(12) United States Patent
Van Wagenen et al.

(10) Patent No.: US 6,660,753 B2
(45) Date of Patent: Dec. 9, 2003

(54) HETEROPOLYCYCLIC COMPOUNDS AND THEIR USE AS METABOTROPIC GLUTAMATE RECEPTOR ANTAGONISTS

(75) Inventors: Bradford Van Wagenen, Salt Lake City, UT (US); Thomas M. Stormann, Salt Lake City, UT (US); Scott T. Moe, Salt Lake City, UT (US); Susan M. Sheehan, Salt Lake City, UT (US); Donald A. McLeod, Salt Lake City, UT (US); Daryl L. Smith, Salt Lake City, UT (US); Methvin Benjamin Isaac, Ontario (CA); Abdelmalik Slassi, Ontario (CA)

(73) Assignee: NPS Pharmaceuticals, Inc., Salt Lake City, UT (US)

(*) Notice: Subject to any disclaimer, the term of this patent is extended or adjusted under 35 U.S.C. 154(b) by 0 days.

(21) Appl. No.: 10/076,618

(22) Filed: Feb. 19, 2002

(65) Prior Publication Data

US 2003/0055085 A1 Mar. 20, 2003

Related U.S. Application Data

(63) Continuation-in-part of application No. PCT/US00/22618, filed on Aug. 18, 2000.
(60) Provisional application No. 60/269,847, filed on Feb. 21, 2001, and provisional application No. 60/149,464, filed on Aug. 19, 1999.

(51) Int. Cl.[7] .................... C07D 401/02; A61K 31/44
(52) U.S. Cl. .................... 514/340; 546/269.1
(58) Field of Search .............. 546/269.1; 514/340

(56) References Cited

U.S. PATENT DOCUMENTS

| | | | | |
|---|---|---|---|---|
| 3,647,809 A | * | 3/1972 | Reiter et al. | 546/256 |
| 4,022,901 A | | 5/1977 | Narayanan et al. | |
| 5,554,630 A | * | 9/1996 | Teuber et al. | 514/338 |

FOREIGN PATENT DOCUMENTS

| | | | | |
|---|---|---|---|---|
| WO | WO 94/22846 A1 | 10/1994 | | |
| WO | WO 94/22846 | * 10/1994 | ......... | C07D/277/64 |
| WO | WO 97/03967 A1 | 2/1997 | | |
| WO | WO 97/0396706096 | * 2/1997 | ......... | C07D/213/81 |
| WO | WO 98 17652 A | 4/1998 | | |
| WO | WO 98/57969 | * 12/1998 | ......... | C07D/413/04 |
| WO | WO 99 02497 A | 1/1999 | | |
| WO | WO 99/26927 A2 | 6/1999 | | |
| WO | WO 01 12627 A | 2/2001 | | |

OTHER PUBLICATIONS

Krasovitskij et al, Chemical Abstracts, vol. 123, No. 22, Abstract 299726w,608h, p. 477, Nov. 27, 1995.*
Yurugi et al, Chemical Pharmaceutical Bulletin, vol. 21, No. 8, pp. 1641–1650, 1973.*
William W. Paudler and James E. Kuder; "The Conversion of Imidazo[1,5–a]pyridines into 3–(2–Pyridyl)–1,2,4–oxadiazoles"; Conversion of Imadazopyridines into Pyridyloxadiazoles; Aug. 1967; pp. 2430–2433; vol. 32; U.S.
T. Ross Kelly and Fengrui Lang; "Total Synthesis of Dimethyl Sulfomycinamate"; Tetrahedron Letters, 1995; pp. 5319–5322; vol. 36, No. 30; Elsevier Science Ltd., U.K.
Wei Huang, et al., "A Novel Improved Procedure for the Synthesis of Oxazoles"; Tetrahedron; 1996; pp. 10131–10136; vol. 52, No. 30; Elsevier Science Ltd., U.K.
Mark A. Massa, et al.; Synthesis of Novel Substituted Pyridines as Inhibitors of Endothelin Converting Enzyme–1 (ECE–1); Biorganic & Medicinal Chemistry Letters; 1998; pp. 2117–2122; vol. 8; Elsevier Science Ltd.
Luciano Vio, et al.; Note–"low antihypertensive activity"; Journal; 5807502; EN; 321; 1988; pp. 713–717; Beilstein Institut zur Foerderung der Chemischen Wissenschaften; Weinheim Germany.
Helene Perrier, et al., "Substituted Furans as Inhibitors of the PDE4 Enzyme"; Biorganic & Medicinal Chemistry Letters; 1999; pp. 323–326; vol. 9; Elsevier Science Ltd.
M. Ohkubo et al.; "Studies on Cerebral Protective Agents; VII. Synthesis of Novel 4–Acrylazole Derivatives with Anti–anoxic Activity", Chem. Pharmaceutical Bulletin; Jun. 1995; pp. 947–954; vol. 43; No. 6;.Pharmaceutical Society of Japan.
W. Pei et al.; "Convenient Synthesis of 2–Alkyl (Aryl)–4, 5–diphenyloxazoles and 2–Alkyl (Aryl)–4 phenyloxazoles"; Synthesis; Sep. 1998; pp. 1298–304; No. 9; China.
C. Montoliu et al.; "Activation of the Metabotropic Glutamate Receptor mGluR5 Prevents Glutamate Toxicity in Primary Cultures of Cerebellar Neurons"; The Journal of Pharmacology and Experimental Therapeutics; May 2, 1997; pp. 643–647; vol. 281; The American Society for Pharmacology and Experimental Therapeutics; United States of America.

* cited by examiner

*Primary Examiner*—Zinna Northington Davis
(74) *Attorney, Agent, or Firm*—Foley & Lardner

(57) ABSTRACT

The present invention provides compounds and pharmaceutical compositions that act as antagonists at metabotropic glutamate receptors, and that are useful for treating neurological diseases and disorders. Methods of preparing the compounds also are disclosed.

58 Claims, No Drawings

HETEROPOLYCYCLIC COMPOUNDS AND THEIR USE AS METABOTROPIC GLUTAMATE RECEPTOR ANTAGONISTS

CROSS-REFERENCE TO RELATED PATENT APPLICATIONS

This application is a continuation-in-part of International Patent Application PCT US00/22618, filed on Aug. 18, 2000, which claims priority to U.S. Provisional Patent Application Ser. No. 60/149,464, filed on Aug. 19, 1999; and a continuation-in-part of U.S. Provisional Application Ser. No. 60/269,847, filed Feb. 21, 2001.

FIELD OF THE INVENTION

The present invention provides compounds that are active at metabotropic glutamate receptors, particularly compounds that are active as antagonists at metabotropic glutamate receptors, more particularly at the mGluR5 glutamate receptor.

BACKGROUND OF THE INVENTION

Recent advances in the elucidation of the neurophysiological roles of metabotropic glutamate receptors have established these receptors as promising drug targets in the therapy of acute and chronic neurological and psychiatric disorders and diseases. However, the major challenge to the realization of this promise has been the development of metabotropic glutamate receptor subtype-selective compounds.

Glutamate is the major excitatory neurotransmitter in the mammalian central nervous system (CNS). Glutamate produces its effects on central neurons by binding to and thereby activating cell surface receptors. These receptors have been divided into two major classes, the ionotropic and metabotropic glutamate receptors, based on the structural features of the receptor proteins, the means by which the receptors transduce signals into the cell, and pharmacological profiles.

The metabotropic glutamate receptors (mGluRs) are G protein-coupled receptors that activate a variety of intracellular second messenger systems following the binding of glutamate. Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase $A_2$; increases in arachidonic acid release; and increases or decreases in the activity of voltage- and ligand-gated ion channels. Schoepp et al., Trends Pharmacol. Sci. 14:13 (1993); Schoepp, Neurochem. Int. 24:439 (1994); Pin et al., Neuropharmacology 34:1 (1995).

Eight distinct mGluR subtypes, termed mGluR1 through mGluR8, have been identified by molecular cloning. See, for example, Nakanishi, Neuron 13:1031 (1994); Pin et al., Neuropharmacology 34:1 (1995); Knopfel et al., J. Med. Chem. 38:1417 (1995). Further receptor diversity occurs via expression of alternatively spliced forms of certain mGluR subtypes. Pin et al., PNAS 89:10331 (1992); Minakami et al., BBRC 199:1136 (1994); Joly et al., J. Neurosci. 15:3970 (1995).

Metabotropic glutamate receptor subtypes may be subdivided into three groups, Group I, Group II, and Group III mGluRs, based on amino acid sequence homology, the second messenger systems utilized by the receptors, and by their pharmacological characteristics. Nakanishi, Neuron 13:1031 (1994); Pin et al., Neuropharmacology 34:1 (1995); Knopfel et al., J. Med. Chem. 38:1417 (1995).

Group I mGluRs comprise mGluR1, mGluR5, and their alternatively spliced variants. The binding of agonists to these receptors results in the activation of phospholipase C and the subsequent mobilization of intracellular calcium. Electrophysiological measurements have been used to demonstrate these effects, for example, in Xenopus oocytes that express recombinant mGluR1 receptors. See, for example, Masu et al., Nature 349:760 (1991); Pin et al., PNAS 89:10331 (1992). Similar results have been achieved with oocytes expressing recombinant mGluR5 receptors. Abe et al., J. Biol. Chem. 267:13361 (1992); Minakami et al., BBRC 199:1136 (1994); Joly et al., J. Neurosci. 15:3970 (1995). Alternatively, agonist activation of recombinant mGluR1 receptors expressed in Chinese hamster ovary (CHO) cells stimulates PI hydrolysis, cAMP formation, and arachidonic acid release as measured by standard biochemical assays. Aramori et al., Neuron 8:757 (1992).

By comparison, the activation of mGluR5 receptors, expressed in CHO cells, stimulates PI hydrolysis and subsequent intracellular calcium transients, but no stimulation of cAMP formation or arachidonic acid release is observed. Abe et al., J. Biol. Chem. 267:13361 (1992). However, activation of mGluR5 receptors expressed in LLC-PK1 cells results in PI hydrolysis and increased cAMP formation. Joly et al., J. Neurosci. 15:3970 (1995). The agonist potency profile for Group I mGluRs is quisqualate>glutamate=ibotenate>(2S, 1'S,2'S)-2-carboxycyclopropyl)glycine (L-CCG-I)>(1S,3R)-1-aminocyclopentane-1,3-dicarboxylic acid (ACPD). Quisqualate is relatively selective for Group I receptors, as compared to Group II and Group III mGluRs, but it also is a potent activator of ionotropic AMPA receptors. Pin et al., Neuropharmacology 34:1, Knopfel et al., J. Med. Chem. 38:1417 (1995).

The lack of subtype-specific mGluR agonists and antagonists has impeded elucidation of the physiological roles of particular mGluRs, and the mGluR-associated pathophysiological processes that affect the CNS have yet to be defined. However, work with the available non-specific agonists and antagonists has yielded some general insights about the Group I mGluRs as compared to the Group II and Group III mGluRs.

Attempts at elucidating the physiological roles of Group I mGluRs suggest that activation of these receptors elicits neuronal excitation. Various studies have demonstrated that ACPD can produce postsynaptic excitation upon application to neurons in the hippocampus, cerebral cortex, cerebellum, and thalamus, as well as other brain regions. Evidence indicates that this excitation is due to direct activation of postsynaptic mGluRs, but it also has been suggested that activation of presynaptic mGluRs occurs, resulting in increased neurotransmitter release. Baskys, Trends Pharmacol. Sci. 15:92 (1992); Schoepp, Neurochem. Int. 24:439 (1994); Pin et al., Neuropharmacology 34:1 (1995).

Pharmacological experiments implicate Group I mGluRs as the mediators of this excitatory mechanism. The effects of ACPD can be reproduced by low concentrations of quisqualate in the presence of ionotrophicGluR antagonists. Hu et al., Brain Res. 568:339 (1991); Greene et al., Eur. J. Pharmacol. 226:279 (1992). Two phenylglycine compounds known to activate mGluR1, namely (S)-3-hydroxyphenylglycine ((S)-3HPG) and (S)-3,5- dihydroxyphenylglycine ((S)-DHPG), also produce excitation. Watkins et al., *Trends Pharmacol. Sci.* 15:33 (1994). In addition, the excitation can be blocked by (S)-4-carboxyphenylglycine ((S)-4CPG), (S)-4-carboxy-3-hydroxyphenylglycine ((S)-4C3HPG), and (+)-alpha-methyl-4-carboxyphenylglycine ((+)-MCPG), compounds known to be mGluR1 antagonists. Eaton et al., *Eur. J. Pharmacol.* 244:195 (1993); Watkins et al., *Trends Pharmacol. Sci.* 15:333 (1994).

Metabotropic glutamate receptors have been implicated in a number of normal processes in the mammalian CNS. Activation of mGluRs has been shown to be required for induction of hippocampal long-term potentiation and cerebellar long-term depression. Bashir et al., *Nature* 363:347 (1993); Bortolotto et al., *Nature* 368:740 (1994); Aiba et al., *Cell* 79:365 (1994); Aiba et al., *Cell* 79:377 (1994). A role for mGluR activation in nociception and analgesia also has been demonstrated. Meller et al., *Neuroreport* 4: 879 (1993). In addition, mGluR activation has been suggested to play a modulatory role in a variety of other normal processes including synaptic transmission, neuronal development, apoptotic neuronal death, synaptic plasticity, spatial learning, olfactory memory, central control of cardiac activity, waking, motor control, and control of the vestibulo-ocular reflex. Generally, see Nakanishi, *Neuron* 13: 1031 (1994); Pin et al., *Neuropharmacology* 34:1; Knopfel et al., *J. Med. Chem.* 38:1417 (1995).

Metabotropic glutamate receptors also have been suggested to play roles in a variety of pathophysiological processes and disease states affecting the CNS. These include stroke, head trauma, anoxic and ischemic injuries, hypoglycemia, epilepsy, and neurodegenerative diseases such as Alzheimer's disease. Schoepp et al., *Trends Pharmacol. Sci.* 14:13 (1993); Cunningham et al., *Life Sci.* 54:135 (1994); Hollman et al., *Ann. Rev. Neurosci.* 17:31 (1994); Pin et al., *Neuropharmacology* 34:1 (1995); Knopfel et al., *J. Med. Chem.* 38:1417 (1995). Much of the pathology in these conditions is thought to be due to excessive glutamate-induced excitation of CNS neurons. Because Group I mGluRs appear to increase glutamate-mediated neuronal excitation via postsynaptic mechanisms and enhanced presynaptic glutamate release, their activation probably contributes to the pathology. Accordingly, selective antagonists of Group I mGluR receptors could be therapeutically beneficial, specifically as neuroprotective agents, analgesics, or anticonvulsants.

Preliminary studies assessing therapeutic potentials with the available mGluR agonists and antagonists have yielded seemingly contradictory results. For example, it has been reported that application of ACPD onto hippocampal neurons leads to seizures and neuronal damage (Sacaan et al., *Neurosci. Lett.* 139:77 (1992); Lipparti et al., *Life Sci.* 52:85 (1993). Other studies indicate, however, that ACPD inhibits epileptiform activity, and also can exhibit neuroprotective properties. Taschenberger et al., *Neuroreport* 3:629 (1992); Sheardown, *Neuroreport* 3:916 (1992); Koh et al., *Proc. Natl. Acad. Sci. USA* 88:9431 (1991); Chiamulera et al., *Eur. J. Pharmacol.* 216:335 (1992); Siliprandi et al., *Eur. J. Pharmacol.* 219:173 (1992); Pizzi et al., *J. Neurochem.* 61:683 (1993).

It is likely that these conflicting results are due to the lack of selectivity of ACPD, which causes activation of several different mGluR subtypes. In the studies finding neuronal damage it appears that Group I mGluRs were activated, thereby enhancing undesirable excitatory neurotransmission. In the studies showing neuroprotective effects it appears that activation of Group II and/or Group III mGluRs occurred, inhibiting presynaptic glutamate release, and diminishing excitatory neurotransmission.

This interpretation is consistent with the observation that (S)-4C3HPG, a Group I mGluR antagonist and Group II mGluR agonist, protects against audiogenic seizures in DBA/2 mice, while the Group II mGluR selective agonists DCG-IV and L-CCG-I protect neurons from NMDA- and KA-induced toxicity. Thomsen et al., *J. Neurochem.* 62:2492 (1994); Bruno et al., *Eur. J. Pharmacol.* 256:109 (1994); Pizzi et al., *J. Neurochem.* 61:683 (1993).

Based on the foregoing, it is clear that a lack of potency and selectivity limits the value of the mGluR agonists and antagonists now available. In addition, most currently available compounds are amino acids or amino-acid derivatives which have limited bioavailabilities, thereby hampering in vivo studies to assess mGluR physiology, pharmacology, and therapeutic potential. On the other hand, compounds that selectively inhibit activation of metabotropic glutamate receptor Group I subtypes are indicated for treatment of neurological disorders and diseases such as senile dementia, Parkinson's disease, Alzheimer's disease, Huntington's Chorea, pain, epilepsy, head trauma, anoxic and ischemic injuries, and psychiatric disorders such as anxiety, schizophrenia and depression.

Accordingly, a need exists for potent mGluR agonists and antagonists that display a high selectivity for a mGluR subtype, particularly a Group I receptor subtype.

SUMMARY OF THE INVENTION

The present invention, provides metabotopic glutamate receptor-active compounds, which exhibit a high degree of potency and selectivity for individual metabotropic glutamate receptor subtypes, and processes of making these compounds.

Further, this invention provides pharmaceutical compositions containing compounds which exhibit a high degree of potency and selectivity for individual metabotropic glutamate receptor subtypes, and to provide methods of making these pharmaceutical compositions.

Another aspect of the invention is to provide methods of inhibiting activation of an mGluR Group I receptor, specifically mGluR5. In particular, a medical condition associated with metabotropic glutamate receptors includes: stroke; head; trauma; anoxic; injury; ischemic; injury; hypoglycemia; epilepsy; pain; migraine headaches; Parkinson's disease; senile dementia; Huntington's Chorea; and Alzheimer's disease.

The invention provides methods of treating a disease associated with excitatory activation of an mGluR Group I receptor and of inhibiting neuronal damage caused by excitatory activation of an mGluR Group I receptor, specifically wherein the mGluR Group I receptor is mGluR5 Finally, the present invention provides potent antagonists of Group I mGluRs, specifically mGluR5.

According to a first aspect of the invention, these antagonists may be represented by compounds of the general formula:

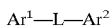

wherein $Ar^1$ is an optionally substituted heteroaromatic moiety and $Ar^2$ is an optionally substituted benzene ring. The L moiety is a group that not only covalently binds to the $Ar^1$ and $Ar^2$ moieties, and facilitates adoption of the correct spatial orientation of $Ar^1$ and $Ar^2$, but also itself may interact with the protein, to effect receptor binding.

In one embodiment of the invention, L is selected from the group consisting of —NH—, —S—, —O—, —CO—, —CONH—, —CONHCH$_2$—, —CH$_2$CONH—, —CNHNH—, —CNHNHCH$_2$—, —C═NO—CH$_2$—, —CH$_2$NHCH$_2$—, —CH$_2$CH$_2$NH—, —NHCH$_2$CO—, —NHCH$_2$CHOH—, —NHCNHNH.—, —NHCONH—, cyclopentane, cyclopentadiene, furan, thiofuran, pyrrolidine, pyrrole, 2-imidazoline, 3-imidazoline, 4-imidazoline, imidazole, pyrazoline, pyrazolidine, imidazolidine, oxazole, 2-oxazole, thiazole, isoxazole, isothiazole, 1H-1,2,4-triazole, 1H-1,2,3-triazole, 1,2,4-oxathiazole, 1,3,4-oxathiazole, 1,4,2-dioxazole, 1,4,2-oxathiazole, 1,2,4-oxadiazole, 1,2,4-thiadiazole, 1,2,5-oxadiazole, 1,2,5-thiadiazole, 1,3,4-oxadiazole, 1,3,4-thiadiazole, 1H-tetrazole, cyclohexane, piperidine, tetrahydropyridine, 1,4-dihydropyridine, pyridine, benzene, tetrahydropyran, 3,4-dihydro-2H-pyran, 2H-pyran, 4H-pyran, tetrahydrothiopyran, 3,4-dihydro-2H-thiopyran, 2H-thiin, 4H-thiopyran, morpholine, thiomorpholine, piperazine, pyridazine, pyrimidine, pyrazine, 1,2,4-triazine, 1,2,3-triazine, 1,3,5-triazine, and 1,2,4,5-tetrazine.

In another embodiment of the invention, Ar$^1$ is selected from the group consisting of phenyl, benzyl, naphthyl, fluorenyl, anthrenyl, indenyl, phenanthrenyl, and benzonaphthenyl, and Ar$^2$ is selected from the group consisting of thiazoyl, furyl, pyranyl, 2H-pyrrolyl, thienyl, pyrroyl, imidazoyl, pyrazoyl, pyridyl, pyrazinyl, pyrimidinyl, pyridazinyl, benzothiazole, benzimidazole, 3H-indolyl, indolyl, indazoyl, purinyl, quinolizinyl, isoquinolyl, quinolyl, phthalizinyl, naphthyridinyl, quinazolinyl, cinnolinyl, isothiazolyl, quinoxalinyl indolizinyl, isoindolyl, benzothienyl, benzofuranyl, isobenzofuranyl, and chromenyl.

According a second aspect of the invention, these antagonists may be represented by compounds of Formula I:

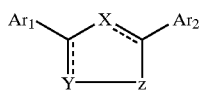

I wherein
---- represents a double or single bond;
X, Y, and Z are independently selected from the group consisting of: N; O; S;
and CR$_1$ and at least one of X, Y, and Z is a heteroatom;
wherein
R$_1$ is selected from the group consisting of: H; alkyl; —CF$_3$; —OR$_2$; —SR$_2$; —NR$_2$R$_3$; ═O; ═S; ═NR$_2$; and ═CR$_2$R$_3$; and
wherein
R$_2$ and R$_3$ may be independently selected from the group consisting of: H; alkyl; haloalkyl; alkyloxy; alkylamine; cycloalkyl;
heterocycloalkyl; aryl; heteroaryl; alkylaryl; alkyl-heteroaryl; haloaryl;
alkyloxyaryl; alkenylaryl; alkenyloxyaryl; and halo-heteroaryl; and Ar$_1$ and Ar$_2$ are independently selected from the group consisting of: aryl and heteroaryl, and at least one of Ar$_1$ and Ar$_2$ is substituted with at least one substituent G;
wherein
G is selected from the group consisting of: haloalkyl; heteroaryl;
cycloalkene; alkenyl; alkynyl; A-alkenyl; A-alkynyl; alkyloxy; A-alkyloxy; —R$_2$OR$_3$; —R$_2$OC(O)R$_3$; (CH$_2$)$_m$—NR$_2$R$_3$; —OCH$_2$CH(Cl)CH$_2$Cl; and substituted aryl wherein the aryl substituent is R$_4$, and wherein
A is a linker selected from the group consisting of: CH$_2$O; NH; S;
SO; SO$_2$ ; NSO$_2$ ; OSO$_2$ ; and —C(NR$_2$)NR$_3$;
m is selected from 0 and 1; and
R$_4$ is selected from the group consisting of: halo; —OR$_2$; —SR$_2$; —SOR$_2$; —SO$_2$R$_2$; —SO$_2$NR$_2$R$_3$; —R$_2$OR$_3$; —R$_2$SR$_3$; —OCOR$_2$; —OCONR$_2$R$_3$; —NR$_2$COR$_3$; —NR$_2$CO$_2$R$_3$; —CN; —NO$_2$; —C(NR$_2$)NR$_3$; —CO$_2$R$_2$R$_3$; —CONR$_2$R$_3$;
—C(O)R$_2$; —CH(OR$_2$)R$_3$; —CH$_2$(OR$_2$); —A—(CH$_2$)$_m$—NR$_2$R$_3$; NR$_2$R$_3$; aryl;
aralkyl; heteroaryl; and heteroaralkyl; and
Ar$_1$, Ar$_2$, and the substituent G are optionally further substituted with one or more substituents selected independently from the group consisting of R$_2$ and R$_4$;
with the proviso that when ---- represents a double bond, then either of Ar$_1$ or
Ar$_2$ is pyridyl and the compound is not:
3-(2-Pyridyl)-5-(2-nitrophenyl)-1,2,4-oxadiazole,
3-(2-Pyridyl)-5-(2-chlorophenyl)-1,2,4-oxadiazole,
3-(4-Pyridyl)-5-(2-chlorophenyl)-1,2,4-oxadiazole
3-(3-Pyridyl)-5-(2-chlorophenyl)-1,2,4-oxadiazole,
3-(4-Pyridyl)-5-(4-chlorophenyl)-1,2,4-oxadiazole,
3-(2-Pyridyl)-5-(3-ethoxyphenyl)-1,2,4-oxadiazole,
3-(2-Pyridyl)-5-[3-(trifluoromethyl)phenyl]-1,2,4-oxadiazole,
3-(2-Pyridyl)-5-(2-bromo-5-methoxyphenyl)-1,2,4-oxadiazole,
3-(2-chlorophenyl)-5-(4-pyridyl)-1,2,4-oxadiazole,
3-(2-ethoxyphenyl)-5-(3-pyridyl)-1,2,4-oxadiazole,
3-styryl-5-(4-pyridyl)-1,2,4-oxadiazole, 3-(3-Pyridyl)-5-(4-aminophenyl)-1,2,4-oxadiazole,
3-(3-Pyridyl)-5-(4-chlorophenoxymethyl)-1,2,4-oxadiazole,
3-(4-Pyridyl)-5-(4-chlorophenoxymethyl)-1,2,4-oxadiazole,
3-(3-Pyridyl)-5-(2-pyridyl)-1,2,4-oxadiazole,
3-(4-Pyridyl)-5-(3-pyridyl)-1,2,4-oxadiazole,
3-(4-Pyridyl)-5-(4-pyridyl)-1,2,4-oxadiazole,
3-(2-ethyl-4-pyridyl)-5-(2-hydroxyphenyl)-1,2,4-oxadiazole,
3-(2-ethyl-4-pyridyl)-5-(4-pyridyl)-1,2,4-oxadiazole,
3-(2-ethyl-4-pyridyl)-5-(2-ethyl-4-pyridyl)-1,2,4-oxadiazole,
3-(2-ethyl-4-pyridyl)-5-(4-chlorophenylmethyl)-1,2,4-oxadiazole,
3-(2-pyridyl)-5-(4-nitrophenyl)-1,2,4-oxadiazole,
3-(2-pyridyl)-5-(4-aminophenyl)-1,2,4-oxadiazole,
3-(3-pyridyl)-5-(4-nitrophenyl)-1,2,4-oxadiazole,
3-(3-pyridyl)-5-(4-aminophenyl)-1,2,4-oxadiazole,
3-(2-pyridyl)-5-{2-[2-(N,N,dimethylamino)-ethyl]oxyphenyl}-1,2,4-oxadiazole,
3-(4-pyridyl)-5-{2-[2-(N,N,dimethylamino)-ethyl]oxyphenyl}-1,2,4-oxadiazole,
3-(2-pyridyl)-5-phenyl-1,2,4-oxadiazole,
2-(4-methoxyphenyl)-4-(2-pyridyl)-1,3-oxazole,
3-(2-pyridyl)-5-(2-chlorophenyl)-1,2,4,-triazole,
3-(2-pyridyl)-5-(2,6-dichlorophenyl)-1,2,4,-triazole,
2-(2-pyridyl)-5-[3-(3-methoxy-4-cyclopentoxy)phenyl]-furan, 2-(3-pyridyl)-5-[3-(3-methoxy-4-cyclopentoxy)phenyl]-furan, or 2-(4-pyridyl)-5-[3-(3-methoxy-4-cyclopentoxyphenyl)]-furan.

In another aspect of the invention, antagonists of Formula II are provided.

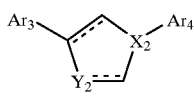

wherein

---- represents a double or single bond;

$X_2$ is selected from N and C, and $Y_2$ is selected from the group consisting of: N;

O; S; and $CR_5$, and at least one of $X_2$ and $Y_2$ is a heteroatom;

wherein $R_5$ is selected from the group consisting of: H; alkyl; —$CF_3$; —$OR_6$; —$SR_6$;

$NR_6R_7$; =O; =S; —=$NR_6$; and =$CR_6R_7$; and wherein $R_6$ and $R_7$ may be independently selected from the group consisting of: H; alkyl; haloalkyl; alkyloxy; alkylamine; cycloalkyl;

heterocycloalkyl; aryl; heteroaryl; alkylaryl; alkylheteroaryl; haloaryl;

alkyloxyaryl; alkenylaryl; alkenyloxyaryl; and halohetroaryl; and $Ar_3$ and $Ar_4$ are independently selected from the group consisting of aryl and heteroaryl and one, or both, of $Ar_3$ and $Ar_4$ is optionally substituted with one or more substituents $G_2$;

wherein $G_2$ is selected from the group consisting of: haloalkyl; heteroaryl;

cycloalkene; alkenyl; alkynyl; A-alkenyl; A-alkynyl; alkyloxy; A-alkyloxy; —$R_6OR_7$; —$R_6OC(O)R_7$; —$(CH_2)_m$—$NR_6R_7$; —$OCH_2CH(Cl)CH_2Cl$; and substituted aryl wherein the aryl substituent is $R_8$; and wherein A is a linker selected from the group consisting of: $CH_2O$; NH; S; SO; $SO_2$; $NSO_2$; $OSO_2$; and —$C(NR_6)NR_7$;

m is selected from 0 and 1; and $R_8$ is selected from the group consisting of: halo; —$OR_6$; —$SR_6$; —$SOR_6$; —$SO_2R_6$; —$SO_2NR_6R_7$; —$R_6OR_7$ $R_6SR_7$; —$OCOR_6$; —$OCONR_6R_7$; —$NR_6COR_7$; —$NR_6CO_2R_7$; —CN; —$NO_2$; —$C(NR_6)NR_7$; —$CO_2R_6R_7$; —$CONR_6R_7$; —C(O)$R_6$; —CH(O$R_6$)$R_7$; —$CH_2$(O$R_6$); —A—(CH$_2$)$_m$—$NR_6R_7$; $NR_6R_7$; aryl;

aralkyl; heteroaryl; and heteroaralkyl; and $Ar_3$, $Ar_4$, and the substituent $G_2$ are optionally further substituted with one or more substituents selected independently from the group consisting of: $R_6$ and $R_8$.

Another aspect of the invention is to provide processes for making the compounds of the present invention.

A further aspect of the invention is to provide a method of inhibiting activation of an mGluR Group I receptor, specifically mGluR5, comprising treating a cell containing said mGluR Group I receptor with an effective amount of a compound of the present invention.

Yet another aspect of the invention is to provide a method of inhibiting neuronal damage caused by excitatory activation of an mGluR Group I receptor, in particular mGluR5, comprising treating neurons with an effective amount of a compound of the present invention.

A further aspect of the invention is to provide a method of treating a disease associated with Group I mGluR activation or amenable to therapeutic intervention with a mGluR Group I antagonist, for example, a disease associated with glutamate-induced neuronal damage, which method comprises the step of administering to a patient, in need of such treatment, for example, a patient suffering from said disease, or at risk of suffering from said disease, a therapeutically effective non-toxic amount of a compound of the present invention. In a particular aspect of the invention a therapeutically effective amount of the present invention would be an amount which selectively antagonizes an mGluR Group I receptor, in particular the mGluR5 receptor.

Other aspects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DEFINITIONS

The term "alkyl" as used herein refers to straight- and branched-chain alkyl radicals containing from 1, 2, 3, 4, 5, or 6 carbon atoms and includes methyl, ethyl and the like.

The term "aryl" as used herein refers to a monocyclic aromatic group such as phenyl and the like or a benzo-fused aromatic group such as indanyl, naphthyl, fluorenyl and the like.

The term "heteroaryl" refers to aromatic compounds containing one or more hetero atoms such as pyridyl, furyl, thienyl and the like or a benzofused aromatic containing one or more heteroatoms such as indolyl, quinolinyl and the like.

The term "heteroatom" as used herein refers to non-carbon atoms such as N, O, S and the like.

The term "cycloalkyl" as used herein refers to a carbocyclic ring containing of 3, 4, 5, 6, 7, or 8 carbons and includes cyclopropyl, cyclohexyl and the like.

The term "heterocycloalkyl" as used herein refers to 3, 4, 5, 6, 7, or 8 membered rings containing 1, 2, or 3 heteroatoms selected from the group consisting of N, S, and O and includes piperidine, piperizine, pyran and the like.

The term "halo" as used herein refers to the halogen radicals fluoro, chloro, bromo, and iodo.

The term "haloalkyl" as used herein refers to an alkyl substituted with one or more halogens, such as bromoethyl, chloromethyl, trichloromethyl and the like.

The term "alkoxy" as used herein refers to a straight- or branched-chain alkoxy containing 1, 2, 3, 4, 5 or 6 carbon atoms and includes methoxy, ethoxy and the like.

The term "alkyloxy" as used herein refers to an alkyl substituted with a hydroxy group such as hydroxyethyl, hydroxypropyl and the like.

The term "alkenyl" as used herein refers to a straight or branched-chain alkyl containing one or more double bonds such as propenyl, vinyl and the like.

The term "aralkyl" as used herein refers to an alkyl substituted with an aryl such as benzyl, phenethyl and the like.

The term "alkylamine" as used herein refers to an alkyl substituted with an amine such as aminomethyl, or dimethylaminoethyl and the like.

The term "alkylaryl" as used herein refers to an aryl substituted with an alkyl group such as methylphenyl, isopropylnaphthyl and the like.

The term "alkylheteroaryl" as used herein refers to a heteroaryl substituted with an alkyl group. Particular examples include methylpyridine, ethylfuran, and the like.

The term "alkynyl" as used herein refers to a straight or branched-chain alkyl containing one or more double bonds such as ethynyl, propynyl, vinyl and the like.

The term "haloaryl" as used herein refers to an aryl substituted with a halogen such as bromophenyl, chlorophenyl and the like.

The term "alkyloxyaryl" as used herein refers to an aryl substituted with an alkyloxy group such as hydroxyethylphenyl and the like.

The term "alkenyloxyaryl" as used herein refers to an aryl susbtituted with an alkenyloxy group such as propenyloxy phenyl and the like.

The term "haloheteroaryl" as used herein refers to a heteroaryl substituted with a halogen. A particular example is 4-chloropyridine.

The term "cycloalkene" as used herein refers to a 3, 4, 5, 6, 7, or 8-member ring, which contains one or more double bonds, and may contain a heteroatom. Particular examples include cyclohexene, tetrahydropyridine and the like.

The term "alkenylaryl" as used herein refers to an aryl substituted with an alkenyl group. A particular example is vinyl benzene.

DETAILED DESCRIPTION OF THE INVENTION

The present invention provides compounds that are potent and selective antagonists of mGluR5. The compounds contemplated by the invention can be represented by the general formula:

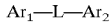

where $Ar^1$ is an optionally substituted heterocyclic moiety and $Ar^2$ is an optionally substituted carbocyclic moiety. The G moiety is a group that not only covalently binds to the $Ar^1$ and $Ar^2$ moieties and facilitates adoption of the correct spatial orientation of $Ar^1$ and $Ar^2$, but may itself interact with the protein to allow receptor binding.

The $Ar^1$ moiety is generally defined as a heterocyclic moiety, and the $Ar^2$ moiety is generally defined as a carbocylic moiety. $Ar^1$ and $Ar^2$ can be monocyclic or fused bicyclic groups. $Ar^2$ is preferably defined as an aryl or alkaryl moiety. $Ar^1$ is preferably defined as a heterocyclic, heteroaryl or heteroarylalkyl moiety. The ring systems encompassed by $Ar^1$ can contain up to four heteroatoms, independently selected from the group consisting of N, S, and O. When $Ar^1$ is a heteroaryl ring or ring system, it preferably contains one or two heteroatoms. At least one of the heteroatoms preferably is nitrogen (N). The heterocyclic or fused heterocylic moiety preferably is selected from the group consisting of quinolyl, quinazolyl, quinoxalyl, 2-pyrimidyl, 4-pyrimidyl, 5-pyrimidyl, 2-pyridyl, 3-pyridyl, 4-pyridyl, and pyrazyl.

Monocyclic $Ar^1$ groups include, but are not limited to: thiazoyl, furyl, pyranyl, 2H-pyrrolyl, thienyl, pyrroyl, imidazoyl, pyrazoyl, pyridyl, pyrazinyl, pyrimidinyl, and pyridazinyl moieties. Monocyclic $Ar^2$ group include but are not limited to phenyl and benzyl. Fused bicyclic $Ar^2$ include, but are not limited to, naphthyl, fluorenyl, anthrenyl, indenyl, phenanthrenyl, and benzonaphthenyl. Fused bicyclic $Ar^1$ groups include, but are not limited to: benzothiazole, benzimidazole, 3H-indolyl, indolyl, indazoyl, purinyl, quinolizinyl, isoquinolyl, quinolyl, phthalizinyl, naphthyridinyl, quinazolinyl, cinnolinyl, isothiazolyl, quinoxalinyl indolizinyl, isoindolyl, benzothienyl, benzofuranyl, isobenzofuranyl, and chromenyl moieties. $Ar^1$ preferably is a 2-pyridyl moiety. $Ar^2$ preferably is a substituted phenyl moiety.

The $Ar^1$ and $Ar^2$ moieties optionally may independently be substituted with one or more moieties selected from the group consisting of halogen, $C_1$–$C_3$ alkyl, $C_1$–$C_3$ O-alkyl, —OH, —OCF$_3$, —COOR, —COR, —SOR, —SO$_2$NRR', —NRR', —CN, —CF$_3$,—CO—NRR', —A—(CH$_2$)$_n$—NRR', wherein A is C, O, N, SO, SO$_2$ , and R and R' are independently selected from the group consisting of $C_1$–$C_3$ alkyl, H, cycloalkyl, heterocycloalkyl, aryl, and n is 1, 2, 3, or 4.

The L moiety is generally made up of 1–14 atoms. L can be independently selected from the group of atoms: C, H, N, O, and S.

The L moiety can thus be made of a non-cyclic moiety. Several examples of these are —NH— (amine), —S— (thioether), —O— (ether), —CO— (ketone), —CONH— (amide), —CONHCH$_2$—, —CH$_2$CONH—, —CNHNH— (amidine), —CNHNHCH$_2$—, —C=NO—CH$_2$— (methoxime), —CH$_2$NHCH$_2$—, —CH$_2$CH$_2$NH—, —NHCH$_2$CO—, —NHCH$_2$CHOH—, —NHCNHNH.— (guanidine), and —HCONH— (urea), for example.

The atomic arrangement in the L moiety can also be made to form a five-membered ring. Several examples of these are cyclopentane, cyclopentadiene, furan, thiofuran, pyrrolidine, pyrrole, 2-imidazoline, 3-imidazoline, 4-imidazoline, imidazole, pyrazoline, pyrazolidine, imidazolidine, oxazole, 2-oxazole, thiazole, isoxazole, isothiazole, 1H-1,2,4-triazole, 1H-1,2,3-triazole, 1,2,4-oxathiazole, 1,3,4-oxathiazole, 1,4,2-dioxazole, 1,4,2-oxathiazole, 1,2,4-oxadiazole, 1,2,4-thiadiazole, 1,2,5-oxadiazole, 1,2,5-thiadiazole, 1,3,4-oxadiazole, 1,3,4-thiadiazole, and 1H-tetrazole, for example. The 1,2,4-oxadiazole is most preferred.

The atomic arrangement in the L moiety can also be made to form a six-membered ring. Several examples of these are cyclohexane, piperidine, tetrahydropyridine, 1,4-dihydropyridine, pyridine, benzene, tetrahydropyran, 3,4-dihydro-2H-pyran, 2H-pyran, 4H-pyran, tetrahydrothiopyran, 3,4-dihydro-2H-thiopyran, 2H-thiin, 4H-thiopyran, morpholine, thiomorpholine, piperazine, pyridazine, pyrimidine, pyrazine, 1,2,4-triazine, 1,2,3-triazine, 1,3,5-triazine, and 1,2,4,5-tetrazine, for example.

The atomic arrangement in the L moiety can also be made to form a five- or six-membered ring containing one or more carbonyl groups. Several examples of these are 2-azetidinone, 1,2-diazetidin-3-one, cyclopentanone, 2-cyclopentenone, 2-pyrrolidinone, 3-pyrrolin-2-one, succinimide, maleimide, 3-pyrazolidinone, 2-imidazolidone, 4-imidazolin-2-one, 2H-imidazol-2-one, 4-imidazolinone, 3-pyrazolin-5-one, hydantoin, 1H-imidazole-2,5-dione, 2-oxazoline-4-one, 2-oxazolidinone, 3-oxazolin-5-one, 3(2H)-isoxazolone, 2,4-oxazolidinedione, 1,2,4-triazoline-3,5-dione, 2,4-dihydro-3H-1,2,4-triazol-3-one, 2H-pyran-2-one, 2(1H)-pyridone, 2(1H)-pyrazinone, 4(3H)-pyrimidone, 3,4-dihydropyrimidin-4-one, glutarimide, 4,6-(1H,5H)-pyrimidinedione, 1,3,5-triazin-2(1H)-one, and cyanuric acid, for example.

In a preferred embodiment, L comprises a heterocyclic 5-membered ring system. Preferably, L is an oxazole or an 1,2,4-oxadiazole ring. The L moiety may have either one of two possible orientations with respect to the Arl and Ar² groups. Thus, for example, the invention prefers compounds having the configuration 4-(Ar¹)-2-(Ar²)-oxazole or 3-(Ar¹)-5-(Ar²)-1,2,4-oxadiazole.

According to one aspect of the invention, compounds of Formula I are provided.

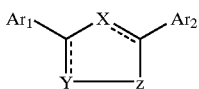

Formula I contains a five member ring containing three variables X, Y, and Z. There are attached to this five member ring two substituents, $Ar_1$ and $Ar_2$. The five member ring may contain 0, 1 or 2 double bonds as denoted by the dotted lines in Formula 1. In a preferred embodiment of the invention, the five member ring has 2 double bonds.

When the five member ring contains two double bonds, however, then either of $Ar_1$ or $Ar_2$ is pyridyl and the following compounds are excluded from this invention: 3-(2-Pyridyl)-5-(2-nitrophenyl)-1,2,4-oxadiazole, 3-(2-Pyridyl)-5-(2-chlorophenyl)-1,2,4-oxadiazole, 3-(4-Pyridyl)-5-(2-chlorophenyl)-1,2,4-oxadiazole, 3-(4-Pyridyl)-5-(4-chlorophenyl)-1,2,4-oxadiazole, 3-(2-Pyridyl)-5-(3-methoxyphenyl)-1,2,4-oxadiazole, 3-(2-Pyridyl)-5-[3-(trifluoromethyl)phenyl]-1,2,4-oxadiazole, 3-(2-Pyridyl)-5-(2-bromo-5-methoxyphenyl)-1,2,4-oxadiazole, 3-(2-chlorophenyl)-5-(4-pyridyl)-1,2,4-oxadiazole, 3-(2-ethoxyphenyl)-5-(3-pyridyl)-1,2,4-oxadiazole, 3-styryl-5-(4-pyridyl)-1,2,4-oxadiazole, 3-(3-Pyridyl)-5-(4-aminophenyl)-1,2,4-oxadiazole,3-(3-Pyridyl)-5-(4-chlorophenoxymethyl)-1,2,4-oxadiazole, 3-(4-Pyridyl)-5-(4-chlorophenoxymethyl)-1,2,4-oxadiazole, 3-(3-Pyridyl)-5-(2-pyridyl)-1,2,4-oxadiazole, 3-(4-Pyridyl)-5-(3-pyridyl)-1,2,4-oxadiazole, 3-(4-Pyridyl)-5-(4-pyridyl)-1,2,4-oxadiazole, 3-(2-ethyl-4-pyridyl)-5-(2-hydroxyphenyl)-1,2,4-oxadiazole, 3-(2-ethyl-4-pyridyl)-5-(4-pyridyl)-1,2,4-oxadiazole, 3-(2-ethyl-4-pyridyl)-5-(2-ethyl-4-pyridyl)-1,2,4-oxadiazole, 3-(2-ethyl-4-pyridyl)-5-(4-chlorophenylmethyl)-1,2,4-oxadiazole, 3-(2-pyridyl)-5-(4-nitrophenyl)-1,2,4-oxadiazole, 3-(2-pyridyl)-5-(4-aminophenyl)-1,2,4-oxadiazole, 3-(3-pyridyl)-5-(4-nitrophenyl)-1,2,4-oxadiazole, 3-(3-pyridyl)-5-(4-aminophenyl) -1,2,4-oxadiazole, 3-(2-pyridyl)-5-{2-[2-(N,N,dimethylamino)-ethyl]oxyphenyl}-1,2,4-oxadiazole, 3-(4-pyridyl)-5-{2-[2-(N,N,dimethylamino)-ethyl]oxyphenyl}-1,2,4-oxadiazole, 3-(2-pyridyl)-5-phenyl-1,2,4-oxadiazole, 2-(4-methoxyphenyl) -4-(2-pyridyl)-1,3-oxazole, 3-(2-pyridyl)-5-(2-chlorophenyl)-1,2,4,-triazole, 3-(2-pyridyl)-5-(2,6-dichlorophenyl)-1,2,4,-triazole, 2-(2-pyridyl)-5-[3-(3-methoxy-4-cyclopentoxy)phenyl]-furan, 2-(3-pyridyl)-5-[3-(3-methoxy-4-cyclopentoxy)phenyl]-furan, or 2-(4-pyridyl)-5-[3-(3-methoxy-4-cyclopentoxyphenyl)]-furan. This proviso excludes known compounds that coincidentally contain structural features that are common to elements of general formula $Ar_1$—L—$Ar_2$ or Formula I. Although none of these known compounds has been recognized heretofore as a metabotropic glutamate receptor antagonist, a subset of these is implicated in the literature as active agents in pharmaceutical compositions. These include: 3-(2-Pyridyl)-5-(2-chlorophenyl)-1,2,4-oxadiazole, 3-(4-Pyridyl)-5-(2-chlorophenyl)-1,2,4-oxadiazole, 3-(3-Pyridyl)-5-(2-chlorophenyl)-1,2,4-oxadiazole, 3-(4-Pyridyl)-5-(4-chlorophenyl)-1,2,4-oxadiazole, 3-(2-chlorophenyl)-5-(4-pyridyl)-1,2,4-oxadiazole, 3-(2-ethoxyphenyl)-5-(3-pyridyl)-1,2,4-oxadiazole, 3-styryl-5-(4-pyridyl)-1,2,4-oxadiazole, 3-(3-Pyridyl)-5-(4-aminophenyl)-1,2,4-oxadiazole, 3-(3-Pyridyl)-5-(4-chlorophenoxymethyl)-1,2,4-oxadiazole, 3-(4-Pyridyl)-5-(4-chlorophenoxymethyl)-1,2,4-oxadiazole, 3-(4-Pyridyl)-5-(3-pyridyl)-1,2,4-oxadiazole, 3-(4-Pyridyl)-5-(4-pyridyl)-1,2,4-oxadiazole, 3-(2-ethyl-4-pyridyl)-5-(2-hydroxyphenyl)-1,2,4-oxadiazole, 3-(2-ethyl-4-pyridyl)-5-(4-pyridyl)-1,2,4-oxadiazole, 3-(2-ethyl-4-pyridyl)-5-(2-ethyl-4-pyridyl)-1,2,4-oxadiazole, 3-(2-ethyl-4-pyridyl)-5-(4-chlorophenylmethyl)-1,2,4-oxadiazole, 3-(2-pyridyl)-5-(4-nitrophenyl)-1,2,4-oxadiazole, 3-(2-pyridyl)-5-(4-aminophenyl)-1,2,4-oxadiazole, 3-(3-pyridyl)-5-(4-nitrophenyl)-1,2,4-oxadiazole, 3-(3-pyridyl)-5-(4-aminophenyl) -1,2,4-oxadiazole, 3-(2-pyridyl)-5-{2-[2-(N,N,dimethylamino)-ethyl]oxyphenyl}-1,2,4-oxadiazole, 3-(4-pyridyl)-5-{2-[2-(N,N,dimethylamino)-ethyl]oxyphenyl}-1,2,4-oxadiazole2-(2-pyridyl)-5-[3-(3-methoxy-4-cyclopentoxy) phenyl]-furan, 2-(3-pyridyl)-5-[3-(3-methoxy-4-cyclopentoxy)phenyl]-furan, and 2-(4-pyridyl)-5-[3-(3-methoxy-4-cyclopentoxyphenyl)]-furan. Such compounds are excluded from the pharmaceutical composition of the present invention.

In embodiments of the invention, variables X, Y, and Z are independently selected from N, O, S, and substituted carbon, designated CRi, wherein Ri is as defined above. At least one of X, Y, or Z must be a heteroatom. In a preferred embodiment of the invention more than one of X, Y, and Z are heteroatoms. In one aspect of the invention two of X, Y, and Z are heteroatoms, while in another aspect of the invention all three of X, Y, and Z are heteroatoms. In a preferred embodiment of the invention at least one of X, Y, and Z, is N. In a more preferred embodiment of the invention two of X, Y and Z are N. In a further preferred embodiment of the invention, X is N, Y is N and Z is O.

According to a further aspect of the invention the groups $Ar_1$ and $Ar_2$ are independently selected from aryl and heteroaryl. Particular embodiments of the invention include those wherein $Ar_1$ and $Ar_2$ are independently selected from 5- and 6-member aryl and heteroaryl rings. In more particular embodiments of the invention $Ar_1$ and $Ar_2$ are selected from 6-member aryl and heteroaryl rings. Still more particular embodiments of the invention include those where $Ar_1$ and $Ar_2$ are independently selected from phenyl, pyridyl, furanyl, thienyl, pyrazinyl, pyrimidinyl, pyridazinyl, pyrrolyl, pyrazolyl, imidazolyl, triazolyl, thiazolyl. In a preferred embodiment of the invention, $Ar_1$ is selected from phenyl and pyridyl. In a more preferred embodiment of the invention, $Ar_1$ is selected from pyridyl. In an even more preferred embodiment, $Ar_1$ is selected from 2-pyridyl. In another preferred embodiment, $Ar_2$ is selected from phenyl and pyridyl. In a suitable embodiment, $Ar_2$ is phenyl. In another suitable embodiment, $Ar_2$ is 3-pyridyl.

According to another aspect of the invention at least one of $Ar_1$ and $Ar_2$ is substituted with at least one substituent G. In preferred embodiments of the invention, $Ar_2$ is substituted with G. Suitable embodiments of the invention include those where G is selected from the group consisting of: haloalkyl; heteroaryl; cycloalkene; alkenyl; alkynyl; A-alkenyl; A-alkynyl; alkyloxy; A-alkyloxy; $R_2OR_3$; —$R_2OC(O)R_3$; $(CH_2)_m$—$NR_2R_3$; —$OCH_2CH(Cl)CH_2Cl$; and substituted aryl, wherein $R_2$ and $R_3$ are as defined above.

In one embodiment of the invention, G is haloalkyl.

In another embodiment of the invention, G is heteroaryl wherein heteroaryl is selected from the group consisting of: pyridyl; furanyl; thienyl; pyrazinyl; pyrimidinyl; pyridazinyl; pyrrolyl; pyrazolyl; imidazolyl; triazolyl; and thiazolyl.

In a preferred embodiment of the invention, G is selected from the group consisting of: pyridyl; furanyl; thienyl; and pyrimidinyl. In a more preferred embodiment of the invention, G is selected from the group consisting of: 2-pyridyl; 3-pyridyl; 4-pyridyl; 3-thienyl; 5-pyrimidinyl; and 3-furanyl.

In yet another preferred embodiment of the invention, G is cycloalkene. In a further preferred embodiment of the invention G is selected from 5- and 6- member carbocyclic and heterocyclic rings containing one or more double bonds. In a still further preferred embodiment of the invention, G is a 6-member herterocyle containing one double bond. In yet a further embodiment, G is 3-(1,2,5,6-tetrahydropyridyl). In a suitable embodiment G, is N-substituted 3-(1,4,5,6-tetrahydropyridyl), for example 3-N-benzyl-(1,2,5,6-tetrahydropyridyl).

According to another aspect of the invention, G is alkenyl. In a more particular embodiment of the invention, G is selected from the group consisting of: vinyl; 2-methylvinyl; propenyl; and butenyl.

According to another aspect of the invention, G is alkynyl. In a more particular embodiment of the invention, G is selected from propargyl and butynyl.

According to yet another aspect of the invention, G is selected from the group consisting of: A-alkenyl; and A-alkynyl; wherein an alkenyl, or alkynyl, respectively, is linked to $Ar_1$ or $Ar_2$ though A. In particular embodiments of the invention, A is selected from the group consisting of: $CH_2O$; NH; S; SO; $SO_2$; $NSO_2$; $OSO_2$; and —$C(NR_2)NR_3$. In a more particular embodiment of the invention, A is selected from O and NH. In a still more particular embodiment of the invention, G is —OHCH2CH=CH2.

In a still further embodiment of the invention, G is selected from the group consisting of: alkyloxy; and A-alkyloxy; wherein alkyloxy is a straight or branched chain alkyl radical substituted with a hydroxy group and A is a linker. In a more particular embodiment of the invention the alkyloxy group is linked to $Ar_1$ or $Ar_2$ through A, and A is selected from the group consisting of: $CH_2O$; NH; S; SO; $SO_2$; $NSO_2$; $OSO_2$; and —$C(NR_2)NR_3$. In a more particular embodiment of the invention, A is 0, and alkyloxy is selected from hydroxymethyl, hydroxyethyl, and hydroxypropyl. In a more particular embodiment G is—$OCH_2CH_2CH_2OH$.

In a further embodiment of the invention, G is $R_2OCOR_3$. In a particular embodiment of the invention, G is an alkylester, wherein the ester links to $Ar_1$ or $Ar_2$ through an alkyl group. In a more particular embodiment of the invention, G is —$CH_2OC(O)H$.

In still a further embodiment of the invention, G is $(CH_2)_m$—$NR_2R_3$, wherein m is 0 or 1. In a particular embodiment of the invention, G is $(CH_2)_m$—$NR_2R_3$, and $R_2$ and $R_3$ are independently selected from H, alkyl, alkyloxy, alkylamine, cycloalkyl, heterocycloalkyl, aryl, heteroaryl, alkylaryl, alkylheteroaryl, haloaryl, alkyloxyaryl, alkenylaryl, alkenyloxyaryl, haloheteroaryl. In a more particular embodiment of the invention, $R_2$ and $R_3$ are independently selected from H, and alkyl. In a further embodiment of the invention, $R_2$ and $R_3$ are independently selected from H and methyl.

According to another aspect of the invention, G is aryl substituted with a substituents $R_4$. In particular, the aryl group is selected from the group consisting of: phenyl; naphthyl; anthrenyl; and fluorenyl. The substituent $R_4$ is selected from the group consisting of: halo; —$OR_2$; —$SR_2$; —$SOR_2$; —$SO_2R_2$; —$SO_2NR_2R_3$; —$R_2OR_3$; $R_2SR_3$; —$OCOR_2$; —$OCONR_2R_3$; —$NR_2COR_3$; —$NR_2CO_2R_3$; —CN; —$NO_2$; OH; —$R_2OH$; —$C(NR_2)NR_3$; —$CO_2R_2R_3$; —$CONR_2R_3$; —$C(O)R_2$; —$CH(OR_2)R_3$; —$CH_2(OR_2)$; —A—$(CH_2)_m$—$NR_2R_3$; $NR_2R_3$; aryl; aralkyl; heteroaryl; and heteroaralkyl. In a preferred embodiment, aryl is phenyl. In a further preferred embodiment, $R_4$ is selected from the group consisting of halo; $NR_2R_3$; alkoxy; and CN. In a further preferred embodiment of the invention, $R_4$ is selected from the group consisting of F; NH2; methoxy.

According to another aspect of the invention, each of $Ar_1$, $Ar_2$, and G is optionally further substituted with one or more substituents selected from $R_2$ and $R_4$. In a preferred embodiment of the invention, $Ar_1$ is further substituted with a substituent selected from the group consisting of: H; alkyl; haloalkyl; alkyloxy; alkylamine; halo; —$OR_2$; —$SR_2$; —$SOR_2$; —$SO_2R_2$; —$SO_2NR_2R_3$; —$R_2OR_3$; $R_2SR_3$; —$OCOR_2$; —$OCONR_2R_3$; —$NR_2COR_3$; —$NR_2CO_2R_3$; —CN; —$NO_2$; —$C(NR_2)NR_3$; —$CO_2R_2R_3$; —$CONR_2R_3$; —$C(O)R_2$; —$CH(OR_2)R_3$; —$CH_2(OR_2)$; —A—$(CH_2)_m$—$NR_2R_3$; $NR_2R_3$; aryl; aralkyl; heteroaryl; heteroaralkyl; cycloalkyl; heterocycloalkyl; alkylaryl; alkylheteroaryl; haloaryl; alkyloxyaryl; alkenylaryl; alkenyloxyaryl; and haloheteroaryl. In a further preferred embodiment of the invention, $Ar_1$ is is further substituted with a substituent selected from the group consisting of: halo and cyano.

In another aspect of the invention wherein $Ar_1$ is 2-pyridyl, the further substituent is located at the 5-position of $Ar_1$. In a further embodiment of the invention, $Ar_1$ is 5-fluoro-2-pyridyl. In yet another embodiment of the invention, $Ar_1$ is 5-cyano-2-pyridyl.

According to a further aspect of the invention, $Ar_2$ is further substituted with one or more substituents selected from the group consisting of: H; alkyl; haloalkyl; alkyloxy; alkylamine; halo; —$OR_2$; —$SR_2$; —$SOR_2$; —$SO_2R_2$; —$SO_2NR_2R_3$; —$R_2OR_3$; —$R_2SR_3$; —$OCOR_2$; —$OCONR_2R_3$; —$NR_2COR_3$; —$NR_2CO_2R_3$; —CN; —$NO_2$; —$C(NR_2)NR_3$; —$CO_2R_2R_3$; —$CONR_2R_3$; —$C(O)R_2$; —$CH(OR_2)R_3$; —$CH_2(OR_2)$; —A—$(CH_2)_m$—$NR_2R_3$; $NR_2R_3$; aryl; aralkyl; heteroaryl; heteroaralkyl; cycloalkyl; heterocycloalkyl; alkylaryl; alkylheteroaryl; haloaryl; alkyloxyaryl; alkenylaryl; alkenyloxyaryl; and haloheteroaryl. In a preferred embodiment of the invention, $Ar_2$ is further substituted with one or more substituents selected from the group consisting of: alkyl; alkoxy; alkyloxy; hydroxy; halo; cyano; and nitro. In a more preferred embodiment of the invention $Ar_2$, has a further substituent selected from the group consisting of: cyano; fluoro; chloro; bromo; iodo; and methoxy.

In a more preferred embodiment of the invention, $Ar_2$ is phenyl or 3-pyridyl, and is substituted with the substituent G at the meta position and a further substituent at the other meta position.

In another embodiment of the invention, the substituent G is optionally further substituted with one or more substituents selected from the group consisting of: H; alkyl; haloalkyl; alkyloxy; alkylamine; halo; —$OR_2$; —$SR_2$; —$SOR_2$; —$SO_2\ R_2$; —$SO_2NR_2R_3$; —$R_2OR_3$ $R_2SR_3$; —$OCOR_2$; —$OCONR_2R_3$; —$NR_2COR_3$; —$NR_2CO_2R_3$; —CN; —$NO_2$; —$C(NR_2)NR_3$; —$CO_2R_2R_3$; —$CONR_2R_3$; —$C(O)R_2$; —$CH(OR_2)R_3$; —$CH_2(OR_2)$; —A—$(CH_2)_m$—$NR_2R_3$; $NR_2R_3$; aryl; aralkyl; heteroaryl; heteroaralkyl; cycloalkyl; heterocycloalkyl; alkylaryl; alkylheteroaryl; haloaryl; alkyloxyaryl; alkenylaryl; alkenyloxyaryl; and haloheteroaryl. In a more preferred embodiment of the invention, G is optionally further substituted with one or more substituents selected from the group consisting of: alkyl; alkoxy; alkenyl; halo; and cyano. In a particular G is —$OCH_2CH_2CH_2OH$, and is further substituted with chloro, to give —$OCH_2CH(Cl)CH_2OH$.

In one aspect of the invention, specific compounds of formula I include:
3-(2-pyridyl)-5-(3-methoxyphenyl)-1,2,4-oxadiazole (B1),
3-(2-pyridyl)-5-(3,5-dichlorophenyl)-1,2,4-oxadiazole (B2),
3-(2-pyridyl)-5-(3-chlorophenyl)-1,2,4-oxadiazole (B3),
3-(2-pyridyl)-5-(2-chlorophenyl)-1,2,4-oxadiazole (B5),
3-(2-pyridyl)-5-[3-(trifluoromethyl)phenyl]-1,2,4-oxadiazole (B6),
3-(2-pyridyl)-5-(3-methylphenyl)-1,2,4-oxadiazole (B9),
3-(2-pyridyl)-5-(1-naphthyl)-1,2,4-oxadiazole (B10),
3-(2-pyridyl)-5-[3-(trifluoromethoxy)phenyl]-1,2,4-oxadiazole (B11),
3-(2-pyridyl)-5-(2,3-difluorophenyl)-1,2,4-oxadiazole (B16),
3-(2-pyridyl)-5-(2,5-difluorophenyl)-1,2,4-oxadiazole (B17),
3-(2-pyridyl)-5-(3,5-difluorophenyl)-1,2,4-oxadiazole (B18),
3-(2-pyridyl)-5-(3-cyanophenyl)-1,2,4-oxadiazole (B21),
3-(2-pyridyl)-5-(3,5-dimethoxyphenyl)-1,2,4-oxadiazol (B23),
3-(2-pyridyl)-5-(2,3-dichlorophenyl)-1,2,4-oxadiazole (B25),
3-(2-pyridyl)-5-(3-chloro-5-cyanophenyl)-1,2,4-oxadiazole (B26),
3-(2-pyridyl)-5-(3-fluoro-5-cyanophenyl)-1,2,4-oxadiazole (B27),
3-(2-pyridyl)-5-(3-chloro-5-fluorophenyl)-1,2,4-oxadiazole (B28),
3-(5-chloropyrid-2-yl)-5-(3-cyanophenyl)-1,2,4-oxadiazole (B29) 3-(5-fluoropyrid-2-yl)-5-(3-cyanophenyl)-1,2,4-oxadiazole (B30),
3-(5-fluoropyrid-2-yl)-5-(3-cyano-5-fluorophenyl)-1,2,4-oxadiazole (B31),
3-(3-fluoropyrid-2-yl)-5-(3-cyanophenyl)-1,2,4-oxadiazole (B32),
3-(5-fluoropyrid-2-yl)-5-(3,5-dimethoxyphenyl)-1,2,4-oxadiazole (B33),
3-(5-methoxypyrid-2-yl)-5-(3-cyanophenyl)-1,2,4-oxadiazole (B34),
3-(2-quinolinyl)-5-(3-cyanophenyl)-1,2,4-oxadiazole (B35),
3-(3-chloro-5-trifluoro methylpyrid-2-yl)-5-(3-cyanophenyl)-1,2,4-oxadiazole (B36),
3-(2-pyridyl)-5-(5-chloro-2-methoxyphenyl)-1,2,4-oxadiazole (B37),
3-(2-pyridyl)-5-(2-chloro-5-methylthiophenyl)-1,2,4-oxadiazole (B39),
3-(2-pyridyl)-5-(2-bromo-5-methoxyphenyl)-1,2,4-oxadiazole (B42),
3-(2-pyridyl)-5-(2,5,6-trifluorophenyl)-1,2,4-oxadiazole (B45),
3-(2-pyridyl)-5-(3-nitrophenyl)-1,2,4-oxadiazole (B19),
3-(2-pyridyl)-5-(3-bromophenyl)-1,2,4-oxadiazole (B22), and pharmaceutically acceptable salts thereof.
In a further aspect of the invention, specific compounds of Formula I include:
2-(3,5-dichlorophenyl)-4-(2-pyridyl)-1,3-oxazole,
2-(3-chlorophenyl)-4-(2-pyridyl)-1,3-oxazole (B50),
2-(3-methoxyphenyl)-4-(2-pyridyl)-1,3-oxazole,
2-(2-chlorophenyl)-4-(2-pyridyl)-1,3-oxazole,
2-(3-trifluorophenyl)-4-(2-pyridyl)-1,3-oxazole,
2-(3-methylphenyl)-4-(2-pyridyl)-1,3-oxazole,
2-(1-naphthyl)-4-(2-pyridyl)-1,3-oxazole,
2-(3-trifluoromethoxyphenyl)-4-(2-pyridyl)-1,3-oxazole,
2-(2,3-difluorophenyl)-4-(2-pyridyl)-1,3-oxazole,
2-(2,5-difluorophenyl)-4-(2-pyridyl)-1,3-oxazole,
2-(3,5-difluorophenyl)-4-(2-pyridyl)-1,3-oxazole,
2-(3-cyanophenyl)-4-(2-pyridyl)-1,3-oxazole (B52),
2-(3,5-dimethoxyphenyl)-4-(2-pyridyl)-1,3-oxazole,
2-(2,3-dichlorophenyl)-4-(2-pyridyl)-1,3-oxazole,
2-(3-chloro-5-cyanophenyl)-4-(2-pyridyl)-1,3-oxazole,
2-(3-fluoro-5-cyanophenyl)-4-(2-pyridyl)-1,3-oxazole,
2-(3-chloro-5-fluorophenyl)-4-(2-pyridyl)-1,3-oxazole,
2-(3-c yanophenyl)-4-(5-chloropyrid-2-yl)-1,3-oxazole,
2-(3-cyanophenyl)-4-(5-fluoropyrid-2-yl)-1,3-oxazole,
2-(3-cyano-5-fluorophenyl)-4-(5-fluoropyrid-2-yl)-1,3-oxazole,
2-(3-cyanophenyl)-4-(3-fluoropyrid-2-yl)-1,3-oxazole,
2-(3,5-dimethoxyphenyl)-4-(5-fluoropyrid-2-yl)-1,3-oxazole,
2-(3-cyano phenyl)-4-(5-meth oxy pyrid-2-yl)-1,3-oxazole,
2-(3-cyanophenyl)-4-(2-quinolinyl)-1,3-oxazole,
2-(3-cyanophenyl)-4-(3-chloro-5-trifluoromethylpyrid-2-yl)-1,3-oxazole,
2-(5-chloro-2-methoxyphenyl)-4-(2-pyridyl)-1,3-oxazole,
2-(2-chloro-5-methylthiophenyl)-4-(2-pyridyl)-1,3-oxazole,
2-(2-bromo-5-methoxyphenyl)-4-(2-pyridyl)-1,3-oxazole,
2-(2,5,6-trifluorophenyl)-4-(2-pyridyl)-1,3-oxazole,
2-[3-chlorophenyl]-4-[pyridin-2-yl]-1,3-oxazole,
2-(2,5,6-trifluorophenyl)-4-(2-pyridyl)-1,3-oxazole,
2-(3-nitrophenyl)-4-(2-pyridyl-1,3-oxazole,
2-(3-bromophenyl)-4-(2-pyridyl)-1,3-oxazole (B51) and pharmaceutically acceptable salts thereof.
In still a further aspect of the invention, the compounds of the formula I include:
3-(2-Pyridyl)-5-(3-allyloxy-5-(methoxycarbonyl)phenyl)-1,2,4-oxadiazole (B77),
3-(2-Pyridyl)-5-(3-N,N-dimethylaminophenyl)-1,2,4-oxadiazole (B82),
3-(2-Pyridyl)-5-(3-cyano-5-(4-pyridyl)phenyl)-1,2,4-oxadiazole (B101),
3-(2-Pyridyl)-5-[2-methoxy-5-(4-pyridyl)phenyl]-1,2,4-oxadiazole (B102),
3-(2-pyridyl)-5-[2-fluoro-5-(4-pyridyl)phenyl]-1,2,4-oxadiazole (B103),
3-(2-Pyridyl)-5-(3-fluoro-5-(4-pyridyl)phenyl)-1,2,4-oxadiazole (B104),
3-(2-Pyridyl)-5-(3-fluoro-5-(3-pyridyl)phenyl)-1,2,4-oxadiazole (B105),
3-(2-Pyridyl)-5-[2-fluoro-5-(3-pyridyl)phenyl]-1,2,4-oxadiazole (B106),
3-(2-Pyridyl)-5-[2-methoxy-5-(3-pyridyl)phenyl]-1,2,4-oxadiazole (B107),
3-(2-Pyridyl)-5-(3-cyano-5-(3-pyridyl)phenyl)-1,2,4-oxadiazole (B108),
3-(5-Fluoro-2-pyridyl)-5-(3-fluoro-5-(3-pyridyl)phenyl)-1,2,4-oxadiazole (B109),
3-(2-Pyridyl)-5-[5-(3-pyridyl-pyrid-3-yl)]-]-1,2,4-oxadiazole (B111),
3-(5-Fluoropyrid-2-yl)]-5-[5-(3-pyridyl-pyrid-3-yl)]-]-1,2,4-oxadiazole (B110),
3-(5-Cyanopyrid-2-yl)-5-(3-(pyrid-3-yl)phenyl)-1,2,4-oxadiazole (B112),
3-(5-Cyanopyrid-2-yl)-5-(3-fluoro-5-(pyrid-3-yl)phenyl)-1,2,4-oxadiazole (B113),
3-(2-Pyridyl)-5-(3-cyano-5-(2-pyridyl)phenyl)-1,2,4-oxadiazole (B124),
3-(2-Pyridyl)-5-[2-methoxy-5-(2-pyridyl)phenyl]-1,2,4-oxadiazole (B125),
3-(-2-Pyridyl)-5-[2-fluoro-5-(2-pyridyl)phenyl]-1,2,4-oxadiazole (B126),
3-(2-Pyridyl)-5-[(3-(3-fuorophenyl)-5-fluorophenyl)]-1,2,4-oxadiazole (B114),
3-(2-Pyridyl)-5-(3-cyano-5-(3-thiophene)phenyl)-1,2,4-oxadiazole (B115), 3-(2-Pyridyl)-5-[5-(3-thienyl)-pyrid-3-yl]-1,2,4-oxadiazole (B116),
3-(2-Pyridyl)-5-[5-(3-furyl)-pyrid-3-yl]-1,2,4-oxadiazole (B117),
3-(2-Pyridyl)-5-[5-(3-methoxyphenyl)-pyrid-3-yl]-1,2,4-oxadiazole (B119),
3-(2-Pyridyl)-5-(3-cyano-5-(5-pyrimidyl)phenyl)-1,2,4-oxadiazole (B120),
3-(2-Pyridyl)-5-(3-cyano-5-(3-aminophenyl)phenyl)-1,2,4-oxadiazole (B121),
3-(2-Pyridyl)-5-(3-cyano-5-(3-fluorophenyl)phenyl)-1,2,4-oxadiazole (B122),
3-(2-Pyridyl)-5-[5-(5-pyrimidyl)-pyrid-3-yl]-1,2,4-oxadiazole (B123),
3-(2-Pyridyl)-5-(3-aminomethyl-5-cyanophenyl)-1,2,4-oxadiazole (B127),
3-(2-Pyridyl)-5-[5[(2-propenyl)-pyrid-3-yl]-1,2,4-oxadiazole (B128),
3-(2-Pyridyl)-5-(3-cyano-5-vinylphenyl)-1,2,4-oxadiazole (B129),
3-(2-Pyridyl)-5-(3-cyano-5-(2-hydroxyethyl)phenyl)-1,2,4-oxadiazole (B130),
3-(2-Pyridyl)-5-(3-cyano-5-(2,3-dichloropropoxy)phenyl)-1,2,4-oxadiazole (B131),
3-(2-Pyridyl)-5-(3-allyloxy-5-carboxyphenyl)-1,2,4-oxadiazole (B135),
3-(2-Pyridyl)-5-(3-allyloxy-5-cyanophenyl)-1,2,4-oxadiazole (B136),
3-(2-Pyridyl)-5-(5-cyano-3-[3-hydroxypropyn-1-yl]phenyl)-1,2,4-oxadiazole (B142),
3-(2-Pyridyl)-5-(2-N-methylaminophenyl)-1,2,4-oxadiazole (B144), and
3-(2-Pyridyl)-5-[5-(3-N-benzyl-1,2,5,6,tetrahydropyridine)-pyrid-3-yl]-1,2,4-oxadiazole (B143), and pharmaceutically acceptable salts thereof.

In yet a further aspect of the invention, the following compounds of Formula I are provided:
3-(5-Methyl-pyrid-2-yl)-5-(3-cyanophenyl)-1,2,4-oxadiazole (B57),
3-(5-Cyano-pyrid-2-yl)-5-(3-cyanophenyl)-1,2,4-oxadiazole (B58),
3-(2-Pyridyl)-5-(5-bromo-2-methoxyphenyl)-1,2,4-oxadiazole (B62),
3-(2-Pyridyl)-5-(5-bromo-2-fluorophenyl)-1,2,4-oxadiazole (B63),
3-(2-Pyridyl)-5-(5-cyano-2-fluorophenyl)-1,2,4-oxadiazole (B64),
3-(2-Pyridyl)-5-(5-bromopyrid-3-yl)-1,2,4-oxadiazole (B65),
3-(2-Pyridyl)-5-(5-chloro-pyrid-3-yl)-1,2,4-oxadiazole (B66),
3-(5-Cyanopyrid-2-yl)-5-(5-bromo-pyrid-3-yl)-1,2,4-oxadiazole (B67),
3-(5-Fluoropyrid-2-yl)-5-(5-bromo-pyrid-3-yl-1,2,4-oxadiazole (B68),
3-(2-Pyridyl)-5-(2-thiomethoxy-pyrid-3-yl)]-1,2,4-oxadiazole (B69),
3-(2-Pyridyl)-5-(5-methylpyrid-3-yl)-1,2,4-oxadiazole (B70),
3-(2-Pyridyl)-5-(5-methoxypyrid-3-yl)-1,2,4-oxadiazole (B72),
3-(2-Pyridyl)-5-(3-cyano-5-methylphenyl)-1,2,4-oxadiazole (B73),
3-(2-Pyridyl)-5-(3-fluoro-5-bromophenyl)-1,2,4-oxadiazole (B74),
3-(2-Pyridyl)-5-(3-iodo-5-bromophenyl)-1,2,4-oxadiazole (B75),
3-(5-Fluoro-2-pyridyl)-5-(3-fluoro-5-bromophenyl)-1,2,4-oxadiazole (B76),
3-(2-Pyridyl)-5-(3-iodo-5-(methylphenylester)-1,2,4-oxadiazole (B78),
3-(2-Pyridyl)-5-(3-methoxy-5-(methoxycarbonyl)phenyl)-1,2,4-oxadiazole (B79),
3-(2-Pyridyl)-5-(3-bromo-5-cyanophenyl)-1,2,4-oxadiazole (B80),
3-(2-Pyridyl)-5-(5-cyano-3-iodophenyl)-1,2,4-oxadiazole (B81),
3-(5-Cyano-2-pyridyl)-5-(3-bromophenyl)-1,2,4-oxadiazole (B59),
3-(5-Cyano-2-pyridyl)-5-(3-cyano-5-fluorophenyl)-1,2,4-oxadiazole (B60),
3-(5-Cyano-2-pyridyl)-5-(3-bromo-5-fluorophenyl)-1,2,4-oxadiazole (B61),
3-(2-Pyridyl)-5-(5-cyano-2-methoxyphenyl)-1,2,4-oxadiazole (B97),
3-(2-Pyridyl)-5-(2-cyano-5-methoxyphenyl)-1,2,4-oxadiazole (B98),
3-(2-Pyridyl)-5-(5-cyano-pyrid-3-yl)-1,2,4-oxadiazole (B99),
3-(2-Pyridyl)-5-(3-cyano-5-(methoxycarbonyl)phenyl)-1,2,4-oxadiazole (B100),
3-(2-Pyridyl)-5-(5-phenyl-pyrid-3-yl)-1,2,4-oxadiazole (B118),
3-(2-Pyridyl)-5-(3-cyano-5-methoxyphenyl)-1,2,4-oxadiazole (B134),
3-(2-Pyridyl)-5-(3-cyano-5-hydroxyphenyl)-1,2,4-oxadiazole (B137),
3-(2-Pyridyl)-5-(3-cyano-5-propoxyphenyl)-1,2,4-oxadiazole (B141),
2-(3-Cyanophenyl)-4-(pyridin-2-yl)-1,3-thiazole (B146),
2-(3-Bromo-5-iodophenyl)-4-pyridin-2-yl)-1,3-oxazole (B147),
2-(2-Pyridyl)-5-(3-iodophenyl)-1,3,4-oxadiazole (B148),
2-(2-Pyridyl)-5-(3-cyanophenyl)-1,3,4-oxadiazole (B149),
2-(2-Pyridyl)-5-(3-cyanophenyl)-1,3,4-triazole (B150),
3-(5-Chloropyrid-2-yl)-5-(3-cyano-5-fluorophenyl)-1,2,4-oxadiazole (B83),
3-(5-Chloropyrid-2-yl)-5-(3-cyano-5-chlorophenyl)-1,2,4-oxadiazole (B84),
3-(5-Chloropyrid-2-yl)-5-(3-chloro-5-fluorophenyl)-1,2,4-oxadiazole (B85),
3-(5-Chloropyrid-2-yl)-5-(3-cyano-5-methoxyphenyl)-1,2,4-oxadiazole (B86),
3-(5-Fluoropyrid-2-yl)-5-(3-cyano-5-chlorophenyl)-1,2,4-oxadiazole (B87),
3-(5-Fluoropyrid-2-yl)-5-(3-fluoro-5-chlorophenyl)-1,2,4-oxadiazole (B88),
3-(5-Fluoropyrid-2-yl)-5-(3-cyano-5-methoxyphenyl)-1,2,4-oxadiazole (B89),
3-(5-Cyanopyrid-2-yl)-5-(3-cyano-5-chlorophenyl)-1,2,4-oxadiazole (B90),
3-(5-Cyanopyrid-2-yl)-5-(3-fluoro-5-chlorophenyl)-1,2,4-oxadiazole (B91)
3-(5-Cyanopyrid-2-yl)-5-(3-cyano-5-methoxyphenyl)-1,2,4-oxadiazole (B92),
3-(5-Fluoropyrid-2-yl)-5-(3,5-di-cyanophenyl)-1,2,4-oxadiazole (B93),
3-(3-(4-Dimethylaminobutoxy)-pyrid-2-yl)-5-(3-cyano-5-fluorophenyl)-1,2,4-oxadiazole (B94),
3-(3-(5-Dimethylaminopentyloxy)-pyrid-2-yl)-5-(3-Cyano-5-fluorophenyl)-1,2,4oxadiazole (B95), and
[3-(3-(6-Dimethylaminohexyloxy)-pyrid-2-yl)-5-(3-cyano-5-fluorophenyl)-1,2,4-oxadiazole (B96).

The present invention also provides compounds that are potent and selective antagonists of mGluR5, which may be represented by Formula II.

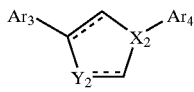

According to another aspect of the invention there is a five member ring containing two variables $X_2$, and $Y_2$. There are attached to this five member ring two substituents, $Ar_3$ and $Ar_4$. The five member ring may contain 0, 1, or 2 double bonds as denoted by the dotted lines in Formula II. In a preferred embodiment of the invention, the five member ring has two double bonds.

In embodiments of the invention, the variable $X_2$ is selected from the group consisting of: N and C, and the variable $Y_2$ is selected from the group consisting of: N; O; S; and $CR_5$, wherein at least one of $X_2$, and $Y_2$ must be a heteroatom. In the case where $Y_2$ is $CR_5$, $R_5$ is selected from the group consisting of: H; alkyl; —$CF_3$; —$OR_6$; —$SR_6$; $NR_6R_7$; —C(O); —C(S); —C=$NR_6$; and =$CR_6R_7$, wherein $R_6$ and $R_7$ may be independently selected from the group consisting of: H; alkyl; haloalkyl; alkyloxy; alkylamine; cycloalkyl; heterocycloalkyl; aryl; heteroaryl; alkylaryl; alkylheteroaryl; haloaryl; alkyloxyaryl; alkenylaryl; alkenyloxyaryl; and haloheteroaryl. In preferred embodiments of the invention, both $X_2$ and $Y_2$ are heteroatoms. In a further preferred embodiment of the invention, $X_2$ is N. In a still more preferred embodiment of the invention $Y_2$ is N. In a more preferred embodiment of the invention, $X_2$ and $Y_2$ are both N.

According to another aspect of the invention, the group $Ar_3$ and $Ar_4$, are independently selected from the group consisting of aryl and heteroaryl. Particular embodiments of the invention include those wherein $Ar_3$ and $Ar_4$ are independently selected from 5- and 6-member aryl and heteroaryl rings. In more particular embodiments of the invention, $Ar_3$ and $Ar_4$ are selected from 6-member aryl and heteroaryl rings. Still more particular embodiments of the invention include those where $Ar_3$ and $Ar_4$ are independently selected from phenyl, pyridyl, furanyl, thienyl, pyrazinyl, pyrimidinyl, pyridazinyl, pyrrolyl, pyrazolyl, imidazolyl, triazolyl, and thiazolyl. In a preferred embodiment of the invention, $Ar_3$ and $Ar_4$ are independently selected from phenyl and pyridyl. In a more preferred embodiment of the invention, one of $Ar_3$ and $Ar_4$ is phenyl and one is pyridyl.

According to still a another embodiment of the invention, $Ar_3$ and $Ar_4$ are optionally substituted with one or more substituents $G_2$, wherein $G_2$ is selected from the group consisting of: haloalkyl; heteroaryl; cycloalkene; alkenyl; alkynyl; A-alkenyl; A-alkynyl; alkyloxy; A-alkyloxy; —$R_6OR_7$; —$R_6OC(O)R_7$; $(CH_2)_m$—$NR_6R_7$; —$OCH_2CH$(Cl)$CH_2Cl$; and substituted aryl wherein the aryl substituent is $R_8$. In a particular embodiment wherein one, or both, of $Ar_3$ and $Ar_4$ are substituted with $G_2$, $G_2$ is selected from the group consisting of: A-alkenyl; Alkynyl; and A-alkyloxy, and A is selected from the group consisting of: $CH_2O$; NH; S; SO; $SO_2$ ; $OSO_2$ ; $NSO_2$; and —C($NR_6$)$NR_7$. In a more particular embodiment, $G_2$ is $(CH_2)_m$—$NR_6R_7$. In an embodiment of the invention, $G_2$ is substituted aryl and the substituent $R_8$ is selected from the group consisting of: halo; —$OR_6$; —$SR_6$; —$SOR_6$; —$SO_2R_6$; —$SO_2NR_6R_7$; —$R_6OR_7$ $R_6SR_7$; —$OCOR_6$; —$OCONR_6R_7$; —$NR_6COR_7$; —$NR_6CO_2R_7$; —CN; —$NO_2$; —C($NR_6$)$NR_7$; —$CO_2R_6R_7$; —$CONR_6R_7$; —C(O)$R_6$; —CH($OR_6$)$R_7$; —$CH_2(OR_6)$; —A—$(CH_2)_m$—$NR_6R_7$; $NR_6R_7$; aryl; aralkyl; heteroaryl; and heteroaralkyl.

In a further embodiment of the invention, each of $Ar_3$ and $Ar_4$ and $G_2$ is further substituted with one or more substituents selected from $R_6$, and $R_8$. In a preferred embodiment of the invention, each of $Ar_3$ and $Ar_4$ is independently further substituted with one or more substituents selected from the group consisting of: H; alkyl; haloalkyl; alkyloxy; alkylamine; halo; —$OR_6$; —$SR_6$; —$SOR_6$; —$SO_2$ $R_6$; —$SO_2NR_6R_6$; —$R_6OR_7$ $R_6SR_7$; —$OCOR_6$; —$OCONR_6R_7$; —$NR_6COR_7$; —$NR_6CO_2R_7$; —CN; —$NO_2$; —C($NR_6$)$NR_7$; —$CO_2R_6R_7$; —$CONR_6R_7$; —C(O)$R_6$; —CH($OR_6$)$R_7$; —$CH_2(OR_6)$; —A—$(CH_2)_m$—$NR_6R_7$; $NR_6R_7$; aryl; aralkyl; heteroaryl; heteroaralkyl; cycloalkyl; heterocycloalkyl; alkylaryl; alkylheteroaryl; haloaryl; alkyloxyaryl; alkenylaryl; alkenyloxyaryl; and haloheteroaryl.

According to a further aspect of the invention, $Ar_3$ and $Ar_4$ are independently substituted with a substituent selected from the group consisting of halo and cyano.

In specific embodiments of the invention, the compounds of formula II include:
4-(3-Cyanophenyl)-1-(2-pyridyl)-1H-imidazole (B151)
1-(3-Cyanophenyl)-4-(2-pyridyl)-1H-imidazole (B152).

Testing of Compounds for mGluR Group I Antagonist Activity

The pharmacological properties of the compounds of the invention can be analyzed using standard assays for functional activity. Examples of glutamate receptor assays are well known in the art, for example, see Aramori et al., Neuron 8:757 (1992); Tanabe et al., Neuron 8:169 (1992); Miller et al, J. Neuroscience 15: 6103 (1995); Balazs, et al., J. Neurochemistry 69:151 (1997). The methodology described in those publications is incorporated herein by reference.

Conveniently, the compounds of the invention can be studied by means of an assay that measures the mobilization of intracellular calcium, $[Ca^{2+}]_i$ in cells expressing mGluR5 that can bind the compounds. A well-known cell line which is suitable for this purpose is described in Miller et al., J. Neuroscience 15: 6103 (1995), the contents of which are hereby incorporated by reference. It has been shown that exposure to rat astrocytes to the growth factors, basic fibroblast growth factor, EGF, or transforming growth factor-α markedly increased the protein expression and functional activity of endogenous mGluR5 (Miller et al., J. Neuroscience, 15(9): 6103–6109, 1995).

In brief, primary astrocyte cultures were prepared from 3–5 day old Sprague-Dawley rat pups using a modification of Miller et al. were plated on poly-L lysine coated flasks in Dulbecco's modified Eagle's medium (DMEM) containing fetal calf serum (FCS). For cuvette analysis, cultures were up-regulated with growth factors in flasks for 3–5 days, then harvested and prepared for measurement of $[Ca^{2+}]_i$ mobilization as previously described (Nemeth et al., 1998).

For FLIPR analysis, cells were seeded on poly-D lysine coated clear bottom 96-well plates with black sides and analysis of $[Ca^{2+}]_i$ mobilization was performed 3 days following the growth factor up-regulation.

FLIPR experiments were done using a laser setting of 0.800 W and a 0.4 second CCD camera shutter speed. Each FLIPR experiment was initiated with 180 μL of buffer present in each well of the cell plate. After each addition of compound, the fluorescence signal was sampled 50 times at 1 second intervals followed by 3 samples at 5 second intervals. Responses were measured as the peak height of the response within the sample period.

$EC_{50}$ and $IC_{50}$ determinations were made from data obtained from 8 point concentration response curves (CRC) performed in duplicate. Agonist CRC were generated by scaling all responses to the maximal response observed for the plate. Antagonist block of the agonist challenge was normalized to the average response of the agonist challenge in 14 control wells on the same plate. A detailed protocol for testing the compounds of the invention is provided below at Example 11.

Preparation of Pharmaceutical Compositions Containing mGluR Antagonists, and Their Use in Treating Neurological Disorders The compounds of the present invention may be useful for treating neurological disorders or diseases. While these compounds typically will be used in therapy for human patients, they also can be used in veterinary medicine, to treat similar or identical diseases.

In therapeutic and/or diagnostic applications, the compounds of the invention can be formulated for a variety of modes of administration, including systemic and topical or localized administration. Techniques and formulations generally may be found in REMINGTON'S PHARMACEUTICAL SCIENCES (18th ed.), Mack Publishing Co. (1990).

The compounds according to the invention are effective over a wide dosage range. For example, in the treatment of adult humans, dosages from about 0.01 to about 1000 mg, preferably from about 0.5 to about 100 mg, per day may be used. A most preferable dosage is about 2 mg to about 70 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/disphosphate, polygalacturonate, salicylate, stearate, subacetate, succinate, sulfate, tannate, tartrate, or teoclate. Other pharmaceutically acceptable salts may be found, for example, in REMINGTON'S PHARMACEUTICAL SCIENCES (18th ed.), supra.

Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-release form as is known to those skilled in the art. Techniques for formulation and administration may be found in REMINGTON'S PHARMACEUTICAL SCIENCES; (18th ed.), supra. Suitable routes may include oral, buccal, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intraperitoneal, intranasal, or intraocular injections, inter alia.

For injection, the agents of the invention may be formulated in aqueous solutions, preferably in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

The present invention will be understood more readily by reference to the following examples, which are provided by way of illustration and are not intended to be limiting of the present invention.

Tables 1, 2, and 3 summarize specific exemplified compounds of the present invention.

TABLE 1

| | |
|---|---|
| B1 | 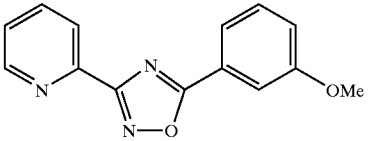 |
| B2 | 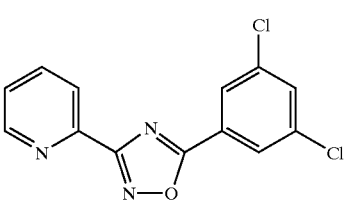 |
| B3 | 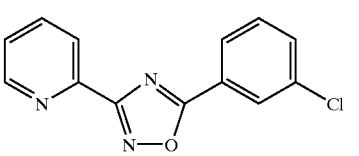 |
| B4 | 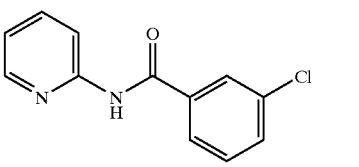 |
| B5 | 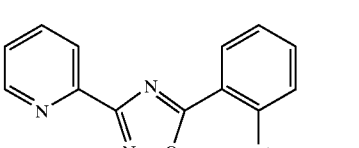 |
| B6 | 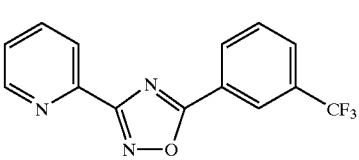 |
| B7 | 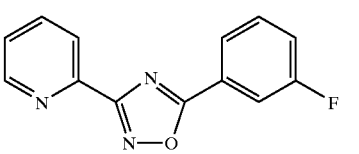 |
| B8 | 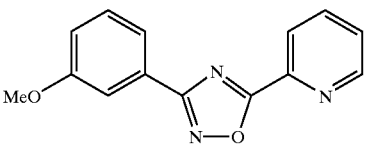 |

TABLE 1-continued

| | |
|---|---|
| B9 | 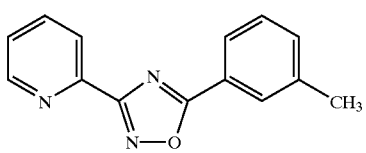 |
| B10 | 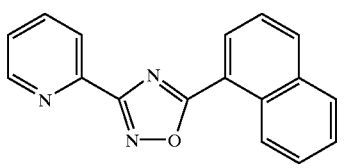 |
| B11 | 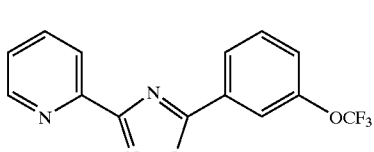 |
| B12 | 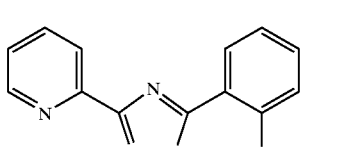 |
| B13 | 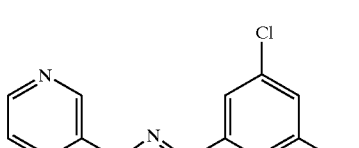 |
| B15 | 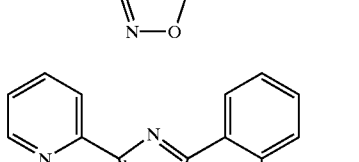 |
| B16 | 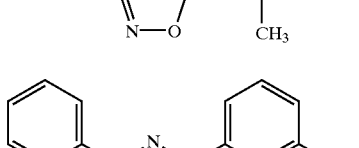 |
| B17 | 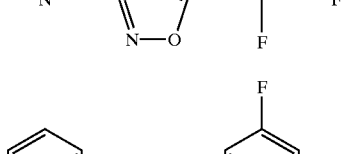 |
| B18 | 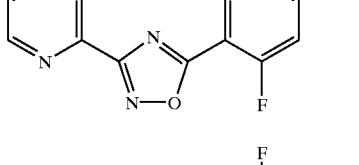 |

TABLE 1-continued
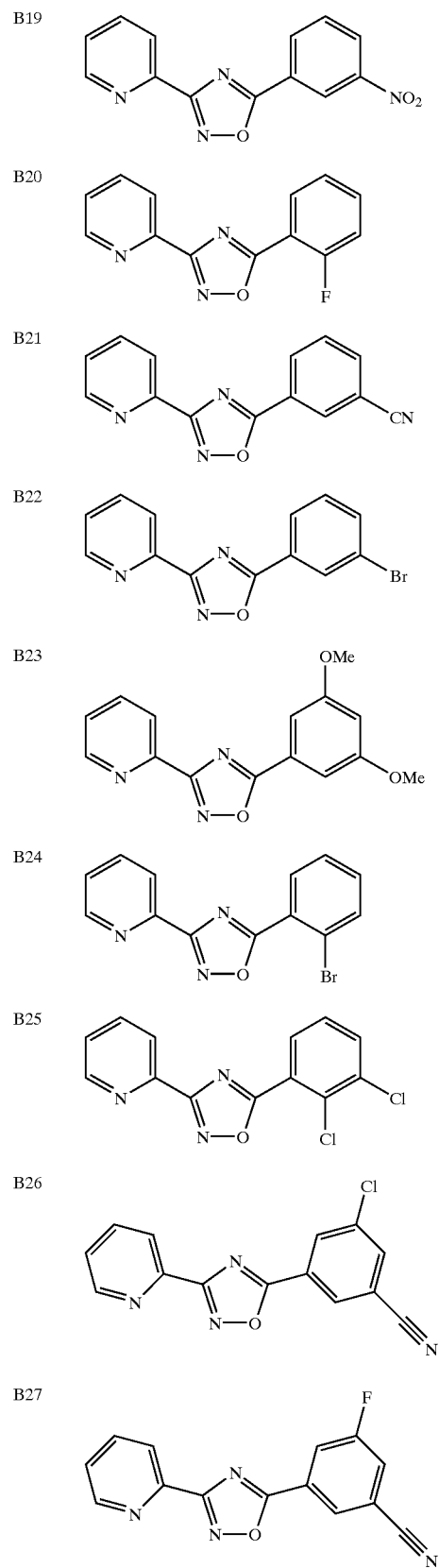
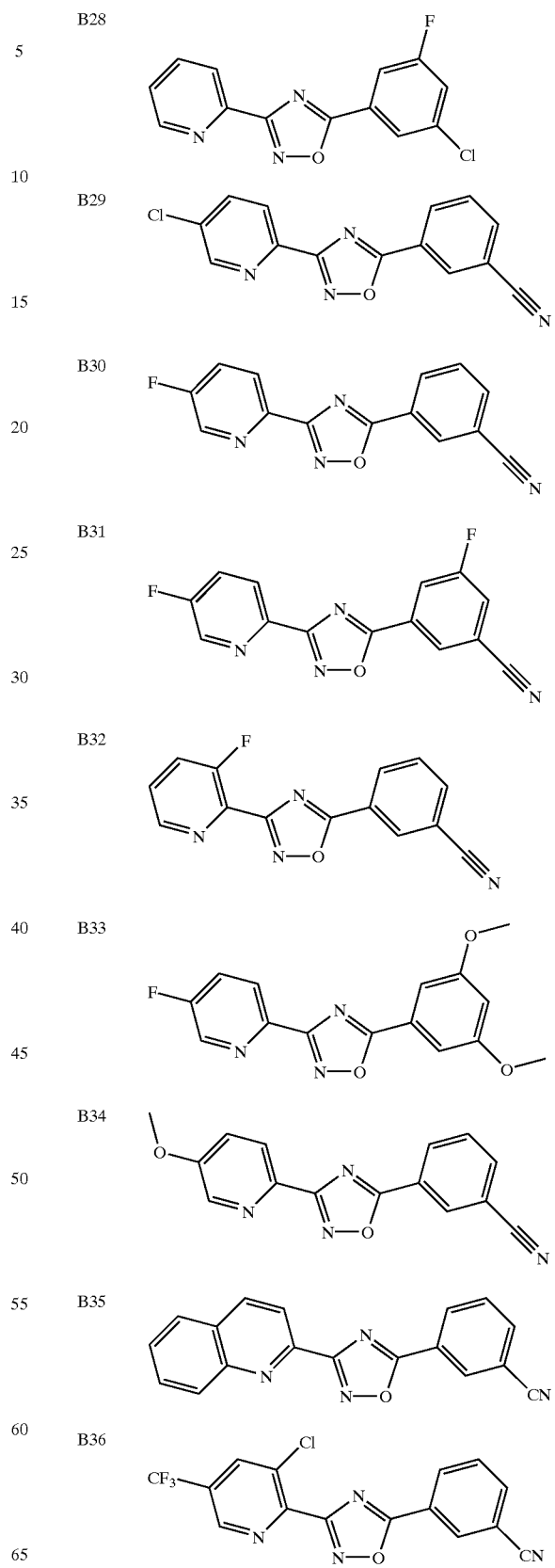

TABLE 1-continued
| | |
|---|---|
| B37 | 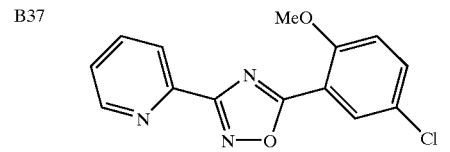 |
| B38 | 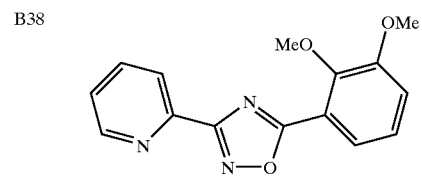 |
| B39 | 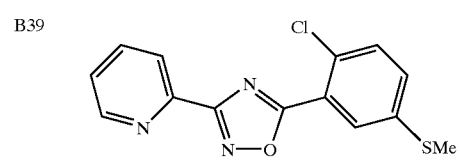 |
| B40 | 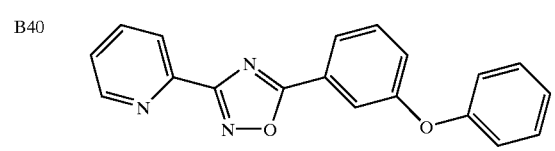 |
| B41 | 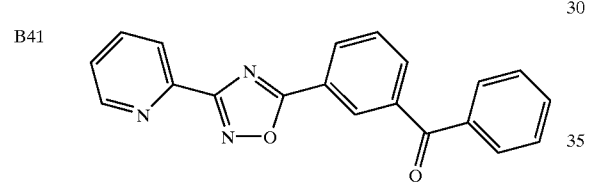 |
| B42 | 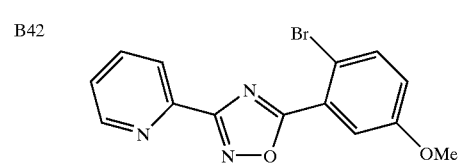 |
| B43 | 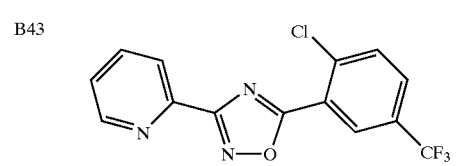 |
| B44 | 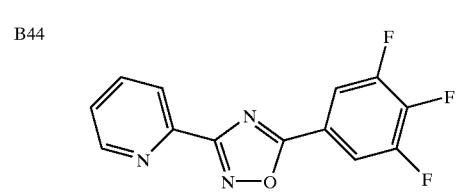 |
| B45 | 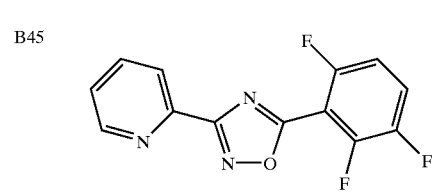 |
| B46 |  |
| B47 | 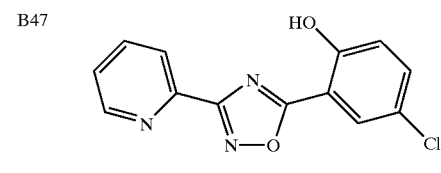 |
| B48 | 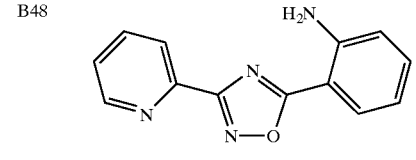 |
| B49 | 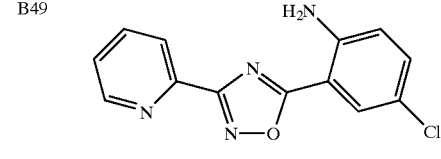 |
| B50 | 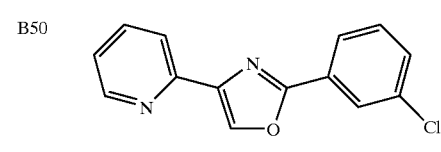 |
| B51 | 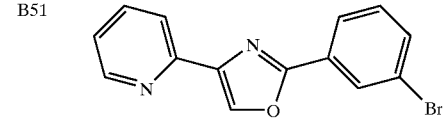 |
| B52 | 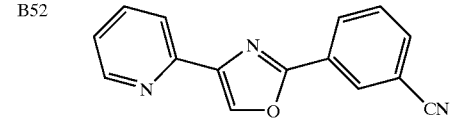 |
| B53 | 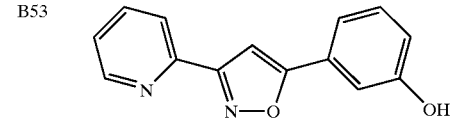 |
| B54 | 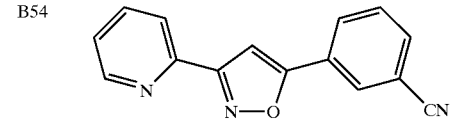 |
| B55 | 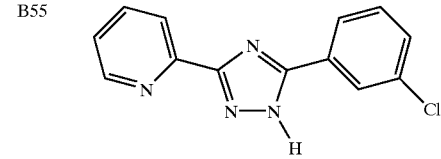 |

| | |
|---|---|
| TABLE 1-continued | TABLE 2-continued |
| B56 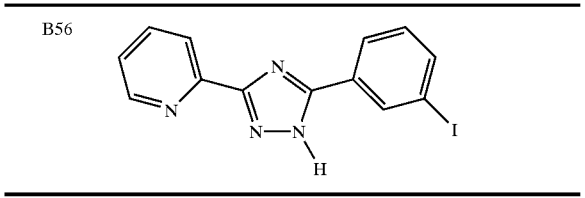 | B65 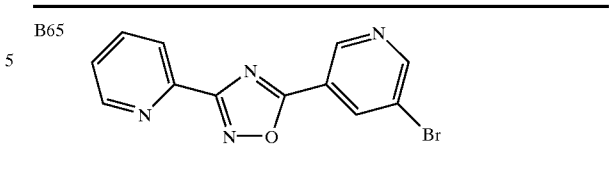 |
| TABLE 2 | B66 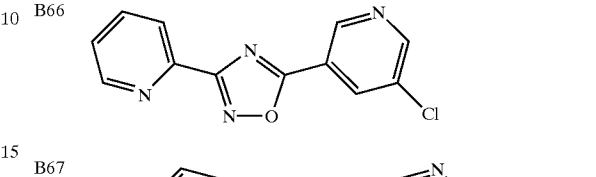 |
| B57 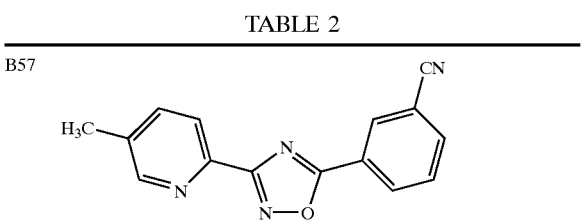 | B67 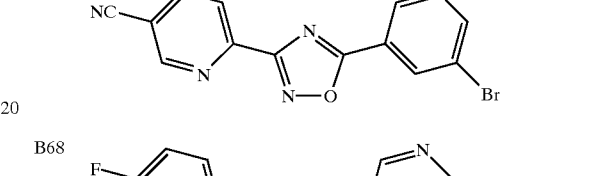 |
| B58 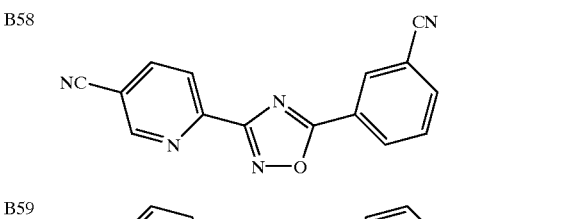 | B68 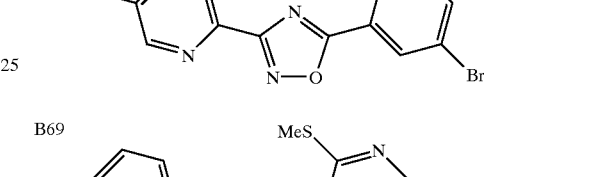 |
| B59 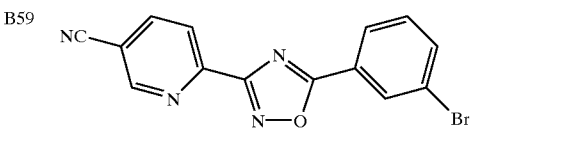 | B69 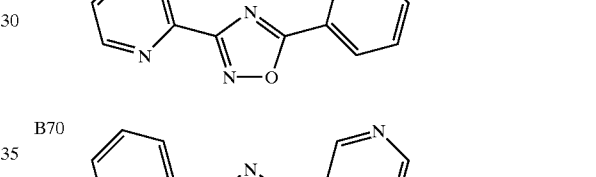 |
| B60 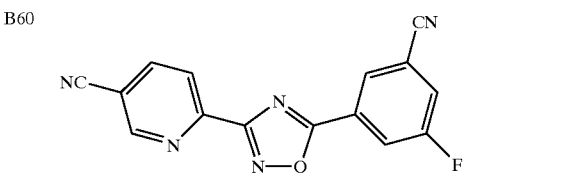 | B70 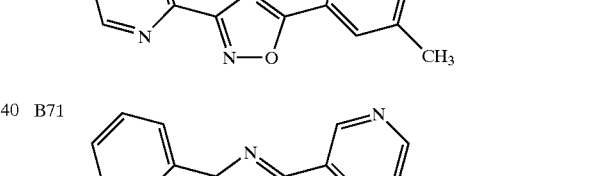 |
| B61 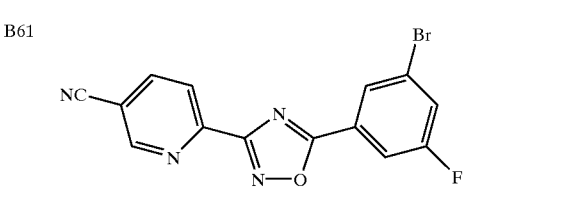 | B71 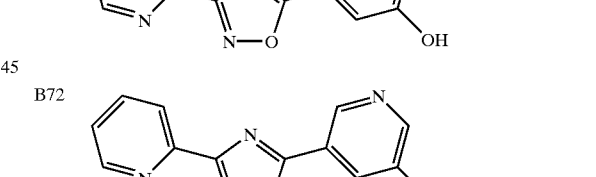 |
| B62 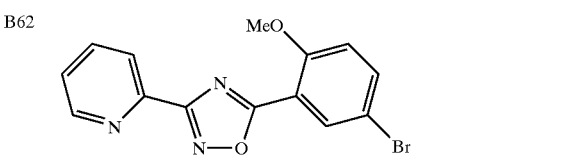 | B72 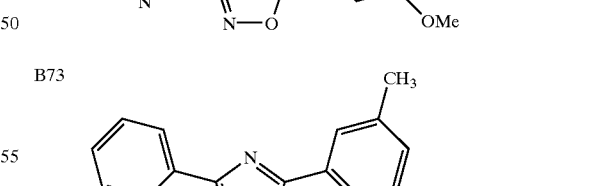 |
| B63 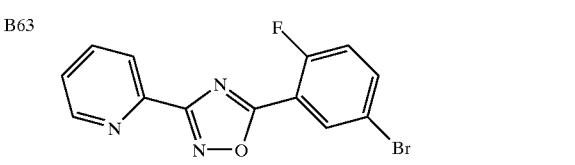 | B73 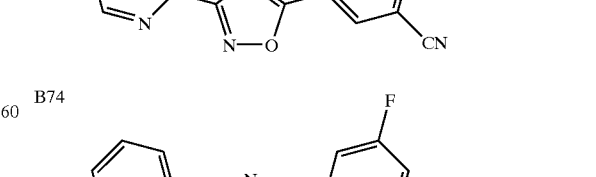 |
| B64 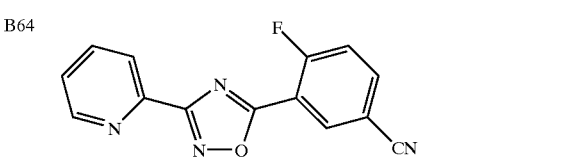 | B74 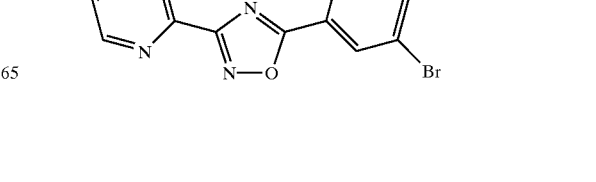 |

TABLE 2-continued
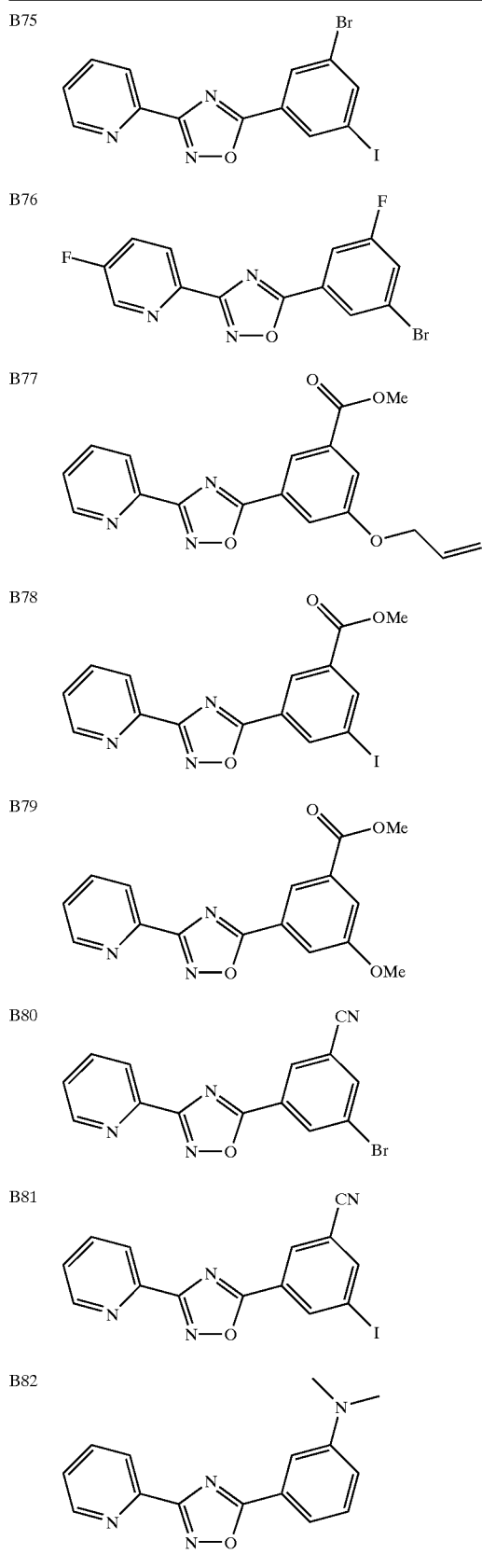
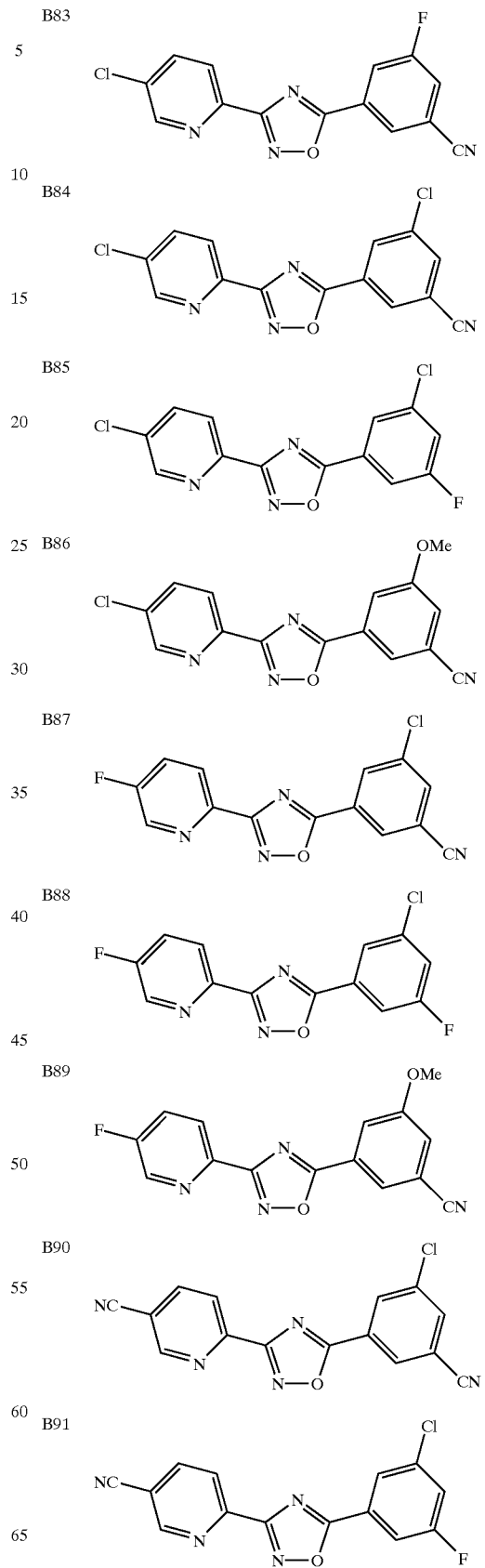

TABLE 2-continued
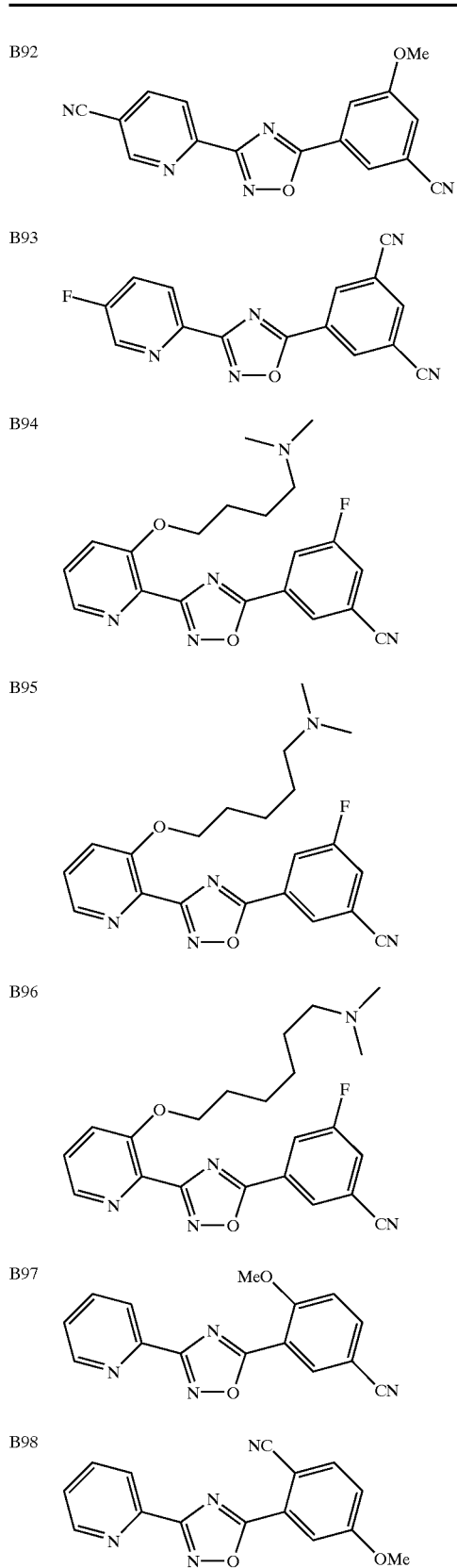
TABLE 2-continued
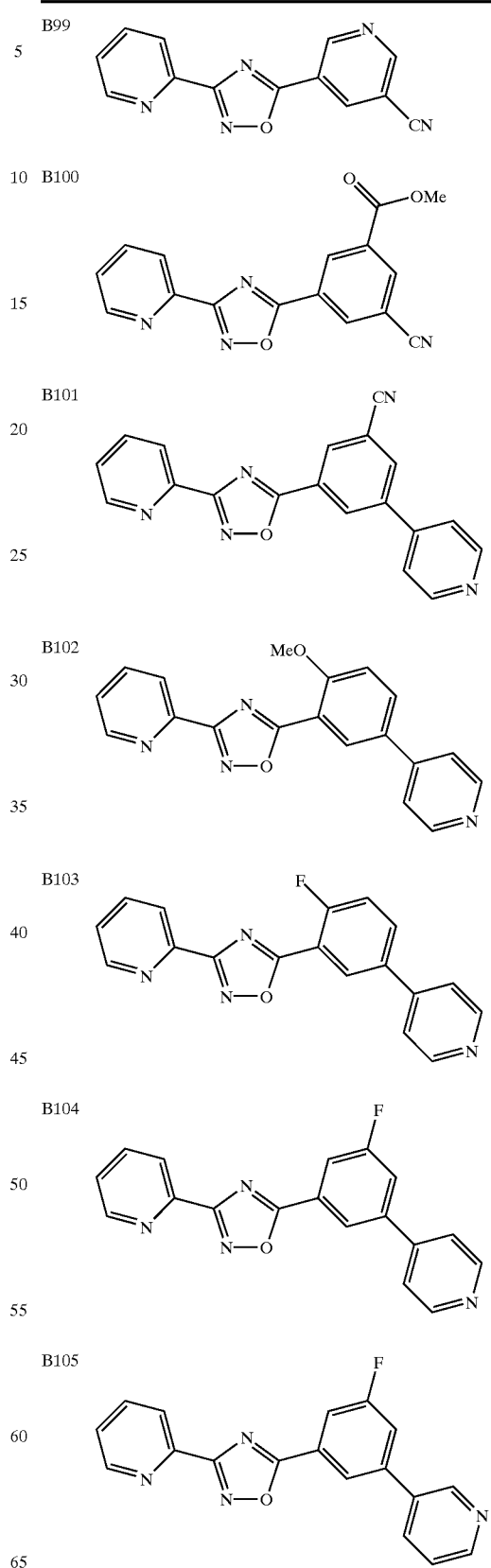

TABLE 2-continued
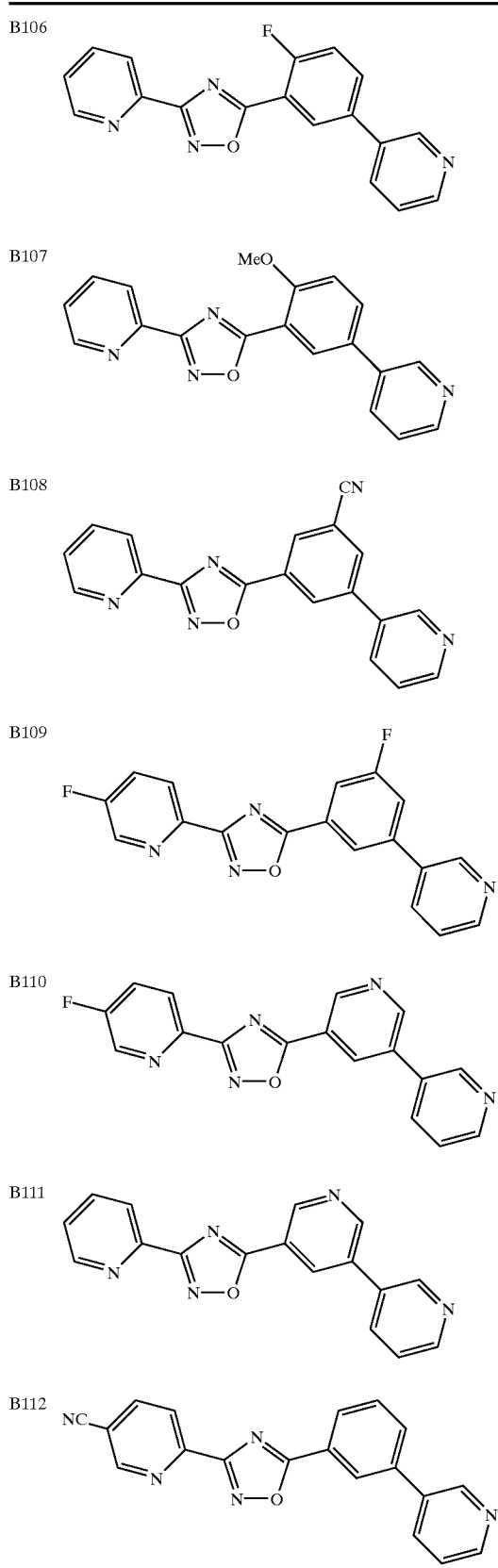
TABLE 2-continued
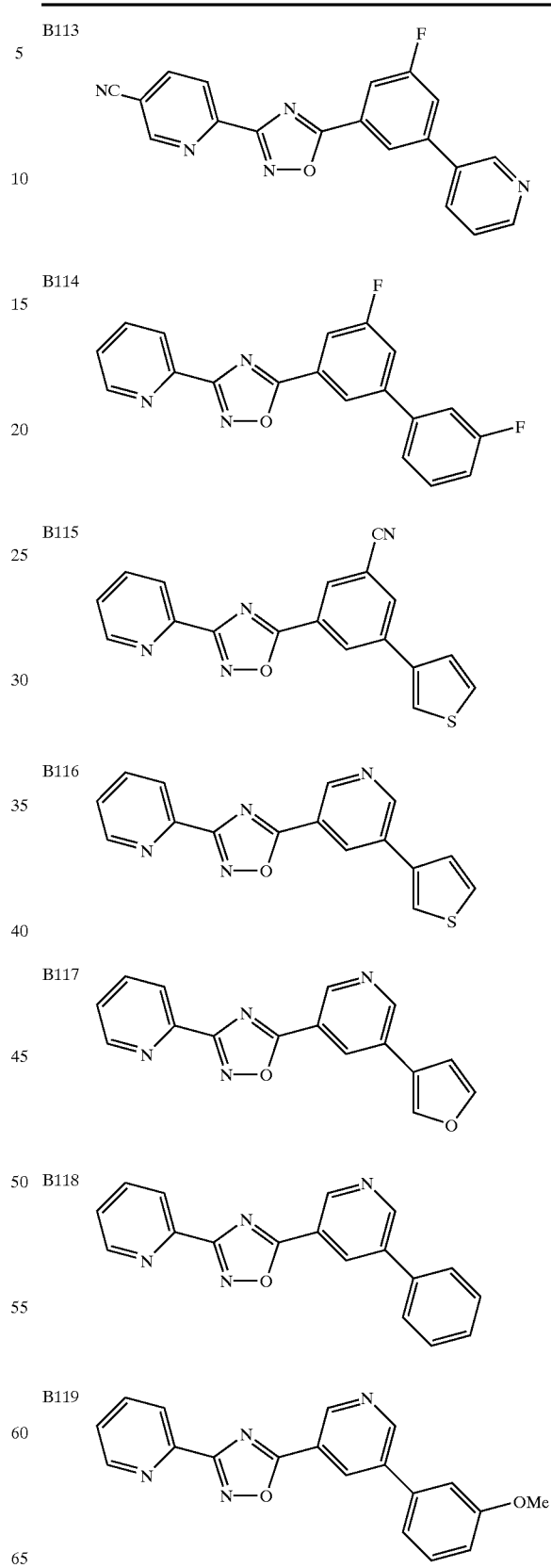

TABLE 2-continued
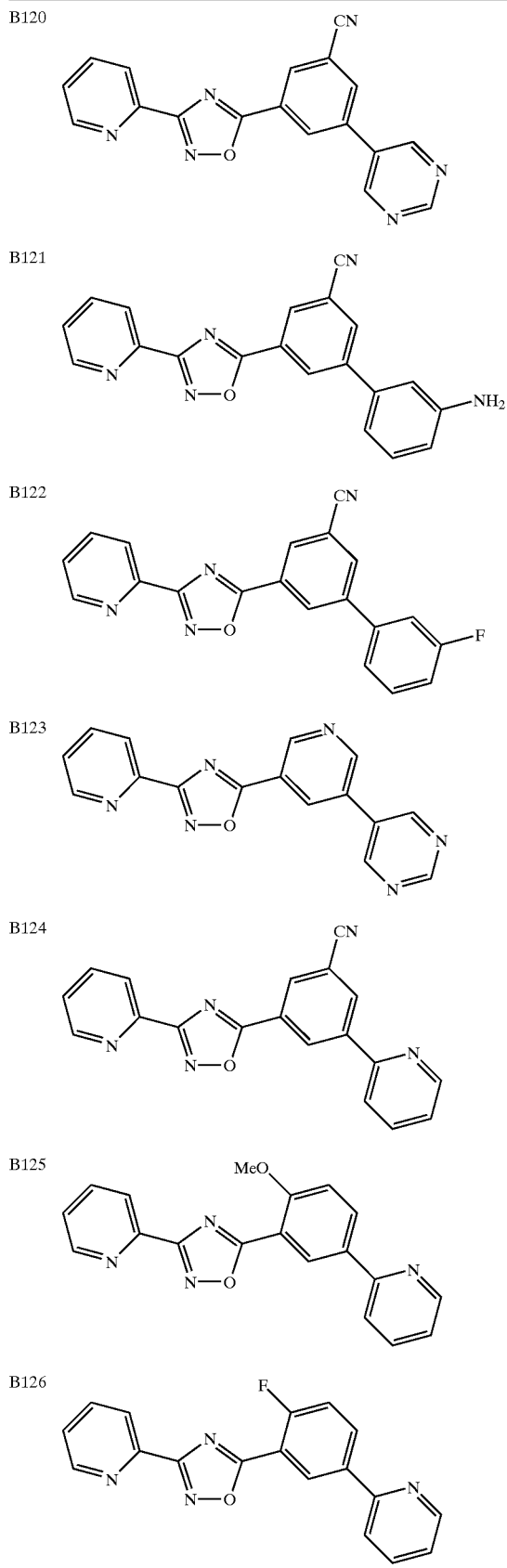
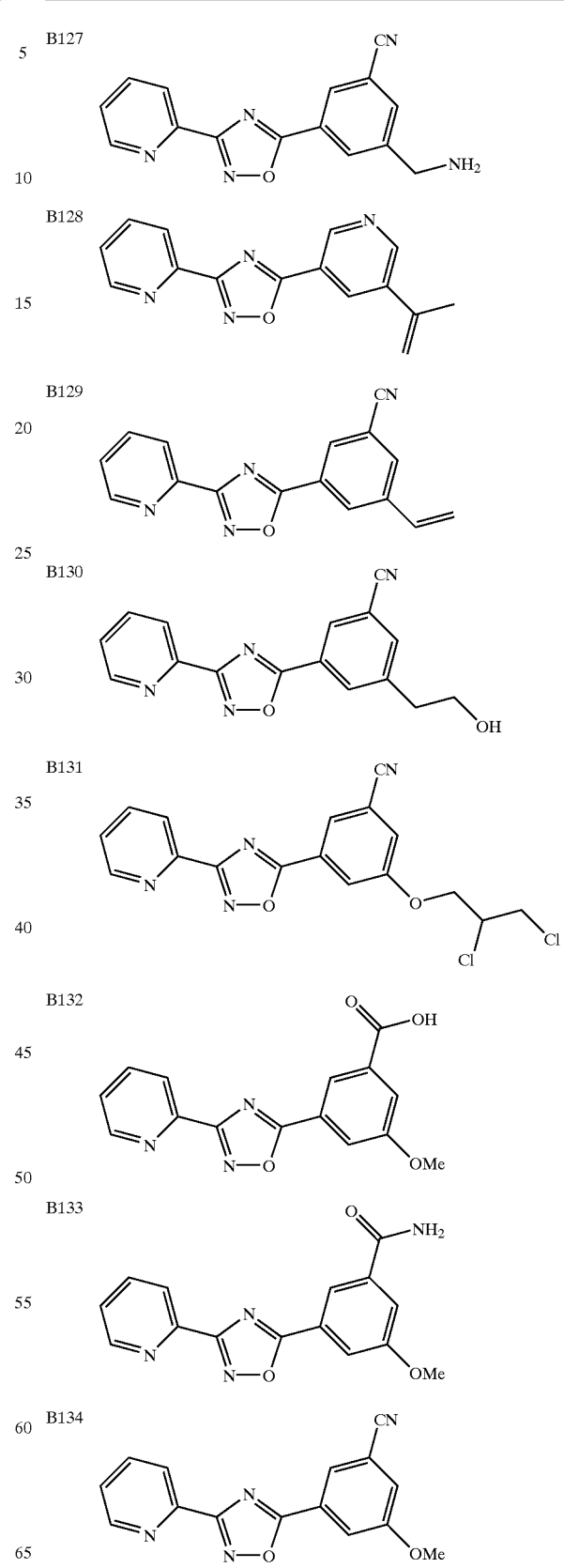

TABLE 2-continued
| B135 | 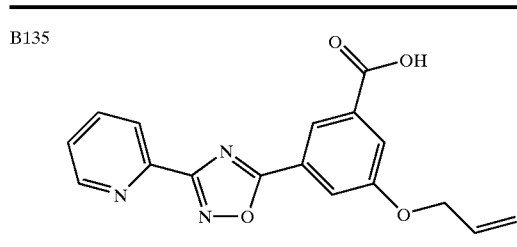 |
| --- | --- |
| B136 | 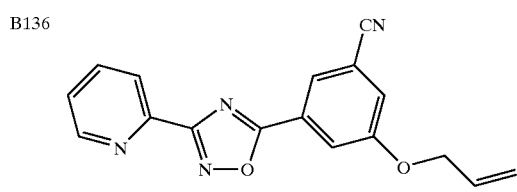 |
| B137 | 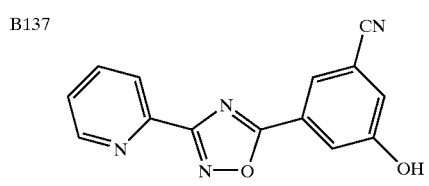 |
| B138 | 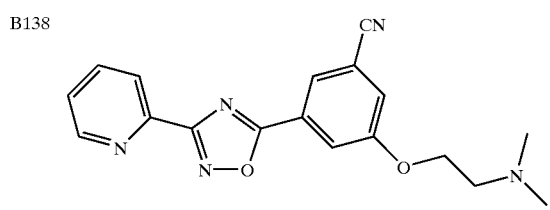 |
| B139 | 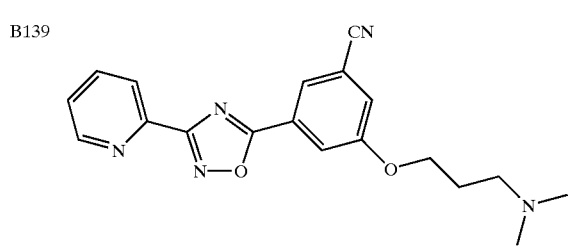 |
| B140 | 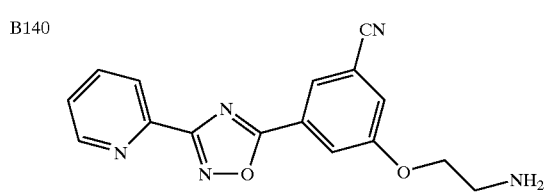 |
| B141 | 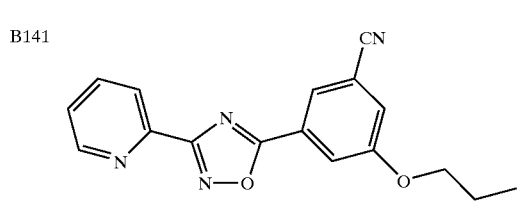 |
TABLE 2-continued
| B142 | 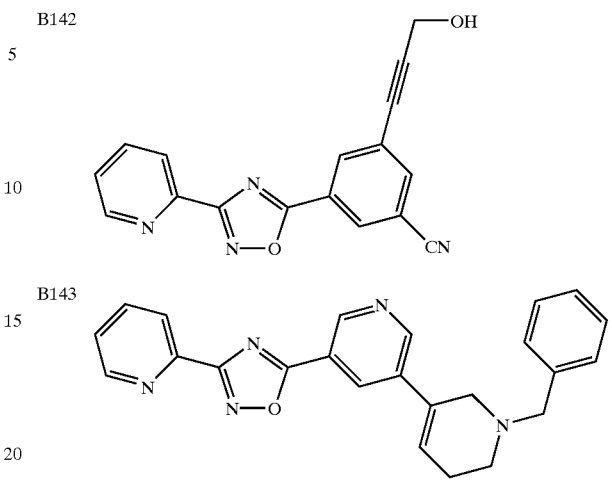 |
| --- | --- |
| B143 | |
| B144 | 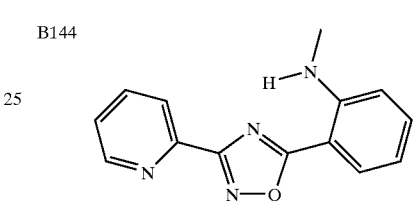 |
| B145 | 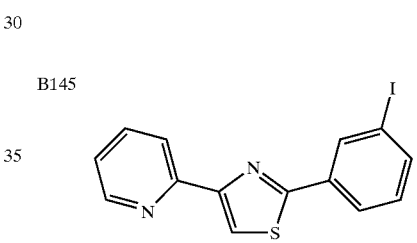 |
| B146 | 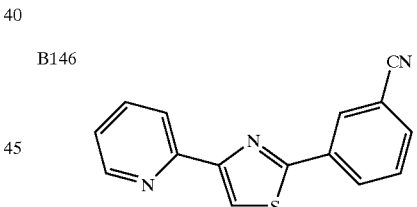 |
| B147 | 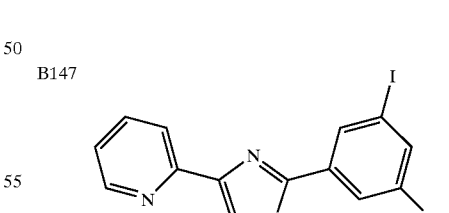 |
| B148 | 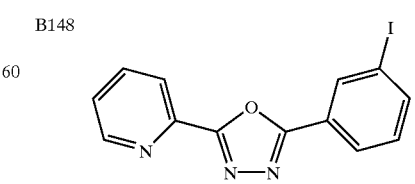 |

TABLE 2-continued
B149 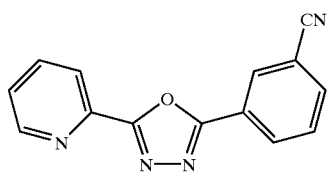
B150 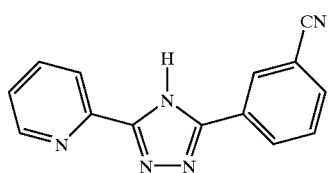
TABLE 2-continued
B151 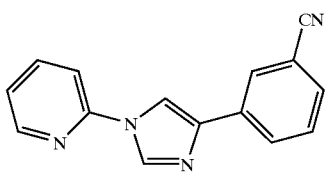
B152 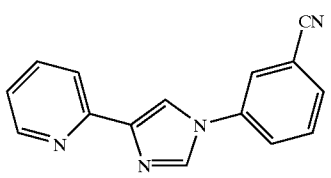
TABLE 3
B153 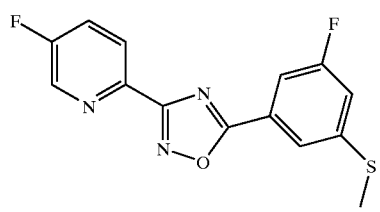
B154 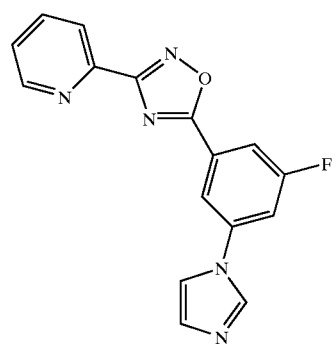
B250 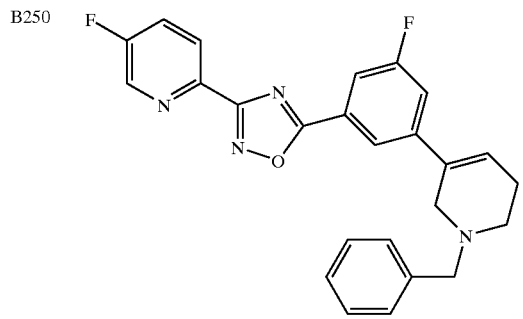

TABLE 3-continued
B212 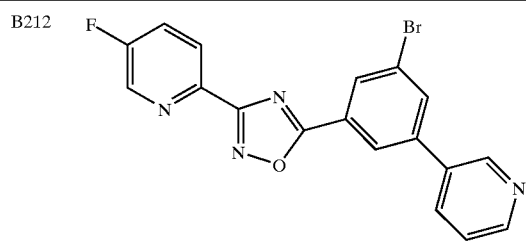
B251 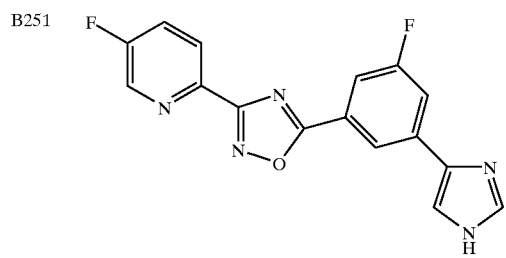
B213 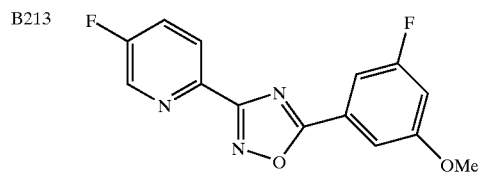
B252 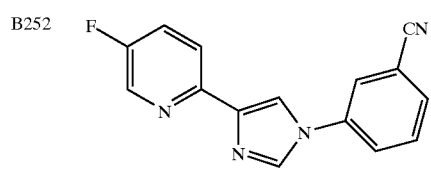
B253 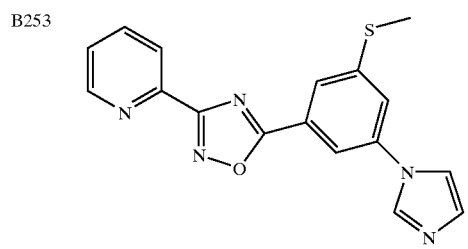
B254 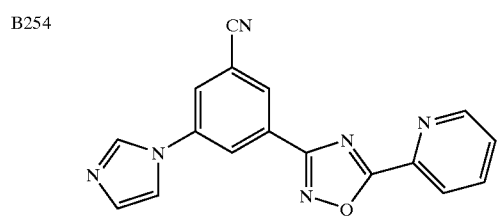
B255 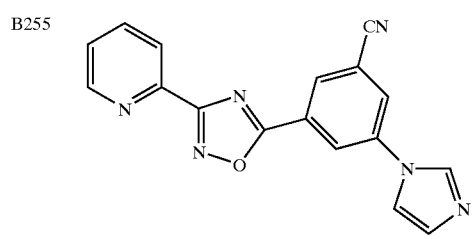

TABLE 3-continued
B269 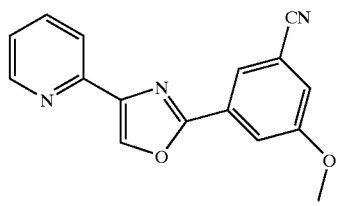
B272 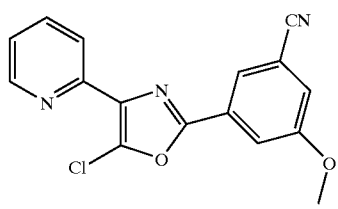
B216 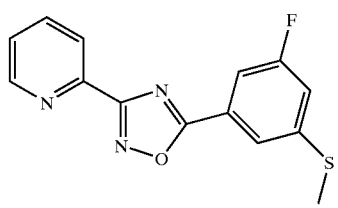
B217 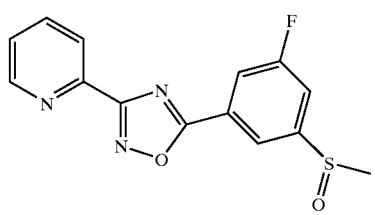
B214 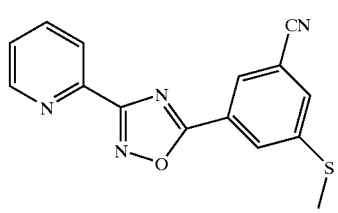
B215 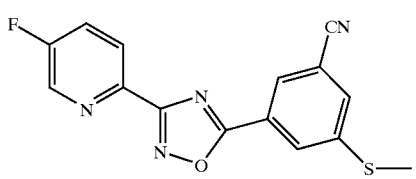
B218 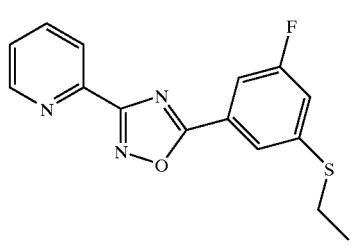

TABLE 3-continued
B219 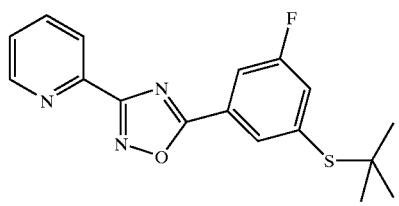
B155 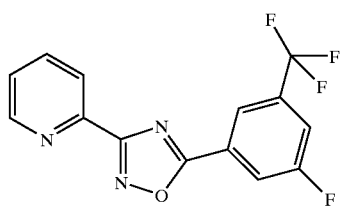
B156 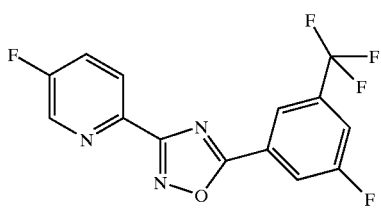
B223 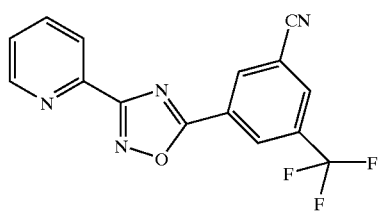
B224 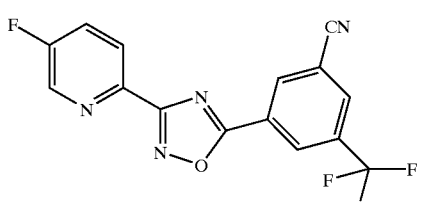
B258 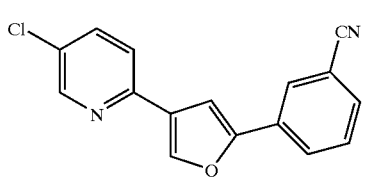
B257 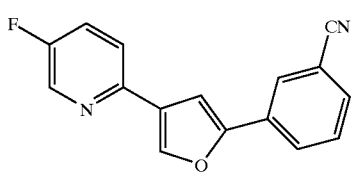
B256 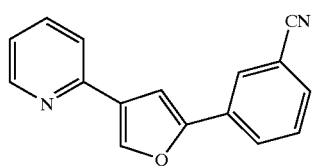

TABLE 3-continued
B244 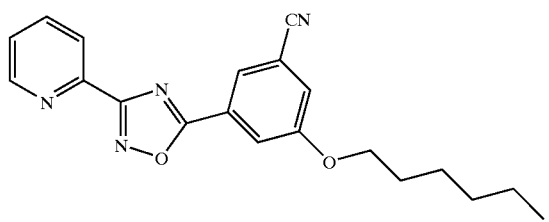
B167 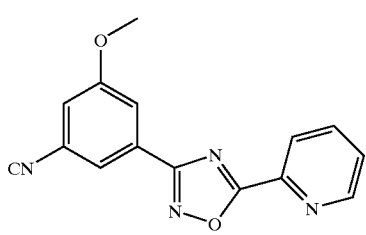
B168 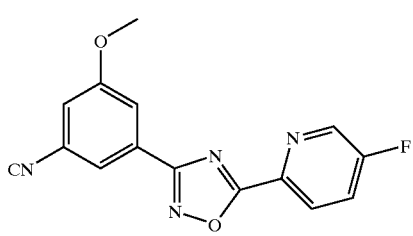
B169 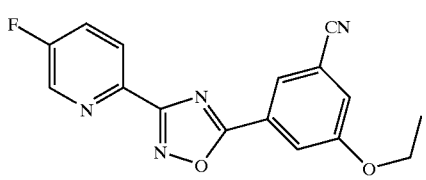
B170 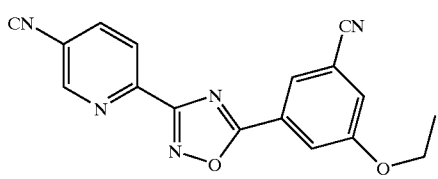
B171 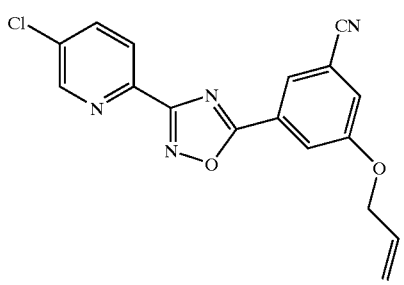

TABLE 3-continued
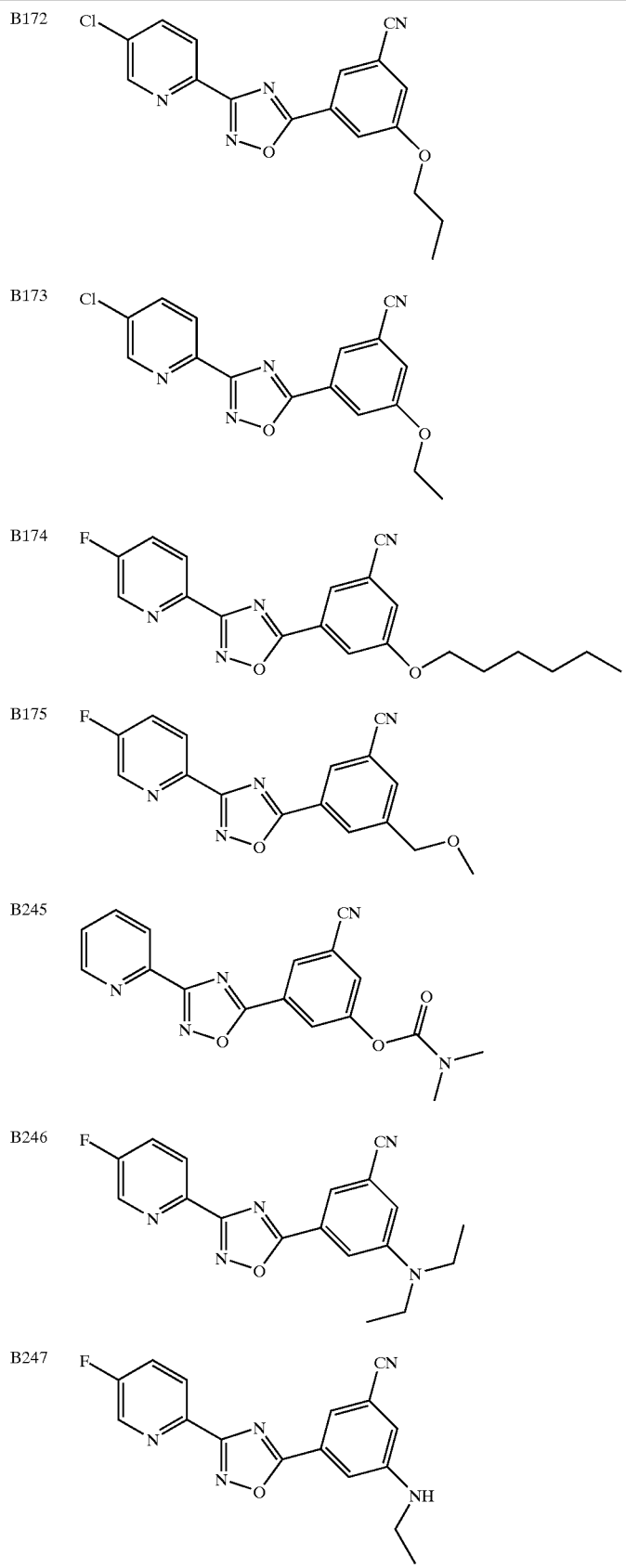

TABLE 3-continued
B260 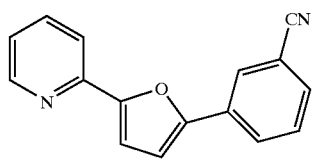
B261 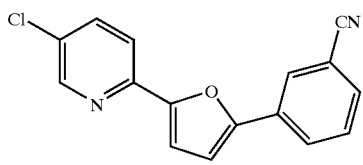
B263 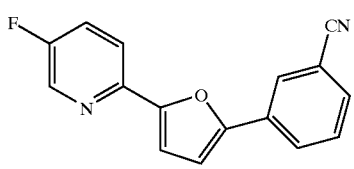
B262 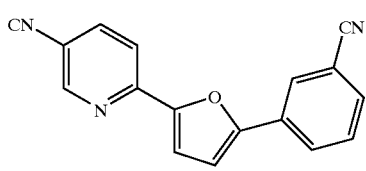
B259 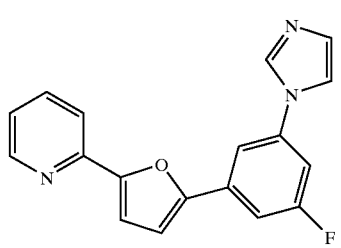
B264 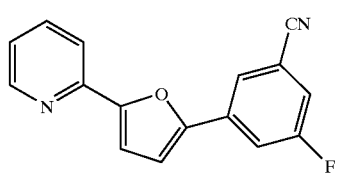
B274 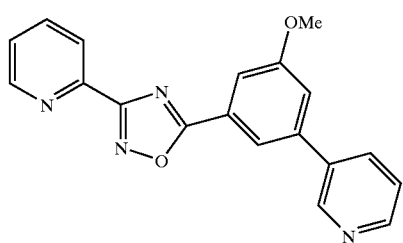

TABLE 3-continued
B275 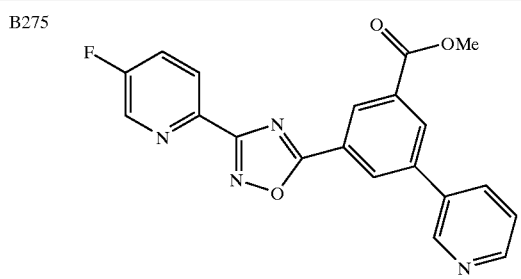
B276 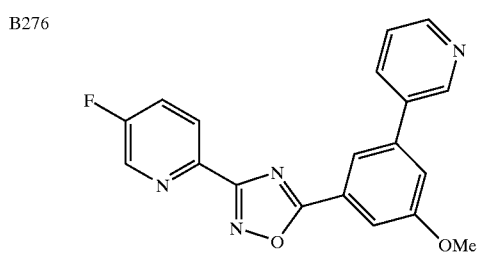
B277 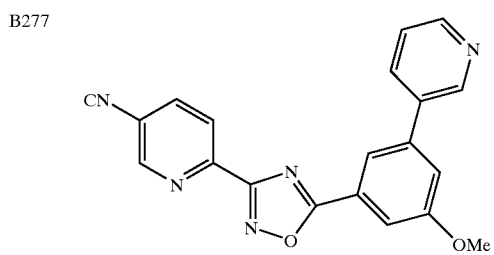
B278 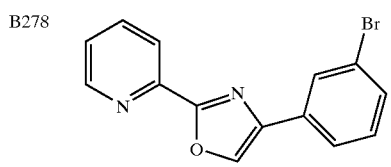
B279 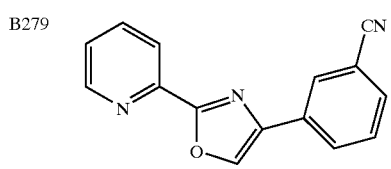
B280 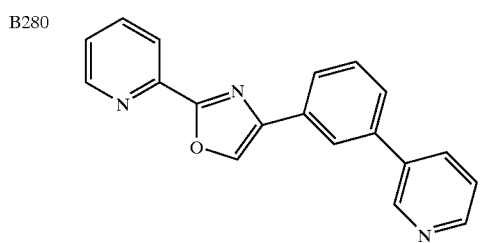
B220 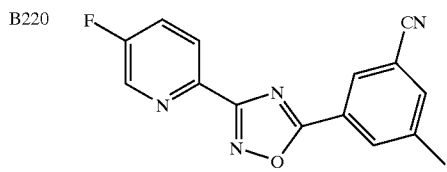

TABLE 3-continued
B221 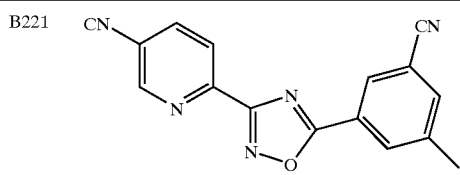
B265 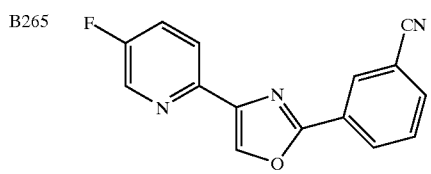
B267 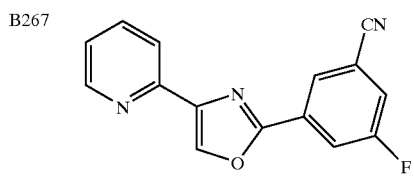
B266 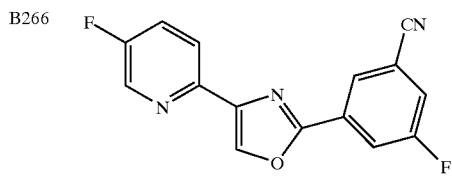
B268 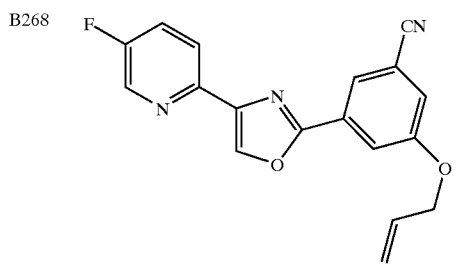
B270 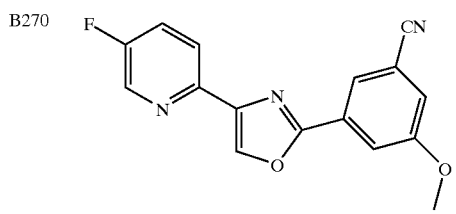
B271 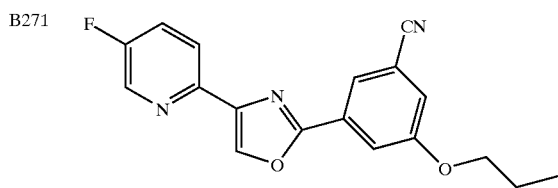
B222 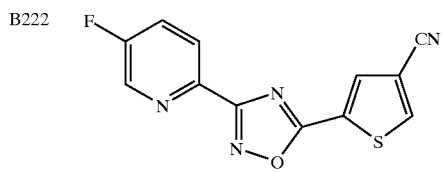

TABLE 3-continued
B176 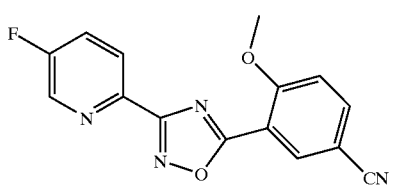
B177 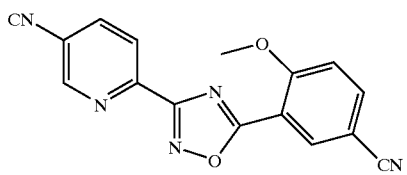
B225 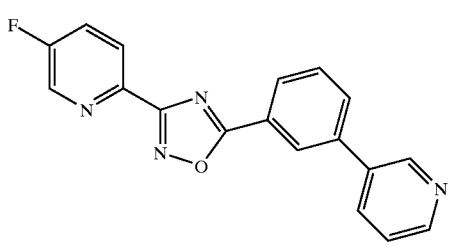
B226 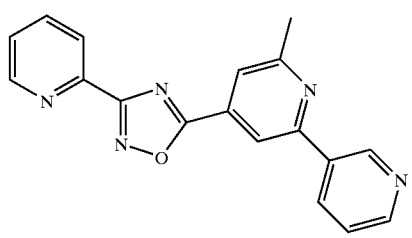
B227 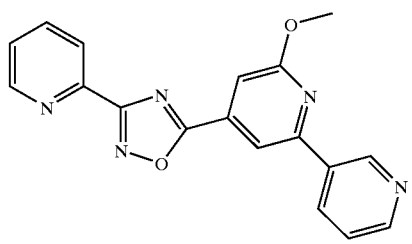
B181 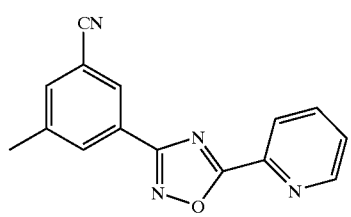
B182 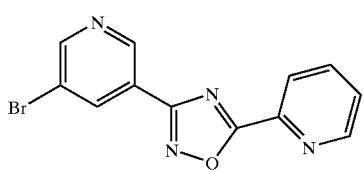

TABLE 3-continued
B228 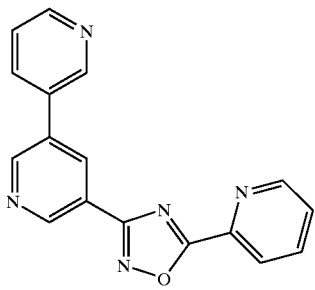
B183 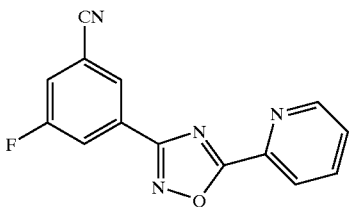
B184 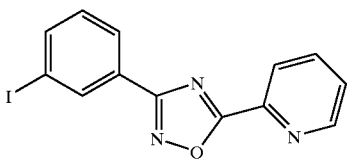
B186 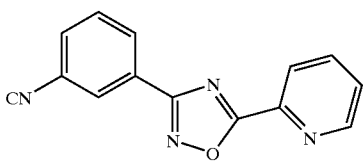
B187 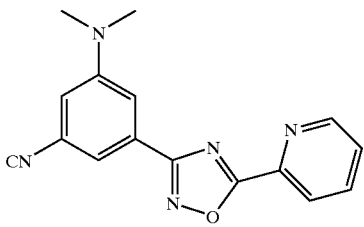
B188 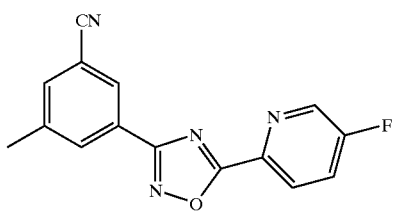
B189 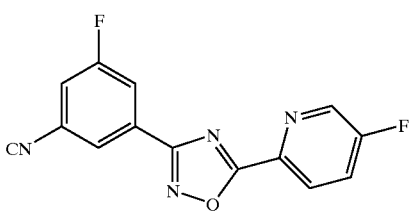

TABLE 3-continued
B229 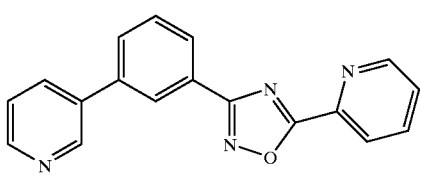
B190 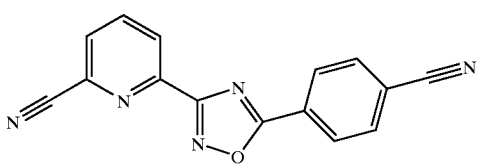
B191 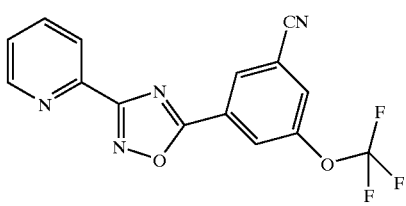
B192 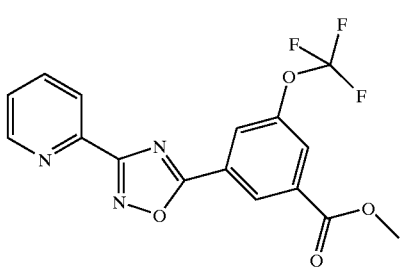
B193 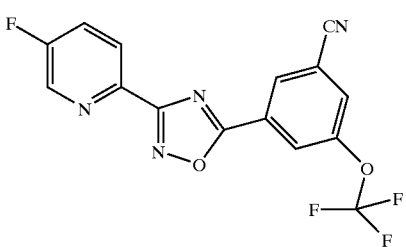
B194 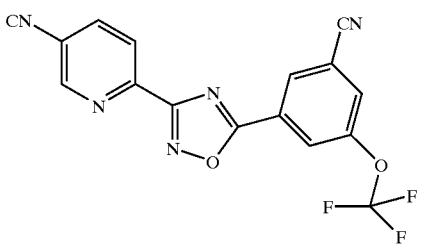
B195 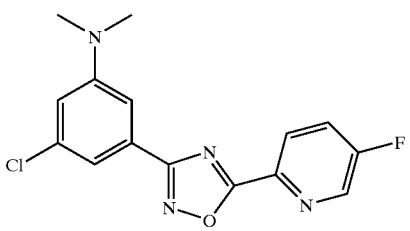

TABLE 3-continued
B230 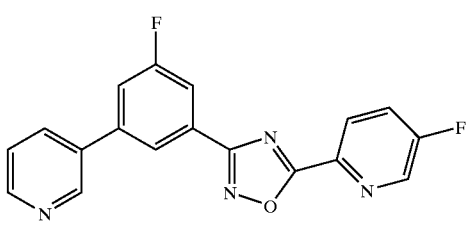
B197 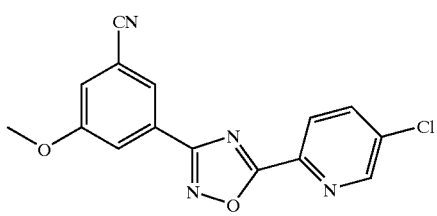
B196 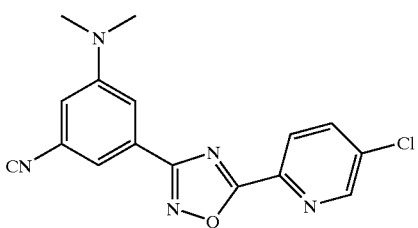
B198 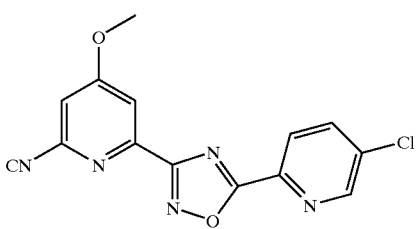
B200 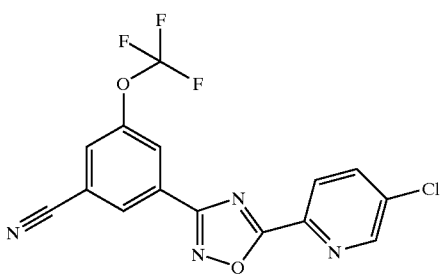
B201 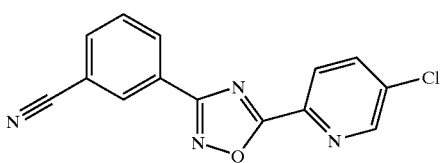
B202 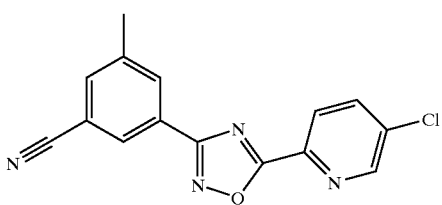

TABLE 3-continued
B203 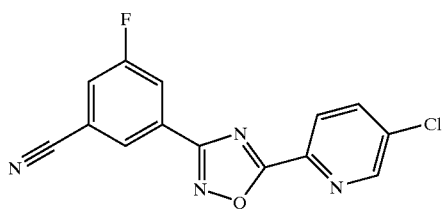
B199 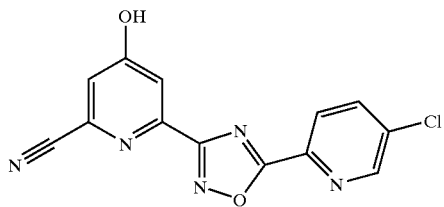
B204 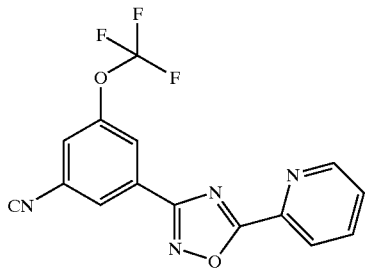
B205 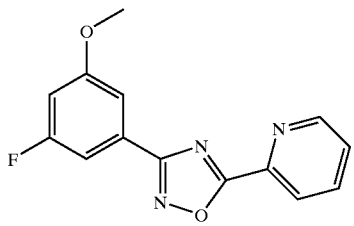
B206 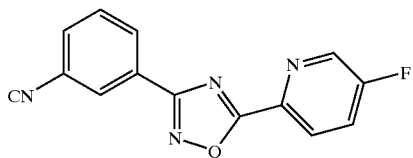
B208 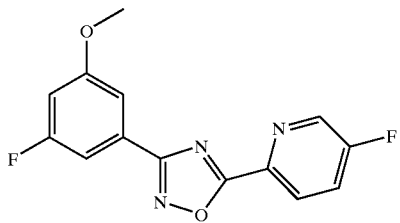

TABLE 3-continued
B207 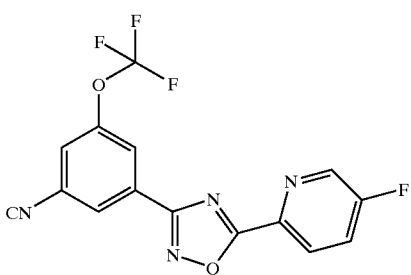
B209 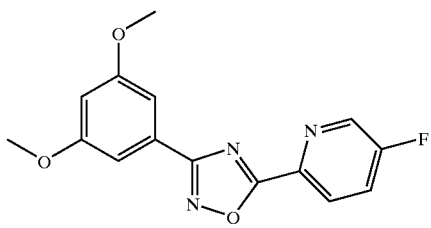
B248 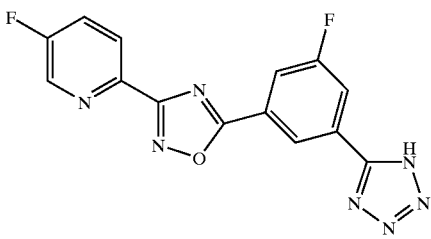
B249 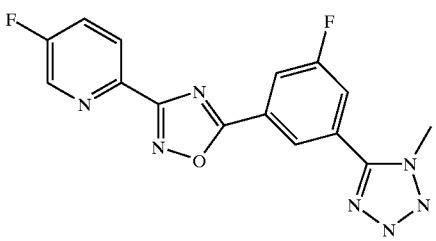
B210 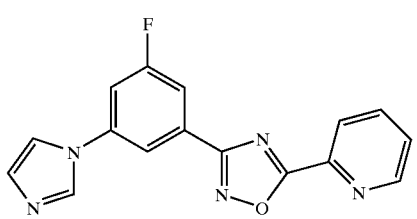
B231 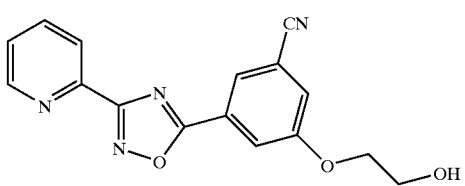
B157 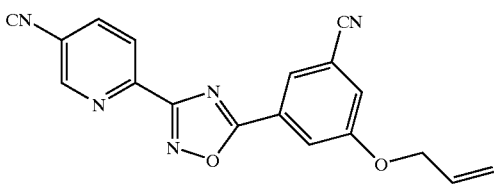

TABLE 3-continued
B158 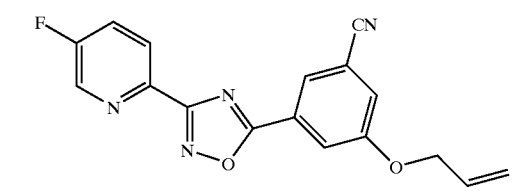
B159 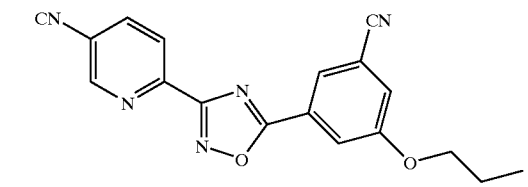
B160 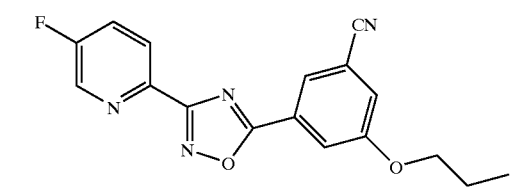
B232 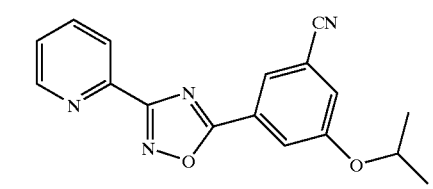
B233 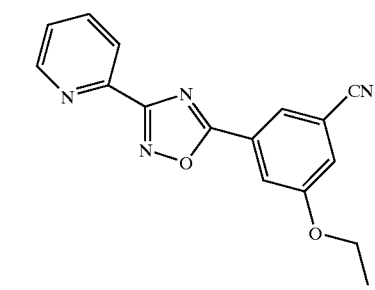
B234 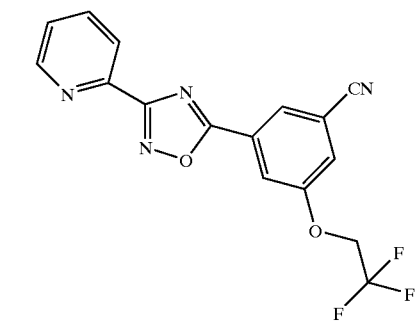
B161 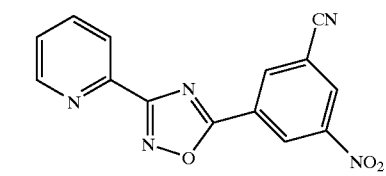

TABLE 3-continued
| | |
|---|---|
| B162 | 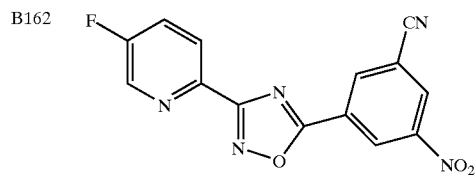 |
| B235 | 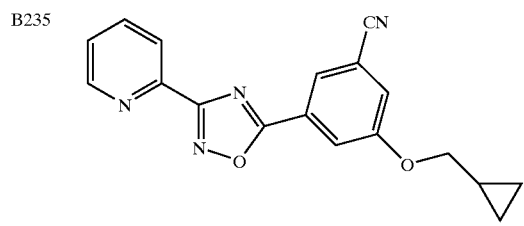 |
| B236 | 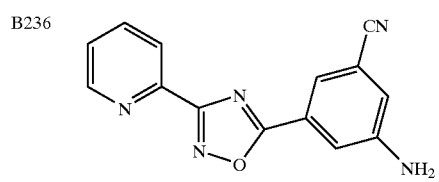 |
| B237 | 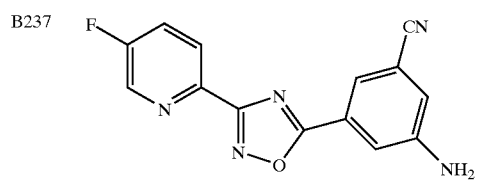 |
| B238 | 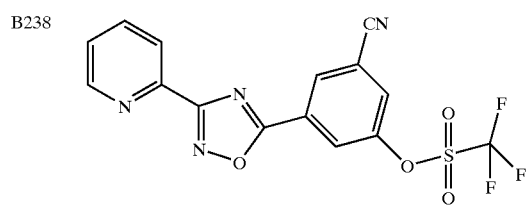 |
| B239 | 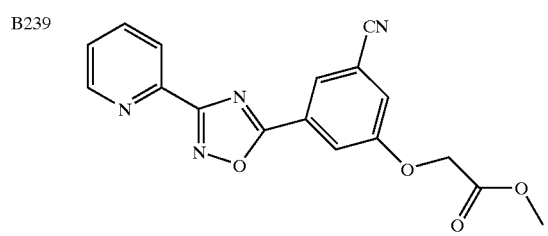 |
| B240 | 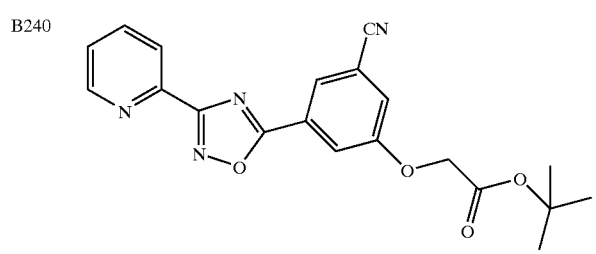 |

TABLE 3-continued

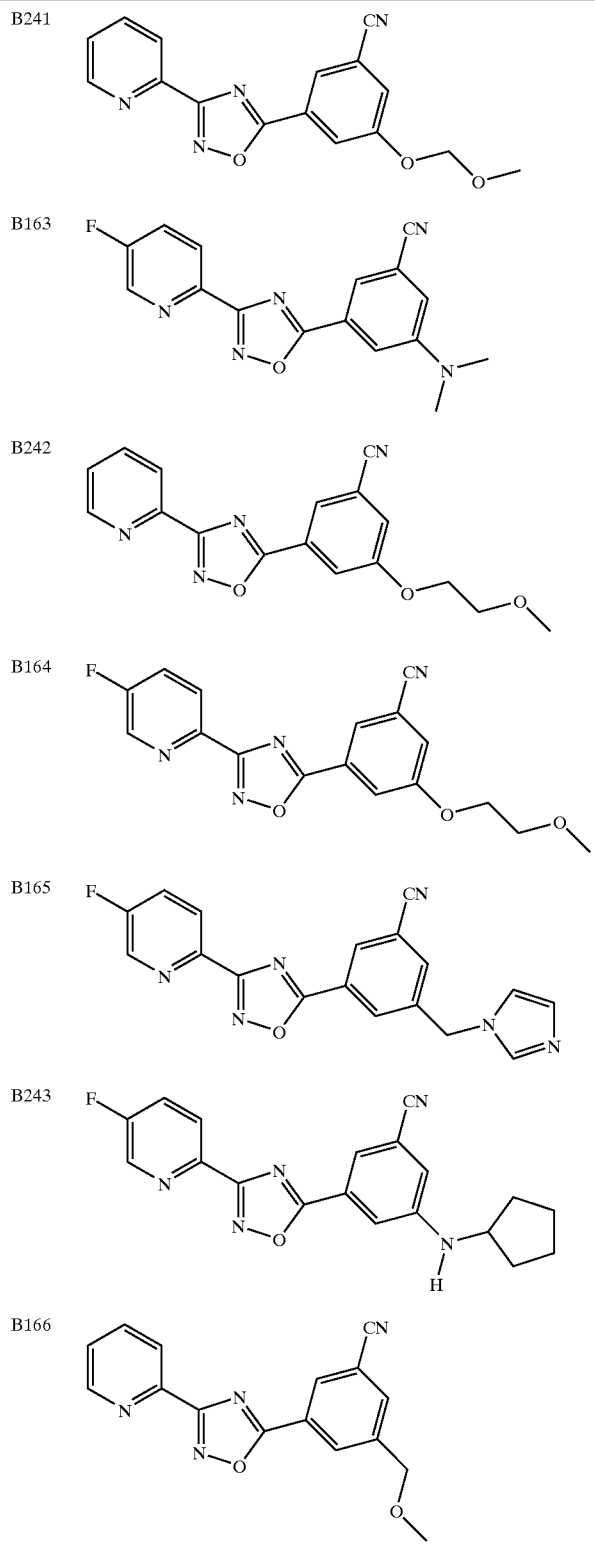

Preparation of mGluR Group I Antagonists

Many starting materials for preparing the compounds of the present invention are available from commercial sources, such as Aldrich Chemical Company (Milwaukee, Wis.). Moreover, compounds of the invention are readily prepared, from available precursors, using straightforward transformations which are well known in the art. The skilled artisan will recognize that mGluR Group I antagonists, according to the invention, can be prepared via methodology that is well known, using widely recognized techniques of organic chemistry. Suitable reactions are described in standard textbooks of organic chemistry. For example, see March, ADVANCED ORGANIC CHEMISTRY, 2d ed., McGraw Hill (1977).

More specifically, compounds of the invention generally can be prepared by formation of the G moiety between two precursor compounds containing suitable $Ar^1$ and $Ar^2$ moieties. When the linker contains a 1,2,4-oxadiazole, the heterocycle may be formed using well known techniques, such as reaction between an amidoxime and an acid chloride, or by the reaction of an amidoxime and an acylimidazole. An illustration of such a transformation is provided in Examples 4 and 5, below.

Amidoximes can be prepared using well known techniques by the reaction of an $Ar^1$ substituted nitrile with hydroxylamine. An illustration of such a transformation is provided below in Example 1.

reaction with, for example, thionyl chloride or oxalyl chloride.

In the case where the linker contains a 1,3-oxazole, compounds were prepared using a procedure similar to that given by Kelly et al., *J. Org. Chem.* 61, 4623–4633 (1996). Thus, 3,5-disubstituted-1,3-oxazoles were prepared by mixing a haloketone with carboxamide in refluxing toluene for 3 days. The resulting mixture was allowed to cool to room temperature, the solvent was removed and the residue was purified.

Scheme 1 illustrates a method for synthesizing compounds of the present invention. In particular, the method illustrated by scheme 1 is used for making the following exemplified compounds: B77–B81, B86, B89, B101, B108, B115, B120–B122, B124, B129–B141.

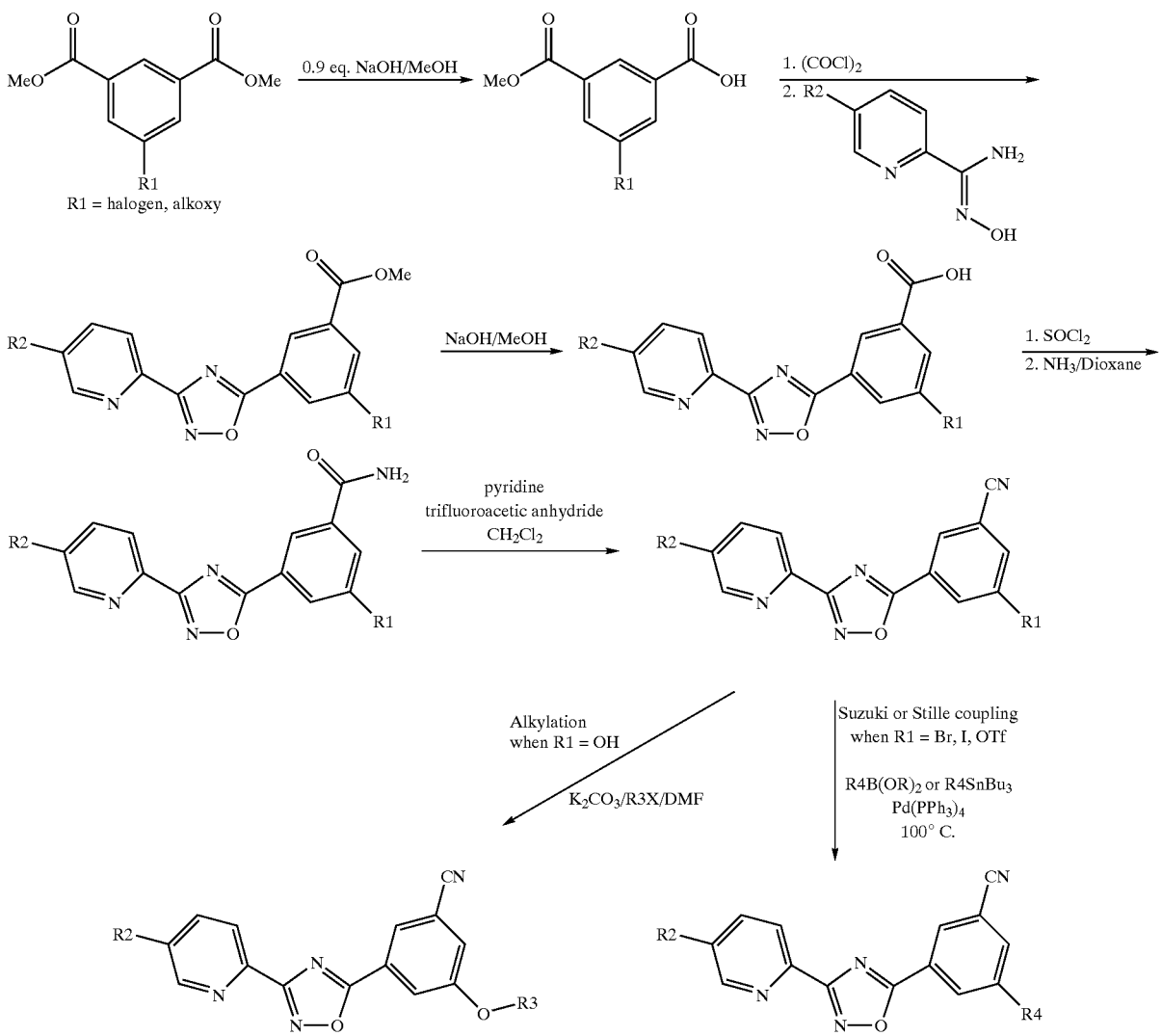

Scheme 1

In most cases, the precursor $Ar^2$ acid chlorides are readily available, or may be prepared using straightforward techniques of organic chemistry. For example, carboxylic acids may be converted into the corresponding acid chlorides by Scheme 2 illustrates another method for synthesizing compounds of the present invention. In particular, the method of scheme 2 is used to make the exemplified compound B144.

Scheme 2

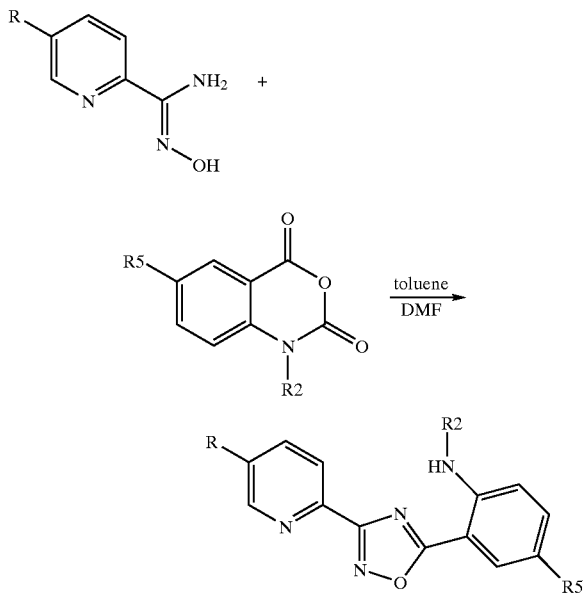

Scheme 3 illustrates a further method for synthesizing compounds of the present invention. In particular, the method of scheme 3 is used to make the following exemplified compounds: B57–B76, B82-B85, B87, B88, B90, B91, B93–B100, B102–B107, B109–B114, B116–B119, B123, B125–B128, B142, B143.

Other compounds of the present invention may readily be prepared by modifications to the reactions exemplified in the Schemes above, as will be appreciated by the skilled artisan.

EXAMPLES

General Experimental Methods

Capillary gas chromatographic and mass spectral data were obtained using a Hewlett-Packard (HP) 5890 Series II Gas Chromatograph coupled to an HP 5971 Series Mass Selective Detector [Ultra-2 Ultra Performance Capillary Column (crosslinked 5% PhMe silicone); column length, 25 m; column i.d., 0.20 mm; helium flow rate, 60 mL/min; injector temp., 250° C.; temperature program, 20° C./min from 125 to 325° C. for 10 min, then held constant at 325° C. for 6 min]. Thin-layer chromatography was performed using Analtech Uniplate 250-$\mu$m silica gel HF TLC plates. UV light sometimes in conjunction with ninhydrin and Dragendorff's spray reagents (Sigma Chemical Co.) were used for detecting compounds on the TLC plates. Most reagents used in reactions were purchased from the Aldrich Chemical Co. (Milwaukee, Wis.), Sigma Chemical Co. (Saint Louis, Mo.), Fluka Chemical Corp. (Milwaukee, Wis.), Fisher Scientific (Pittsburgh, Pa.), TCI America (Portland, Oreg.), or Lancaster Synthesis (Windham, N.H.).

Scheme 3

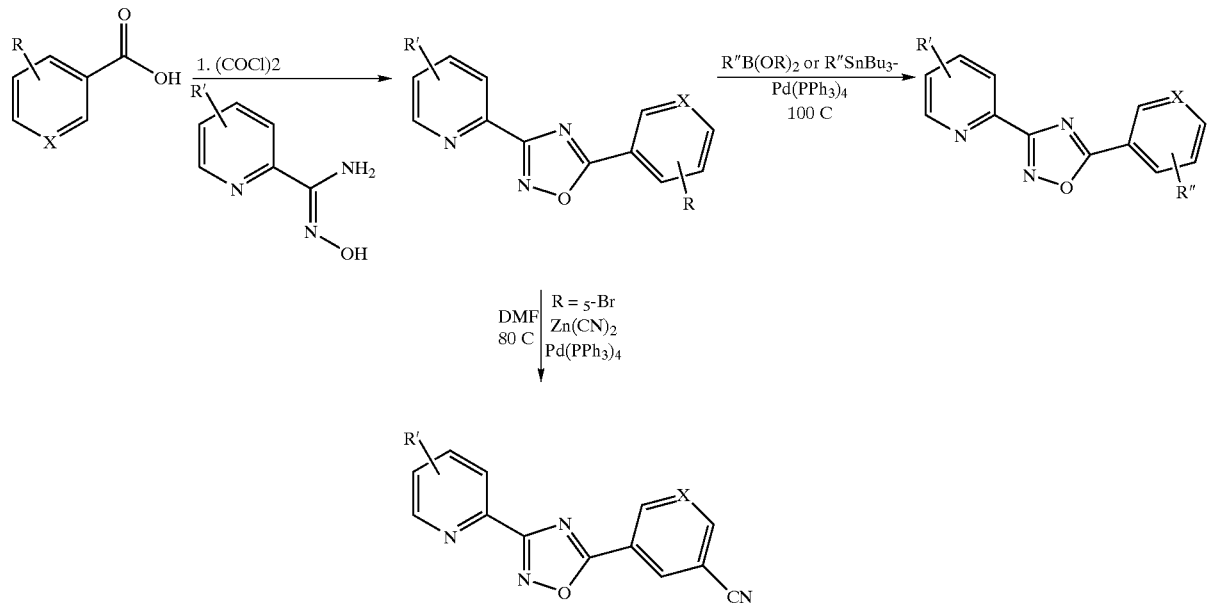

Example 1

Synthesis of Amidoxime Intermediates

Pyrid-2-ylamidoxime

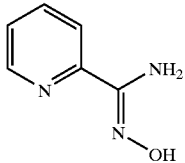

Using the general procedure of Shine et al., *J. Heterocyclic Chem.* (1989) 26:125–128, hydroxylamine hydrochloride (7.65 g, 110 mmol) in ethanol (100 mL) was treated with a 10N solution of sodium hydroxide (11 mL, 110 mmol). A precipitate quickly formed and the reaction mixture was stirred at room temperature for 30 min. The inorganic precipitate was filtered and rinsed with ethanol (100 mL). The filtrate and ethanol washings were combined and treated with 2-cyanopyridine (10.4 g, 100 mmol). The reaction mixture was then heated at reflux for 20 hours. After cooling, the volatiles were removed in vacuo, to afford 13.3 g (97%) of pyrid-2-ylamidoxime.

5-Methyl-pyrid-2-ylamidoxime

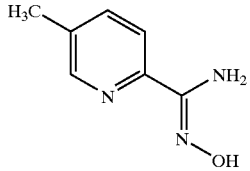

A mixture of 2-bromo-5-methylpyridine (2.001 g, 11.63 mmol), zinc cyanide (830 mg, 7 mmol), zinc (dust, 35 mg, 0.53 mmol), [1,1'-bis(diphenylphosphino)ferrocene] dichloropalladium(II), complex with dichloromethane (1:1) (192.5 mg, 0.24 mmol) in N,N-dimethylformamide (10 mL) was heated at reflux for 16 hours. After cooling, the reaction was diluted with ethyl acetate and extracted with water and brine. The organic solution was filtered through a plug of silica gel, washing dichloromethane. Removal of the solvent in vacuo, afforded 770 mg (56%) of 5-methyl-2-cyanopyridine.

Using the general procedure for the synthesis of amidoximes, 5-methyl-2-cyano-pyridine (770 mg, 6.5 mmol), 5M hydroxylamine hydrochloride (1.5 mL, 7.5 mmol) in ethanol (10 mL), and 10N sodium hydroxide (0.75 mL, 7.5 mmol), were heated at reflux for 18 hours. Standard work up afforded 594 mg (60%) of 5-methylpyrid-2-ylamidoxime.

5-Cyanopyrid-2-ylamidoxime

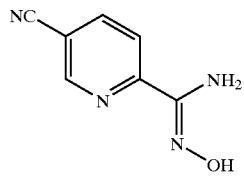

In a similar fashion, a mixture of 2,5-dicyanopyridine (740mg, 5.74 mmol), 5M hydroxyamine hydrochloride (1.15 mL, 5.75 mmol) and 1M sodium hydroxide (5.74 mL, 5.74 mmol) in ethanol (10 mL) was heated at 80° C. for 5 minutes. The precipitate was collected by filtration to afford 555 mg (60%) of 5-cyanopyrid-2-ylamidoxime.

5-Fluoropyrid-2-ylamidoxime

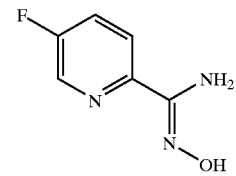

A mixture of 2-cyano-5-chloropyridine (1 g, 7.22 mmol) and potassium fluoride (1.26 g, 21.68 mmol) in 1-methyl-2-pyrrolidinone (25 mL) was heated at reflux for 18 hours. After cooling, the reaction was diluted with ethyl acetate and extracted with water and brine. The organic solvents were then removed in vacuo. Silica gel chromatography of the residue afforded 425 mg (48%) of 2-cyano-5-fluoropyridine.

Using the general procedure for the synthesis of amidoximes, 2-cyano-5-fluoropyridine (425 mg, 3.48 mmol), 5M hydroxylamine hydrochloride (0.79 ml, 3.95 mmol) in ethanol (5 mL), and 10N sodium hydroxide (0.398 mL, 3.98 mmol) were heated at reflux for 24 hours. Standard work up afforded 330 mg (61%) of 5-fluoropyrid-2-ylamidoxime.

5-Tert-Butoxycarbonyl-pyrid-2-ylamidoxime

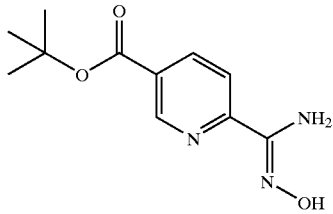

A suspension of 6-cyanonicotinic acid (535 mg, 3.6 mmol) in dichloromethane (8 mL) at 0° C. was treated with 2M oxalyl chloride (3.6 mL, 7.2 mmol, dichloromethane) and a catalytic amount of N,N-dimethylformamide. The reaction was then stirred at room temperature for 2 hours. The solvent was removed in vacuo and the residue dissolved in dichloromethane (10 mL). The resulting solution was treated with pyridine (2 mL) and tert-butanol (0.8 mL) and the reaction mixture stirred overnight at room temperature. The reaction mixture was diluted with dichloromethane (200 mL) and washed sequentially with saturated sodium bicarbonate (50 mL) and brine (50 mL). The organic layer was dried over anhydrous sodium sulfate, filtered and the solvent removed in vacuo. Silica gel chromatography, using a gradient of 5% to 10% ethyl acetate in hexane, afforded 623 mg (84%) of 5-tert-butoxycarbonyl-2-cyano-pyridine, as a yellow solid.

Using the general procedure for the synthesis of amidoximes, 5-tert-butoxycarbonyl-2-cyano-pyridine (623 mg, 3.05 mmol) and 5M hydroxylamine hydrochloride (0.69 mL, 3.4 mmol) in ethanol (7 mL) and 10N sodium hydroxide (0.34 mL, 3.4 mmol), were heated at reflux for 18 hours. Standard work up afforded 570 mg (79%) of 5-tert-butoxycarbonylpyrid-2-ylamidoxime.

3-Cyano-5-methoxypyrid-2-ylamidoxime

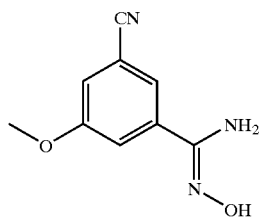

A solution of dimethyl-5-hydroxylsophthalate (6 g, 28.6 mmol) and potassium carbonate (9 g, 65.4 mmol) in acetone (120 mL) was prepared. To this, methyl iodide (4 mL, 63.7 mmol) was added and the reaction was left stirring overnight at ambient temperature. The reaction mixture was filtered and then concentrated. The residue was dissolved in ethyl acetate and washed with water and saturated brine, dried over anhydrous sodium sulfate, filtered, and concentrated. 6.4 g (quantitative) of dimethyl-5-methoxy-isophthalate was isolated as an off-white solid.

A solution of dimethyl-5-methoxy-isophthalate (2.5 g, 11.1 mmol) in tetrahydrofuran/methanol (56 mL/20 mL) was treated with 2.0 N sodium hydroxide (12 mL, 25 mmol). The reaction was left stirring for 15 hours at room temperature. After the solution was concentrated, the solid was dissolved in water and acidified with 2.0 N hydrogen chloride. Ethyl acetate was used to extract the precipitate, which was then washed with brine and dried over anhydrous sodium sulphate. After removal of solvent in vacuo, a total of 2.5 g (quantitative) of 5-methoxyisophthalic acid was isolated.

A solution of 5-methoxyisophthalic acid (2.5g, 13.8 mmol) in dichloromethane (20 mL) was treated with 2M oxalyl chloride (38 mL, 76.6 mmol) and a few drops of DMF. After stirring for 17 hours, the reaction was concentrated in vacuo and then the resulting brown oil was transferred into a cold, stirred solution of ammonium hydroxide in ethyl acetate (70 mL/200 mL) with a small amount of dichloromethane. The reaction was allowed to proceed for 1 hour, after which a precipitate formed. Water (100 mL) and ethyl acetate (1500 mL) were combined with the reaction in a separatory funnel, and the organic layer was collected, washed with brine and dried over sodium sulphate. The remaining solid in the aqueous layer was isolated by filtration, washed with water, and dried. The organic layer was filtered and concentrated and then triturated with hexanes. A total of 2.5g (quantitative) of the 5-methoxyisophthalamide was isolated.

A suspension of the 5-methoxyisophthalamide (3.1 g, 16 mmol) in a dichloromethane (27 mL) at 0° C. was treated with pyridine (5.2 mL, 65 mol) and then trifluoroacetic anhydride drop-wise (5.4 mL, 39 mmol). The reaction was stirred at 0° C. for 20 minutes and then stirred overnight at ambient temperature. The reaction mixture was washed with water and saturated brine, dried over anhydrous sodium sulfate, filtered and concentrated. Silica gel chromatography using hexanes:ethyl acetate:dichloromethane afforded 940 mg (46%) of the 5-methoxyisophthalonitrile as a white solid.

Using the general procedure for the synthesis of amidoximes, 5-methoxyisophthalonitrile (600 mg, 3.8 mmol), 5M hydroxylamine hydrochloride (0.76 ml, 3.8 mmol) in ethanol (6 mL), and 1N sodium hydroxide (3.8 mL, 3.8 mmol) were heated at reflux for 3 hours. Standard work up and column chromatography using 30–40% ethyl acetate/hexanes afforded 329 mg (45%) of 3-cyano-5-methoxyphenyl-amidoxime.

3-Cyano-5-fluorophenylamidoxime

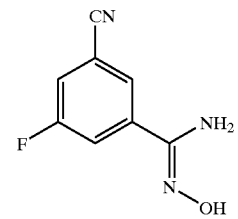

5-Fluoro-isophthalonitrile (730 mg, 5 mmol) and 5M hydroxylamine hydrochloride (1 mL, 5 mmol) in ethanol (10 mL) and 1N sodium hydroxide (5 mL, 5 mmol), were heated at reflux for 30 minutes. Standard work up followed by column chromatography afforded 473 mg (52.8%) of 3-cyano-5-fluorophenylamidoxime 5-Bromopyrid-3-yl-amidoxime

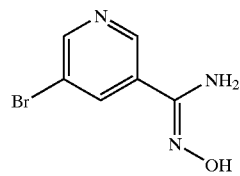

5-Bromonicotinonitrile (982 mg, 5.4 mmol) and 5M hydroxylamine hydrochloride (1.098 mL, 5.4 mmol) in ethanol (5 mL) and 1N sodium hydroxide (5.4 mL, 5.4 mmol), were heated at reflux for 5 minutes. Standard work up afforded 925 mg (79.3%) of 5-bromopyrid-3-yl-amidoxime.

3-Cyano-5-methylphenylamidoxime

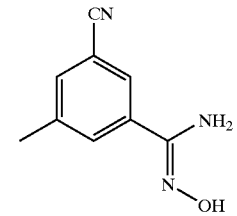

3,5-Dicyanotoluene (1000 mg, 7.04 mmol) and 5M hydroxylamine hydrochloride (1.4 mL, 7.04 mmol) in ethanol (5 mL) and 1 N sodium hydroxide (7.04 mL, 7.04 mmol), were heated at reflux for 12 minutes. Standard work up followed by column chromatography afforded 215 mg (17.4%) of 3-cyano-5-methylphenylamidoxime.

3-Cyanophenylamidoxime

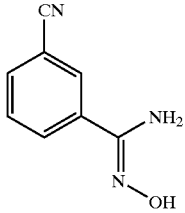

Isophthalonitrile (640 mg, 5 mmol) and 5M hydroxylamine hydrochloride (1 mL, 5 mmol) in ethanol (5 mL) and 1N sodium hydroxide (5 mL, 5 mmol), were heated at reflux for 2.5 hours. Standard work up followed by column chromatography afforded 650 mg (80.7%) of 3-cyanophenylamidoxime.

3-Iodophenylamidoxime

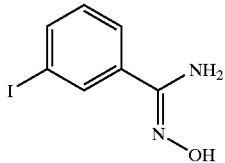

3-Iodobenzonitrile (1145 mg, 5 mmol) and 5M hydroxylamine hydrochloride (1 mL, 5 mmol) in ethanol (5 mL) and 1Nsodium hydroxide (5 mL, 5 mmol), were heated at reflux for 2.5 hours. Standard work up followed by column chromatography afforded 920 mg (70.2%) of 3-iodophenylamidoxime.

3-Cyano-5-dimethylaminophenylamidoxime

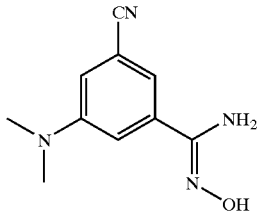

5-Dimethylaminoisophthalonitrile (856 mg, 5 mmol) and 5M hydroxylamine hydrochloride (1 mL, 5 mmol) in ethanol (10 mL) and 1N sodium hydroxide (5 mL, 5 mmol), were heated at reflux for 30 minutes. Standard work up followed by column chromatography afforded 280 mg (27.4%) of 3-cyano-5-dimethylaminophenylamidoxime.

6-Cyano-pyrid-2-yl-amidoxime

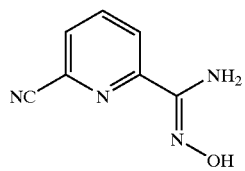

2,6-Dictanopyridine (3.87 g, 30 mmol) and 5M hydroxylamine hydrochloride (6 mL, 30 mmol) in ethanol (50 mL) and 1N sodium hydroxide (30 mL, 30 mmol), were heated at reflux for 10 minutes. Standard work up followed by column chromatography afforded 2.87 g (59%) of 6-cyano-pyrid-2-yl-amidoxime.

3-Bromo-5-fluorophenylamidoxime

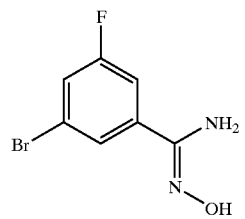

3-Bromo-5-fluorobenzonitrile (1.9 g, 9.5 mmol) and 5M hydroxylamine hydrochloride (4 mL, 20 mmol) in ethanol (20 mL) and 1N sodium hydroxide (20 mL, 20 mmol), were heated at reflux for 1 hour. Standard work up followed by column chromatography afforded 721 mg (32.6%) of 3-bromo-5-fluorophenylamidoxime.

3-Fluoro-5-methoxyphenylamidoxime

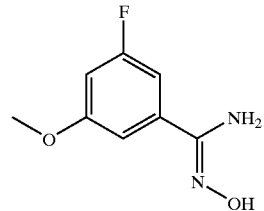

3-Fluoro-5-methoxybenzonitrile (379 mg, 2.5 mmol) and 5M hydroxylamine hydrochloride (0.5 mL, 2.5 mmol) in ethanol (2.5 mL) and 1N sodium hydroxide (2.5 mL, 2.5 mmol), were heated at reflux for 1 hour. Standard work up afforded 431 mg (93.4%) of 3-fluoro-5-methoxyphenylamidoxime.

3,5-dimethoxyphenylamidoxime

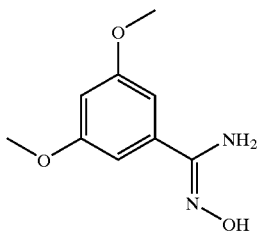

3,5-dimethoxybenzonitrile (228 mg, 1.4 mmol) and 5M hydroxylamine hydrochloride (0.336 mL, 1.68 mmol) in ethanol (2 mL) and 1N sodium hydroxide (1.68 mL, 1.68 mmol), were heated at reflux overnight. Standard work up afforded 250 mg (91%) of 3,5-dimethoxyphenylamidoxime.

3-Fluoro-5-(1H-imidazol-1-yl)phenyl-amidoxime

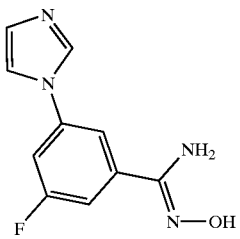

3-Fluoro-5-(1H-imidazol-1-yl)benzonitrile (950 mg, 5.08 mmol) and 5M hydroxylamine hydrochloride (1.02 mL, 5.08 mmol) in ethanol (5 mL) and 1N sodium hydroxide (5.08 mL, 5.08 mmol), were heated at reflux for 1 hour and 20 minutes. Standard work up afforded 901 mg (81.4%) of 3-bromo-5-fluorophenylamidoxime.

6-Cyano-4-methoxypyrid-2-yl-amidoxime

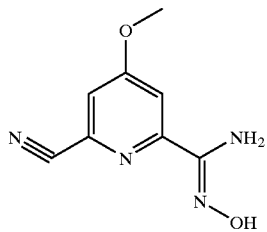

Chelidamic acid monohydrate (2.01 g, 10 mmol) was mixed with 1M HCl (20 mL, 20 mmol, ether) in ethanol (50 mL) and heated at 85° C. for 24 hours. The solvent was removed in vacuo and mixed with ethyl acetate and water. The ethyl acetate layer was dried and concentrated. The residue was triturated with hexanes and ether to give 1.6 g (66%) diethyl 4-hydroxy-2,6-pyridinedicarboxylate.

To a suspension of 60% sodium hydride (0.351 g, 8.77 mmol) in dimethylformamide(7.5 mL), a solution of diethyl 4-hydroxy-2,6-pyridinedicarboxylate (1.4 g, 5.85 mmol) in dimethylformamide (9 mL) was added dropwise under argon at room temperature and the reaction mixture was stirred for 5 minutes. Iodomethane (1.245 g, 8.77 mmol) was added and the reaction was stirred at room temperature for 20 hours. The mixture was poured into water and extracted with dichloromethane. The dichloromethane layer was dried, concentrated to give 1.45 g (97.8%) diethyl 4-methoxy-2,6-pyridinedicarboxylate.

Diethyl 4-methoxy-2,6-pyridinedicarboxylate (1.45 g, 5.73 mmol) was stirred with concentrated ammonium (40 mL) at room temperature for 10 minutes. The precipitate was filtered to give 0.93 g (83%) of 4-methoxypyridine-2,6-dicarboxamide.

4-methoxypyridine-2,6-dicarboxamide (900 mg, 4.6 mmol) was mixed with trifluoroacetic anhydride (2.32 g, 11.1 mmol) and pyridine (1.6 g, 20.2 mmol) in dichloromethane (20 mL) and stirred overnight at room temperature. The reaction mixture was diluted with dichloromethane and washed with water. Standard work up, afforded 461 mg of 2,6-dicyano-4-methoxypyridine.2,6-Dicyano-4-methoxypyridine (460 mg, 2.89 mmol) and 5M hydroxylamine hydrochloride (0.578 mL, 2.89 mmol) in ethanol (3 mL) and 1N sodium hydroxide (2.89 mL, 2.89 mmol), were stirred at room temperature overnight. Standard work up afforded 180 mg (32.4%) of 6-cyano-4-methoxypyrid-2-yl-amidoxime.

3-Methoxybenzamidoxime

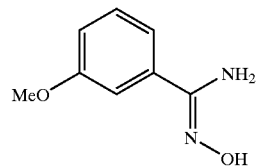

Using the general procedure for the synthesis of amidoximes, hydroxylamine hydrochloride (7.65 g, 110 mmol), sodium hydroxide (11 mL of 10 N, 110 mmol), and 3-methoxybenzylnitrile (12.2 mL, 100 mmol) afforded 9.9 g (60%) of 3-methoxybenzamidoxime.

5-Chloropyrid-2-ylamidoxime

A mixture of 2,5-dichloropyridine (1.48 g, 10 mmol), zinc cyanide (705 mg, 6 mmol), zinc (dust, 29 mg, 0.45 mmol), [1,1'-bis(diphenylphosphino)ferrocene] dichloropalladium (II), complex with dichloromethane (1:1) (0.18 g, 0.22 mmol) in N,N-dimethylformamide (10 mL) was heated at reflux for 5 hours. After cooling, the reaction was diluted with ethyl acetate and extracted with water and brine. Silica gel chromatography afforded 735 mg (53%) of 2-cyano-5-chloropyridine.

Using the general procedure for the synthesis of amidoximes, 2-cyano-5-chloropyridine (735 mg, 5.3 mmol), a solution of hydroxylamine hydrochloride (1.2 mL of 5 M, 6 mmol) in ethanol (7 mL), and sodium hydroxide (0.61 mL of 10 N, 6.1 mmol), were heated at reflux for 24 hours. Standard work up afforded 707 mg (77%) of 5-chloropyrid-2-ylamidoxime.

5-Methoxypyrid-2-ylamidoxime

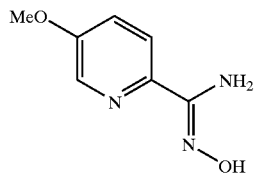

A solution of 2-cyano-5-fluoropyridine (0.65 g, 5.3 mmol) in sodium methoxide (1.83 mL of 25% wt. solution in methanol, 7.95 mmol) was stirred at 0° C. for 1.5 hours and 2 hours at ambient temperature. The reaction was then diluted with ethyl acetate and washed with water and brine. Removal of the solvent in vacuo afforded 304 mg (43%) of 2-cyano-5-methoxypyridine.

Using the general procedure for the synthesis of amidoximes, 2-cyano-5-methoxypyridine (270 mg, 2.01 mmol), a solution of hydroxylamine hydrochloride (0.457 ml of 5 M, 2.28 mmol) in ethanol (4 mL), and sodium hydroxide (0.230 mL of 10 N, 2.30 mmol) were heated at reflux for 24 hours. Standard work up afforded 79 mg (24%) of 5-methoxypyrid-2-ylamidoxime.

3-Fluoropyrid-2-ylamidoxime

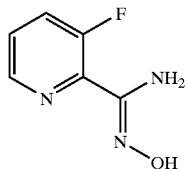

A mixture of 2,3-dichloropyridine (1.48 g, 10 mmol), zinc cyanide (705 mg, 6 mmol,), zinc (dust, 29 mg, 0.45 mmol), [1,1'-bis(diphenylphosphino)ferrocene] dichloropalladium (II), complex with dichloromethane (1:1) (0.18 g, 0.22 mol) in N,N-dimethylformamide (10 mL) was heated at reflux for 5 hours. After cooling, the reaction was diluted with ethyl acetate and extracted with water and brine. Removal of the solvent and silica gel chromatography afforded 1.05 g (76%) of 2-cyano-3-chloropyridine.

A solution of 2-cyano-3-chloropyridine (1 g, 7.22 mmol) in 1-methyl-2-pyrrolidinone (25 mL) was treated with potassium fluoride (1.26 g, 21.68 mmol) and heated at reflux for 18 hours. After cooling, the reaction was diluted with ethyl acetate and extracted with water and brine. Silica gel chromatography afforded 442 mg (50%) of 2-cyano-3-fluoropyridine.

Using the general procedure for the synthesis of amidoximes, 2-cyano-3-fluoropyridine (442 mg, 3.62 mmol), a solution of hydroxylamine hydrochloride (0.82 mL of 5 M, 4.1 mmol) in ethanol (5 mL), and sodium hydroxide (0.415 ml of 10N, 4.15 mmol) were heated at reflux for 24 hours. Standard work up afforded 368 mg (66%) of 3-fluoropyrid-2-ylamidoxime.

Quinol-2-ylamidoxime

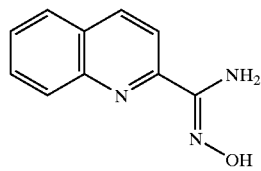

Using the general procedure for the synthesis of amidoximes, 2-quinolinecarbonitrile (1.02 g, 6.6 mmol), a solution of hydroxylamine hydrochloride (1.44 mL of 5 N solution, 7.2 mmol) in ethanol (10 mL), and sodium hydroxide (0.72 mL of 10 N solution, 7.2 mmol) were heated at reflux for 18 hours. Standard work up afforded 990 mg (80%) of quinol-2-ylamidoxime.

Example 2

Synthesis of Carboxylic Acid Intermediates

5-Allyloxy-3-(methoxycarbonyl)benzoic Acid

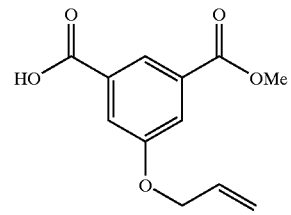

A stirred suspension of dimethyl 5-hydroxyisophthlate (5.0 g, 23.8 mmol) and potassium carbonate (7.5 g, 54.5 mmol) in acetone (120 mL) was treated with allyl bromide (4.6 mL, 53.0 mmol). The mixture was stirred at room temperature for 3 days. The mixture was then filtered and concentrated. The residue was dissolved in ethyl acetate and washed with water and brine. The remaining organic solution was dried over anhydrous sodium sulfate, filtered, and concentrated. Trituration with hexane afforded 5.0 g (84%) of dimethyl 5-allyloxy-isophthalate A mixture of dimethyl 5-allyloxy-isophthalate (3.7 g, 14.9 mmol) in methanol (75 mL) was treated with 1M sodium hydroxide (13.4 mL, 13.4 mmol) and the reaction stirred at room temperature for 16 hours. The mixture was concentrated under vacuum and the resulting residue was dissolved in water. The aqueous layer was washed with ethyl acetate (3x), and then acidified (pH 1) by the addition of aqueous HCl. The aqueous solution was then extracted with ethyl acetate. The organic extract was dried over anhydrous sodium sulfate, filtered and concentrated to afford 2.6 g (74%) of 3-allyloxy-5-(methoxycarbonyl)benzoic acid.

3-Methoxycarbonyl-5-methoxybenzoic Acid

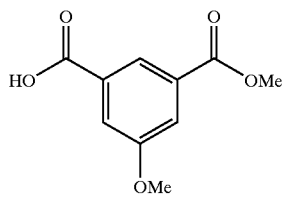

In a similar fashion, dimethyl 5-hydroxyisophthlate (1.0 g, 4.8 mmol), potassium carbonate (1.5 mg, 10.9 mmol), and methyl iodide (0.7 mL, 10.6 mmol) in acetone (25 mL) afforded 1.1 g (99%) of dimethyl 5-methoxyisophthalate. Hydrolysis and standard work up afforded 0.7 g (68%) of 3-methoxycarbonyl-5-methoxybenzoic acid.

3-Bromo-5-cyanobenzoic Acid

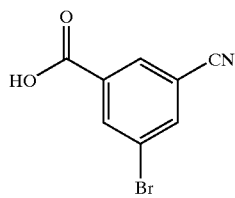

A mixture of 3-bromo-5-iodobenzoic acid (9.0 g) in methanol (40 mL) was treated with 1M HCl in diethyl ether (27.5 mL). The reaction was heated overnight at 40° C. The solvent was then removed in vacuo, and the residue dissolved in ethyl acetate. The organic solution was washed with saturated sodium bicarbonate, dried over anhydrous sodium sulfate, filtered and concentrated to afford 8.8 g (94%) of methyl 3-bromo-5-iodobenzoate.

A solution of methyl 3-bromo-5-iodobenzoate (4.5 g, 13.2 mmol) in N,N-dimethylformamide (36 mL) was treated with zinc cyanide (1.7 g, 14.5 mmol) and tetrakis (triphenylphosphine)palladium(0) ($Pd(PPh_3)_4$, 1.5 g, 1.3 mmol). The reaction mixture was heated, under an argon atmosphere, for 1 hour at 80° C. After cooling the mixture was diluted with ethyl acetate. The resulting organic solution was washed with water (3×), saturated brine, dried over anhydrous sodium sulfate, filtered and concentrated in vacuo. Silica gel chromatography using a gradient of hexane to 10% ethyl acetate in hexane afforded 1.9 g (61%) of methyl 3-bromo-5-cyanobenzoate.

Hydrolysis of the methyl ester (1.9 g, 8.0 mmol) in methanol (20 mL) and 1M sodium hydroxide (8.0 mL, 8.0 mmol), afforded, after standard work up 1.6 g (88%) of 3-bromo-5-cyanobenzoic acid.

3-Methoxycarbonyl-5-iodobenzoic Acid

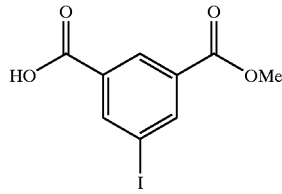

In a similar fashion, hydrolysis of dimethyl-5-iodoisophthlate (4.5 g, 14.058 mmol) in methanol (60 mL) with 1M NAOH (12.6 mL, 12.6 mmol) afforded, after standard work up 3.43 g (80%) of 3-methoxycarbonyl-5-iodobenzoic acid.

3-Cyano-5-iodobenzoic Acid

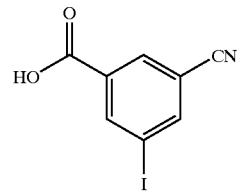

A solution of 3-methoxycarbonyl-5-iodobenzoic acid (3 g, 10 mmol) in thionyl chloride (2 mL) was heated for 2 hours at 60° C. The reaction mixture was cooled and concentrated in vacuo. The intermediate acid chloride was then diluted with tetrahydrofuran (10 mL) and cooled to 0° C. The mixture was then treated with a solution of 2M ammonia (20 mL, 40 mmol, methanol) and the reaction stirred for 1 hour at 0° C. The mixture was then filtered and the solvent removed in vacuo. Recrystallization from methanol afforded 2.5 g (82%) of 3-methoxycarbonyl-5-iodobenzamide, as a white solid.

A mixture of 3-methoxycarbonyl-5-iodobenzamide (2.5 g, 8.2 mmol) in thionyl chloride (2 mL) was heated for 2 hours at 90° C. The reaction mixture was cooled and concentrated in vacuo. Silica gel chromatography afforded 670 mg (29%) of methyl-3-cyano-5-iodobenzoate, as a white solid.

A solution of methyl-3-cyano-5-iodobenzoate (640 mg, 2.3 mmol) in tetrahydrofuran (8 mL) was treated with 0.5M LiOH (5.5 mL, 2.75 mmol) and methanol. The reaction mixture was heated at reflux for 1 hour. The solvent was concentrated in vacuo and the mixture treated with 1N HCl. The resulting white precipitate was filtered and the filtrate was extracted with dichloromethane. The residue and the extracted filtrate were combined and concentrated in vacuo to afford 590 mg (94%) of 3-cyano-5-iodobenzoic acid, as a white solid.

5-fluoro-3-(thiomethyl)benzoic Acid

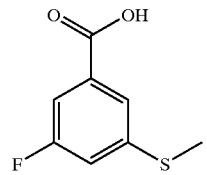

1-Bromo-3,5-difluorobenzene (1.00 g, 5.18 mmol) was dissolved in anhydrous DMF (10 mL). The solution was chilled in an ice bath, and NaSMe (0.36 g, 5.18 mmol) was added. After 30 minutes the reaction mixture was poured into water (100 mL) and extracted with hexanes. The organic phase was washed with water and brine, dried ($MgSO_4$), filtered, and concentrated to provide the title compound as a colourless oil. The crude product was used directly in the next step. Using the standard cyanation procedure, 5-cyano-3-fluoro-1-(thiomethyl)benzene was prepared as a yellow oil. The crude product was used directly in the next step. Using the standard saponification procedure, the title compound was prepared in 0.60 g yield (63% over 3 steps) as a colourless solid.

3-Fluoro-5-(1H-imidazol-1-yl)benzoic Acid

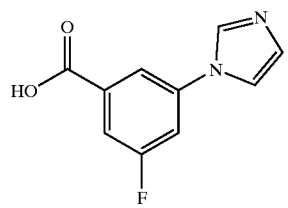

1-Bromo-3,5-difluorobenzene (1.00 g, 5.18 mmol) was dissolved in anhydrous DMF (10 mL). The solution was chilled in an ice bath. Imidazole (0.36 g, 5.18 mmol) and $K_2CO_3$ (0.72 g, 5.18 mmol) were added. The reaction mixture was stirred at room temperature for 16 hours, and at 80° C. for 24 hours. The reaction mixture was poured into water (100 mL) and extracted with EtOAc. The organic phase was washed with brine, dried ($MgSO_4$), filtered, and concentrated. The intermediate 3-Fluoro-5-Bromo-(1H-imidazol-1-yl)-benzene was used directly in the next step. Using the standard cyanation procedure, 3-Fluoro-5-cyano-(1H-imidazol-1-yl)-benzene was prepared as a colourless solid. The crude product was used directly in the next step. Using the standard saponification procedure, the title compound was prepared as a colourless solid. The crude product was used directly in the next step.

3-Iodo-5-Trifluoromethylbenzoic Acid

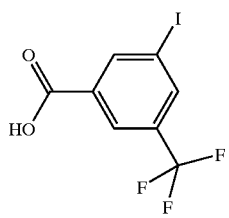

The title product was prepared according to the literature procedure (Fujiki, Kanji; Kashiwagi, Mitsuyoshi; Miyamoto, Hideyuki; Sonoda, Akinari; Ichikawa, Junji; et al *J. Fluorine Chem.* 1992, 57, 307–321) from 3,5-bis (trifluoromethyl)benzene (7.3 mL, 47 mmol) and iodine (11.95 g, 47 mmol) in 30% oleum (30 mL) at 55 degrees for 15h. Quenching with ice was followed by extraction of the crude product into ether, sequential washing of the aqueous layer with sodium sulfite (1M) and water. Sodium hydroxide (!N, ~150 mL) was added to the crude ether solution until pH basic, the layers were separated and the aqueous layer was then acidified using HCl (12N, ~10 mL, pH acidic). Extraction into ether followed by drying over magnesium sulfate yielded the crude acid (4.3 g, 29%). The material was insufficiently pure for use, so the product was esterified using acetyl chloride in methanol, purified using flash chromatography (silica gel, 20% dichloromethane in hexane) and hydrolyzed with sodium hydroxide in methanol yielding 2.95 g (69%) of pure 3-iodo-5-Trifluoromethylbenzoic acid.

3-Allyloxy-5-cyanobenzoic Acid

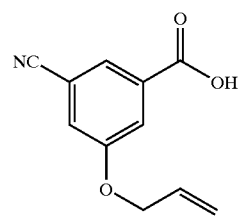

A suspension of 3-allyloxy-5-(methoxycarbonyl)benzoic acid (5.5 mg, 23 mmol) in thionyl chloride (30 mL) was heated at reflux for 2 hours. The excess thionyl chloride was then removed in vacuo and the intermediate acid chloride dissolved in dichloromethane (25 mL). After cooling to 0° C. the solution was treated with 0.5 M ammonia in 1,4-dioxane (100 mL) and then allowed to warm to room temperature. After 2 hours of stirring the solvent was removed in vacuo and the residue was titurated with water. The precipitate was collected, washed with water, and dried in vacuo to afford the 5.0 g (92%) of methyl 3-(allyloxy)-(5-aminocarbonyl)benzoate as a white solid.

A suspension of methyl 3-(allyloxy)-(5-aminocarbonyl) benzoate (5.0 g, 21 mmol) in a dichloromethane (70 mL) at 0° C. was treated with pyridine (3.5 mL, 43 mmol) and then trifluoroacetic anhydride drop-wise (3.6 mL, 25 mmol). The reaction was stirred at 0° C. for 20 minutes and then stirred overnight at ambient temperature. The reaction mixture was washed with water and saturated brine, dried over anhydrous sodium sulfate, filtered and concentrated. Silica gel chromatography using a 10% ethyl acetate/hexanes afforded 3.8 g (81%) of methyl 3-(allyloxy)-5-cyanobenzoate as a white solid.

A solution of methyl 3-(allyloxy)-5-cyanobenzoate (1.5 g, 6.9 mmol) in methanol-tetrahydrofuran (1:2, 30 mL) was treated with 0.5 N lithium hydroxide (17 mL, 8.3 mmol). The reaction was stirred at 70° C. for 30 minutes and then the solvent was removed in vacuo. The residue was dissolved in a small amount of water and then acidified (pH~4) by the addition of 2N hydrogen chloride. The precipitate was collected and dried to afford 1.0 g (74%) of 3-allyloxy-5-cyanobenzoic acid as a white solid.

3-Cyano-5-propoxybenzoic Acid

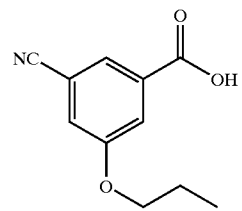

A suspension of 3-allyloxy-5-(methoxycarbonyl)benzoic acid (5.5 mg, 23 mmol) in thionyl chloride (30 mL) was heated at reflux for 2 hours. The excess thionyl chloride was then removed in vacuo and the intermediate acid chloride dissolved in dichloromethane (25 mL). After cooling to 0° C. the solution was treated with 0.5 M ammonia in 1,4-dioxane (100 mL) and then allowed to warm to room temperature. After 2 hours of stirring the solvent was removed in vacuo and the residue was titurated with water. The precipitate was collected, washed with water, and dried in vacuo to afford the 5.0 g (92%) of methyl 3-(allyloxy)-(5-aminocarbonyl)benzoate as a white solid.

Methanol (20 mL) and dichloromethane (20 mL) were added to round bottom flask that contained methyl 3-(allyloxy)-(5-aminocarbonyl)benzoate (2.0 g, 8.5 mmol) and palladium(10 wt. % on activated carbon, 200 mg) under argon. The flask was evacuated using a water aspirator and then filled with hydrogen from a balloon. The balloon filled was hydrogen was attached to the flask as the reaction stirred for 2 hours. The palladium on carbon was remove by filtration through celite. The solvent was removed using a roto-evaporator and then the sample was dried under vacuum to afford 2.0 (97%) of methyl 3-(aminocarbonyl)-5-propoxybenzoate as a white solid.

A suspension of methyl 3-(aminocarbonyl)-5-propoxybenzoate (2.0 g, 8.2 mmol) in a dichloromethane (25 mL) at 0° C. was treated with pyridine (1.3 mL, 17 mmol) and then trifluoroacetic anhydride dropwise (1.4 mL, 9.9 mmol). The reaction was stirred at 0° C. for 20 minutes and then stirred overnight at ambient temperature. The reaction mixture was washed with water and saturated brine, dried over anhydrous sodium sulfate, filtered and concentrated. Silica gel chromatography using a 40% dichloromethane/hexanes afforded 1.5 g (84%) of methyl 3-cyano-5-propoxybenzoate as a white solid.

A solution of methyl 3-cyano-5-propoxybenzoate (1.5 g, 6.8 mmol) in methanol-tetrahydrofuran (1:2, 30 mL) was treated with 0.5 M lithium hydroxide (16 mL, 8.2 mmol). The reaction was stirred at 70° C. for 30 minutes and then the solvent was removed in vacuo. The residue was dissolved in a small amount of water and then acidified (pH~4) by the addition of 2N hydrogen chloride. The precipitate was collected and dried to afford 1.2 g (86%) of 3-cyano-5-propoxybenzoic acid.

3-Cyano-5-nitrobenzoic Acid

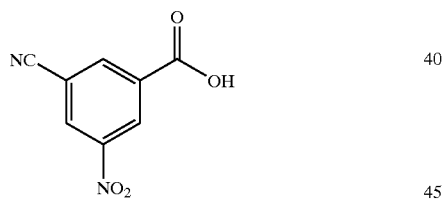

Using the same procedure as for 3-allyloxy-5-cyanobenzoic acid, 3-cyano-5-nitrobenzoic acid (2.0 g, 10.7 mmol) was prepared from mono-methyl 5-nitroisophthalate (5.0 g, 22 mmol).

3-Cyano-5-dimethylaminobenzoic Acid

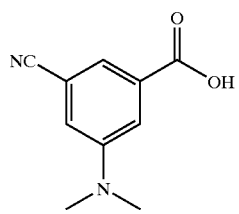

Methyl 3-cyano-2-nitrobenzoate (6.0g, 29 mmol) and tin(II) chloride dihydrate (26 g, 12 mmol) in methanol (100 mL) were heated at reflux for 3 hours. The reaction mixture was transferred into a 1 L Erlenmeyer flask equipped with a stirring bar and containing ice. While stirring the reaction mixture, 1N sodium hydroxide was added until pH~4–5. At this point solid sodium bicarbonate was added until pH~8. The mixture was transferred to a separatory funnel and extracted with ethyl acetate. The organic layer was washed with water and saturated brine, dried over anhydrous sodium sulfate, filtered and concentrated. Silica gel chromatography using 30% ethyl acetate/hexanes afforded 2.4 g (47%) of methyl 3-amino-5-cyanobenzoate as a light brown solid.

Formaldehyde, 37 wt. % solution in water, (4.3 mL, 57 mmol), solid sodium cyanoborohydride (752 mg, 11 mmol), and then acetic acid (909 µL, 16 mmol) were added to methyl 3-amino-5-cyanobenzoate (500 mg, 2.8 mmol) in acetonitrile (10 mL). After stirring at ambient temperature for 5 hours, the reaction mixture was transferred to a separatory funnel and then ethyl acetate was added. The organic layer was washed with water and saturated brine, dried over anhydrous sodium sulfate, filtered, and concentrated. Silica gel chromatography using 15% ethyl acetate/hexanes afforded 390 mg (55%) methyl-3-cyano-5-dimethylaminobenzoate.

A solution of methyl-3-cyano-5-dimethylaminobenzoate (318 mg, 1.6 mmol) in tetrahydrofuran (5 mL) was treated with 0.5 N lithium hydroxide (3.7 mL, 1.9 mmol). The reaction was stirred at 70° C. for 30 minutes and then the solvent was removed in vacuo. The residue was dissolved in a small amount of water and then acidified by the dropwise addition of 2 N hydrogen chloride until a white precipitate no longer formed. Following extraction of the aqueous layer with diethyl ether, the organic layer was then washed with water and saturated brine, dried over anhydrous sodium sulfate, filtered, and concentrated to afford 308 mg (quantitative) of 3-cyano-5-dimethylaminobenzoic acid.

3-cyano-5-(2-methoxyethoxy)benzoic Acid

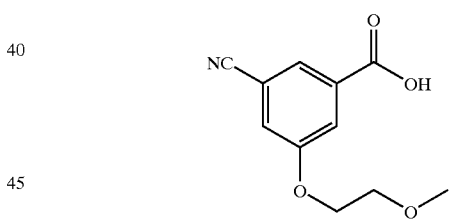

A mixture of methyl 3-allyloxy-5-cyanobenzoate (1.5 g, 6.9 mmol) and tetrabutylammonium iodide (2.8 g, 7.6 mmol) in dichloromethane (38 mL) at −78° C., under argon, was treated with a solution of 1M boron trichloride in dichloromethane (24 mL, 24 mmol). After 5 minutes at −78° C., the reaction mixture was stirred at ambient temperature for 1 hour. The reaction was then quenched with ice water and stirred for an additional 30 minutes. The organic layer was washed with saturated sodium bicarbonate, dried over anhydrous sodium sulfate, filtered and concentrated. Silica gel chromatography using a gradient of 20–30% ethyl acetate/hexanes afforded 811 mg (67%) of methyl 3-cyano-5-hydroxybenzoate as a light yellow solid.

A mixture of methyl 3-cyano-5-hydroxybenzoate (302 mg, 1.7 mmol), potassium carbonate (471 mg, 3.4 mmol) and 2-chloroethyl methyl ether (309 µL mg, 3.4 mmol) in N,N-dimethylformamide (4 mL) was heated in a sealed vial at 140° C. for 15 minutes. The reaction was cooled, diluted with ethyl acetate, washed with water and saturated brine, filtered and concentrated. Filtration through silica gel using dichloromethane afforded 375 mg (93%) of methyl 3-cyano-5-(2-methoxyethoxy) benzoate.

A solution of methyl 3-cyano-5-(2-methoxyethoxy) benzoate (375 mg, 1.6 mmol) in tetrahydrofuran (4 mL) was treated with 0.5 N lithium hydroxide (3.8 mL, 1.9 mmol). The reaction was stirred at 70° C. for 30 minutes and then the solvent was removed in vacuo. The residue was dissolved in a small amount of water and then acidified with 2 N hydrogen chloride until pH~2. Following extraction of the aqueous layer with ethyl acetate, the organic layer washed with water and saturated brine, dried over anhydrous sodium sulfate, filtered, and concentrated to afford 343 mg (97%) of 3-cyano-5-(2-methoxyethoxy)benzoic acid.

3-cyano-5-(1H-imidazol-1-yl-methyl)benzoic Acid

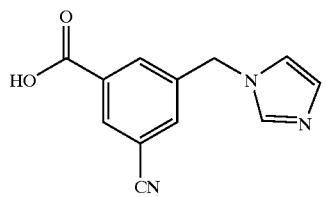

A mixture of methyl 3-(bromomethyl)-5-iodobenzoate (500 mg, 1.4 mmol), potassium carbonate (388 mg, 2.8 mmol), and imidazole (96 mg, 1.4 mmol) in N,N-dimethylformamide (4 mL) was heated at 70° C. for 3 hours. After cooling, the reaction mixture was diluted with water and then extracted with dichloromethane. The organic layer was washed with water and saturated brine, dried over anhydrous sodium sulfate, filtered, and concentrated. Silica gel chromatography using 100% ethyl acetate afforded 242 mg (51%) of methyl 3-(imidazol-1-ylmethyl)-5-iodobenzoate as a white solid.

After bubbling argon into a solution of methyl 3-(imidazol-1-ylmethyl)-5-iodobenzoate (242 mg, 0.70 mmol) in N,N-dimethylformamide (2 mL) for 5 minutes, zinc cyanide (90 mg, 0.77 mmol) and tetrakis(triphenylphosphine)palladium(0) (80 mg, 0.070 mmol) were added. The reaction mixture was heated at 80° C. for 30 minutes under argon. Following cooling, the reaction mixture was diluted with ethyl acetate and then the precipitate that formed was removed by filtration. The filtrate was washed with water and saturated brine, dried over anhydrous sodium sulfate, filtered, and concentrated. The residue was triturated with 20% diethyl ether/hexanes, filtered, and dried in vacuo to afford 150 mg (89%) of 3-cyano-5-(1H-imidazol-1-yl-methyl)benzoate as a white solid.

A solution of 3-cyano-5-(1H-imidazol-1-yl-methyl)benzoate (150 mg, 0.62 mmol) in tetrahydrofuran (2 mL) was treated with 0.5 N lithium hydroxide (1.5 mL, 0.75 mmol). The reaction was stirred at 70° C. for 10 minutes and then the solvent was removed in vacuo. The residue was dissolved in a small amount of water and then acidified (pH~4) by the addition of 2N hydrogen chloride. The precipitate was collected and dried to afford 140 mg (quantitative) of 3-cyano-5-(1H-imidazol-1-yl-methyl) benzoic acid.

3-cyano-5-(methoxymethyl)benzoic Acid

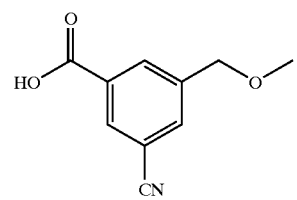

A mixture of methyl 3-(bromomethyl)-5-iodobenzoate (400 mg, 1.1 mmol) and potassium carbonate (311 mg, 2.3 mmol) in methanol/tetrahydrofuran (5 mL/5 mL) was heated at 55° C. for 1 hour. After cooling, the reaction mixture was diluted with water and then extracted with ethyl acetate. The organic layer was washed with water and saturated brine, dried over anhydrous sodium sulfate, filtered, and concentrated. After drying in vacuo, 325 mg (94%) of methyl 3-(methoxymethyl)-5-iodobenzoate was isolated as a white solid.

After bubbling argon into a solution of methyl 3-(methoxymethyl)-5-iodobenzoate (316 mg, 1.03 mmol) in N,N-dimethylformamide (3 mL) for 5 minutes, zinc cyanide (133 mg, 1.13 mmol) and tetrakis(triphenylphosphine) palladium(0) (119 mg, 0.010 mmol) were added. The reaction mixture was heated at 80° C. for 15 minutes under argon. Following cooling, the reaction mixture was diluted with ethyl acetate and then the precipitate that formed was removed by filtration. The filtrate was washed with water and saturated brine, dried over anhydrous sodium sulfate, filtered, and concentrated. Silica gel chromatography using 10–30% ethyl acetate/hexanes afforded 184 mg (86%) of methyl 3-cyano-5-(methoxymethyl)benzoate as a colorless oil.

A solution of methyl 3-cyano-5-(methoxymethyl) benzoate (184 mg, 0.75 mmol) in tetrahydrofuran (2.1 mL) was treated with 0.5 N lithium hydroxide (1.8 mL, 0.90 mmol). The reaction was stirred at 70° C. for 30 minutes and then after cooling the solvent was removed in vacuo. The residue was dissolved in a small amount of water and then acidified with 2 N hydrogen chloride until pH~2–3. Following extraction of the aqueous layer with ethyl acetate, the organic layer washed with water and saturated brine, dried over anhydrous sodium sulfate, filtered, and concentrated to afford 145 mg (quantitative) of 3-cyano-5-(methoxymethyl) benzoic acid.

3-cyano-5-ethoxybenzoic Acid

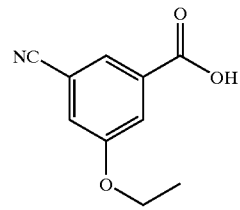

A solution of methyl 3-cyano-5-hydroxybenzoate (270 mg, 1.5 mmol) and potassium carbonate (482 mg, 3.4 mmol) in acetone (5.5 mL) was prepared. To this, ethyl iodide (272 µL, 3.4 mmol) was added and the reaction was heated at 52° C. for 2.5 hours. The reaction mixture was concentrated, re-dissolved in ethyl acetate and washed with water and saturated brine. The organic solvent layer was collected, dried over anhydrous sodium sulphate, filtered, and concentrated. 321 mg (99%) of methyl 3-cyano-5-ethoxybenzoate was isolated as a light brown solid.

Methyl 3-cyano-5-ethoxybenzoate (312 mg, 1.5 mmol) was hydrolyzed as previously described to afford 290 mg (quantitative) of 3-cyano-5-ethoxybenzoic acid as an off-white solid.

3-cyano-5-propoxybenzoic Acid

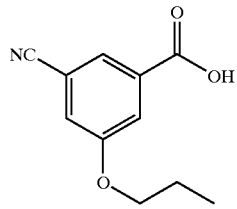

A solution of methyl 3-cyano-5-hydroxybenzoate (200 mg, 1.3 mmol) and potassium carbonate (357 mg, 2.6 mmol) in acetone (4.0 mL) was prepared. To this, propyl iodide (245 μL, 2.5 mmol) was added and the reaction was heated at 50° C. for 5 hours. The reaction mixture was concentrated, re-dissolved in ethyl acetate and washed with water and saturated brine. The organic solvent layer was collected, dried over anhydrous sodium sulphate, filtered, and concentrated. 222 mg (90%) of methyl 3-cyano-5-propoxybenzoate was isolated as a light brown solid.

Methyl 3-cyano-5-propoxybenzoate (222 mg, 1.0 mmol) was hydrolyzed as previously described to afford 169 mg (80%) of 3-cyano-5-propoxybenzoic acid as an off-white solid.

3-cyano-5-hexyloxybenzoic Acid

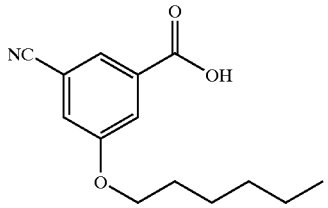

A solution of methyl 3-cyano-5-hydroxybenzoate (170 mg, 0.95 mmol) and potassium carbonate (304 mg, 2.2 mmol) in acetone (4.0 mL) was prepared. To this, 1-bromohexane (300 μL, 2.1 mmol) was added and the reaction was heated at 50° C. overnight. The reaction mixture was concentrated, re-dissolved in ethyl acetate and washed with water and saturated brine. The organic solvent layer was collected, dried over anhydrous sodium sulphate, filtered, and concentrated. Trituration with hexanes afforded 250 mg (quantitative) of methyl 3-cyano-5-hexyloxybenzoate as a light brown solid.

Methyl 3-cyano-5-ethoxybenzoate (250 mg, 0.95 mmol) was hydrolyzed as previously described to afford 247 mg (quantitative) of 3-cyano-5-hexyloxybenzoic acid as an off-white solid.

4-Amino-3-bromo-5-trifluoromethoxybenzoic Acid

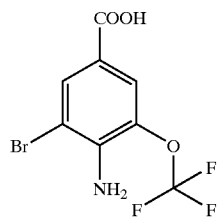

To a solution of 4-amino-3-trifluoromethoxybenzoic acid (5 g, 22.6 mmoles) in acetic acid (50 mL), bromine(3.98 g, 24.9 mmoles) in acetic acid(10 mL) was added dropwise at room temperature. After the reaction mixture was kept stirring for one hour, water was added into the mixture. The solid was filtered and washed with water to give 4-amino-3-bromo-5-trifluoromethoxybenzoic acid (3.9 g, 54.9%).

3-Bromo-5-trifluoromethoxybenzoic Acid

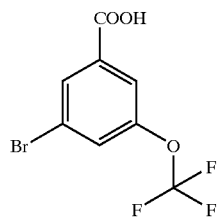

4-Amino-3-bromo-5-trifluoromethoxybenzoic acid (1.5 g, 5 mmoles) was mixed with ethanol (15 mL) at 0° C. and then concentrated sulfuric acid (2.26 g, 10.2 mmoles) wad added. The sodium nitrite (0.38 g, 5.5 mmoles) water solution (1.2 mL) was added dropwise at 0° C. for 1 hour. After the reaction mixture was warmed to room temperature and then heated to reflux for 45 minutes, water was added. The mixture was extracted with dichloromethane. The dichloromethane layer was dried and concentrated. The residue was dissolved in 1M sodium hydroxide and extracted with ether. The aqueous solution was acidified with 2M HCl to pH=2 to give 3-bromo-5-trifluoromethoxybenzoic acid (1.08 g, 75.5%).

3-Cyano-5-trifluoromethoxybenzoic Acid

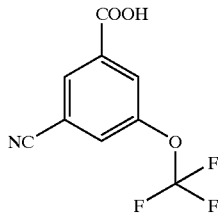

To an ether solution of 3-bromo-5-trifluoromethoxybenzoic acid (1.08 g, 3.79 mmloes), tirmethylsilylmethyl azide was added in and stirred at room temperature for 10 minutes. The reaction was quenched with methanol and passed column with 2% ethyl acetate in hexanes to give colorless oil (0.84 g). This colorless oil was mixed with zinc cyanide (0.33 g, 2.8 mmoles) and tetrakis (triphenylphosphine)palladium(0) (Pd(PPh$_3$)$_4$, 467 mg, 0.404 mmol) in N,N-dimethylformamide(10 mL) under argon at 85° C. overnight. The reaction mixture was diluted with dichloromethane and washed with water twice. The dichloromethane layer was dried and concentrated. The residue was mixed with 1M sodium hydroxide (8 mL) and methanol (4 mL) and stirred at room temperature for 2 hours. The mixture was acidified with 1M HCl to pH=1~2 and extracted with ethyl acetate. The ethyl acetate layer was washed with Brine and concentrated. The residue was passed column with 2% ethyl acetate in hexanes to give 3-cyano-5-trifluoromethoxybenzoic acid, which contained 3-[imino(methoxy)methyl]-5-trifluoromethoxybenzoic acid (3:1, 145 mg, 16.6%)

3-Fluoro-5-(3-pyridyl)benzoic Acid

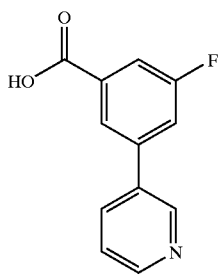

A solution of 3-Bromo-5-fluorobenzoic acid (2.00 g, 9.13 mmol) in thionyl chloride (16 ml) and dimethylformamide (0.4 ml) was stirred at 80° C. for 1 h. The reaction mixture was concentrated in-vacuo and the residue was dissolved in methanol (15 ml) and left stirring at room temperature overnight. The reaction mixture was concentrated in-vacuo, and the residue was dissolved in ethyl acetate (50 ml). Organic phase was sequentially washed with water (50 ml), saturated sodium bicarbonate (50 ml, aqueous), water (50 ml) and brine (50 ml), dried (sodium sulfate), filtered and concentrated in-vacuo to provide the title compound (1.97 g, 92%) as yellow oil.

To the solution of Methyl-3-bromo-5-fluorobenzoate (1.97 g, 8.44 mmol) in toluene (40 ml) added Pyridine-3-boronic acid-1,3-propanediol ester (1.79 g, 7.63 mmol), potassium carbonate (11.66 g, 84.4 mmol) and tetrakis (triphenylphoshine)palladium (0) (0.49, 0.42 mmol), sequentially. The resulting brownish yellow reaction mixture was heated at 120° C. under argon overnight. The reaction mixture was cooled to room temperature, filtered through a pad of celite and concentrated in-vacuo. The residue was purified on silica gel using 1% methanol in dichloromethane to isolate the title compound (0.92 g, 47%) as a yellow solid.

In a 100 ml round bottom flask equipped with stir bar added Methyl-3-fluoro-5-(3-pyridyl)benzoate (0.92 g, 3.93 mmol), methanol (10 ml) and sodium hydroxide (5.89 ml, 5.89 mmol, 1N aqueous). Stirred the resulting mixture at 50° C. for 2 h. The reaction mixture was cooled to room temperature, concentrated in-vacuo and the residue was dissolved in methanol (20 ml). To this mixture added hydrochloric acid (1N diethyl ether) dropwise and stirred at room temperature for 10 min. The reaction mixture was concentrated in-vacuo and the residue was triturated with diethyl ether to provide the crude hydrochloride salt of title compound (1.00 g) as an off white solid.

3-Bromo-5-(3-pyridyl)benzoic Acid

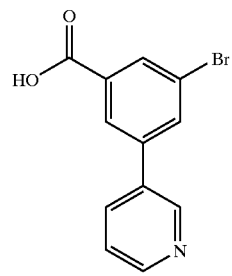

A solution of 3-Bromo-5-iodobenzoic acid (5.00 g, 15.3 mmol) in methanol (30 ml) and hydrochloric acid (15.3 ml, 15.3 mmol, 1N diethyl ether) was stirred at room temperature for 48 h. The reaction mixture was concentrated in-vacuo and the residue was diluted with dichloromethane (100 ml). The organic phase was sequentially washed with sodium hydroxide (100 ml, 1N aqueous), water (100 ml) and brine (100 ml), dried (sodium sulfate), filtered and concentrated in-vacuo. The crude residue was dissolved in 10% ethyl acetate in hexanes (100 ml) and filtered through a pad of silica gel. Upon concentrating in-vacuo, isolated the methyl ester (4.98 g, 95%) as yellowish white solid.

To the solution of Methyl-3-bromo-5-iodobenzoate (2.00 g, 5.87 mmol) in toluene (50 ml) added Pyridine-3-boronic acid-1,3-propanediol ester (1.24 g, 7.63 mmol), potassium carbonate (8.11 g, 58.7 mmol) and tetrakis (triphenylphoshine)palladium (0) (0.34, 0.29 mmol), sequentially. The resulting brownish yellow reaction mixture was heated at 80° C. under argon for 10 h. The reaction mixture was cooled to room temperature, filtered through a pad of celite and concentrated in-vacuo. The residue was purified on silica gel using 3% methanol in dichloromethane to isolate Methyl-3-bromo-5-(3-pyridyl)benzoate (1.16 g, 67%) as a white solid.

In a 100 ml round bottom flask equipped with stir bar added Methyl-3-bromo-5-(3-pyridyl)benzoate (1.16 g, 3.96 mmol), methanol (15 ml) and sodium hydroxide (5.94 ml, 5.94 mmol, 1N aqueous). Stirred the resulting mixture at 50° C. for 2 h. The reaction mixture was cooled to room temperature, concentrated in-vacuo and the residue was dissolved in methanol (20 ml). To this mixture added hydrochloric acid (1N diethyl ether) dropwise and stirred at room temperature for 10 min. The reaction mixture was concentrated in-vacuo and the residue was triturated with diethyl ether to provide the crude hydrochloride salt of title compound (1.50 g) as a white solid.

3-Fluoro-5-methoxybenzoic Acid

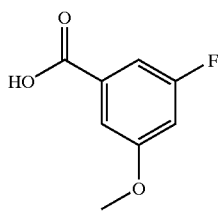

In a 250 ml round bottom flask equipped with stir bar added 3,5-Difluorobenzonitrile (4.2 g, 30.4 mmol), sodium methoxide (10.4 ml, 45.6 mmol, 25% methanol) and dimethylformamide (40 ml). Stirred the resulting reaction mixture at room temperature, overnight. The reaction mixture was concentrated in-vacuo and residue was dissolved in dichloromethane (200 ml). The organic phase was washed sequentially with water (150 ml) and brine (150 ml), dried (sodium sulfate) and concentrated in-vacuo. The crude residue was purified on silica gel using 10% diethyl ether in hexanes to isolate 3-Fluoro-5-methoxybenzonitrile (1.63 g) as a white solid.

In a 50 ml round bottom flask equipped with stir bar and reflux condensor added 3-Fluoro-5-methoxybenzonitrile (0.62 g, 4.10 mmol), methanol (6.2 ml) and sodium hydroxide (6.2 ml, 6N aqueous). Stirred the resulting reaction mixture at 100° C. overnight. Reaction mixture was cooled to room temperature and concentrated in-vacuo. The residue was diluted with dichloromethane (100 ml) and acidified using hydrochloric acid (1N aqueous). The organic phase was separated, sequentially washed with water (100 ml) and brine (100 ml), dried (sodium sulfate) and concentrated in-vacuo, to yield the title compound (0.64g, 91%) as a white solid.

3-Cyano-5-thiomethylbenzoic Acid

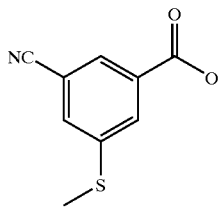

3-bromo-5-thiomethylbenzoic acid (519.6 mg, 2.1 mmol) was dissolved in diethyl ether (20 mL). Diazomethane in diethyl ether was added to the benzoic acid solution until the mixture ceased to bubble and a yellow colour persisted. Glacial acetic acid was added dropwise to this solution until the yellow colour disappeared. The reaction was washed with saturated sodium bicarbonate and brine, dried over anhydrous sodium sulfate and solvent was removed in vacuo to yield 537 mg (98%) of 3-bromo-5-thiomethylester as a colourless oil. 3-bromo-5-thiomethylester (536 mg, 2.05 mmol) was dissolved in anhydrous N,N-dimethylformamide (5 mL) in an argon atmosphere. Zinc cyanide (42 mg, 0.36 mmol) and tetrakis (triphenylphosphine) palladium(0) (41 mg, 0.356 mmol) was added to the reaction mixture, which was stirred at 80° C. for 10 hours. After cooling to room temperature, the reaction was diluted with water and extracted with ethyl acetate. The organic extracts were washed with brine, dried over anhydrous sodium sulfate and the solvent was removed in vacuo. The compound was purified by column chromatography on silica to yield 356 mg (85%) of 3-cyano-5-thiomethylester, which was a white solid.

3-cyano-5-thiomethylester (360 mg, 1.74 mol) was dissolved in anhydrous tetrahydrofuran (22 mL) and 21.6 mL of aqueous lithium hydroxide (0.5 M) and 11 mL of methanol was added. The reaction was refluxed for 45 minutes. The reaction was cooled and the solvent was removed in vacuo. The mixture was diluted with water and washed with ethyl acetate. The aqueous layer was then acidified to pH 1 with HCl (1M) and extracted with ethyl acetate. The organic extractions were combined and dried over anhydrous sodium sulfate and solvent was removed in vacuo to give 330 mg (98%) of 3-cyano-5-thiomethylbenzoic acid as a white solid.

5-Fluoro-3-thiomethylbenzoic Acid

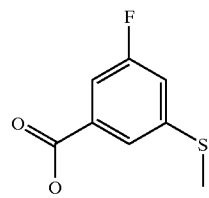

A solution of 3,5-difluorbromobenzene (1.0 g, 5.18 mmol) in N,N-dimethylformamide (15 mL) was cooled to 0° C. and sodiumthiomethoxide (363 mg, 5.18 mmol) was added. The reaction stirred for 30 minutes before the mixture was diluted with water and extracted with hexanes. The organic extracts were washed with brine and dried over anhydrous sodium sulphate. Solvent was removed in vacuo and the product was eluted through an SPE tube (10 g) with hexanes to yield 618 mg (54%) of a colourless oil.

The 5-Fluoro-3-thiomethylbromobenzene (618 mg, 2.80 mmol) was dissolved in N,N-dimethylformamide (6 mL) and zinc cyanide (329 mg, 2.80 mmol) and tetrakis (triphenylphosphine)palladium (0) (324 mg, 0.28 mmol) were added to the solution. The reaction was stirred at 80° C. for 12 hours. The reaction mixture was cooled to R.T., diluted with water and extracted with ethyl acetate, washed with brine, dried over anhydrous sodium sulphate and the solvent was removed in vacuo. Silica gel chromatography using 5% ethyl acetate in hexanes afforded 430 mg (92%) of a white solid, 5-Fluoro-3-cyanothiomethylbenzene (430 mg, 2.57 mmol) that was dissolved in water (6.0 ml) and aqueous sodium hydroxide (6M, 6.0 mL) and refluxed for 12 hours. The reaction mixture was acidified to pH 3 and extracted with ethyl acetate. The organic extracts were washed with brine, dried over anhydrous sodium sulphate and the solvent was removed in vacuo to yield 470 mg (98%) of the title compound as a white solid.

5-Fluoro-3-thioethylbenzoic Acid

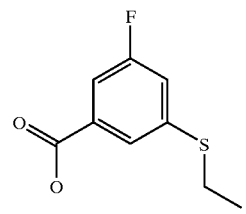

A solution of 3,5-difluorobromobenzene (1.0 g, 5.18 mmol) in N,N-dimethylformamide (15 mL) was cooled to 0° C. and sodiumthioethoxide (436 mg, 5.18 mmol) was added. The reaction stirred for 30 minutes before the mixture was diluted with water and extracted with hexanes. The organic extracts were washed with brine and dried over anhydrous sodium sulphate. Solvent was removed in vacuo and the product was eluted through an SPE tube (10 g) with hexanes to yield 366 mg (30%) of a colourless oil, 5-Fluoro-3-thioethylbromobenzene (365 mg, 1.55 mmol) that was dissolved in N,N-dimethylformamide (5 mL) and zinc cyanide (182 mg, 1.55 mmol) and tetrakis (triphenylphosphine)palladium (0) (179 mg, 0.16 mmol) were added to the solution. The reaction was stirred at 80° C. for 3 hours. The reaction mixture was cooled to R.T., diluted with water and extracted with ethyl acetate, washed with brine, dried over anhydrous sodium sulphate and solvent was removed in vacuo. Silica gel chromatography using 5% ethyl acetate in hexanes afforded 241mg (86%) of a white solid, 5-Fluoro-3-cyanothioethylbenzene (240 mg, 1.32 mmol) that was dissolved in water (3.0 ml) and aqueous sodium hydroxide (6M, 3.0 mL) and refluxed for 12 hours. The reaction mixture was acidified to pH 3 and extracted with ethyl acetate. The organic extracts were washed with brine, dried over anhydrous sodium sulphate and the solvent was removed in vacuo to yield 274 mg (103%) of an off-white solid.

3-Chloro-5-cyanobenzoic Acid

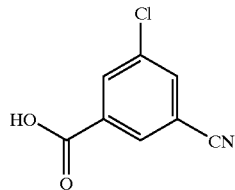

A mixture of methyl 3,5-dichlorobenzoate (14.66 g, 71.5 mmol), zinc cyanide (5.04 g, 42.9 mmol) zinc (dust, 0.21 g, 3.21 mmol), [1,1'Bis(diphenylphosphino)ferrocene] dichloropalladium(II), complex with dichloromethane (1:1) (1.3 g, 1.57 mmol) in N,N-dimethylformamide (70 mL) was heated at reflux for 5 hours. After cooling the reaction was diluted with ethyl acetate and extracted with water and brine. Silica gel chromatography afforded 2.34g (17%) methyl 2-chloro-5-cyanobenzoate.

The intermediate ester was treated with a solution of sodium hydroxide (7.5 mL of 4 N solution, 30 mmol) in methanol (50 mL) and stirred at ambient temperature for 18 hours. The solvent was removed in vacuo and the residue dissolved in ethyl acetate. The organic solution was washed with 5% HCl and brine. Removal of the solvent afforded 1.8 g (83%) of 3-chloro-5-cyanobenzoic acid.

3-Chloro-5-fluorobenzoic Acid

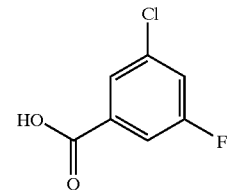

A mixture of 1-bromo-3-chloro-5-fluorobenzene (25.0 g, 120 mmol), zinc cyanide (8.45 g, 72 mmol) zinc (dust, 235 mg, 3.6 mmol), [1,1'Bis(diphenylphosphino)ferrocene] dichloropalladium(II), complex with dichloromethane (1:1) (1.5 g, 1.8 mmol) in N,N-dimethylformamide (70 ml) was heated at reflux for 1 hour. After cooling the reaction was diluted with ethyl acetate and extracted with water and brine. Silica gel chromatography afforded 15.9g (85%) 3-chloro-5-fluorobenzonitrile.

The intermediate nitrile was treated with a solution of sodium hydroxide (100 mL of 10 N solution, 1 mol) in 100 mL water and heated at reflux for 2 hours. After this time the solution was cooled and acidified with concentrated hydrochloric acid. Extraction with dichloromethane and evaporation of the solvent, afforded 15.14g (85%) of 3-chloro-5-fluorobenzoic acid.

3-Fluoro-5-cyanobenzoic Acid

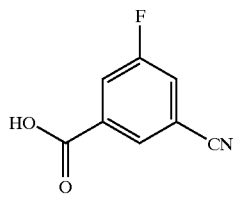

3-Chloro-5-fluorobenzoic acid (13.74g, 78.7 mmol) was treated with 50 ml thionyl chloride and heated at reflux for 2 hours. The excess thionyl chloride was removed in vacuo and the residue treated with 100 ml dry methanol to afford 13.6g (92%) of methyl 3-chloro-5-fluorobenzoate.

A mixture of the methyl 3-chloro-5-fluorobenzoate, zinc cyanide (8.46g, 72.3 mmol) zinc (dust, 235 mg, 3.6 mmol), [1,1'bis(diphenylphosphino)ferrocene] dichloropalladium (II), complex with dichloromethane (1:1) (1.5 g, 1.8 mmol) in N,N-dimethylformamide (70 ml) was heated at reflux for 1 hour. The reaction was cooled to ambient temperature and diluted with ethyl acetate. The organic solution was extracted with water and brine and concentrated in vacuo, to afford crude methyl 3-chloro-5-cyanobenzoate.

The crude methyl 3-chloro-5-cyanobenzoate was treated with a solution of sodium hydroxide (45 ml of 4 N solution, 180 mmol) in methanol (350 mL) at ambient temperature for 4 hours. The solvent was removed in vacuo and the residue dissolved in ethyl acetate. The organic solution was washed with 5% aqueous HCl and brine. Silica gel chromatography afforded 7.0 g (54%) of 3-fluoro-5-cyanobenzoic acid.

Example 3

Synthesis of 3-Chlorobenzhydrazide for Triazole Syntheses

3-Chlorobenzhydrazide

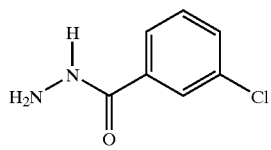

A mixture of 3-chlorobenzoic acid (0.5 g, 3.19 mmol), 1,3-diccyclohexylcarbodiimide (0.72 g, 3.51 mmol), 4-dimethylaminopyridine (0.04 g, 0.32 mmol) in ethanol was stirred at ambient temperature for 1.5 hour. The white solid was filtered off and the filtrate diluted with dichloromethane (100 mL). The organic solution was washed with 1N sodium hydrogen sulfate (100 mL), saturated sodium bicarbonate (100 mL), water (100 mL) and brine (100 mL). The organic phase was dried over anhydrous magnesium sulfate and filtered. The filtrate was concentrated in vacuo. The crude residue was dissolved in ethanol (15 mL) and treated with hydrazine monohydrate (0.46 mL, 9.58 mmol). The resulting clear solution was stirred overnight at ambient temperature. The reaction mixture was then concentrated to dryness in vacuo. Silica gel chromatography of the residue, using 3% methanol in dichloromethane, afforded 0.29 g (53%) of 3-chlorobenzhydrazide as a white solid.

Example 4

3-(2-Pyridyl)-5-(3,5-dichlorophenyl)-1,2,4-oxadiazole

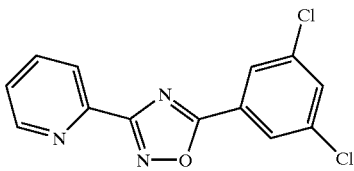

B2

A mixture of 3,5-dichlorobenzoyl chloride (2.1 g, 10 mmol) and pyrid-2-ylamidoxime (1.37 g, 10 mmol) in pyridine (5 mL) was heated in sealed tube at 190° C. for 2 hours. After this time, the reaction mixture was added to ice cold water to precipitate the oxadiazole. The solid was collected by filtration, washed with water and then recrystallized from ethanol to yield 2.1 g (72%) of 3-(2-pyridyl)-5-(3,5-dichlorophenyl)-1,2,4-oxadiazole: mp 162–166° C.; GC/EI-MS gave m/z (rel. int.) 291 ($M^+$, 38), 293 (25), 261 (1), 173 (6), 145 (13), 120 (100), 90 (20), 78 (28), 51 (15).

3-(2-Pyridyl)-5-(3-chlorophenyl)-1,2,4-oxadiazole

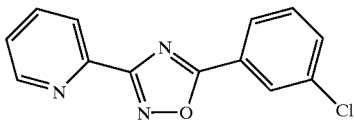

B3

Using the general procedure for the synthesis of 1,2,4-oxadiazoles, 3-chlorobenzoyl chloride (127 μL, 1 mmol) and pyrid-2-ylamidoxime (137 mg, 1 mmol) in pyridine (1 mL) were heated at reflux for 4 hours. Standard work up afforded 156 mg (61%) of 3-(2-pyridyl)-5-(3-chlorophenyl)-1,2,4-oxadiazole: mp 136–140° C.; GC/EI-MS gave m/z (rel. int.) 257 ($M^+$, 64), 259 (21), 227 (3), 120 (100), 111 (22), 90 (24), 78 (32), 75 (26), 51 (20).

3-(2-Pyridyl)-5-(3-methoxyphenyl)-1,2,4-oxadiazole

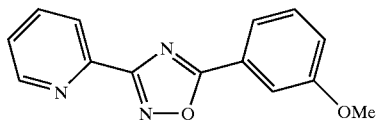

B1

Using the general procedure for the synthesis of 1,2,4-oxadiazoles, 3-anisoyl chloride (151 uL, 1 mmol) and pyrid-2-ylamidoxime (137 mg, 1 mmol) in pyridine (1 mL) were heated at reflux for 4 hours. Standard work up afforded 200 mg (79%) of 3-(2-pyridyl)-5-(3-methoxyphenyl)-1,2,4-oxadiazole: mp 96–99° C.; GC/EI-MS gave m/z (rel. int.) 253 ($M^+$, 100), 223 (3), 179 (3), 135 (74), 133 (90), 92 (27), 78 (29), 77 (32), 64 (23), 63 (23).

3-(2-Pyridyl)-5-(2-chlorophenyl)-1,2,4-oxadiazole

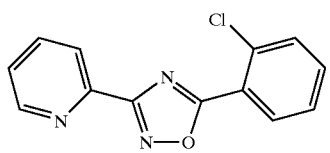

B5

Using the general procedure for the synthesis of 1,2,4-oxadiazoles, 2-chlorobenzoyl chloride (127 μL, 1 mmol) and pyrid-2-ylamidoxime (137 mg, 1 mmol) in pyridine (1 mL) were heated at reflux for 4 hours. Standard work up afforded 157 mg (61%) of 3-(2-pyridyl)-5-(2-chlorophenyl)-1,2,4-oxadiazole: mp 93–94° C.; GC/EI-MS gave m/z (rel. int.) 257 ($M^+$, 76), 259 (26), 227 (4), 139 (11), 120 (100), 111 (21), 90 (27), 78 (35), 75 (29), 51 (21).

3-(2-Pyridyl)-5-[3-(trifluoromethyl)phenyl]-1,2,4-oxadiazole

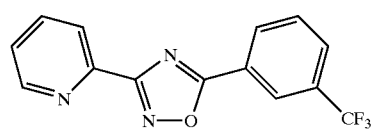

B6

Using the general procedure for the synthesis of 1,2,4-oxadiazoles, 3-(trifluoromethyl)benzoyl chloride (151 μL, 1 mmol) and pyrid-2-ylamidoxime (137 mg, 1 mmol) in pyridine (1 mL) were heated at reflux for 16 hours. Standard work up afforded 233 mg (80%) of 3-(2-pyridyl)-5-[3-(trifluoromethyl)phenyl]-1,2,4-oxadiazole: mp 116–118° C.; GC/EI-MS gave m/z (rel. int.) 291 ($M^+$, 81), 272 (7), 173 (6), 145 (25), 120 (100), 90 (20), 78 (23), 51 (11).

3-(2-Pyridyl)-5-(3-fluorophenyl)-1,2,4-oxadiazole

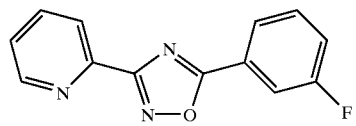

B7

Using the general procedure for the synthesis of 1,2,4-oxadiazoles, 3-fluorobenzoyl chloride (122 μL, 1 mmol) and pyrid-2-ylamidoxime (137 mg, 1 mmol) in pyridine (1 mL) were heated at reflux for 16 hours. Standard work up afforded 176 mg (73%) of 3-(2-pyridyl)-5-(3-fluorophenyl)-1,2,4-oxadiazole: mp 88–98° C.; GC/EI-MS gave m/z (rel. int.) 241 ($M^+$, 95), 211 (5), 120 (100), 107 (13), 95 (30), 90 (21), 78 (27), 75 (19), 51 (15).

3-(2-Pyridyl)-5-(3-methylphenyl)-1,2,4-oxadiazole

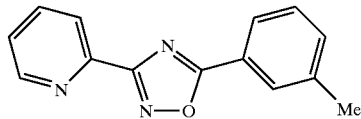

B9

Using the general procedure for the synthesis of 1,2,4-oxadiazoles, 3-toluoyl chloride (264 μL, 2 mmol) and pyrid- 2-ylamidoxime (274 mg, 2 mmol) in pyridine (1 mL) were heated in a sealed tube at 200° C. for 2 hours. Standard work up afforded 387 mg (82%) of 3-(2-pyridyl)-5-(3-toluoyl)-1,2,4-oxadiazole: mp 127–128° C.; GC/EI-MS gave m/z (rel. int.) 237 (M⁺, 100), 222 (2), 207 (8), 120 (68), 117 (24), 91 (29), 90 (29), 78 (32), 65 (26), 51 (23).

3-(2-Pyridyl)-5-(1-naphthyl)-1,2,4-oxadiazole

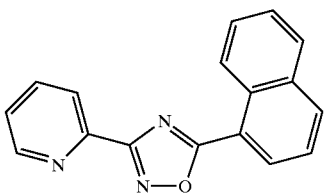

Using the general procedure for the synthesis of 1,2,4-oxadiazoles, 1-naphthoyl chloride (150 μL, 1 mmol) and pyrid-2-ylamidoxime (137 mg, 1 mmol) in pyridine (1 mL) were heated in a sealed tube at 200° C. for 3 hours. Standard work up afforded 50 mg (18%) of 3-(2-pyridyl)-5-(1-naphthyl)-1,2,4-oxadiazole: mp 132–136° C.; GC/EI-MS gave m/z (rel. int.) 273 (M⁺, 75), 195 (5), 169 (88), 153 (100), 139 (12), 127 (66), 126 (29), 105 (23), 78 (14), 51 (14).

3-(2-Pyridyl)-5-[3-(trifluoromethoxy)phenyl]-1,2,4-oxadiazole

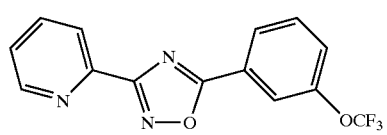

Using the general procedure for the synthesis of 1,2,4-oxadiazoles, 3-(trifluoromethoxy)benzoyl chloride (220 mg, 1 mmol), and pyrid-2-ylamidoxime (137 mg, 1 mmol) in pyridine (1 mL) were heated in a sealed tube at 200° C. for 3 hours. Standard work up afforded 175 mg (57%) of 3-(2-pyridyl)-5-[3-(trifluoromethoxy)phenyl]-1,2,4-oxadiazole: mp 86–88° C.; GC/EI-MS gave m/z (rel. int.) 307 (M⁺, 73), 277 (3), 222 (3), 189 (6), 161 (5), 120 (100), 78 (21), 69 (17), 51 (10).

3-(2-Pyridyl)-5-(2,3-difluorophenyl)-1,2,4-oxadiazole

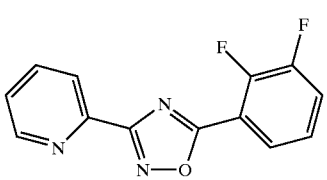

Using the general procedure for the synthesis of 1,2,4-oxadiazoles, 2,3-difluorobenzoyl chloride (124 μL, 1 mmol) and pyrid-2-ylamidoxime (137 mg, 1 mmol) in pyridine (1 mL) were heated at 100° C. for 16 hours. Standard work up afforded 158 mg (61%) of 3-(2-pyridyl) -5-(2,3-difluorophenyl)-1,2,4-oxadiazole: mp 120–121° C.; GC/EI-MS gave m/z (rel. int) 259 (M⁺, 97), 229 (5), 228 (4), 141 (11), 120 (100), 113 (26), 90 (27), 78 (34), 51 (17).

3-(2-Pyridyl)-5-(2,5-difluorophenyl)-1,2,4-oxadiazole

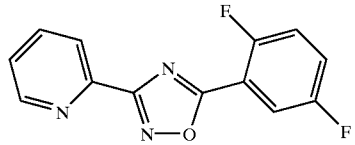

Using the general procedure for the synthesis of 1,2,4-oxadiazoles, 2,5-difluorobenzoyl chloride (124 μL, 1 mmol) and pyrid-2-ylamidoxime (137 mg, 1 mmol) in pyridine (1 mL) were heated at 100° C. for 16 hours. Standard work up afforded 3-(2-pyridyl)-5-(2,5-difluorophenyl)-1,2,4-oxadiazole: mp 120–126° C.; GC/EI-MS gave m/z (rel. int) 259 (M⁺, 91), 229 (5), 228 (4), 141 (13), 120 (100), 113 (25), 90 (23), 78 (27), 51 (14).

3-(2-Pyridyl)-5-(3,5-difluorophenyl)-1,2,4-oxadiazole

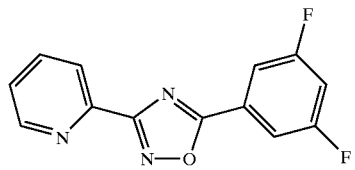

Using the general procedure for the synthesis of 1,2,4-oxadiazoles, 3,5-difluorobenzoyl chloride (1.25 mL, 10 mmol) and pyrid-2-ylamidoxime (1.37 g, 10 mmol) in pyridine (5 mL) were heated in a sealed tube at 200° C. for 4 hours. Standard work up afforded 1.2 g (46%) of 3-(2-pyridyl)-5-(3,5-difluorophenyl)-1,2,4-oxadiazole: mp 115–119° C.; GC/EI-MS gave m/z (rel. int) 259 (M⁺, 100), 229 (4), 228 (5), 141 (9), 125 (13), 113 (30), 90 (19), 78 (27), 63 (23), 51 (15).

3-(2-Pyridyl)-5-(3-cyanophenyl)-1,2,4-oxadiazole

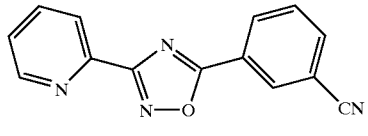

Using the general procedure for the synthesis of 1,2,4-oxadiazoles, 3-cyanobenzoyl chloride (165 mg, 1 mmol) and pyrid-2-ylamidoxime (137 mg, 1 mmol) in pyridine (1 mL) were heated at 100° C. for 72 hours. Standard work up afforded 158 mg (64%) of 3-(2-pyridyl) -5-(3-cyanophenyl)-1,2,4-oxadiazole: mp 148–149° C.; GC/EI-MS gave m/z (rel. int.) 248 (M⁺, 85), 218 (5), 130 (6), 120 (100), 114 (9), 102 (28), 90 (26), 78 (37), 75 (19), 51 (30).

3-(2-Pyridyl)-5-(3,5-dimethoxyphenyl)-1,2,4-oxadiazole

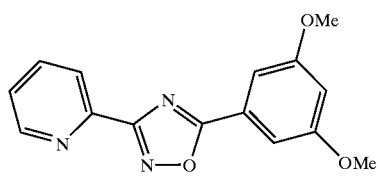

B23

Using the general procedure for the synthesis of 1,2,4-oxadiazoles, 3,5-dimethoxybenzoyl chloride (200 mg, 1 mmol) and pyrid-2-ylamidoxime (137 mg, 1 mmol) in pyridine (1 mL) were heated at 100° C. for 72 hours. Standard work up afforded 210 mg (74%) of 3-(2-pyridyl)-5-(3,5-dimethoxyphenyl)-1,2,4-oxadiazole: mp 145–148° C.; GC/EI-MS gave m/z (rel. int.) 283 ($M^+$, 100), 253 (3), 165 (69), 163 (19), 137 (36), 122 (33), 107 (17), 90 (10), 78 (25), 63 (19), 51 (19).

3-(2-Pyridyl)-5-(2,3-dichlorophenyl)-1,2,4-oxadiazole

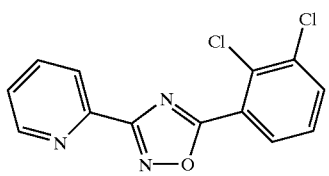

B25

Using the general procedure for the synthesis of 1,2,4-oxadiazoles, 2,3-dichlorobenzoyl chloride (209 mg, 1 mmol) and pyrid-2-ylamidoxime (137 mg, 1 mmol) in pyridine (1 mL) were heated at 100° C. for 48 hours. Standard work up afforded 236 mg (81%) of 3-(2-pyridyl)-5-(2,3-dichlorophenyl)-1,2,4-oxadiazole: mp 128–133° C.; GC/EI-MS gave m/z (rel. int.) 291 ($M^+$, 66), 293 (43), 256 (6), 173 (10), 145 (11), 120 (100), 90 (19), 78 (27), 51 (14).

3-(2-Pyridyl)-5-(3-chloro-5-cyanophenyl)-1,2,4-oxadiazole

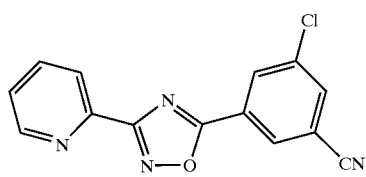

B26

3-Chloro-5-cyanobenzoic acid (0.82 g, 4.97 mmol) was treated with a solution of oxalyl chloride (10 mL of 2.5 M in dichloromethane, 25 mmol) and a catalytic amount of N,N-dimethylformamide. The reaction was stirred at ambient temperature for 2.5 hours. The excess oxalyl chloride was removed in vacuo to afford 3-chloro-5-cyanobenzoyl chloride.

Using the general procedure for the synthesis of 1,2,4-oxadiazoles, the 3-chloro-5-cyanobenzoyl chloride and pyrid-2-ylamidoxime (682 mg, 5 mmol, 1 equivalent) in pyridine (5 mL) were heated in a sealed tube at 175° C. for 4 hours. Standard work up and recrystallization from 2-propanol afforded 250 mg (19%) of 3-(2-pyridyl) -5-(3-chloro-5-cyanophenyl)-1,2,4-oxadiazole: GC/EI-MS gave m/z (rel. int.) 282 ($M^+$, 100), 283 (18), 284 (34), 251 (4), 136 (10), 120 (53), 100 (10), 78 (15), 51 (6).

3-(2-Pyridyl)-5-(3-fluoro-5-cyanophenyl)-1,2,4-oxadiazole

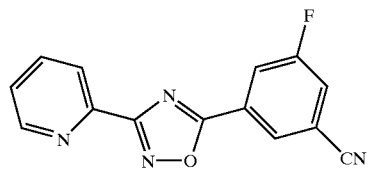

B27

3-Fluoro-5-cyanobenzoic acid (2.5 g, 15.14 mmol) was treated with a solution of oxalyl chloride (30 mL of 2.5 M in dichloromethane, 75 mmol) and a catalytic amount of N,N-dimethylformamide. The reaction was stirred at ambient temperature for 2.5 hours. The excess oxalyl chloride was removed in vacuo to afford 3-fluoro-5-cyanobenzoyl chloride.

Using the general procedure for the synthesis of 1,2,4-oxadiazoles, the 3-fluoro-5-cyanobenzoyl chloride and pyrid-2-ylamidoxime (2.076 g, 15.15 mmol, 1 equivalent) in pyridine (5 mL) were heated in a sealed tube at 175° C. for 4 hours. Standard work up and recrystallization from 2-propanol afforded 1.5 g (37%) of 3-(2-pyridyl)-5-(3-fluoro-5-cyanophenyl)-1,2,4-oxadiazole: GC/EI-MS gave m/z (rel. int.) 266 ($M^+$, 81), 267 (13), 235 (5), 132 (12), 120 (100), 100 (18), 90 (18), 78 (35), 51 (20).

3-(2-Pyridyl)-5-(3-chloro-5-fluorophenyl)-1,2,4-oxadiazole

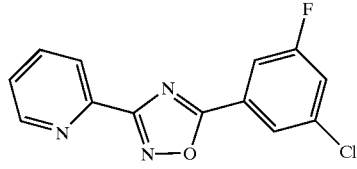

B28

3-Chloro-5-fluorobenzoic acid (400 mg, 2.3 mmol) was treated with a solution of oxalyl chloride (4.6 mL of 2.5 M in dichloromethane, 11.5 mmol) and a catalytic amount of N,N-dimethylformamide. The reaction was stirred at ambient temperature for 2.5 hours. The excess oxalyl chloride was removed in vacuo to afford 3-chloro-5-fluorobenzoyl chloride.

Using the general procedure for the synthesis of 1,2,4-oxadiazoles, the 3-chloro-5-fluorobenzoyl chloride and pyrid-2-ylamidoxime (314 mg, 2.3 mmol, 1 equivalent) in pyridine (5 mL) were heated in a sealed tube at 175° C. for 4 hours. Standard work up and recrystallization from 2-propanol afforded 250 mg (39%) of 3-(2-pyridyl) -5-(3-chloro-5-fluorophenyl)-1,2,4-oxadiazole: GC/EI-MS gave m/z (rel. int.) 275($M^+$, 89), 276 (14), 277 (29), 129 (26), 120 (100), 109 (7), 90 (20), 78 (31), 51 (14).

3-(5-Chloropyrid-2-yl)-5-(3-cyanophenyl)-1,2,4-oxadiazole

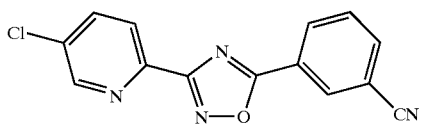

B29

Using the general procedure for the synthesis of 1,2,4-oxadiazoles, 3-cyanobenzoyl chloride (675 mg, 4 mmol) and 5-chloropyrid-2-ylamidoxime (686 mg, 4 mmol) in pyridine (5 mL) were heated in a sealed tube at 175° C. for 4 hours. Standard work up and recrystallization from 2-propanol afforded 357 mg (32%) of 3-(5-chloropyrid-2-yl)-5-(3-cyanophenyl)-1,2,4-oxadiazole: GC/EI-MS gave m/z (rel. int.) 282 ($M^+$, 85), 283 (14), 284 (27), 156 (31), 154 (100), 112 (19), 102 (30), 76 (28), 64 (13).

3-(5-Fluoropyrid-2-yl)-5-(3-cyanophenyl)-1,2,4-oxadiazole

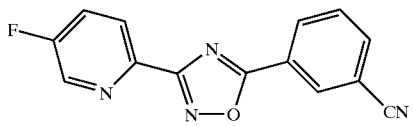

B30

Using the general procedure for the synthesis of 1,2,4-oxadiazoles, 3-cyanobenzoyl chloride (0.534 g, 3.2 mmol) and 5-fluoropyrid-2-ylamidoxime (0.5 g, 3.2 mmol) in pyridine (5 mL) were heated in a sealed tube at 175° C. for 4 hours. Standard work up and recrystallization from 2-propanol afforded 370 mg (43%) of 3-(5-fluoropyrid-2-yl)-5-(3-cyanophenyl)-1,2,4-oxadiazole: GC/EI-MS gave m/z (rel. int.) 266 ($M^+$, 100), 267 (10), 138 (80), 114 (8), 102 (19), 96 (22), 76 (17), 57 (8).

3-(5-Fluoropyrid-2-yl)-5-(3-cyano-5-fluorophenyl)-1,2,4-oxadiazole

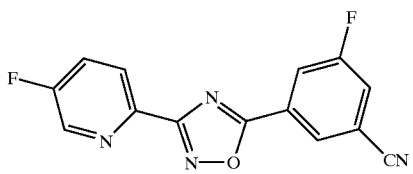

B31

3-Fluoro-5-cyanobenzoic acid (1.0 g, 6 mmol) was treated with a solution of oxalyl chloride (12 mL of 2.5 M in dichloromethane, 30 mmol) and a catalytic amount of N,N-dimethylformamide. The reaction was stirred at ambient temperature for 2.5 hours. The excess oxalyl chloride was removed in vacuo to afford 3-fluoro-5-cyanbenzoyl chloride.

Using the general procedure for the synthesis of 1,2,4-oxadiazoles, the 3-fluoro-5-cyanbenzoyl chloride (1.1 g, 6 mmol) and 5-fluoropyrid-2-ylamidoxime (0.93 g, 6 mmol) in pyridine (5 mL) were heated in a sealed tube at 175° C. for 4 hours. Standard work up and recrystallization from 2-propanol afforded 0.41 g (24%) of 3-(5-fluoropyrid-2-yl)-5-(3-cyano-5-fluorophenyl)-1,2,4-oxadiazole: GC/EI-MS gave m/z (rel. int.) 284 ($M^+$, 100), 285 (16), 253 (2), 138 (99), 120 (23), 108 (16), 96 (25), 82 (15), 57 (11).

3-(3-Fluoropyrid-2-yl)-5-(3-cyanophenyl)-1,2,4-oxadiazole

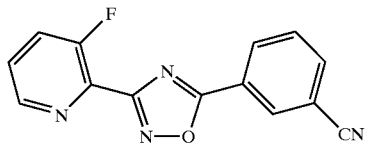

B32

Using the general procedure for the synthesis of 1,2,4-oxadiazoles, 3-cyanobenzoyl chloride (107 mg, 0.64 mmol) and 3-fluoropyrid-2-ylamidoxime (0.1 g, 0.64 mmol) in pyridine (5 mL) were heated in a sealed tube at 175° C. for 4 hours. Standard work up, silica gel chromatography, and recrystallization from 2-propanol, afforded 32 mg (19%) of 3-(3-fluoropyrid-2-yl)-5-(3-cyanophenyl)-1,2,4-oxadiazole: GC/EI-MS gave m/z (rel. int.) 266 ($M^+$, 75), 267 (12), 138 (100), 114 (11), 102 (19), 96 (17), 76 (16), 57 (5), 51 (5).

3-(5-Fluoropyrid-2-yl)-5-(3,5-dimethoxyphenyl)-1,2,4-oxadiazole

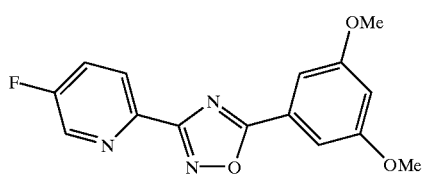

B33

Using the general procedure for the synthesis of 1,2,4-oxadiazoles, 3,5-dimethoxybenzoyl chloride (0.10 g, 0.5 mmol) and 5-fluoropyrid-2-ylamidoxime (78 mg, 0.5 mmol) in pyridine (3 mL) were heated in a sealed tube at 175° C. for 4 hours. Standard work up, silica gel chromatography, and recrystallization from 2-propanol afforded 94 mg (62%) of 3-(5-fluoropyrid-2-yl)-5-(3,5-dimethoxyphenyl)-1,2,4-oxadiazole: GC/EI-MS gave m/z (rel. int.) 301 ($M^+$, 100), 302 (17), 165 (41), 137 (23), 122 (27), 96 (15), 77 (11), 63 (12).

3-(5-Methoxypyrid-2-yl)-5-(3-cyanophenyl)-1,2,4-oxadiazole

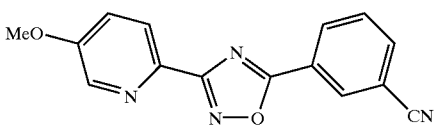

B34

Using the general procedure for the synthesis of 1,2,4-oxadiazoles, 3-cyanobenzoyl chloride (79 mg, 0.47 mmol) and 5-methoxypyrid-2-ylamidoxime (79 mg, 0.47 mmol) in pyridine (2.5 mL) were heated in a sealed tube at 175° C. for 4 hours. Standard work up, silica gel chromatography, and recrystallization from 2-propanol afforded 59 mg (45%) of 3-(5-methoxypyrid-2-yl)-5-(3-cyanophenyl)-1,2,4-oxadiazole: GC/EI-MS gave m/z (rel. int.) 278 ($M^+$, 100), 279 (16), 150 (56), 128 (7), 107 (21), 102 (17), 80 (12), 64 (5).

3-(2-Quinolinyl)-5-(3-cyanophenyl)-1,2,4-oxadiazole

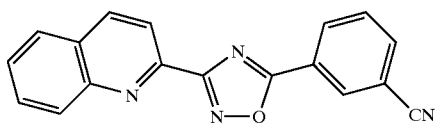

B35

Using the general procedure for the synthesis of 1,2,4-oxadiazoles, 3-cyanobenzoyl chloride (68 mg, 0.41 mmol) and quinol-2-ylamidoxime (75.9 mg, 0.405 mmol) in pyridine (0.5 mL) were heated in a sealed tube at 165° C. for 22 hours. Standard work up, recrystallization from ethanol, and solid phase extraction (SPE) afforded 23.7 mg (20%) of 3-(2-quinolinyl)-5-(3-cyanophenyl)-1,2,4-oxadiazole. $_1$H-NMR (CDCl$_3$), δ (ppm): 8.62 (s, 1H), 8.54 (d, 1H), 8.36 (d, 2H), 8.28 (d, 1H), 7.90 (d, 2H), 7.80 (t, 1H), 7.72 (t, 1H), 7.64 (t, 1H).

3-(3-chloro-5-trifluoromethylpyrid-2-yl)-5-(3-cyanophenyl)-1,2,4-oxadiazole

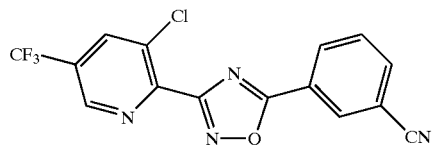

B36

Using the general procedure for the synthesis of 1,2,4-oxadiazoles, 3-cyanobenzoyl chloride (66 mg, 0.40 mmol) and 3-chloro-5-trifluoromethylpyrid-2-ylamidoxime (96.5 mg, 0.403 mmol) in pyridine (0.5 mL) were heated in a sealed tube at 165° C. for 22 hours. Standard work up and solid phase extraction (SPE) afforded 45.9 mg (33%) of 3-(3-chloro-5-trifluoromethylpyrid-2-yl)-5-(3-cyanophenyl)-1,2,4-oxadiazole. $^1$H-NMR (CDCl$_3$), δ (ppm): 8.99 (s, 1H), 8.57 (s, 1H), 8.49 (d, 1H), 8.19 (s, 1H), 7.92 (d, 1H), 7.72 (t, 1H).

3-(2-pyridyl)-5-(5-chloro-2-methoxyphenyl)-1,2,4-oxadiazole

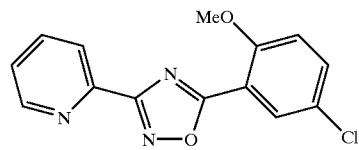

B37

5-Chloro-O-anisic acid (187 mg, 1 mmol) was treated with a solution of oxalyl chloride (1.5 mL of 2 M in dichloromethane, 3 mmol) and a catalytic amount of N,N-dimethylformamide. The reaction was stirred at ambient temperature for 2 hours. The excess oxalyl chloride was removed in vacuo to afford 5-chloro-2-methoxybenzoyl chloride.

Using the general procedure for the synthesis of 1,2,4-oxadiazoles, the 5-chloro-2-methoxybenzoyl chloride and pyrid-2-ylamidoxime (137 mg, 1 mmol) in pyridine (1 mL) were heated at 115° C. for 17 hours. Standard work up, and silica gel chromatography afforded 49 mg (17%) of 3-(2-pyridyl)-5-(5-chloro-2-methoxyphenyl)-1,2,4-oxadiazole. $^1$H-NMR (CDCl$_3$), δ (ppm): 4.00(s, 3H), 7.03 (d, J=8.9 Hz, 1H), 7.42–7.47 (m, 1H), 7.50 (dd, J=8.9 Hz, 2.8 Hz, 1H), 7.87 (ddd, J=1.4 Hz, 7.4 Hz, 8.2 Hz, 1H), 8.22 (d, J=8.2 Hz, 1H), 8.28 (d, J=2.4 Hz, 1H), 8.84 (m, 1H).

3-(2-pyridyl)-5-(2,3-dimethoxyphenyl)-1,2,4-oxadiazole

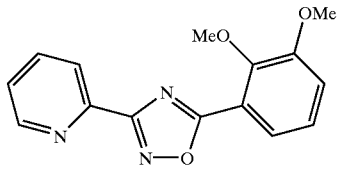

B38

2,3-Dimethoxybenzoic acid (182 mg, 1 mmol) was treated with a solution of oxalyl chloride (1.5 mL of 2 M in dichloromethane, 3 mmol) and a catalytic amount of N,N-dimethylformamide. The reaction was stirred at ambient temperature for 2 hours. The excess oxalyl chloride was removed in vacuo to afford 2,3-dimethoxybenzoyl chloride.

Using the general procedure for the synthesis of 1,2,4-oxadiazoles, the 2,3-dimethoxybenzoyl chloride and pyrid-2-ylamidoxime (137 mg, 1 mmol) in pyridine (1 mL) were heated at 115° C. for 17 hours. Standard work up and silica gel chromatography afforded 120 mg (42%) of 3-(2-pyridyl)-5-(2,3-dimethoxyxyphenyl)-1,2,4-oxadiazole.

3-(2-pyridyl)-5-(2-chloro-5-methylthiophenyl)-1,2,4-oxadiazole

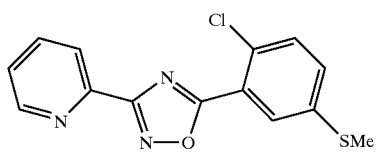

B39

2-Chloro-5-methylthiobenzoic acid (182 mg, 1 mmol) was treated with a solution of oxalyl chloride (1.5 mL of 2 M in dichloromethane, 3 mmol) and a catalytic amount of N,N-dimethylformamide. The reaction was stirred at ambient temperature for 2 hours. The excess oxalyl chloride was removed in vacuo to afford 2-chloro-5-methylthiobenzoyl chloride.

Using the general procedure for the synthesis of 1,2,4-oxadiazoles, the 2-chloro-5-methylthiobenzoyl chloride and pyrid-2-ylamidoxime (137 mg, 1 mmol) in pyridine (1 mL) were heated at 115° C. for 17 hours. Standard work up and silica gel chromatography afforded 250 mg (82%) of 3-(2-pyridyl)-5-(2-chloro-5-methylthiophenyl)-1,2,4-oxadiazole. $^1$H-NMR (CDCl$_3$), δ (ppm): 7.37(dd, J=2.4 Hz, 8.2 Hz, 1H), 7.40–7.50 (m, 2H), 7.89 (ddd, J=1.4 Hz, 7.4 Hz, 8.2 Hz, 1H), 8.05 (d, J=2.4 Hz, 1H), 8.23 (dd, J=2.2 Hz, 8.0 Hz, 1× H), 8.85 (m, 1H).

3-(2-Pyridyl)-5-(3-phenoxyphenyl)-1,2,4-oxadiazole

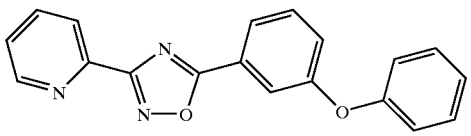

B40

3-Phenoxybenzoic acid (214 mg, 1.0 mmol) was treated with a solution of oxalyl chloride (1.5 mL of 2 M in dichloromethane, 3 mmol) and a catalytic amount of N,N-dimethylformamide. The reaction was stirred overnight at ambient temperature. The excess oxalyl chloride was removed in vacuo to afford 3-phenoxybenzoyl chloride.

Using the general procedure for the synthesis of 1,2,4-oxadiazoles, the 3-phenoxybenzoyl chloride and pyrid-2-ylamidoxime (137 mg, 1 mmol) in pyridine (1 mL) were heated in a sealed vial overnight at 110° C. Standard work up afforded 118 mg (37%) of 3-(2-pyridyl)-5-(3-phenoxyphenyl)-1,2,4-oxadiazole as a white solid.

3-(2-Pyridyl)-5-(3-benzoylphenyl)-1,2,4-oxadiazole

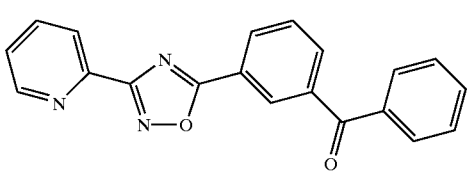

B41

3-Benzoylbenzoic acid (226 mg, 1.0 mmol) in dichloromethane (1.5 mL) was treated with a solution of oxalyl chloride (1.5 mL of 2 M in dichloromethane, 3 mmol) and a catalytic amount of N,N-dimethylformamide. The reaction was stirred overnight at ambient temperature. The excess oxalyl chloride was removed in vacuo to afford 3-benzoylbenzoyl chloride.

Using the general procedure for the synthesis of 1,2,4-oxadiazoles, the 3-benzoylbenzoyl chloride and pyrid-2-ylamidoxime (137 mg, 1 mmol) in pyridine (1 mL) were heated in a sealed vial overnight at 110° C. Standard work up and filtration through silica gel (with dichloromethane) afforded 200 mg (61%) of 3-(2-pyridyl)-5-(3-benzoylphenyl)-1,2,4-oxadiazole as a white solid. $^1$H NMR (CDCl$_3$), δ (ppm): 8.85 (d, 1H), 8.68 (m, 1H), 8.53 (dd, 1H), 8.23 (d, 1H), 8.07 (m, 1H), 7.88 (m, 3H), 7.70 (m, 2H), 7.49 (m, 3H).

3-(2-Pyridyl)-5-(2-bromo-5-methoxyphenyl)-1,2,4-oxadiazole

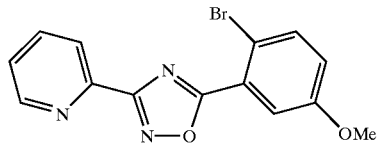

B42

2-Bromo-5-methoxybenzoic acid (231 mg, 1.0 mmol) in dichloromethane (1.5 mL) was treated with a solution of oxalyl chloride (1.5 mL of 2 M in dichloromethane, 3 mmol) and a catalytic amount of N,N-dimethylformamide. The reaction was stirred overnight at ambient temperature. The excess oxalyl chloride was removed in vacuo to afford 2-bromo-5-methoxybenzoyl chloride.

Using the general procedure for the synthesis of 1,2,4-oxadiazoles, the 2-bromo-5-methoxybenzoyl chloride and pyrid-2-ylamidoxime (137 mg, 1 mmol) in pyridine (1 mL) were heated in a sealed vial overnight at 110° C. Standard work up and filtration through silica gel (with dichloromethane) afforded 147 mg (44%) of 3-(2-pyridyl)-5-(2-bromo-5-methoxyphenyl)-1,2,4-oxadiazole. $^1$H NMR (CDCl$_3$), δ (ppm): 8.85 (d, 1H), 8.24 (d, 1H), 7.89 (m, 1H), 7.65 (m, 2H), 7.47 (m, 1H), 6.99 (m, 1H), 3.89 (s, 3H).

3-(2-Pyridyl)-5-(2-chloro-5-(trifluoromethyl)phenyl)-1,2,4-oxadiazole

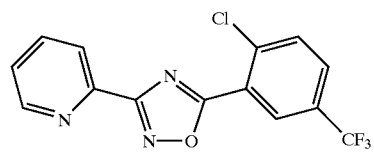

B43

2-Chloro-5-(trifluoromethyl)benzoic acid (224 mg, 1.0 mmol) in dichloromethane (1.5 mL) was treated with a solution of oxalyl chloride (1.5 mL of 2 M in dichloromethane, 3 mmol) and a catalytic amount of N,N-dimethylformamide. The reaction was stirred overnight at ambient temperature. The excess oxalyl chloride was removed in vacuo to afford 2-chloro-5-(trifluoromethyl)benzoyl chloride.

Using the general procedure for the synthesis of 1,2,4-oxadiazoles, the 2-chloro-5-(trifluoromethyl)benzoyl chloride and pyrid-2-ylamidoxime (137 mg, 1 mmol) in pyridine (1 mL) were heated in a sealed vial overnight at 110° C. Standard work up and filtration through silica gel (with dichloromethane) afforded 136 mg (42%) of 3-(2-pyridyl)-5-(2-chloro-5-(trifluoromethyl)phenyl)-1,2,4-oxadiazole as a beige solid. $^1$H NMR (CDCl$_3$), δ (ppm): 8.87 (d, 1H), 8.56 (s, 1H), 8.25 (d, 1H), 7.89 (m, 1H), 7.78 (m, 2H), 7.50 (m, 1H).

3-(2-Pyridyl)-5-(3,4,5-trifluorophenyl)-1,2,4-oxadiazole

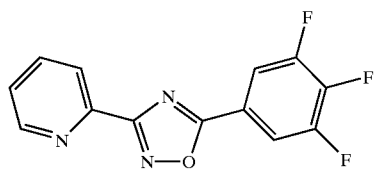

B44

3,4,5-Trifluorobenzoic acid (0.176 g, 1.0 mmol) in dichloromethane (1.5 mL) was treated with a solution of oxalyl chloride (1.5 mL of 2 M in dichloromethane, 3 mmol) and a catalytic amount of N,N-dimethylformamide. The reaction was stirred overnight at ambient temperature. The excess oxalyl chloride was removed in vacuo to afford 3,4,5-trifluorobenzoyl chloride.

Using the general procedure for the synthesis of 1,2,4-oxadiazoles, the 3,4,5-trifluorobenzoyl chloride and pyrid-2-ylamidoxime (137 mg, 1 mmol) in pyridine (1 mL) were heated in a sealed vial overnight at 110° C. Standard work up and silica gel chromatography (with 10–30% ethyl acetate in hexane) afforded 15 mg (5%) of 3-(2-pyridyl)-5-(3,4,5-trifluorophenyl)-1,2,4-oxadiazole as a white solid.

3-(2-pyridyl)-5-(2,5,6-trifluorophenyl)-1,2,4-oxadiazole

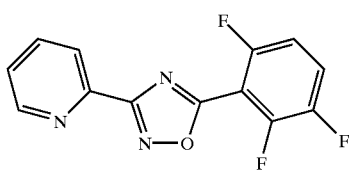

B45

2,5,6-Trifluorolbenzoic acid (176 mg, 1 mmol) was treated with a solution of oxalyl chloride (1.5 mL of 2 M in dichloromethane, 3 mmol) and a catalytic amount of N,N-dimethylformamide. The reaction was stirred at ambient temperature for 16 hours. The excess oxalyl chloride was removed in vacuo to afford 2,5,6-trifluorolbenzoyl chloride.

A solution of the intermediate 2,5,6-trifluorolbenzoyl chloride and pyrid-2-ylamidoxime (137 mg, 1 mmol) in dichloromethane was stirred at ambient temperature for 0.5 hours. Silica gel chromatography afforded 151 mg (51%) of N-[(2,5,6-trifluorobenzoyl) oxy]pyridine-2-carboximidamide.

A solution of N-[(2,5,6-trifluorobenzoyl)oxy]pyridine-2-carboximidamide (50 mg, 0.169 mmol) in pyridine (0.3 mL) was heated at 115° C. for 17 hours. Standard work up, and silica gel chromatography, afforded 9.5 mg (20%) of 3-(2-pyridyl)-5-(2,5,6-trifluorophenyl)-1,2,4-oxadiazole.

3-(3-Methoxyphenyl)-5-(2-pyridyl)-1,2,4-oxadiazole

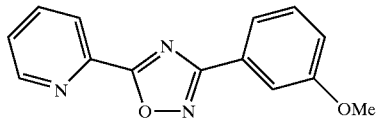

B8

Using modifications of the method of Shine et al., *J. Heterocyclic Chem.* (1989) 26:125–128, a solution of picolinic acid (123 mg, 1 mmol) in pyridine (1 mL) was treated with 1,1'-carbonyldiimidazole (162 mg, 1 mmol) and the reaction stirred at ambient temperature until the evolution of carbon dioxide ceased (30 min). The intermediate acylimidazole was then treated with 3-methoxybenzamidoxime (166 mg, 1 mmol) and the reaction heated at reflux for 1 hour. Ice cold water was added to the reaction mixture to precipitate the oxadiazole. The solid was collected by filtration, washed with water and dried to afford 80 mg (32%) of 3-(3-methoxyphenyl)-5-(2-pyridyl)-1,2,4-oxadiazole: mp 90–94° C.; GC/EI-MS gave m/z (rel. int.) 253 ($M^+$, 100), 254 (17), 179 (2), 175 (2), 149 (77), 133 (33), 119 (4), 106 (29), 78 (45), 51 (18).

3-(Pyrid-2-yl)-5-(2-hydroxyphenyl)-1,2,4-oxadiazole

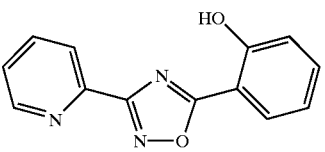

B46

Using the method of Korbonits et al., *J. Chem. Soc. Perkin Trans. I* (1982) 759–766, a mixture of ethyl salicylate (200 mg, 1.2 mmol), pyrid-2-ylamidoxime (82.5 mg, 0.6 mmol), 21% sodium ethoxide (19.4 mL, 6 mmol) in ethanol (12 mL) was heated at reflux for 16 hours. After cooling, the reaction mixture was diluted with dichloromethane (50 mL) and washed with water and saturated sodium hydrocarbonate. The organic layer was dried with sodium sulfate and concentrated in vacuo. Recrystallization from diethyl ether afforded 15 mg (5%) of 3-(Pyrid-2-yl)-5-(2-hydroxyphenyl)-1,2,4-oxadiazole.

3-(2-pyridyl)-5-(5-chloro-2-hydroxyphenyl)-1,2,4-oxadiazole

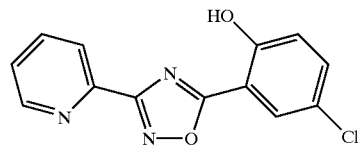

B47

In a similar fashion, methyl 5-chloro-2-hydroxybenzoate (372 mg, 2 mmol), pyrid-2-ylamidoxime (137 mg, 1 mmol), 21% sodium ethoxide (32.4 mL, 10 mmol) in ethanol (20 mL) were heated at reflux for 16 hours. Standard work up and recrystallization from diethyl ether afforded 14.2 mg (5%) of 3-(2-pyridyl)-5-(5-chloro-2-hydroxyphenyl)-1,2,4-oxadiazole.

3-(2-pyridyl)-5-(2-aminophenyl)-1,2,4-oxadiazole

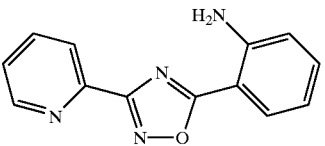

B48

Using modifications from the procedure of Nagahara et al., *Chem. Pharm. Bull.*, (1975) 23:3178–3183, a mixture of isatoic anhydride (163 mg, 1 mmol) and pyrid-2-ylamidoxime (137 mg, 1 mmol) in pyridine (1 mL) was heated at 115° C. for 17 hours. After cooling the reaction, the mixture was diluted with 50 mL of dichloromethane and washed with water and saturated sodium hydrocarbonate. The organic layer was dried over sodium sulfate, filtered through silica gel and concentrated in vacuo. Recrystallization from diethyl ether afforded 45.6 mg (19%) of 3-(2-pyridyl)-5-(2-aminophenyl)-1,2,4-oxadiazole.

3-(2-pyridyl)-5-(2-aminophenyl)-1,2,4-oxadiazole

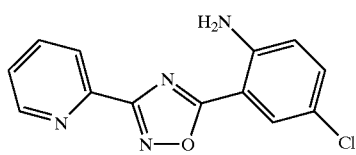

In a similar fashion, 5-chloroisatoic anhydride (197 mg, 1 mmol) and pyrid-2-ylamidoxime (137 mg, 1 mmol) in pyridine (1 mL) was heated at 115° C. for 17 hours. Work up afforded 138 mg (51%) of 3-(2-pyridyl)-5-(2-aminophenyl)-1,2,4-oxadiazole.

2-[3-chlorophenyl]-4-[pyridin-2-yl]-1,3-oxazole

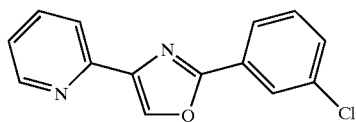

Using the procedures of Kelly et al., *J. Org. Chem.*, (1996) 61:4623–4633, a solution of 2-bromoacetylpyridine (120 mg, 0.6 mmol) in toluene (5 mL) was treated with 3-chlorobenzamide (300 mg, 1.9 mmol) and the mixture heated in a sealed vial at reflux for 60 hours. The mixture was then cooled and the solvent was removed in vacuo. Silica gel chromatography using a gradient of hexane to ethyl acetate afforded 38 mg (9%) of 2-[3-chlorophenyl]-4-[pyridin-2-yl]-1,3-oxazole as a pale yellow solid. $^1$H-NMR (CDCl$_3$), δ (ppm): 8.62 (d, 1H), 8.35 (s, 1H), 8.15 (m, 1H), 8.00 (m, 2H), 7.80 (td, 1H), 7.42 (m, 2H), 7.23 (m, 1H).

2-[3-Bromophenyl]-4-[pyridin-2-yl]-1,3-oxazole

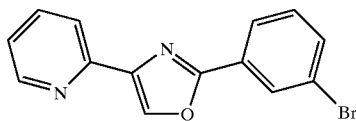

In a similar fashion 2-bromoacetylpyridine (500 mg, 2.5 mmol) and 3-chlorobenzamide (1.2g, 6 mmol) in toluene (10 mL) was heated in a sealed vial at reflux for 60 hours. Work up and silica gel chromatography using a gradient of hexane to ethyl acetate afforded 50 mg (7%) of 2-[3-bromophenyl]-4-[pyridin-2-yl]-1,3-oxazole as a white solid. $^1$H-NMR (CDCl$_3$), δ (ppm): 8.60 (d, 1H), 8.34 (s, 1H), 8.30 (t, 1H), 8.00 (m, 2H), 7.80 (td, 1H), 7.60 (dd, 1H), 7.35 (t, 1H), 7.23 (m, 1H).

2-[3-cyanophenyl]-4-[pyridin-2-yl]-1,3-oxazole

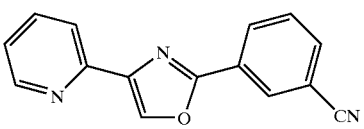

A mixture of 2-[3-bromophenyl]-4-[pyridin-2-yl]-1,3-oxazole (23 mg, 0.076 mmol) and zinc cyanide (112 mg, 0.96 mmol) in N,N-dimethylformamide (2 mL) was treated with Pd(PPh$_3$)$_4$ (74 mg, 0.064 mmol) and heated overnight at 80° C. Standard work up and chromatography afforded 6 mg (32%) of 2-[3-cyanophenyl]-4-[pyridin-2-yl]-1,3-oxazole as a white solid. $^1$H-NMR (CDCl$_3$), δ (ppm): 8.61 (d, 1H), 8.45 (s, 1H), 8.38 (s, 1H), 8.36 (m, 1H), 8.00 (d, 1H), 7.80 (m, 2H), 7.61 (t, 1H), 7.23 (m, 1H).

5-[3-hydroxyphenyl]-3-[pyridin-2-yl]-1,2-oxazole

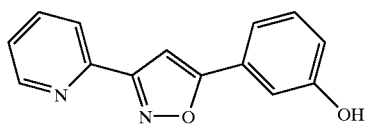

A stirred solution of pyridine-2-carbohydroximoyl chloride (300 mg, 1.9 mmol) and 3-hydroxyphenylacetylene (760 mg, 6.4 mmol) in a 1:1 mixture of THF/CH$_2$Cl$_2$ (10 mL) at 0° C. was treated with triethylamine (2 mL, 1.45 g, 15 mmol). The mixture was allowed to warm to room temperature overnight. The solvent was removed in vacuo. The residue was dissolved in dichloromethane, washed with brine and dried over anhydrous sodium sulphate. Removal of the solvent in vacuo followed by trituration with 10% ethylacetate in hexane afforded 200 mg (44%) of 5-[3-hydroxyphenyl]-3-[pyridin-2-yl]-1,2-oxazole as a beige solid.

5-[3-cyanophenyl]-3-[pyridin-2-yl]-1,2-oxazole

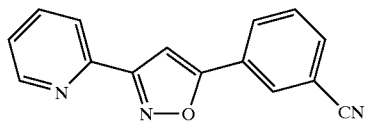

A mixture of 5-[3-trifluoromethanesulfonylphenyl]-3-[pyridin-2-yl]-1,2-oxazole (98 mg, 0.26 mmol), KCN (230 mg, 4 mmol), NiBr$_2$(PPh$_3$)$_2$ (52.4 mg, 0.07 mmol), and PPh$_3$ (42 mg, 0.16 mmol) in acetonitrile (1 mL) was treated with zinc powder (20 mg, 0.3 mmol) and the mixture was heated overnight at 60° C. Silica gel chromatography of the resulting mixture using a gradient of hexane to ethyl acetate afforded 15 mg (23%) of 5-[3-cyanophenyl]-3-[pyridin-2-yl]-1,2-oxazole as a white solid.

3-(2-Pyridyl)-5-(3-chlorophenyl)-1,2,4-triazole

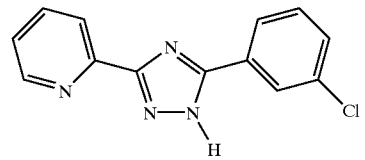

Using the procedures of Browne et al., *Aust. J. Chem.*, (1975) 28:2543–2546, a solution of 2-cyanopyridine (0.1 mL, 1.00 mmol) in methanol (5 mL) was treated with sodium metal (6.9 mg, 0.30 mmol) and stirred for at ambient temperature for 1 hour. After this time, a solution of 3-chlorobenzhyrazide (0.17 g, 1.0 mmol) in methanol (5 mL) was added and the resulting solution heated at reflux for 3 hours. The reaction mixture was concentrated in vacuo, and the resulting yellow solid (100 mg) dissolved in toluene (2 mL). The mixture was heated at 175° C. for 3 hours and then stirred overnight at ambient temperature. Evaporation of the solvent in vacuo and silica gel chromatography using 1% methanol in dichloromethane afforded 29 mg (11%) of 3-(2-pyridyl)-5-(3-chlorophenyl)-1,2,4-triazole as an off-white solid.

3-(2-Pyridyl)-5-(3-iodophenyl)-1,2,4-triazole

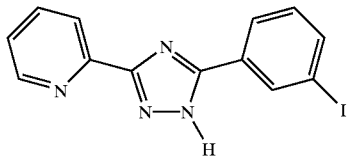

B56

In a similar fashion, 2-cyanopyridine (0.15 mL, 1.53 mmol), sodium metal (10.5 mg, 0.46 mmol) and 3-iodobenzhydrazide (0.40 g, 1.53 mmol) afforded, after work up and chromatography, 210 mg (40%) of 3-(2-pyridyl)-5-(3-iodophenyl)-1,2,4-triazole as a white solid.

Example 5

3-(5-Methyl-pyrid-2-yl)-5-(3-cyanophenyl)-1,2,4-oxadiazole

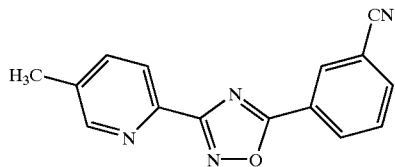

B57

A suspension of 5-methylpyrid-2-ylamidoxime (449.5 mg, 2.97 mmol) in dichloromethane (10 mL) was treated with 3-cyanobenzoyl chloride (495 mg, 2.99 mmol) and the mixture stirred 30 minutes. The solvent was removed in vacuo and the intermediate dissolved in N,N-dimethylformamide (15 mL). The reaction was heated, under an argon atmosphere, for 20 hours at 120° C. After this time, the reaction mixture was cooled and the solvent removed in vacuo. Silica gel chromatography using a gradient of 20% to 75% ethyl acetate in hexane afforded 674 mg (86%) of 3-(5-methyl-pyrid-2-yl)-5-(3-cyanophenyl)-1,2,4-oxadiazole: $^1$H-NMR (CDCl$_3$), δ (ppm):☐8.69 (s, 1H), 8.60 (s, 1H), 8.51 (d, 1H), 8.12 (d, 1H), 7.90 (d, 1H), 7.72 (t, 2H).

3-(5-Cyano-pyrid-2-yl)-5-(3-cyanophenyl)-1,2,4-oxadiazole

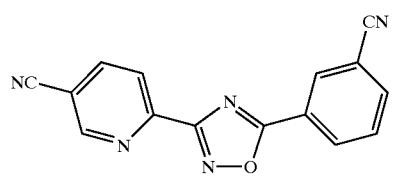

B58

Method A: In a similar fashion, a solution of 5-tert-butoxycarbonylpyrid-2-ylamidoxime (89.5 mg, 0.38 mmol) in dichloromethane (5 mL) was treated with 3-cyanobenzoyl chloride (64.9 mg, 0.39 mmol) and stirred 2 minutes at room temperature. Saturated sodium bicarbonate (1 mL) was added and the resulting mixture stirred vigorously for 30 minutes. The mixture was passed through an EX-TUBE (3 mL) and the product was eluted with dichloromethane (25 mL). The organic wash was concentrated in vacuo, and the intermediate dissolved in N,N-dimethylformamide (2.5 mL). The solution was heated in sealed tube for 21 hours at 120° C. After this time, the reaction mixture was added to ice cold water and the crude oxadiazole collected and dried. Silica gel chromatography using a gradient of 10% to 30% ethyl acetate in hexane afforded 114.2 mg (87%) of 3-(5-tert-butoxycarbonyl-2-pyridyl)-5-(3-cyanophenyl)-1,2,4-oxadiazole.

Method B: A mixture of 3-(5-cyanopyridyl)amidoxime (95mg, 0.586 mmol) 3-cyanobenzoyl chloride (96mg, 0.586 mol) and triethylamine (175 mg, 1.74 mmol) in dichloromethane were stirred for 5 min. Then DMF (1 ml) was added to the reaction mixture. The mixture was heated to 120° C. for 16 hrs. After cooling the mixture was poured into water. The solid was filtered and washed with water, then triturated in ether to provide 125 mg, (78%) of 3-(5-tert-butoxycarbonyl-2-pyridyl) -5-(3-cyanophenyl)-1,2,4-oxadiazole.

A mixture of 3-(5-tert-butoxycarbonylpyrid-2-yl)-5-(3-cyanophenyl)-1,2,4-oxadiazole (114 mg, 0.33 mmol) in formic acid (98%, 6 mL) was heated for 2 days at 45° C. The incomplete reaction was resubjected to additional formic acid (96%, 6 mL) for 1 day at 45° C. Co-evaporation of the solvent in vacuo using toluene afforded 103.6 mg of 3-(5-hydroxycarbonylpyrid-2-yl)-5-(3-cyanophenyl)-1,2,4-oxadiazole, as a white solid.

A suspension of 3-(5-hydroxycarbonylpyrid-2-yl)-5-(3-cyanophenyl)-1,2,4-oxadiazole (49.7 mg, 0.17 mmol) in dichloromethane (5 mL) was treated with 2M oxalyl chloride (0.19 mL, 0.38 mmol, dichloromethane) and a catalytic amount of N,N-dimethylformamide. The reaction was stirred at ambient temperature for 1 hour and solvents removed in vacuo. The acid chloride was dissolved in dichloromethane (5 mL) and treated with concentrated ammonium hydroxide (1 mL) for 1 hour. The aqueous layer was removed and the remaining organic solvent evaporating in vacuo, azeotroping with ethanol.

The crude amide in thionyl chloride (1.5 mL) was heated for 4.5 hours at 80° C. After cooling, the excess thionyl chloride was removed in vacuo and the residue dissolved in dichloromethane. The organic solution was washed with aqueous sodium carbonate and dried by passing through an EX-TUBE. Silica gel chromatography using a gradient of 20% ethyl acetate in hexane to 100% ethyl acetate afforded 22.2 mg (47%) of 3-(5-cyano-pyrid-2-yl)-5-(3-cyanophenyl)-1,2,4-oxadiazole: $^1$H-NMR (CDCl$_3$), δ (ppm):☐9.11 (s, 1H), 8.59 (s, 1H), 8.51 (d, 1H), 8.37 (d, 1H), 8.20 (dd, 1H), 7.94 (d, 1H), 7.75 (t, 1H).

3-(5-Cyano-2-pyridyl)-5-(3-bromophenyl)-1,2,4-oxadiazole

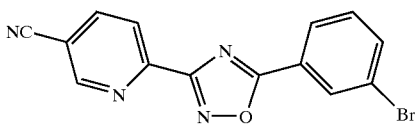

B59

A mixture of 3-bromobenzoyl chloride (0.17 mL, 1.28 mmol) and 5-tert-butoxycarbonylpyrid-2-ylamidoxime (302 mg, 1.27 mmol) in dichloromethane (10 mL) wasstirred at room temperature for 30 minutes. The solvent was removed in vacuo. The intermediate was dissolved in N,N-dimethylformamide (7.5 mL) and heated in sealed tube at 120° C. for 23 hours. The solvent was then removed in vacuo. Silica gel chromatography using a gradient of 5% to 10% ethyl acetate in hexane afforded 329 mg (64%) of 3-(5-tert-butoxycarbonyl-2-pyridyl)-5-(3-bromophenyl)-1,2,4-oxadiazole.

A mixture of 3-(5-tert-butoxycarbonylpyrid-2-yl)-5-(3-bromophenyl)-1,2,4-oxadiazole (100 mg, 0.25 mmol) in formic acid (98%, 6 mL) was heated at 45° C. for 23 hours. Evaporation of the solvent in vacuo followed by trituration with dichloromethane afforded 3-(5-hydroxycarbonylpyrid-2-yl)-5-(3-bromophenyl)-1,2,4-oxadiazole (65.4 mg, 76%) as a white solid.

A mixture of 3-(5-hydroxycarbonylpyrid-2-yl)-5-(3-bromophenyl)-1,2,4-oxadiazole (269.4 mg, 0.78 mmol) in dichloromethane (15 mL) was treated with 2M oxalyl chloride (0.90 mL, 1.8 mmol, dichloromethane) and a catalytic amount N,N-dimethylformaide. The resulting mixture was stirred at ambient temperature for 1.5 hours and the solvent and excess oxalyl chloride removed, in vacuo. The acid chloride in dichloromethane (5 mL) was then treated with solid ammonium chloride (450 mg, 8.4 mmol) and pyridine (1.5 mL, 18.5 mmol). The mixture was stirred vigorously at ambient temperature for 15 hours, and then treated with 2M ammonia (5 mL, 10 mmol, methanol). The solvent was then removed in vacuo, and the residue treated with water. Collection of the precipitate by filtration afforded crude 3-(5-aminocarbonylpyrid-2-yl)-5-(3-bromophenyl)-1,2,4-oxadiazole.

A solution of this intermediate amide in thionyl chloride (5 mL) was heated for 6 hours at 80° C. After cooling, the excess thionyl chloride was removed in vacuo. The residue was dissolved in dichloromethane, washed with aqueous sodium carbonate and dried by passing through an EX-TUBE. Silica gel chromatography using a gradient of 5% to 30% ethyl acetate in hexane, afforded 130.8 mg (51%) of 3-(5-cyano-2-pyridyl)-5-(3-bromophenyl)-1,2,4-oxadiazole: $^1$H-NMR (CDCl$_3$), δ (ppm): 9.10 (s, 1H), 8.45 (s, 1H), 8.36 (d, 1H), 8.18 (m, 2H), 7.78 (dd, 1H), 7.47 (t, 1H).

3-(5-Cyano-2-pyridyl)-5-(3-cyano-5-fluorophenyl)-1,2,4-oxadiazole

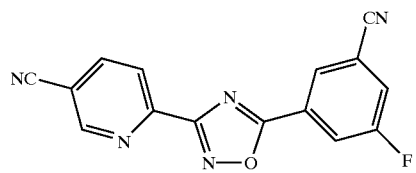

B60

Using the general procedure for the preparation of acid chlorides, 3-cyano-5-fluorobenzoyl chloride was prepared from 3-cyano-5-fluorobenzoic acid (106 mg, 0.63 mmol). The acid chloride in dichloromethane (2.5 mL) was treated with 5-tert-butoxycarbonylpyrid-2-ylamidoxime (149 mg, 0.63 mmol). The mixture stirred at room temperature for 2 hours and the solvent removed in vacuo. The intermediate was dissolved in N,N-dimethylformamide (2.5 mL) and heated in sealed tube for 13 hours at 120° C. After cooling, water was added and the product collected by filtration. Silica gel chromatography using a gradient of 10% to 30% ethyl acetate in hexane afforded 71.2 mg (31%) of 3-(5-tert-butoxycarbonyl-2-pyridyl)-5-(3-cyano-5-fluorophenyl)-1,2,4-oxadiazole.

A mixture of 3-(5-tert-butoxycarbonylpyrid-2-yl)-5-(3-cyano-5-fluorophenyl)-1,2,4-oxadiazole (69 mg, 0.19 mmol) in formic acid (98%, 3.5 mL) was heated at 40° C. for 17 hours. Evaporation of the solvent in vacuo afforded crude 3-(5-hydroxycarbonylpyrid-2-yl)-5-(3-cyano-5-flourophenyl)-1,2,4-oxadiazole as a white solid.

A solution of crude 3-(5-hydroxycarbonylpyrid-2-yl)-5-(3-cyano-5-flourphenyl)-1,2,4-oxadiazole in dichloromethane (5 mL) was treated with 2M oxalyl chloride (0.25 mL, 0.5 mmol, dichloromethane) and a catalytic amount of N,N-dimethylformamide. The mixture was stirred at room temperature for 1.5 hour and the solvent and excess reagent removed in vacuo. The crude product was dissolved in dichloromethane (5 mL) and treated with 0.5M ammonia (2 mL, 1 mmol, dioxane). The mixture was stirred at room temperature for 1 hour and the solvents removed in vacuo. The crude amide, in dichloromethane (2 mL) and pyridine (0.10 mL, 1.23 mmol), was treated with trifluoroacetic anhydride (0.09 mL, 0.64 mmol). The mixture was stirred at room temperature for 12 hours and diluted with dichloromethane. The organic solution was washed with dilute aqueous sodium bicarbonate and brine, and dried over sodium sulfate and silica gel. Filtration and removal of the solvent in vacuo afforded the crude product. Silica gel chromatography using a gradient of 20% to 50% ethyl acetate in hexane, afforded 48.8 mg (88%) of 3-(5-cyano-2-pyridyl)-5-(3-cyano-5-fluorophenyl)-1,2,4-oxadiazole: $^1$H-NMR (CDCl$_3$), δ (ppm): 9.10 (S, 1H), 8.37 (m, 2H), 8.22 (m, 2H), 7.64 (m, 1H).

3-(5-Cyano-2-pyridyl)-5-(3-bromo-5-fluorophenyl)-1,2,4-oxadiazol

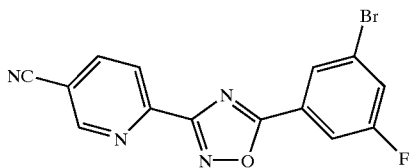
B61

Using the general procedure for the preparation of acid chlorides, 3-bromo-5-fluorobenzoyl chloride was prepared from 3-bromo-5-fluorobenzoic acid chloride (554 mg, 2.52 mmol). The acid chloride in dichloromethane (10 mL) was treated with 5-tert-butoxycarbonylpyrid-2-ylamidoxime (601 mg, 2.53 mmol). The mixture was stirred at room temperature for 30 minutes and the solvent was removed in vacuo. The intermediate was dissolved in DMF (15 mL) and heated in sealed tube at 120° C. for 13 hours. After cooling the solvent was removed in vacuo. Silica gel chromatography using a gradient of 5% to 10% ethyl acetate in hexane, afforded 556 mg of crude 3-(5-tert-butoxycarbonyl-2-pyridyl)-5-(3-bromo-5-fluorophenyl)-1,2,4-oxadiazole.

A mixture of this crude intermediate in formic acid (98%, 20 mL) was heated at 40° C. for 17 hours. Evaporation of the solvent in vacuo afforded 3-(5-hydroxycarbonylpyrid-2-yl)-5-(3-bromo-5-fluorophenyl)-1,2,4-oxadiazole as a white solid.

The crude acid in dichloromethane (20 mL) was treated with 2M oxalyl chloride (1.4 mL, 2.8 mmol, dichloromethane) and a catalytic amount of N,N-dimethylformamide. The mixture was stirred at room temperature for 2 hours and the solvent and excess reagent removed in vacuo. The crude product was dissolved in dichloromethane (25 mL) and and treated with 0.5M ammonia (10 mL, 5 mmol, dioxane) and the mixture stirred at room temperature for 1 hour. Removal of the solvent in vacuo afforded the crude amide.

The crude amide in a mixture of dichloromethane (7.5 mL) and pyridine (0.46 mL, 5.6 mmol) was treated with trifluoroacetic anhydride (0.44 mL, 3.1 mmol). The mixture was stirred at room temperature for 12 hours and then diluted with ethyl acetate. The organic solution was washed with dilute aqueous sodium bicarbonate and brine, and then dried over sodium sulfate and silica gel. Filtration and removal of the solvent in vacuo afforded the crude product. Silica gel chromatography using 10% ethyl acetate in hexane afforded 22 mg (6%) of 3-(5-cyano-2-pyridyl)-5-(3-bromo-5-fluorophenyl)-1,2,4-oxadiazole: $^1$H-NMR (CDCl$_3$), δ (ppm): 9.10 (s, 1H), 8.36 (d, 1H), 8.25 (s, 1H), 8.18 (dd, 1H), 7.91 (dd, 1H), 7.53 (dd, 1H).

3-(2-Pyridyl)-5-(5-bromo-2-methoxyphenyl)-1,2,4-oxadiazole

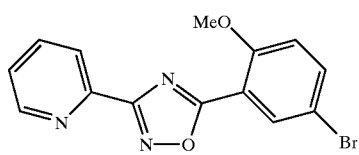
B62

A mixture of 5-bromo-2-methoxybenzoic acid (1.49 g, 6.45 mmol) in dichloromethane (10 mL) was treated with 2M oxalyl chloride (9.7 ml, 19.4 mmol, dichloromethane) and 3 drops of N,N-dimethylformamide. The mixture was stirred 4 hours at room temperature. The solvent and excess reagent were removed in vacuo. The residue was treated with pyrid-2-ylamidoxime (884 mg, 6.45 mmol) and triethylamine (1.95 g, 19.35 mmol) in dichloromethane (10 mL). The mixture was then heated in dimethylformamide (10 mL) for 2 hours at 120° C. Standard work up, afforded 1.2 g (67%) of 3-(2-pyridyl)-5-(5-bromo-2-methoxyphenyl)-1,2,4-oxadiazole.

3-(2-Pyridyl)-5-(5-bromo-2-fluorophenyl)-1,2,4-oxadiazole

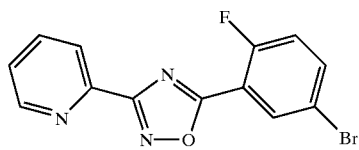
B63

In a similar fashion, 5-bromo-2-fluorobenzoyl chloride was prepared from 5-bromo-2-fluorobenzoic acid (2.19 g, 10 mmol). Treatment of the acid chloride with pyrid-2-ylamidoxime (1.37 g, 10 mmol) and triethylamine (3.03 g, 30 mmol) in dichloromethane (20 mL), followed by heating in dimethylformamide (20 mL) at 120° C. for 2 hours, afforded 3.2 g (100%) of 3-(2-pyridyl)-5-(5-bromo-2-fluorophenyl)-1,2,4-oxadiazole.

3-(2-Pyridyl)-5-(5-cyano-2-fluorophenyl)-1,2,4-oxadiazole

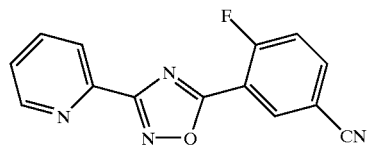
B64

In a similar fashion, 5-cyano-2-fluorobenzoyl chloride was prepared from 5-cyano-2-fluorobenzoic acid (185 mg, 1.12 mmol). Treatment of the acid chloride with pyrid-2-ylamidoxime (1.153 g, 1.12 mmol) and triethylamine (340 mg, 3.36 mmol) in dichloromethane (3 mL), followed by heating in dimethylformamide (2 mL) at 120° C. for 16 hours, afforded 17 mg (6%) of 3-(2-pyridyl)-5-(5-cyano-2-fluorophenyl)-1,2,4-oxadiazole.

3-(2-Pyridyl)-5-(5-bromopyrid-3-yl)-1,2,4-oxadiazole

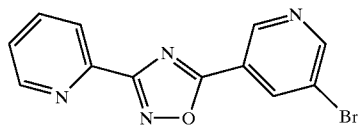
B65

In a similar fashion, 5-bromonicotinoyl chloride was prepared from 5-bromonicotinic acid (2.02 g, 10 mmol). Treatment of the acid chloride with pyrid-2-ylamidoxime (1.37 g, 10 mmol) and triethylamine (4.04 g, 40 mmol) in dichloromethane (20 mL), followed by heating in dimethylformamide (20 mL) at 120° C. for 16 hours. After this time water was added and the precipitate collected and dried. Filtration through silica gel using dichloromethane followed by trituration with hexane afforded 2.58 g (85%) of 3-(2-pyridyl)-5-(5-bromopyrid-3-yl)-1,2,4-oxadiazole.

3-(2-Pyridyl)-5-(5-chloro-pyrid-3-yl)-1,2,4-oxadiazole

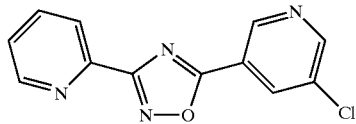

B66

In a similar fashion, 5-chloronicotinoyl chloride was prepared from 5-chloronicotinic acid (157 mg, 1 mmol). Treatment of the acid chloride with pyrid-2-ylamidoxime (137 mg, 1 mmol) and triethylamine (404 mg, 4 mmol) in dichloromethane (2 mL), followed by heating in dimethylformamide (2 mL) at 120° C. for 3 hours afforded 149 mg (58%) of 3-(2-pyridyl)-5-(5-chloro-pyrid-3-yl)-1,2,4-oxadiazole (149 mg, 57.6%).

3-(5-Cyanopyrid-2-yl)-5-(5-bromo-pyrid-3-yl)-1,2,4-oxadiazole

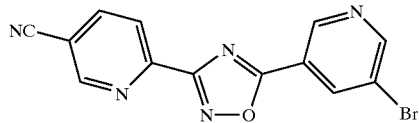

B67

In a similar fashion, 5-bromonicotinoyl chloride was prepared from 5-bromonicotinic acid (262.6 mg, 1.3 mmoles). Treatment of the acid chloride with 5-cyanopyrid-2-ylamidoxime (162 mg, 1 mmol) and triethylamine (404 mg, 4 mmol) in dichloromethane (2 mL), followed by heating in dimethylformamide (2 mL) at 120° C. for 16 hours afforded 230 mg (70%) of 3-(5-cyanopyrid-2-yl)-5-(5-bromo-pyrid-3-yl)-1,2,4-oxadiazole.

3-(5-Fluoropyrid-2-yl)-5-(5-bromo-pyrid-3-yl)-1,2,4-oxadiazole

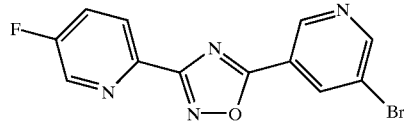

B68

In a similar fashion, 5-bromonicotinoyl chloride was prepared from 5-bromonicotinic acid (202 mg, 1 mmol). Treatment of the acid chloride with 5-fluoropyrid-2-ylamidoxime (155.13 mg, 1 mmol) and triethylamine (404 mg, 4 mmol) in dichloromethane (2 mL), followed by heating in dimethylformamide (2 mL) at 120° C. for 3 hours afforded 216.5 mg (67%) of 3-(5-fluoropyrid-2-yl)-5-(5-bromo-pyrid-3-yl)-1,2,4-oxadiazole.

3-(2-Pyridyl)-5-(2-thiomethoxy-pyrid-3-yl)-1,2,4-oxadiazole

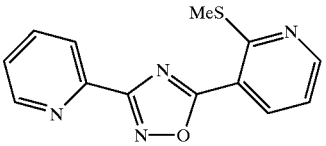

B69

In a similar fashion, 2-thiomethoxynicotinoyl chloride was prepared from 2-thiomethoxynicotinic acid (169 mg, 1 mmol). Treatment of the acid chloride with pyrid-2-ylamidoxime (137mg, 1 mmole) and triethylamine (404 mg, 4 mmol) in dichloromethane (2 mL), followed by heating in dimethylformamide (2 mL) at 120° C. for 16 hours afforded 20 mg (7%) of 3-(2-pyridyl)-5-(2-thiomethoxy-pyrid-3-yl)-1,2,4-oxadiazole.

3-(2-Pyridyl)-5-(5-methylpyrid-3-yl)-1,2,4-oxadiazole

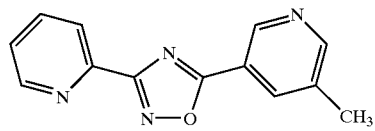

B70

In a similar fashion, 5-methylnicotinoyl chloride was prepared from 5-methyinicotinic acid (548 mg, 4 mmoles). Treatment of the acid chloride with pyrid-2-ylamidoxime (822 mg, 6 mmol) and triethylamine (1.2g, 12 mmol) in dichloromethane (6 mL), followed by heating in dimethylformamide (6 mL) at 120° C. for 2.5 hours, afforded 448 mg (47%) of 3-(2-pyridyl)-5-(5-methyl-pyrid-3-yl)-1,2,4-oxadiazole.

3-(2-Pyridyl)-5-(5-hydroxypyrid-3-yl)-1,2,4-oxadiazole

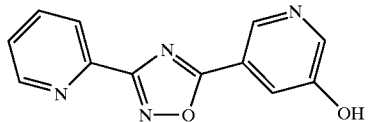

B71

In a similar fashion, 5-hydroxynicotinoyl chloride was prepared from 5-hydroxynicotinic acid hydrochloride, which was obtained form the hydrolysis of 5-hydroxynicotinic acid methyl ester (1.53 g, 10 mmol). Treatment of the acid chloride with pyrid-2-ylamidoxime (1.37 g, 10 mmol) and triethylamine (4.04g, 40 mmol) in dichloromethane (10 mL), followed by heating in dimethylformamide (20 mL) at 120° C. for 2 hours afforded 497 mg (21%) 3-(2-pyridyl)-5-(5-hydroxy-pyrid-3-yl)-1,2,4-oxadiazole.

3-(2-Pyridyl)-5-(5-methoxypyrid-3-yl)-1,2,4-oxadiazole

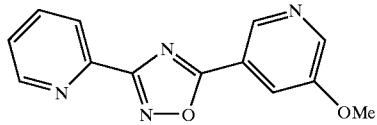
B72

In a similar fashion, 5-methoxynicotinoyl chloride was prepared from 5-methoxynicotinic acid hydrochloride (112.7 mg, 0.59 mmoles). Treatment of the acid chloride with pyrid-2-ylamidoxime (80.8 mg, 0.59 mmol) and triethylamine (0.3 mL) in dichloromethane (2 mL), followed by heating in dimethylformamide (1 mL) at 120° C. for 2.5 hours afforded 25 mg (17%) of 3-(2-pyridyl)-5-(5-methoxy-pyrid-3-yl)-1,2,4-oxadiazole.

3-(2-Pyridyl)-5-(3-cyano-5-methylphenyl)-1,2,4-oxadiazole

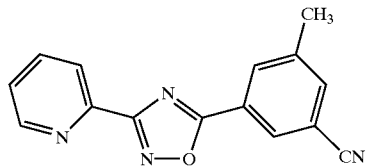
B73

A solution of 5-methylisophalonitrile (1.0 g, 7.03 mmol) in methanol (9 mL) at 64° C. was treated dropwise with a solution of 20% NaOH (0.78 g, 19.5 mmol). The reaction was stirred an additional 14 hours at this temperature. Work up and silica gel chromatography, afforded 0.420 g (37%) of 3-cyano-5-methylbenzamide. The intermediate amide (0.110 g, 0.69 mmol) was treated with 70 wt. % $H_2SO_4$ (3.75 mL) and sodium nitrite (0.071 g, 1.03 mmol) and the mixture stirred at 40° C. for 1 hour. The reaction was cooled and the precipitate collected to afford 0.0447 g (42%) of 3-methyl-5-cyanobenzoic acid.

Using the general procedure for the preparation of acid chlorides, 3-methyl-5-cyanobenzoyl chloride was prepared from 3-methyl-5-cyanobenzoic acid (0.0447 g, 0.28 mmol). The acid chloride and pyrid-2-ylamidoxime (0.038 g, 0.28 mmol) in N,N-dimethylformamide (4 mL) was heated in sealed tube at 120° C. for 12 hours. Standard work up and silica gel chromatography afforded 0.480 g (80%) of 3-(2-pyridyl)-5-(3-cyano-5-methylphenyl)-1,2,4-oxadiazole: $^1H$ NMR (CDCl$_3$), δ (ppm): 8.85 d, 1H), 8.36 (d, 2H), 8.22 (d, 1H), 7.89 (t, 1H), 7.70 (s, 1H), 7.48 (t, 1H), 2.52 (s, 3H),

3-(2-Pyridyl)-5-(3-fluoro-5-bromophenyl)-1,2,4-oxadiazole

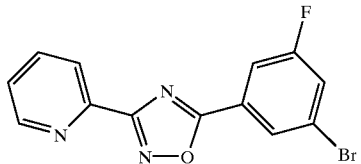
B74

Using the general procedure for the preparation of acid chlorides, 3-fluoro-5-bromobenzoyl chloride was prepared from 3-fluoro-5-bromobenzoic acid (300 mg, 1.369 mmol). The acid chloride was treated with pyrid-2-ylamidoxime (187.7 mg, 1.369 mmol) in pyridine (2 mL) and the mixture heated in sealed tube at 130° C. for 16 hours. After cooling, the reaction was treated with water and the solid collected by filtration. Recrystallization from ethanol afforded 168.3 mg (38%) of 3-(2-pyridyl)-5-(3-fluoro,5-bromophenyl)-1,2,4-oxadiazole: $^1H$-NMR (CDCl$_3$), δ (ppm): 8.82 (d, 1H), 8.25 (s, 1H), 8.21 (d, 1H), 7.92 (td, 2H), 7.50 (m, 2H).

3-(2-Pyridyl)-5-(3-iodo-5-bromophenyl)-1,2,4-oxadiazole

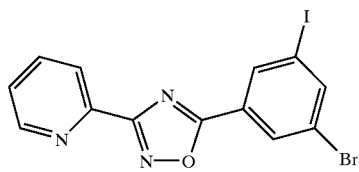
B75

Using the general procedure for the preparation of acid chlorides, 3-iodo-5-bromobenzoyl chloride was prepared from 3-iodo-5-bromobenzoic acid (1.0 g, 3.058 mmol). The acid chloride was treated with pyrid-2-ylamidoxime (419.3 mg, 3.058 mmol) in pyridine (5 mL) and the mixture heated in sealed tube at 130° C. for 16 hours. After cooling, the reaction was treated with water and the solid collected by filtration. Recrystallization from ethanol afforded 140 mg (10.7%) of 3-(2-pyridyl)-5-(3-iodo-5-bromophenyl)-1,2,4-oxadiazole: $^1H$-NMR (CDCl$_3$), δ (ppm): 8.84 (d, 1H), 8.57 (s, 1H), 8.42 (s, 1H), 8.22 (dd, 1H), 8.10 (s, 1H), 7.90 (t, 1H), 7.49 (td, 1H).

3-(5-Fluoro-2-pyridyl)-5-(3-fluoro-5-bromophenyl)-1,2,4-oxadiazole

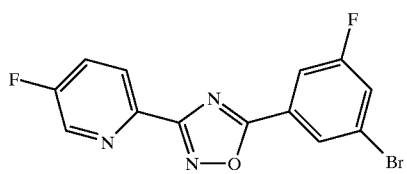
B76

Using the general procedure for the preparation of acid chlorides, 3-fluoro-5-bromobenzoyl chloride was prepared 3-fluoro-5-bromobenzoic acid (350 mg, 1.598 mmol). The acid chloride was treated 5-fluoropyrid-2-ylamidoxime (223 mg, 1.438 mmol) in dimethylformamide (5 mL) and the mixture heated in sealed tube at 130° C. for 16 hours. After cooling, the reaction was treated with water and the solid collected by filtration. Recrystallization from ethanol afforded 218 mg (45%) of 3-(5-fluoro-2-pyridyl)-5-(3-fluoro-5-bromophenyl)-1,2,4-oxadiazole: $^1H$-NMR (CDCl$_3$), δ (ppm): 8.70 (d, 1H), 8.28 (s, 1H), 8.27 (dd, 1H), 7.93 (td, 1H), 7.61 (td, 1H), 7.53 (td, 1H).

3-(2-Pyridyl)-5-(3-allyloxy-5-(methoxycarbonyl)phenyl)-1,2,4-oxadiazole

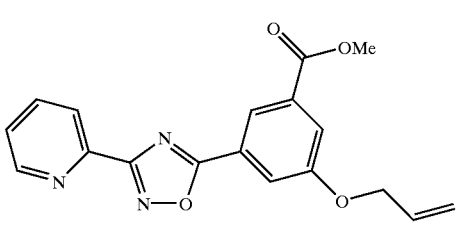
B77

Using the general procedure for the preparation of acid chlorides, 3-allyloxy-5-(methoxycarbonyl) benzoyl chloride was prepared from 3-allyloxy-5-(methoxycarbonyl)benzoic acid (3.24 g, 13.7 mmol). A solution of the acid chloride in dichloromethane (20 mL) at 0° C. was treated with pyrid-2-ylamidoxime (1.9 g, 13.9 mmol) and then stirred at ambient temperature for 2 hours. After this time, the reaction mixture was washed with water and saturated brine, dried over anhydrous sodium sulfate, filtered, and concentrated. The residue was dissolved in N,N-dimethylformamide (50 mL) and heated at 120° C. for 16 hours. Standard work up and silica gel chromatography using hexanes:ethyl acetate:dichloromethane (3.5:0.5:4) afforded 1.8 g (39%) of 3-(2-pyridyl)-5-(3-allyloxy-5-(methoxycarbonyl)phenyl)-1,2,4-oxadiazole: $^1$H NMR (DMSO): δ-8.81 (d, 1H), 8.28 (s, 1H), 8.20 (d, 1H), 8.07 (t, 1H), 7.94 (s, 1H), 7.76 (s, 1H), 7.66 (m, 2H), 6.09 (m, 1H), 5.47 (dd, 1H), 5.33 (dd, 1H), 4.81 (d, 2H), 3.93 (s, 3H).

3-(2-Pyridyl)-5-(3-iodo-5-(methoxycarbonyl)phenyl)-1,2,4-oxadiazole

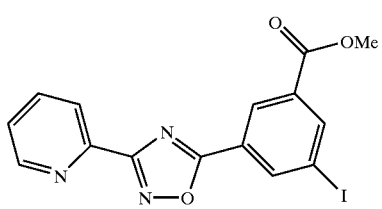
B78

Using the general procedure for the preparation of acid chlorides, 3-iodo-5-(methoxycarbonyl)benzoyl chloride was prepared from 3-iodo-5-(methoxycarbonyl)benzoic acid (1.7 g, 5.554 mmol). The acid chloride was treated with pyrid-2-ylamidoxime (0.685 g, 4.998 mmol) in dimethylformamide (10 mL) and the mixture heated in sealed tube at 130° C. for 16 hours. After cooling, the reaction was treated with water and the solid collected by filtration. Recrystallization from ethanol afforded 357 mg (17.8%) of 3-(2-pyridyl)-5-(3-iodo-5-(methoxycarbonyl)phenyl) -1,2,4-oxadiazole: $^1$H-NMR (CDCl$_3$), δ (ppm): 8.85 (s, 1H), 8.84 (m, 1H), 8.82 (m, 1H), 8.60 (s, 1H), 8.25 (dd, 1H), 7.91 (td, 1H), 7.50 (dd, 1H), 4.05 (s, 3H).

3-(2-Pyridyl)-5-(3-methoxy-5-(methoxycarbonyl)phenyl)-1,2,4-oxadiazole

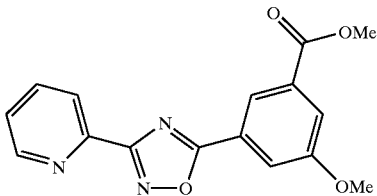
B79

Using the general procedure for the preparation of acid chlorides, 3-methoxy-5-(methoxycarbonyl)benzoyl chloride was prepared from 3-methoxy-5-(methoxycarbonyl)benzoic acid (400 mg, 1.9 mmol). The acid chloride in dichloromethane (20 mL) at 0° C. was treated with pyrid-2-ylamidoxime (261 mg, 1.9 mmol) and the mixture stirred at room temperature for 1 hour. The reaction mixture was then washed with water and saturated brine, dried over anhydrous sodium sulfate, filtered, and concentrated. The residue was dissolved in N,N-dimethylformamide (4 mL) and heated overnight at 110° C. Standard work up and silica gel chromatography using a mixture of hexane:ethyl acetate:dichloromethane (3:1:4) afforded 191.3 mg (32%) of 3-(2-pyridyl)-5-(3-methoxy-5-(methoxycarbonyl)phenyl)-1,2,4-oxadiazole: $^1$H NMR (CDCl$_3$): δ-8.86 (d, 1H), 8.55 (s, 1H), 8.25 (d, 1H), 7.99 (m, 1H), 7.90 (t, 1H), 7.82 (s, 1H), 7.47 (m, 1H), 3.98 (s, 3H), 3.96 (s, 3H).

3-(2-Pyridyl)-5-(3-bromo-5-cyanophenyl)-1,2,4-oxadiazole

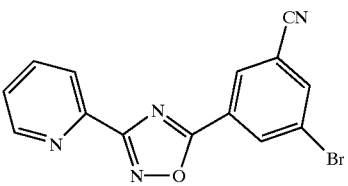
B80

Using the general procedure for the preparation of acid chlorides, 3-bromo-5-cyanobenzoyl chloride was prepared from 3-bromo-5-cyanobenzoic acid (1.6 g, 7.0 mmol). The acid chloride in dichloromethane (20 mL) at 0° C. was treated with pyrid-2-ylamidoxime (965 mg, 7.0 mmol) and the mixture stirred at room temperature for 2 hours. The reaction mixture was washed with water and saturated brine, dried over anhydrous sodium sulfate, filtered, and concentrated. The residue was dissolved in N,N-dimethylformamide (30 mL) and heated overnight at 110° C. Standard work up and silica gel chromatography using a mixture of hexane:ethyl acetate:dichloromethane (3:1:4) afforded 739 g (32%) of 3-(2-pyridyl)-5-(3-bromo-5-cyanophenyl)-1,2,4-oxadiazole: $^1$H NMR (CDCl$_3$): δ-8.87 (d, 1H), 8.70 (s, 1H), 8.52 (s, 1H), 8.23 (d, 1H), 8.03 (s, 1H), 7.92 (t, 1H), 7.51 (m, 1H).

3-(2-Pyridyl)-5-(5-cyano-3-iodophenyl)-1,2,4-oxadiazole

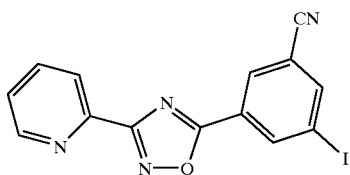

B81

Using the general procedure for the preparation of acid chlorides, 3-cyano-5-iodobenzoyl chloride was prepared from 3-cyano-5-iodobenzoic acid (570 mg, 2.1 mmol). The acid chloride in dichloromethane (5 mL) was treated with pyrid-2-ylamidoxime (287 mg, 2.1 mmol) and triethylamine (1 mL) and the mixture stirred for 1 hour at room temperature. The solvent was removed in vacuo, and the residue dissolved in N,N-dimethylformamide (5 mL). The mixture was heated overnight at 120° C. Removal of the solvent in vacuo, and trituration with 20% ethylacetate in hexane afforded 250 mg (32% yield) of 3-(2-pyridyl)-5-(5-cyano-3-iodophenyl)-1,2,4-oxadiazole: $^1$H-NMR (CDCl$_3$), δ ppm: 8.85 (m, 2H), 8.54 (s, 1H), 8.22 (d, 1H), 8.20 (s, 1H), 7.90 (t, 1H), 7.45 (m, 1H). GC/EI-MS gave m/z 374 (M$^+$)

3-(2-Pyridyl)-5-(3-N,N-dimethylaminophenyl)-1,2,4-oxadiazole

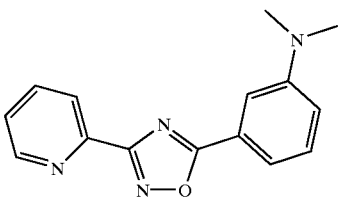

B82

Using the general procedure for the preparation of acid chlorides, 3-dimethylaminobenzoyl chloride was prepared from 3-dimethylaminobenzoic acid (632 mg, 3.1 mmol). The acid chloride in dichloromethane (20 mL) at 0° C. was treated with pyrid-2-ylamidoxime (430 mg, 3.1 mmol). The mixture was then stirred at room temperature for 2 hours. Standard work up afforded a residue which was dissolved in N,N-dimethylformamide (15 mL) and heated overnight at 110° C. After cooling, the solvent was removed in vacuo. The residue was dissolved in dichloromethane and then washed with water and saturated brine, dried over anhydrous sodium sulfate, filtered and concentrated. Silica gel chromatography using a mixture of hexane:ethyl acetate:dichloromethane (3:1:4) followed by trituration with 10% diethyl ether in hexane, afforded 27 mg (3%) of 3-(2-pyridyl)-5-(3-N,N-dimethylaminophenyl)-1,2,4-oxadiazole: $^1$H NMR (CDCl$_3$): δ-8.86 (d, 1H), 8.24 (d, 1H), 7.88 (t, 1H), 7.60 (m, 2H), 7.46 (m, 1H), 7.37 (m, 1H), 6.95 (d, 1H), 3.06 (s, 6H).

3-(5-Chloropyrid-2-yl)-5-(3-cyano-5-fluorophenyl)-1,2,4-oxadiazole

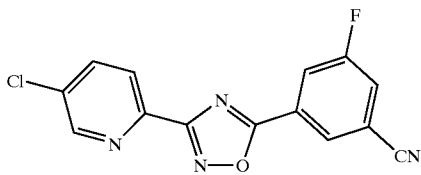

B83

Using the general procedure for the preparation of acid chlorides, 3-cyano-5-fluorobenzoyl chloride was prepared from 3-cyano-5-fluorobenzoic acid (0.10 g, 0.6 mMol). Treatment of the intermediate acid chloride in dichloromethane with 5-chloropyrid-2-ylamidoxime (0.103 g, 0.6 mMol) followed by heating in N,N-dimethylformamide overnight at 110° C. afforded crude product. Standard work up and purification by silica gel chromatography, and recrystallization afforded 30 mg (16%) 3-(5-chloropyrid-2-yl)-5-(3-cyano-5-fluorophenyl)-1,2,4-oxadiazole.

3-(5-Chloropyrid-2-yl)-5-(3-cyano-5-chlorophenyl)-1,2,4-oxadiazole

B84

Using the general procedure for the preparation of acid chlorides, 3-cyano-5-chlorobenzoyl chloride was prepared from 3-cyano-5-chlorobenzoic acid (0.10 g, 0.55 mMol). Treatment of the intermediate acid chloride in dichloromethane with 5-chloropyrid-2-ylamidoxime (0.094 g, 0.55 mMol) followed by heating in N,N-dimethylformamide overnight at 110° C. afforded crude product. Standard work up and purification by silica gel chromatography, and recrystallization afforded 4.5 mg (2.6%) 3-(5-chloropyrid-2-yl)-5-(3-cyano-5-chlorophenyl)-1,2,4-oxadiazole.

3-(5-Chloropyrid-2-yl)-5-(3-chloro-5-fluorophenyl)-1,2,4-oxadiazole

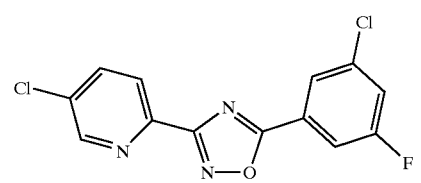

B85

Using the general procedure for the preparation of acid chlorides, 3-chloro-5-fluorobenzoyl chloride is prepared from 3-chloro-5-fluorobenzoic acid using a solution of oxalyl chloride in dichloromethane and a catalytic amount of N,N-dimethylformamide. Treatment of the intermediate acid chloride in dichloromethane with 1 equivalent of 5-chloropyrid-2-ylamidoxime followed by heating in N,N-dimethylformamide overnight at 110° C. affords crude product. Standard work up and purification by one or more methods, including silica gel chromatography, recystallization, and trituration, affords purified 3-(5-chloropyrid-2-yl)-5-(3-chloro-5-fluorophenyl)-1,2,4-oxadiazole.

3-(5-Chloropyrid-2-yl)-5-(3-cyano-5-methoxyphenyl)-1,2,4-oxadiazole

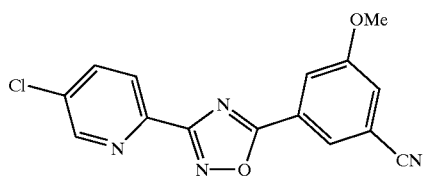

B86

Using the general procedure for the preparation of acid chlorides, 3-cyano-5-methoxybenzoyl chloride is prepared from 3-cyano-5-methoxybenzoic acid using a solution of oxalyl chloride in dichloromethane and a catalytic amount of N,N-dimethylformamide. Treatment of the intermediate acid chloride in dichloromethane with 1 equivalent of 5-chloropyrid-2-ylamidoxime followed by heating in N,N-dimethylformamide overnight at 110° C. affords crude product. Standard work up and purification by one or more methods, including silica gel chromatography, recystallization, and trituration, affords purified 3-(5-chloropyrid-2-yl)-5-(3-cyano-5-methoxyphenyl)-1,2,4-oxadiazole.

3-(5-Fluoropyrid-2-yl)-5-(3-cyano-5-chlorophenyl)-1,2,4-oxadiazole

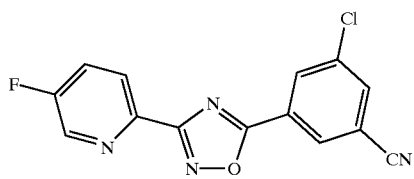

B87

Using the general procedure for the preparation of acid chlorides, 3-cyano-5-chlorobenzoyl chloride was prepared from 3-cyano-5-chlorobenzoic acid (0.10 g, 0.55 mMol). Treatment of the intermediate acid chloride in dichloromethane with 5-flouropyrid-2-ylamidoxime (0.086 g, 0.55 mMol) followed by heating in N,N-dimethylformamide overnight at 110° C. afforded crude product. Standard work up and purification by silica gel chromatography, and recrystallization afforded 1.8 mg (1%) 3-(5-fluoropyrid-2-yl)-5-(3-cyano-5-chlorophenyl)-1,2,4-oxadiazole.

3-(5-Fluoropyrid-2-yl)-5-(3-fluoro-5-chlorophenyl)-1,2,4-oxadiazole

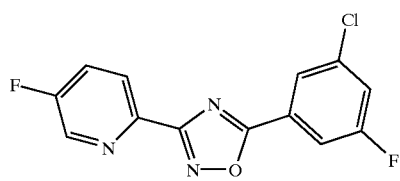

B88

Using the general procedure for the preparation of acid chlorides, 3-chloro-5-fluorobenzoyl chloride is prepared from 3-chloro-5-fluorobenzoic acid using a solution of oxalyl chloride in dichloromethane and a catalytic amount of N,N-dimethylformamide. Treatment of the intermediate acid chloride in dichloromethane with 1 equivalent of 5-fluoropyrid-2-ylamidoxime followed by heating in N,N-dimethylformamide overnight at 110° C. affords crude product. Standard work up and purification by one or more methods, including silica gel chromatography, recystallization, and trituration, affords purified 3-(5-fluororopyrid-2-yl)-5-(3-chloro-5-fluorophenyl)-1,2,4-oxadiazole.

3-(5-Fluoropyrid-2-yl)-5-(3-cyano-5-methoxyphenyl)-1,2,4-oxadiazole

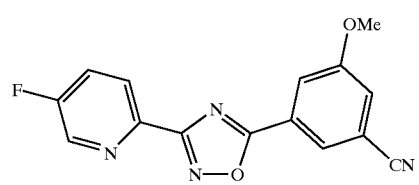

B89

Using the general procedure for the preparation of acid chlorides, 3-cyano-5-methoxybenzoyl chloride is prepared from 3-cyano-5-methoxybenzoic acid using a solution of oxalyl chloride in dichloromethane and a catalytic amount of N,N-dimethylformamide. Treatment of the intermediate acid chloride in dichloromethane with 1 equivalent of 5-fluoropyrid-2-ylamidoxime followed by heating in N,N-dimethylformamide overnight at 110° C. affords crude product. Standard work up and purification by one or more methods, including silica gel chromatography, recystallization, and trituration, affords purified 3-(5-fluororopyrid-2-yl)-5-(3-cyano-5-methoxyphenyl)-1,2,4-oxadiazole.

3-(5-Cyanopyrid-2-yl)-5-(3-cyano-5-chlorophenyl)-1,2,4-oxadiazole

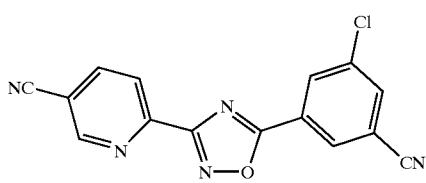

B90

Using the general procedure for the preparation of acid chlorides, 3-cyano-5-chlorobenzoyl chloride was prepared from 3-cyano-5-chlorobenzoic acid (0.10 g, 0.55 mMol). Treatment of the intermediate acid chloride in dichloromethane with 5-cyanopyrid-2-ylamidoxime (0.099 g, 0.55 mMol) followed by heating in N,N-dimethylformamide overnight at 110° C. afforded crude product. Standard work up and purification by silica gel chromatography, and recrystallization afforded 1.1 mg (0.65%) 3-(5-fluoropyrid-2-yl)-5-(3-cyano-5-chlorophenyl)-1,2,4-oxadiazole.

3-(5-Cyanopyrid-2-yl)-5-(3-fluoro-5-chlorophenyl)-1,2,4-oxadiazole

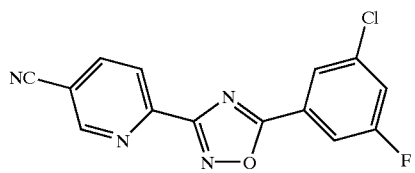

B91

Using the general procedure for the preparation of acid chlorides, 3-chloro-5-fluorobenzoyl chloride is prepared from 3-chloro-5-fluorobenzoic acid using a solution of oxalyl chloride in dichloromethane and a catalytic amount of N,N-dimethylformamide. Treatment of the intermediate acid chloride in dichloromethane with 1 equivalent of 5-cyanopyrid-2-ylamidoxime followed by heating in N,N-dimethylformamide overnight at 110° C. affords crude product. Standard work up and purification by one or more methods, including silica gel chromatography, recystallization, and trituration, affords purified 3-(5-cyanopyrid-2-yl)-5-(3-chloro-5-fluorophenyl)-1,2,4-oxadiazole.

3-(5-Cyanopyrid-2-yl)-5-(3-cyano-5-methoxyphenyl)-1,2,4-oxadiazole

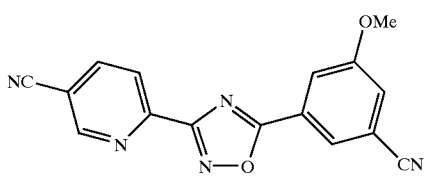

B92

Using the general procedure for the preparation of acid chlorides, 3-cyano-5-methoxybenzoyl chloride is prepared from 3-cyano-5-methoxybenzoic acid using a solution of oxalyl chloride in dichloromethane and a catalytic amount of N,N-dimethylformamide. Treatment of the intermediate acid chloride in dichloromethane with 1 equivalent of 5-cyanopyrid-2-ylamidoxime followed by heating in N,N-dimethylformamide overnight at 110° C. affords crude product. Standard work up and purification by one or more methods, including silica gel chromatography, recystallization, and trituration, affords purified 3-(5-cyanopyrid-2-yl)-5-(3-cyano-5-methoxyphenyl)-1,2,4-oxadiazole.

3-(5-Fluoropyrid-2-yl)-5-(3,5-di-cyanophenyl)-1,2,4-oxadiazole

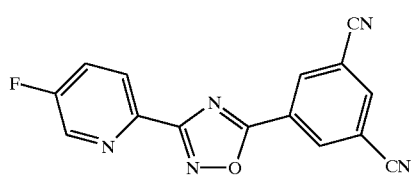

B93

Using the general procedure for the preparation of acid chlorides, 3,5-dicyanobenzoyl chloride is prepared from 3,5-dicyanobenzoic acid using a solution of oxalyl chloride in dichloromethane and a catalytic amount of N,N-dimethylformamide. Treatment of the intermediate acid chloride in dichloromethane with 1 equivalent of 5-fluoropyrid-2-ylamidoxime followed by heating in N,N-dimethylformamide overnight at 110° C. affords crude product. Standard work up and purification by one or more methods, including silica gel chromatography, recystallization, and trituration, affords purified 3-(5-fluoropyrid-2-yl)-5-(3,5-dicyanophenyl)-1,2,4-oxadiazole.

3-(3-(4-Dimethylaminobutoxy)-pyrid-2-yl)-5-(3-cyano-5-fluorophenyl)-1,2,4-oxadiazole

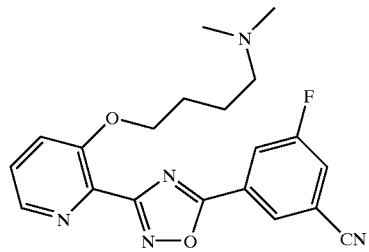

B94

Using the general procedure for the preparation of acid chlorides, 3-cyano-5-fluorobenzoyl chloride is prepared from 3-cyano-5-fluorobenzic acid using a solution of oxalyl chloride in dichloromethane and a catalytic amount of N,N-dimethylformamide. Treatment of the intermediate acid chloride in dichloromethane with 1 equivalent of 3-(4-dimethylaminobutoxy)pyrid-2-ylamidoxime followed by heating in N,N-dimethylformamide overnight at 110° C. affords crude product. Standard work up and purification by one or more methods, including silica gel chromatography, recystallization, trituration, and reversed-phase high-performance liquid chromatography (RP-HPLC) affords purified 3-(3-(4-dimethylaminobutoxy)-pyrid-2-yl)-5-(3-cyano-5-fluorophenyl)-1,2,4-oxadiazole.

Alternatively, treatment of 3-(3-fluoropyrid-2-yl)-5-(3-fluoro-5-cyanophenyl)-1,2,4-oxadiazole with potassium 4-dimethylaminobutoxide in N.N-dimethylformamide with a catalytic amount of 1,4,7,10,13,16-hexaoxacyclooctadecane (18-crown-6) and heating at 110° C. affords crude product. Standard work up and purification by one or more methods, including silica gel chromatography, recystallization, trituration, and reversed-phase high-performance liquid chromatography (RP-HPLC) affords purified 3-(3-(4-dimethylaminobutoxy)-pyrid-2-yl)-5-(3-cyano-5-fluorophenyl)-1,2,4-oxadiazole.

3-(3-(5-Dimethylaminopentyloxy)-pyrid-2-yl)-5-(3-Cyano-5-fluorophenyl)-1,2,4-oxadiazole

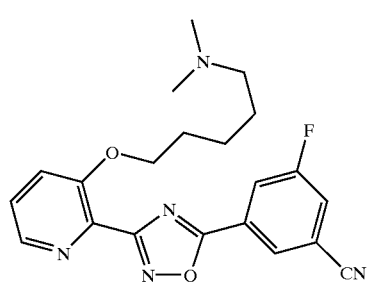

B95

Using the general procedure for the preparation of acid chlorides, 3-cyano-5-fluorobenzoyl chloride is prepared from 3-cyano-5-fluorobenzic acid using a solution of oxalyl chloride in dichloromethane and a catalytic amount of N,N-dimethylformamide. Treatment of the intermediate acid chloride in dichloromethane with 1 equivalent of 3-(5-dimethylaminopentyloxy)pyrid-2-ylamidoxime followed by heating in N,N-dimethylformamide overnight at 110° C. affords crude product. Standard work up and purification by one or more methods, including silica gel chromatography, recystallization, trituration, and reversed-phase high-performance liquid chromatography (RP-HPLC) affords purified 3-(3-(5-dimethylaminopentyloxy)-pyrid-2-yl)-5-(3-cyano-5-fluorophenyl)-1,2,4-oxadiazole.

Alternatively, treatment of 3-(3-fluoropyrid-2-yl)-5-(3-fluoro-5-cyanophenyl)-1,2,4-oxadiazole with potassium 5-dimethylaminopentyloxide in N.N-dimethylformamide with a catalytic amount of 1, 4, 7, 10, 13, 16-hexaoxacyclooctadecane (18-crown-6) and heating at 110° C. affords crude product. Standard work up and purification by one or more methods, including silica gel chromatography, recystallization, trituration, and reversed-phase high-performance liquid chromatography (RP-HPLC) affords purified 3-(3-(5-dimethylaminopentyloxy)-pyrid-2-yl)-5-(3-cyano-5-fluorophenyl)-1,2,4-oxadiazole.

3-(3-(6-Dimethylaminohexyloxy)-pyrid-2-yl)-5-(3-cyano-5-fluorophenyl)-1,2,4-oxadiazole

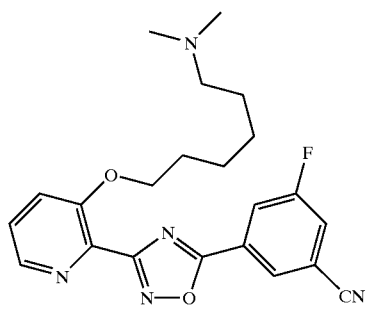

B96

Using the general procedure for the preparation of acid chlorides, 3-cyano-5-fluorobenzoyl chloride is prepared from 3-cyano-5-fluorobenzic acid using a solution of oxalyl chloride in dichloromethane and a catalytic amount of N,N-dimethylformamide. Treatment of the intermediate acid chloride in dichloromethane with 1 equivalent of 3-(6-dimethylaminohexyloxy)pyrid-2-ylamidoxime followed by heating in N,N-dimethylformamide overnight at 110° C. affords crude product. Standard work up and purification by one or more methods, including silica gel chromatography, recystallization, trituration, and reversed-phase high-performance liquid chromatography (RP-HPLC) affords purified 3-(3-(6-dimethylaminohexyloxy)-pyrid-2-yl)-5-(3-cyano-5-fluorophenyl)-1,2,4-oxadiazole.

Alternatively, treatment of 3-(3-fluoropyrid-2-yl)-5-(3-fluoro-5-cyanophenyl)-1,2,4-oxadiazole with potassium 6-dimethylaminohexyloxide in N.N-dimethylformamide with a catalytic amount of 1,4,7,10,13,16-hexaoxacyclooctadecane (18-crown-6) and heating at 110° C. affords crude product. Standard work up and purification by one or more methods, including silica gel chromatography, recystallization, trituration, and reversed-phase high-performance liquid chromatography (RP-HPLC) affords purified 3-(3-(6-dimethylaminohexyloxy)-pyrid-2-yl)-5-(3-cyano-5-fluorophenyl)-1,2,4-oxadiazole.

3-(5-Fluoropyrid-2-yl)-5-(5-fluoro-3-(thiomethyl)phenyl)-1,2,4-oxadiazole

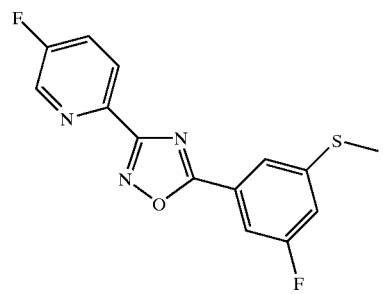

B153

Using the general procedure for the preparation of acid chlorides 5-fluoro-3-(thiomethyl)benzoyl chloride was prepared from 5-fluoro-3-(thiomethyl)benzoic acid using a solution of oxalyl chloride in dichloromethane and a catalytic amount of N,N-dimethylformamide. Treatment of the intermediate acid chloride in dichloromethane with 1 equivalent of 5-fluoropyrid-2-ylamidoxime followed by heating in N,N-dimethylformamide overnight at 110° C. afforded crude product. Standard work up and purification by silica gel chromatography afforded the purified title compound in 52 mg yield (64%) as a colourless solid.

5-(2-Pyridyl)-3-[3-(1H-imidazol-1-yl)-5-Fluorophenyl)]-1,2,4-oxadiazole

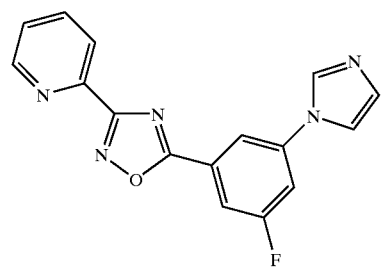

B154

Using the general procedure for the preparation of acid chlorides 3-fluoro-5-(1H-imidazol-1-yl)benzoyl chloride was prepared from 3-fluoro-5-(1H-imidazol-1-yl)benzoic acid using a solution of oxalyl chloride in dichloromethane and a catalytic amount of N,N-dimethylformamide. Treatment of the intermediate acid chloride in dichloromethane with 1 equivalent of 2-pyridylamidoxime followed by heating in N,N-dimethylformamide overnight at 110° C. afforded crude product. Standard work up and purification by silica gel chromatography followed by preperative reversed-phase HPLC afforded the title compound in 6.9 mg yield (5% over 4 steps) as a colourless solid.

3-(2-Pyridyl)-5-(3-cyano-5-trifluoromethylphenyl)-1,2,4-oxadiazole

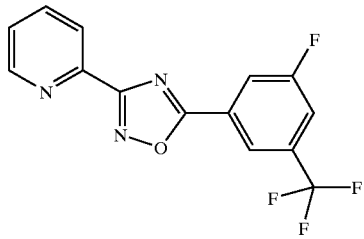

B155

3-Fluoro-5-trifluoromethylbenzoyl chloride (0.11 mL, 0.73 mmol) was added in a dropwise manner to a solution of pyridylamidoxime (99.3 mg, 0.73 mmol) in dichloromethane (10 mL) under argon. The reaction mixture was stirred at room temperature for 10 minutes and the solvent was removed in vacuo. DMF (4 ml) was added to the oily residue and the resulting solution was stirred at 120° C. for 16 h under argon. After the reaction mixture was cooled to room temperature, the solvent was removed in vacuo. Flash chromatography on silica gel (15%–20% ethyl acetate in hexanes) yielded 150 mg (66.9%, GC/MS product RT 7.59 min, 98% purity) of 3-(2-pyridyl)-5-(3-cyano-5-trifluoromethylphenyl)-1,2,4-oxadiazole. $^1$H-NMR (CDCl$_3$), δ (ppm): 8.86 (d, 1H), 8.40 (s, 1H), 8.24 (d, 1H), 8.18 (d, 1H), 7.90 (dt, 1H), 7.59 (d, 1H), 7.49 (m, 1H).

3-(5-Fluoro-2-pyridyl)-5-(3-fluoro-5-trifluoromethylphenyl)-1,2,4-oxadiazole

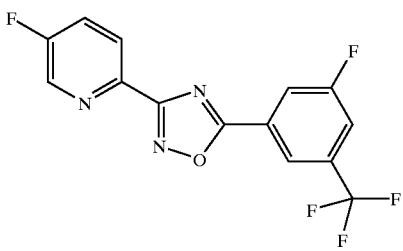

B156

3-Fluoro-5-trifluoromethylbenzoyl chloride (0.10 mL, 0.65 mmol) was added to a solution of 5-fluoropyridylamidoxime (102.9 mg, 0.66 mmol) in dichloromethane (2 mL). The solution was stirred at room temperature for 10 minutes and then concentrated in vacuo. DMF (4 mL) was added to the residue and the resulting solution was stirred at 120° C. for 16 h under argon. After the reaction mixture was cooled to room temperature, the solvent was removed in vacuo. Flash chromatography on silica gel (10%–20% ethyl acetate in hexane) yielded 131.1 mg (62.5%, GC/MSproduct RT 7.34 min, 96% pure) of 3-(5-fluoro-2-pyridyl)-5-(3-fluoro-5-trifluoromethylphenyl)-1,2,4-oxadiazole. $^1$H-NMR (CDCl$_3$), δ (ppm): 8.70 (d, 1H), 8.38 (s, 1H), 8.28 (dd, 1H), 8.17 (d, 1H), 7.60 (dt, 2H).

3-(5-Cyanopyrid-2-yl)-5-(3-alloxy-5-cyanophenyl)-1,2,4-oxadiazole

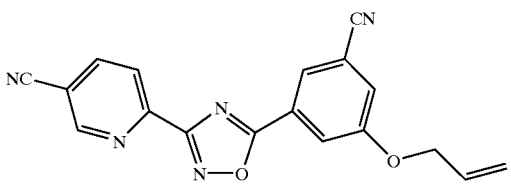

B157

Using the general procedure for the preparation of acid chlorides, 3-allyloxy-5-cyanobenzoyl chloride was prepared from 3-allyloxy-5-cyanobenzoic acid (203 mg, 1.0 mmol). A solution of the acid chloride in dichloromethane (2 mL) at 0° C. was treated with 5-cyanopyrid -2-ylamidoxime (162 mg, 1.0 mmol) and triethylamine (418 μL, 3.0 mmol) and then stirred at ambient temperature for 1 hour. The reaction mixture was washed with water and saturated brine, dried over anhydrous sodium sulfate, filtered, and concentrated. The residue was dissolved in N,N-dimethylformamide (5 mL) and heated at 120° C. for 16 hours. Standard work up and silica gel chromatography using hexanes:ethyl acetate: dichloromethane (3.5:0.5:4) afforded 131 mg (40%) of 3-(5-cyanopyrid-2-yl)-5-(3-allyloxy-5-cyanophenyl)-1,2,4-oxadiazole: $^1$H NMR (CDCl$_3$), δ (ppm): 9.11 (d, 1H), 8.39 (d, 1H), 8.22 (s, 1H), 8.21 (d, 1H), 8.01 (s, 1H), 7.42 (s, 1H), 6.05 (m, 1H), 4.48 (dd, 1H), 4.40 (dd, 1H), 4.69 (d, 2H).

3-(5-fluoropyrid-2-yl)-5-(3-alloxy-5-cyanophenyl)-1,2,4-oxadiazole

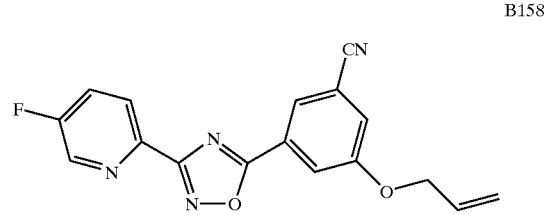

B158

Using the general procedure for the preparation of acid chlorides, 3-allyloxy-5-cyanobenzoyl chloride was prepared from 3-allyloxy-5-cyanobenzoic acid (203 mg, 1.0 mmol). A solution of the acid chloride in dichloromethane (2 mL) at 0° C. was treated with 5-fluoropyrid -2-ylamidoxime (155 mg, 1.0 mmol) and triethylamine (418 μL, 3.0 mmol) and then stirred at ambient temperature for 1 hour. The reaction mixture was washed with water and saturated brine, dried over anhydrous sodium sulfate, filtered, and concentrated. The residue was dissolved in N,N-dimethylformamide (5 mL) and heated at 120° C. for 16 hours. Standard work up and silica gel chromatography using hexanes:ethyl acetate: dichloromethane (3.5:0.5:4) afforded 59 mg (18%) of 3-(5-fluoropyrid-2-yl)-5-(3-allyloxy-5-cyanophenyl)-1,2,4-oxadiazole: $^1$H NMR (CDCl$_3$), δ (ppm): 8.70 (d, 1H), 8.27 (m, 1H), 8.15 (s, 1H), 8.01 (s, 1H), 7.62 (m, 1H), 7.41 (s, 1H), 6.04 (m, 1H), 5.48 (dd, 1H), 5.34 (dd, 1H), 4.69 (d, 2H).

3-(5-Cyanopyrid-2-yl)-5-(3-cyano-5-propoxyphenyl)-1,2,4-oxadiazole

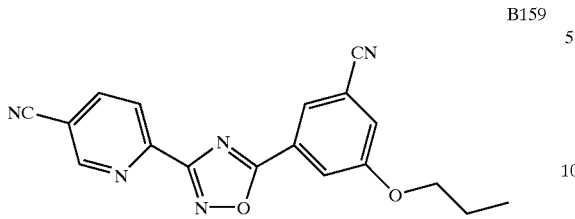

B159

Using the general procedure for the preparation of acid chlorides, 3-cyano-5-propoxybenzoyl chloride was prepared from 3-cyano -5-propoxybenzoic acid (205 mg, 1.0 mmol). A solution of the acid chloride in dichloromethane (2 mL) at 0° C. was treated with 5-cyanopyrid -2-ylamidoxime (162 mg, 1.0 mMol) and triethylamine (418 µL, 3.0 mmol) and then stirred at ambient temperature for 1 hour. The reaction mixture was washed with water and saturated brine, dried over anhydrous sodium sulfate, filtered, and concentrated. The residue was dissolved in N,N-dimethylformamide (5 mL) and heated at 120° C. for 16 hours. Standard work up and silica gel chromatography using hexanes:ethyl acetate: dichloromethane (3.7:0.3:4) afforded 65 mg (20%) of 3-(5-cyanopyrid-2-yl)-5-(3-cyano-5-propoxyphenyl)-1,2,4-oxadiazole: $^1$H NMR (CDCl$_3$), δ (ppm): 9.11 (s, 1H), 8.39 (d, 1H), 8.22 (d, 1H), 8.13 (s, 1H), 7.99 (s, 1H), 7.42 (s, 1H), 4.06 (t, 2H), 1.89 (m, 2H), 1.09 (s, 3H).

3-(5-Fluoropyrid-2-yl)-5-(3-cyano-5-propoxyphenyl)-1,2,4-oxadiazole

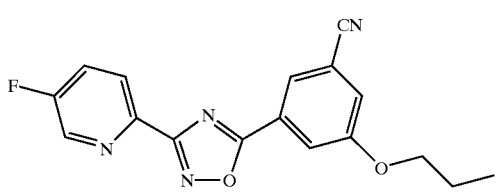

B160

Using the general procedure for the preparation of acid chlorides, 3-cyano-5-propoxybenzoyl chloride was prepared from 3-cyano-5-propoxybenzoic acid (205 mg, 1.0 mmol). A solution of the acid chloride in dichloromethane (2 mL) at 0° C. was treated with 5-fluoropyrid-2-ylamidoxime (155 mg, 1.0 mMol) and triethylamine (418 µL, 3.0 mMol) and then stirred at ambient temperature for 1 hour. The reaction mixture was washed with water and saturated brine, dried over anhydrous sodium sulfate, filtered, and concentrated. The residue was dissolved in N,N-dimethylformamide (5 mL) and heated at 120° C. for 16 hours. Standard work up and silica gel chromatography using hexanes:ethyl acetate: dichloromethane (3.7:0.3:4) afforded 120 mg (37%) of 3-(5-fluoropyrid-2-yl)-5-(3-cyano-5-propoxyphenyl)-1,2,4-oxadiazole: $^1$H NMR (CDCl$_3$), δ (ppm): 8.70 (d, 1H), 8.27 (m, 1H), 8.12 (s, 1H), 7.99 (s, 1H), 7.62 (m, 1H), 7.39 (s, 1H), 4.06 (t, 2H), 1.88 (m, 2H), 1.08 (s, 3H).

3-(2-Pyridyl)-5-(3-cyano-5-nitrophenyl)-1,2,4-oxadiazole

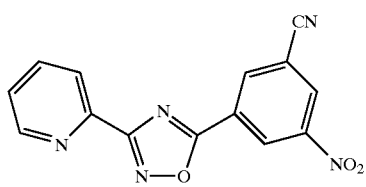

B161

Using the general procedure for the preparation of acid chlorides, 3-cyano-5-nitrobenzoyl chloride was prepared from 3-cyano-5-nitrobenzoic acid (1.0 g, 5.1 mmol). A solution of the acid chloride in dichloromethane (5 mL) at 0° C. was treated with pyrid-2-ylamidoxime (700 mg, 5.1 mMol) and triethylamine (2.1 mL, 15.3 mmol) and then stirred at ambient temperature for 1 hour. The reaction mixture was washed with water and saturated brine, dried over anhydrous sodium sulfate, filtered, and concentrated. The residue was dissolved in N,N-dimethylformamide (5 mL) and heated at 110° C. for 4 hours. Standard work up and silica gel chromatography using hexanes:ethyl acetate: dichloromethane (3.5:0.5:4) afforded 149 mg (50%) of 3-(2-pyridyl)-5-(3-cyano-5-nitrophenyl)-1,2,4-oxadiazole: $^1$H NMR (CDCl$_3$), δ (ppm): 9.35 (d, 1H), 8.91 (s, 1H), 8.89 (d, 1H), 8.75 (s,1H), 8.26 (d, 1H), 7.94 (m, 1H), 7.53 (m, 1H).

3-(5-fluoropyrid-2-yl)-5-(3-cyano-5-nitrophenyl)-1,2,4-oxadiazole

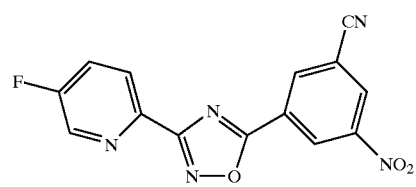

B162

Using the general procedure for the preparation of acid chlorides, 3-cyano-5-nitrobenzoyl chloride was prepared from 3-cyano-5-nitrobenzoic acid (1.0 g, 5.1 mmol). A solution of the acid chloride in dichloromethane (5 mL) at 0° C. was treated with 5-fluoropyrid-2-ylamidoxime (791 mg, 5.1 mMol) and triethylamine (2.1 mL, 15.3 mmol) and then stirred at ambient temperature for 1 hour. The reaction mixture was washed with water and saturated brine, dried over anhydrous sodium sulfate, filtered, and concentrated. The residue was dissolved in N,N-dimethylformamide (5 mL) and heated at 110° C. for 4 hours. Standard work up and silica gel chromatography using hexanes:ethyl acetate: dichloromethane (3.5:0.5:4) afforded 131 mg (8%) of 3-(5-fluoropyrid-2-yl)-5-(3-cyano-5-nitrophenyl)-1,2,4-oxadiazole: $^1$H NMR (CDCl$_3$), δ (ppm): 9.34 (s, 1H), 8.89 (s, 1H), 8.74 (d, 2H), 8.30 (m, 1H), 7.66 (m, 1H).

3-(5-fluoropyrid-2-yl)-5-(3-cyano-5-dimethylaminophenyl)-1,2,4-oxadiazole

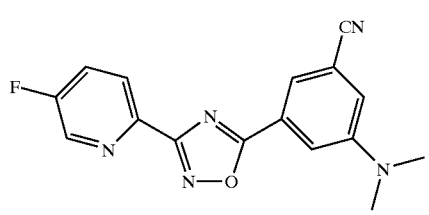

B163

Using the general procedure for the preparation of acid chlorides, 3-cyano-5-dimethylaminobenzoyl chloride was prepared from 3-cyano-5-dimethylaminobenzoic acid (190 mg, 1.0 mmol). A solution of the acid chloride in dichloromethane (3 mL) at 0° C. was treated with 5-fluoropyrid-2-ylamidoxime (155 mg, 1.0 mmol) and triethylamine (697 µL, 5.0 mmol) and then stirred at ambient temperature for 1 hour. The reaction mixture was washed with water and saturated brine, dried over anhydrous sodium sulfate, filtered, and concentrated. The residue was dissolved in N,N-dimethylformamide (5 mL) and heated at 120° C. for 16 hours. After cooling, water was added to the reaction mixture and then the precipitate was collected and dried. Filtration through silica gel using dichloromethane followed by trituration with dichloromethane afforded 14 mg (5%) of 3-(5-fluoropyrid-2-yl)-5-(3-cyano-5-dimethylaminophenyl)-1,2,4-oxadiazole: $^1$H NMR (CDCl$_3$), δ (ppm): 8.70 (d, 1H), 8.27 (m, 1H), 7.81 (s, 1H), 7.70 (s, 1H), 7.62 (m, 1H), 7.08 (s, 1H), 3.11 (s, 6H).

3-(5-fluoropyrid-2-yl)-5-(3-cyano-5-(2-methoxyethoxy)phenyl)-1,2,4-oxadiazole

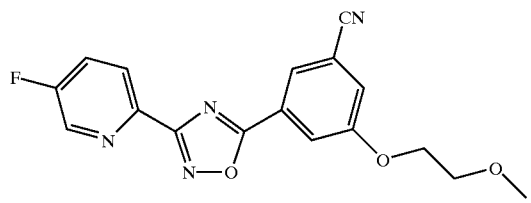

B164

Using the general procedure for the preparation of acid chlorides, 3-cyano-5-(2-methoxyethoxy)benzoyl chloride was prepared from 3-cyano-5-(2-methoxyethoxy)benzoic acid (221 mg, 1.0 mmol). A solution of the acid chloride in dichloromethane (2 mL) at 0° C. was treated with 5-fluoropyrid-2-ylamidoxime (155 mg, 1.0 mmol) and triethylamine (418 µL, 3.0 mmol) and then stirred at ambient temperature for 1 hour. The reaction mixture was washed with water and saturated brine, dried over anhydrous sodium sulfate, filtered, and concentrated. The residue was dissolved in N,N-dimethylformamide (2 mL) and heated at 120° C. for 16 hours. After cooling, water was added to the reaction mixture and then the precipitate was collected and dried. Silica gel chromatography using 40% ethyl acetate/hexanes followed by trituration with diethyl ether afforded 169 mg (50%) of 3-(5-fluoropyrid-2-yl)-5-(3-cyano-5-(2-methoxyethoxy)phenyl)-1,2,4-oxadiazole: $^1$H NMR (CDCl$_3$), δ (ppm): 8.70 (d, 1H), 8.27 (m, 1H), 8.15 (s, 1H), 8.03 (s, 1H), 7.62 (m, 1H), 7.44 (s, 1H), 4.27 (t, 2H), 3.81 (t, 2H), 3.48 (s, 3H).

3-(5-fluoropyrid-2-yl)-5-(3-cyano-5-(1H-imidazol-1-ylmethyl)phenyl)-1,2,4-oxadiazole

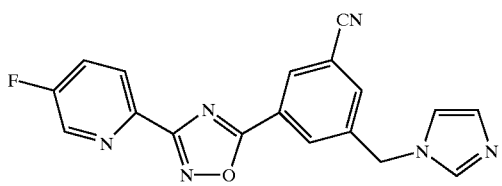

B165

Using the general procedure for the preparation of acid chlorides, 3-cyano-5-(1 H-imidazol-1-yl-methyl)benzoyl chloride was prepared from 3-cyano-5-(1H-imidazol-1-yl-methyl)benzoic acid (140 mg, 0.62 mmol). A solution of the acid chloride in dichloromethane (2 mL) at 0° C. was treated with 5-fluoropyrid-2-ylamidoxime (96 mg, 0.62 mmol) and triethylamine (258 µL, 1.9 mmol) and then stirred at ambient temperature for 1 hour. The reaction mixture was washed with water and saturated brine, dried over anhydrous sodium sulfate, filtered, and concentrated. The residue was dissolved in N,N-dimethylformamide (2 mL) and heated at 120° C. for 16 hours. After cooling, water was added to the reaction mixture and then the precipitate was collected and dried. Silica gel chromatography using 40% ethyl acetate/hexanes followed by trituration with diethyl ether afforded 4 mg (2%) of 3-(5-fluoropyrid-2-yl)-5-(3-cyano-5-(1H-imidazol-1-ylmethyl)phenyl)-1,2,4-oxadiazole: $^1$H NMR (CDCl$_3$), δ (ppm): 8.71 (d, 1H), 8.53 (s, 1H), 8.33 (s, 1H), 8.28 (m, 1H), 7.63 (m, 3H), 7.21 (s, 1H), 6.97 (s, 1H), 5.30 (s, 2H).

3-(2-Pyridyl)-5-(3-cyano-5-(methoxymethyl)phenyl)-1,2,4-oxadiazole

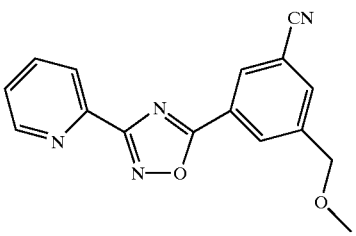

B166

Using the general procedure for the preparation of acid chlorides, 3-cyano-5-(methoxymethyl)benzoyl chloride was prepared from 3-cyano-5-(methoxymethyl)benzoic acid (157 mg, 0.82 mmol). A solution of the acid chloride in dichloromethane (2 mL) at 0° C. was treated with pyrid-2-ylamidoxime (113 mg, 0.82 mmol) and triethylamine (343 µL, 2.5 mmol) and then stirred at ambient temperature for 3 hours. The reaction mixture was washed with water and saturated brine, dried over anhydrous sodium sulfate, filtered, and concentrated. The residue was dissolved in N,N-dimethylformamide (2 mL) and heated at 120° C. for 16 hours. After cooling, water was added to the reaction mixture and the precipitate that formed was collected and dried. The solid was dissolved in dichloromethane and silica gel was added to the solution to remove the dark color. The silica gel was then filtered off and the filtrate was concentrated to dryness. Trituration of the residue with diethyl ether afforded 44 mg (18%) of 3-(2-pyridyl)-5-(3-cyano-5-(methoxymethyl)phenyl)-1,2,4-oxadiazole as a white solid: $^1$H NMR (CDCl$_3$), δ (ppm): 8.87 (d, 1H), 8.50 (s, 2H), 8.23

(d, 1H), 7.94 (m, 1H), 7.89 (s, 1H), 7.50 (m, 1H), 4.59 (s, 2H), 3.49 (s, 3H).

3-(3-cyano-5-methoxyphenyl)-5-(2-pyridyl)-1,2,4-oxadiazole

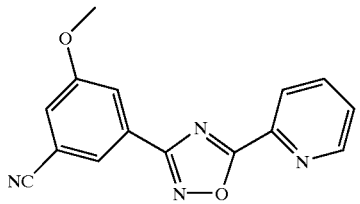

B167

Using the general procedure for the preparation of acid chlorides, picolinoyl chloride was prepared from picolinic acid (300 mg, 2.4 mmol). A solution of the acid chloride in dichloromethane (2 mL) at 0° C. was treated with of 3-cyano-5-methoxyphenyl-amidoxime (100 mg, 0.52 mmol) and triethylamine (1.0 mL, 7.2 mmol) and then stirred at ambient temperature for 1 hour. The reaction mixture was washed with water and saturated brine, dried over anhydrous sodium sulfate, filtered, and concentrated. The residue was dissolved in N,N-dimethylformamide (2 mL) and heated at 120° C. for 16 hours. Standard work up and silica gel chromatography using 10–20% ethyl acetate/hexanes followed by trituration with hexanes afforded 10 mg (7%) of 3-(3-cyano-5-methoxyphenyl)-5-(2-pyridyl)-1,2,4-oxadiazole: $^1$H NMR (CDCl$_3$), δ (ppm): 8.90 (d, 1H), 8.32 (d, 1H), 8.13 (s, 1H), 7.98 (m, 2H), 7.58 (dd, 1H), 7.31 (s, 1H), 3.94 (s, 3H).

3-(3-Cyano-5-methoxyphenyl)-5-(5-fluoropyrid-2-yl)-1,2,4-oxadiazole

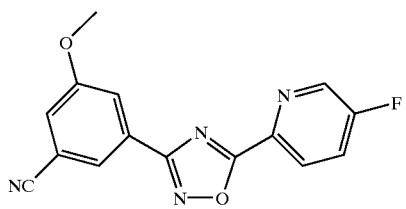

B168

Using the general procedure for the preparation of acid chlorides, 5-fluoro-picolinoyl chloride was prepared from 5-fluoro-picolinic acid hydrochloride (177 mg, 1.0 mmol). A solution of the acid chloride in dichloromethane (2 mL) at 0° C. was treated with of 3-cyano-5-methoxyphenyl-amidoxime (100 mg, 0.52 mmol) and triethylamine (418 μL, 3.0 mmol) and then stirred at ambient temperature for 1 hour. The reaction mixture was washed with water and saturated brine, dried over anhydrous sodium sulfate, filtered, and concentrated. The residue was dissolved in N,N-dimethylformamide (2 mL) and heated at 120° C. for 16 hours. Standard work up and silica gel chromatography using 10–20% ethyl acetate/hexanes followed by trituration with diethyl ether/hexanes afforded 20 mg (19%) of 3-(3-cyano-5-methoxyphenyl)-5-(5-fluoropyrid-2-yl)-1,2,4-oxadiazole: $^1$H NMR (CDCl$_3$), δ (ppm): 8.75 (s, 1H), 8.40 (dd, 1H), 8.13 (s, 1H), 7.96 (s, 1H), 7.68 (m, 1H), 7.38 (s, 1H), 3.94 (s, 3H).

3-(5-fluoropyrid-2-yl)-5-(3-cyano-5-ethoxyphenyl)-1,2,4-oxadiazole

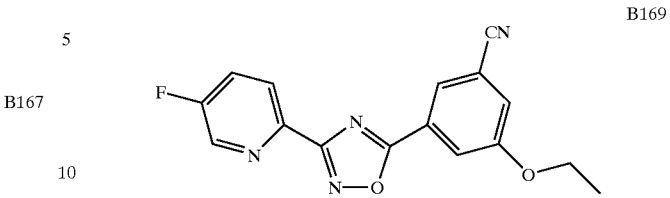

B169

Using the general procedure for the preparation of acid chlorides, 3-cyano-5-ethoxybenzoyl chloride was prepared from 3-cyano-5-ethoxybenzoic acid (145 mg, 0.75 mmol). A solution of the acid chloride in dichloromethane (2 mL) at 0° C. was treated with 5-fluoropyrid-2-ylamidoxime (117 mg, 0.75 mmol) and triethylamine (315 μL, 2.26 mmol) and then stirred at ambient temperature for 1 hour. The reaction mixture was washed with water and saturated brine, dried over anhydrous sodium sulfate, filtered, and concentrated. The residue was dissolved in N,N-dimethylformamide (2 mL) and heated at 120° C. for 16 hours. Standard work up and silica gel chromatography using 5–20% ethyl acetate/hexanes followed by trituration with diethyl ether afforded 54 mg (23%) of 3-(5-fluoropyrid-2-yl)-5-(3-cyano-5-ethoxyphenyl)-1,2,4-oxadiazole: $^1$H NMR (CDCl$_3$), δ (ppm): 8.69 (d, 1H), 8.26 (dd, 1H), 8.12 (s, 1H), 7.97 (s, 1H), 7.60 (m, 1H), 7.38 (s, 1H), 4.16 (q, 2H), 1.49 (t, 3H).

3-(5-Cyanopyrid-2-yl)-5-(3-cyano-5-ethoxyphenyl)-1,2,4-oxadiazole

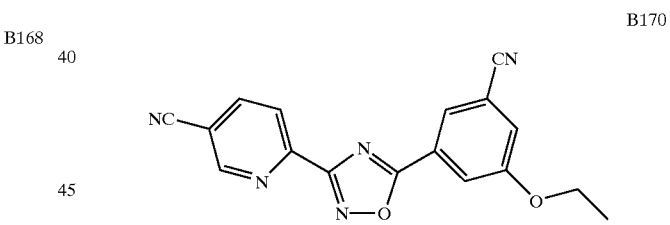

B170

Using the general procedure for the preparation of acid chlorides, 3-cyano-5-ethoxybenzoyl chloride was prepared from 3-cyano-5-ethoxybenzoic acid (145 mg, 0.75 mmol). A solution of the acid chloride in dichloromethane (2 mL) at 0° C. was treated with 5-cyanopyrid-2-ylamidoxime (122 mg, 0.75 mmol) and triethylamine (315 μL, 2.3 mmol) and then stirred at ambient temperature for 1 hour. The reaction mixture was washed with water and saturated brine, dried over anhydrous sodium sulfate, filtered, and concentrated. The residue was dissolved in N,N-dimethylformamide (2 mL) and heated at 120° C. for 16 hours. Standard work up and silica gel chromatography using 5–20% ethyl acetate/hexanes followed by trituration with diethyl ether afforded 85 mg (35%) of 3-(5-cyanopyrid-2-yl)-5-(3-cyano-5-ethoxyphenyl)-1,2,4-oxadiazole: $^1$H NMR (CDCl$_3$), δ (ppm): 9.11 (s, 1H), 8.38 (d, 1H), 8.20 (dd, 1H), 8.13 (s, 1H), 7.98 (d, 1H), 7.40 (s, 1H), 4.17 (q, 2H), 1.50 (t, 3H).

151

3-(5-Chloropyrid-2-yl)-5-(3-allyloxoy-5-cyanophenyl)-1,2,4-oxadiazole

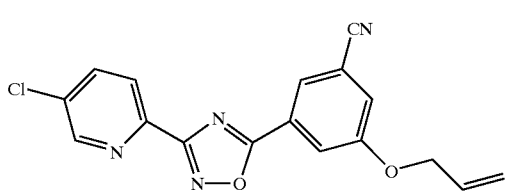

B171

Using the general procedure for the preparation of acid chlorides, 3-allyloxy-5-cyanobenzoyl chloride was prepared from 3-allyloxy-5-cyanobenzoic acid (279 mg, 1.4 mmol). A solution of the acid chloride in dichloromethane (3 mL) at 0° C. was treated with 5-chloropyrid-2-ylamidoxime (231 mg, 1.4 mmol) and triethylamine (574 µL, 4.1 mmol) and then stirred at ambient temperature for 1 hour. The reaction mixture was washed with water and saturated brine, dried over anhydrous sodium sulfate, filtered, and concentrated. The residue was dissolved in N,N-dimethylformamide (3 mL) and heated at 120° C. for 16 hours. Standard work up and silica gel chromatography using 5–20% ethyl acetate/hexanes followed by trituration with diethyl ether afforded 192 mg (42%) of 3-(5-chloropyrid-2-yl)-5-(3-allyloxy-5-cyanophenyl)-1,2,4-oxadiazole: $^1$H NMR (CDCl$_3$), δ (ppm): 8.79 (d, 1H), 8.18 (d, 1H), 8.14 (m, 1H), 7.99 (s, 1H), 7.88 (d, 1H), 7.40 (s, 1H), 6.07 (m, 1H), 5.40 (m, 2H), 4.67 (d, 2H).

3-(5-Chloropyrid-2-yl)-5-(3-cyano-5-propoxyphenyl)-1,2,4-oxadiazole

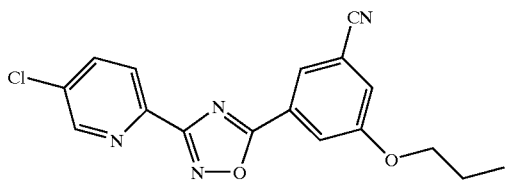

B172

Using the general procedure for the preparation of acid chlorides, 3-cyano-5-propoxybenzoyl chloride was prepared from 3-cyano-5-propoxybenzoic acid (93 mg, 0.45 mmol). A solution of the acid chloride in dichloromethane (2 mL) at 0° C. was treated with 5-chloropyrid-2-ylamidoxime (76 mg, 0.45 mmol) and triethylamine (188 µL, 1.4 mmol) and then stirred at ambient temperature for 1 hour. The reaction mixture was washed with water and saturated brine, dried over anhydrous sodium sulfate, filtered, and concentrated. The residue was dissolved in N,N-dimethylformamide (2 mL) and heated at 120° C. for 16 hours. Standard work up and silica gel chromatography using 10% ethyl acetate/hexanes afforded 7 mg (4%) of 3-(5-chloropyrid-2-yl)-5-(3-cyano-5-propoxyphenyl)-1,2,4-oxadiazole: $^1$H NMR (CDCl$_3$), δ (ppm): 8.80 (d, 1H), 8.18 (d, 1H), 8.11 (s, 1H), 7.98 (s, 1H), 7.88 (dd, 1H), 7.39 (s, 1H), 4.05 (t, 2H), 1.87 (m, 2H), 1.08 (t, 3H).

152

3-(5-Chloropyrid-2-yl)-5-(3-cyano-5-ethoxyphenyl)-1,2,4-oxadiazole

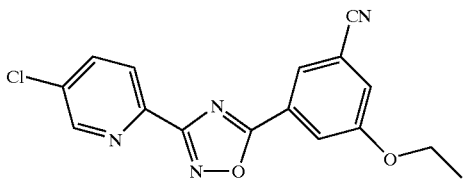

B173

Using the general procedure for the preparation of acid chlorides, 3-cyano-5-ethoxybenzoyl chloride was prepared from 3-cyano-5-ethoxybenzoic acid (189 mg, 0.94 mmol). A solution of the acid chloride in dichloromethane (2 mL) at 0° C. was treated with 5-chloropyrid-2-ylamidoxime (159 mg, 0.94 mmol) and triethylamine (399 µL, 2.9 mmol) and then stirred at ambient temperature for 1 hour. The reaction mixture was washed with water and saturated brine, dried over anhydrous sodium sulfate, filtered, and concentrated. The residue was dissolved in N,N-dimethylformamide (2 mL) and heated at 120° C. for 16 hours. After cooling, water was added to the reaction mixture and then the precipitate was collected and dried. Filtration through silica gel using dichloromethane followed by trituration with diethyl ether afforded 193 mg (62%) of 3-(5-chloropyrid-2-yl)-5-(3-cyano-5-ethoxyphenyl)-1,2,4-oxadiazole: $^1$H NMR (CDCl$_3$), δ (ppm): 8.79 (d, 1H), 8.18 (d, 1H), 8.12 (s, 1H), 7.97 (s, 1H), 7.88 (dd, 1H), 7.38 (s, 1H), 4.16 (q, 2H), 1.49 (t, 3H).

3-(5-Fluoropyrid-2-yl)-5-(3-cyano-5-hexyloxyphenyl)-1,2,4-oxadiazole

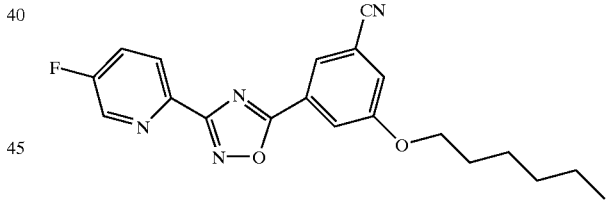

B174

Using the general procedure for the preparation of acid chlorides, 3-cyano-5-hexyloxybenzoyl chloride was prepared from 3-cyano-5-hexyloxybenzoic acid (247 mg, 0.96 mmol). A solution of the acid chloride in dichloromethane (2 mL) at 0° C. was treated with 5-fluoropyrid-2-ylamidoxime (149 mg, 0.96 mmol) and triethylamine (399 µL, 2.9 mmol) and then stirred at ambient temperature for 1 hour. The reaction mixture was washed with water and saturated brine, dried over anhydrous sodium sulfate, filtered, and concentrated. The residue was dissolved in N,N-dimethylformamide (2 mL) and heated at 120° C. for 16 hours. Standard work up and filtration through silica gel using dichloromethane followed by trituration with diethyl ether afforded 75 mg (21%) of 3-(5-fluoropyrid-2-yl)-5-(3-cyano-5-hexyloxyphenyl)-1,2,4-oxadiazole: $^1$H NMR (CDCl$_3$), δ (ppm): 8.69 (d, 1H), 8.27 (dd, 1H), 8.12 (s, 1H), 7.98 (s, 1H), 7.62 (m, 1H), 7.39 (s, 1H), 4.09 (t, 2H), 1.84 (m, 2H), 1.49 (m, 2H), 1.37 (m, 4H), 0.93 (t, 3H).

3-(5-Fluoropyrid-2-yl)-5-(3-cyano-5-(methoxymethyl)phenyl)-1,2,4-oxadiazole

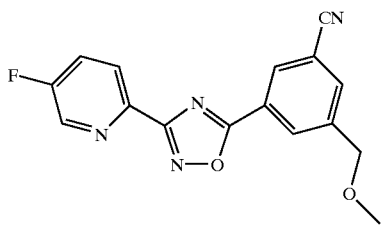

B175

Using the general procedure for the preparation of acid chlorides, 3-cyano-5-(methoxymethyl)benzoyl chloride was prepared from 3-cyano-5-(methoxymethyl)benzoic acid (143 mg, 0.75 mmol). A solution of the acid chloride in dichloromethane (2 mL) at 0° C. was treated with 5-fluoropyrid-2-ylamidoxime (123 mg, 0.75 mmol) and triethylamine (313 µL, 2.2 mmol) and then stirred at ambient temperature for 3 hours. The reaction mixture was washed with water and saturated brine, dried over anhydrous sodium sulfate, filtered, and concentrated. The residue was dissolved in N,N-dimethylformamide (2 mL) and heated at 120° C. for 16 hours. After cooling, water was added to the reaction mixture and the precipitate that formed was collected and dried. The solid was dissolved in dichloromethane and silica gel was added to the solution to remove the dark color. The silica gel was then filtered off and the filtrate was concentrated to dryness. Trituration of the residue with diethyl ether afforded 60 mg (25%) of 3-(5-fluoropyrid-2-yl)-5-(3-cyano-5-(methoxymethyl)phenyl)-1,2,4-oxadiazole as a white solid: $^1$H NMR (CDCl$_3$), δ (ppm): 8.69 (d, 1H), 8.48 (s, 2H), 8.27 (dd, 1H), 7.89 (s, 1H), 7.62 (m, 1H), 4.59 (s, 2H), 3.49 (s, 3H).

3-(5-Fluoro-pyrid-2-yl)-5-(5-cyano-2-methoxyphenyl)-1,2,4-oxadiazole

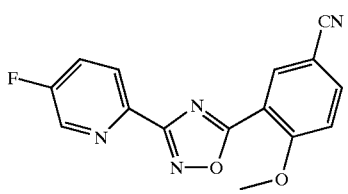

B176

A mixture of 5-cyano-2-methoxybenzoic acid (1.77mg, 1 mmol) in dichloromethane (2 mL) was treated with 2M oxalyl chloride (2 ml, 4 mmol, dichloromethane) and 1 drops of N,N-dimethylformamide. The mixture was stirred 2 hours at room temperature. The solvent and excess reagent were removed in vacuo. The residue was treated with 5-fluoropyrid-2-ylamidoxime (155 mg, 1 mmol) and triethylamine (404 mg, 4 mmol) in dichloromethane (10 mL). The mixture was then heated in dimethylformamide (1 mL) for 3 hours at 120° C. Standard work up, afforded 75 mg (25.3%) of 3-(5-Fluoro-pyrid-2-yl)-5-(5-cyano-2-methoxyphenyl)-1,2,4-oxadiazole. $^1$H NMR (CDCl$_3$), δ (ppm): 8.69 (d, 1H), 8.59 (d, 1H), 8.26 (dd, 1H), 7.85 (dd, 1H), 7.60 (m, 1H), 7.19 (d, 1H), 4.10 (s, 3H).

5-(5-Cyano-2-methoxyphenyl)-3-(5-cyano-pyrid-2-yl)-1,2,4-oxadiazole

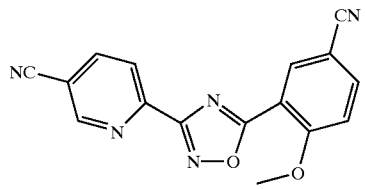

B177

A mixture of 5-cyano-2-methoxybenzoic acid (1.77mg, 1 mmol) in dichloromethane (2 mL) was treated with 2M oxalyl chloride (2 ml, 4 mmol, dichloromethane) and 1 drops of N,N-dimethylformamide. The mixture was stirred 2 hours at room temperature. The solvent and excess reagent were removed in vacuo. The residue was treated with 5-cyanopyrid-2-ylamidoxime (162 mg, 1 mmol) and triethylamine (404 mg, 4 mmol) in dichloromethane (2 mL). The mixture was then heated in dimethylformamide (1 mL) for 3 hours at 120° C. Standard work up, afforded 67 mg (22%) of 5-(5-cyano-2-methoxyphenyl)-3-(5-cyano-pyrid -2-yl)-1, 2,4-oxadiazole. $^1$H NMR (CDCl$_3$), δ (ppm): 9.10 (S, 1H), 8.58 (d, 1H), 8.37 (dd, 1H), 8.19 (dd, 1H), 7.86 (dd, $_1$ H), 7.20 (d, 1H), 4.11 (s, 3H).

3-(5-Fluoro-pyrid-2-yl)-5-(3-bromophenyl)-1,2,4-oxadiazole

B178

To the dichloromethane solution (2 mL) of 5-fluoropyrid-2-ylamidoxime (155 mg, 1 mmol) and triethylamine (404 mg, 4 mmol), 3-bromobenzoyl chloride (1.77mg, 1 mmol) was added at room temperature. The mixture was then heated in dimethylformamide (1 mL) for 40 minutes at 120~130° C. Standard work up, afforded 225 mg (70.3%) of 3-(5-Fluoro-pyrid-2-yl)-5-(3-bromophenyl)-1,2,4-oxadiazole.

5-(3-Chloro-5-methyl-pyrid-4-yl)-3-(2-pyridyl)-1,2,4-oxadiazole

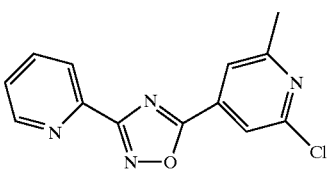

B179

A mixture of 2-chloro-6-methylisonicotinic acid (1.71 g, 10 mmol) in dichloromethane (15 mL) was treated with 2M oxalyl chloride (15 ml, 30 mmol, dichloromethane) and 3 drops of N,N-dimethylformamide. The mixture was stirred 2 hours at room temperature. The solvent and excess reagent were removed in vacuo. The residue was treated with 2-pyridylamidoxime (1.37 g, 10 mmol) and triethylamine (3.03 g, 30 mmol) in dichloromethane (15 mL). The mixture was then heated in dimethylformamide (10 mL) for 1 hours at 120° C. Standard work up, afforded 1.63 g (60%) of 5-(3-chloro-5-methyl-pyrid-4-yl)-3-(2-pyridyl)-1,2,4-oxadiazole.

5-(3-Chloro-5-methoxy-pyrid-4-yl)-3-(2-pyridyl)-1,2,4-oxadiazole

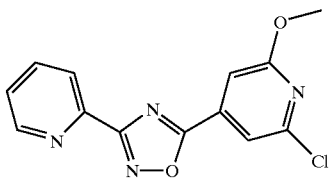

B180

A mixture of 2-chloro-6-methoxyisonicotinic acid (1.87 g, 10 mmol) in dichloromethane (15 mL) was treated with 2M oxalyl chloride (15 ml, 30 mmol, dichloromethane) and 3 drops of N,N-dimethylformamide. The mixture was stirred 2 hours at room temperature. The solvent and excess reagent were removed in vacuo. The residue was treated with 2-pyridylamidoxime (1.37 g, 10 mmol) and triethylamine (3.03 g, 30 mmol) in dichloromethane (15 mL). The mixture was then heated in dimethylformamide (10 mL) for 1 hours at 120° C. Standard work up, afforded 1.63 g (60%) of 3-(2-pyridyl)-5-(3-chloro-5-methoxy-pyrid-4-yl)-1,2,4-oxadiazole.

3-(3-Cyano-5-methylphenyl)-5-(2-pyridyl)-1,2,4-oxadiazole

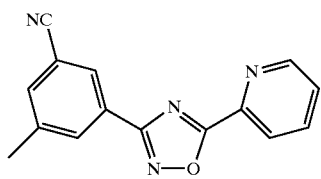

B181

A mixture of picolinic acid (123 mg, 1 mmol) in dichloromethane (2 mL) was treated with 2M oxalyl chloride (2 ml, 4 mmol, dichloromethane). The mixture was stirred 2 hours at room temperature. The solvent and excess reagent were removed in vacuo. The residue was treated with 3-cyano-5-methylphenyl-amidoxime (80 mg, 0.457 mmol) and triethylamine (303 mg, 3 mmol) in dichloromethane (2 mL). The mixture was then heated in dimethylformamide (2 mL) for 1 hours at 120° C. Standard work up, afforded 5.8 mg (4.8%) of 3-(3-cyano-5-methylphenyl)-5-(2-pyridyl)-1,2,4-oxadiazole. $^1$H-NMR (CDCl$_3$), δ (ppm): 8.89 (d, 1H), 8.30 (s,m, 3H), 7.96 (dt, 1H), 7.60 (s,dd, 2H), 2.50 (s, 3H).

3-(5-Bromo-pyrid-3-yl)-5-(2-pyridyl)-1,2,4-oxadiazole

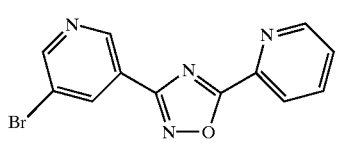

B182

A mixture of picolinic acid (123 mg, 1 mmol) in dichloromethane (2 mL) was treated with 2M oxalyl chloride (2 ml, 4 mmol, dichloromethane). The mixture was stirred 2 hours at room temperature. The solvent and excess reagent were removed in vacuo. The residue was treated with 5-bromopyrid-3-ylamidoxime (216 mg, 1 mmol) and triethylamine (303 mg, 3 mmol) in dichloromethane (2 mL). The mixture was then heated in dimethylformamide (2 mL) for 1 hours at 120° C. Standard work up, afforded 103 mg (34%) of 3-(5-bromo-pyrid-3-yl)-5-(2-pyridyl)-1,2,4-oxadiazole. $^1$H-NMR (CDCl$_3$), δ (ppm): 9.36 (d, 1H), 8.90 (d, 1H), 8.84 (d, 1H), 8.68 (t, 1H), 8.32 (d, 1H), 7.98 (dt, 1H), 7.58 (dd, 1H).

3-(3-Cyano-5-fluorophenyl)-5-(2-pyridyl)-1,2,4-oxadiazole

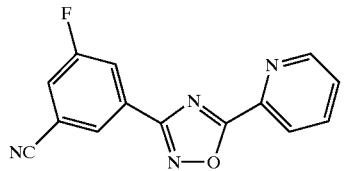

B183

A mixture of picolinic acid (184.6 mg, 1.5 mmol) in dichloromethane (2 mL) was treated with 2M oxalyl chloride (3 ml, 6 mmol, dichloromethane). The mixture was stirred overnight at room temperature. The solvent and excess reagent were removed in vacuo. The residue was treated with 3-cyano-5-fluorophenyl-amidoxime (100 mg, 0.558 mmol) and triethylamine (558 mg, 5.58 mmol) in dichloromethane (2 mL). The mixture was then heated in dimethylformamide (1 mL) for 1 hours at 120° C. Standard work up, afforded 43 mg (28.9%) of 3-(5-cyano-3-fluorophenyl)-5-(2-pyridyl)-1,2,4-oxadiazole. $^1$H-NMR (CDCl$_3$), δ (ppm): 8.89 (d, 1H), 8.34 (s,d, 3H), 8.10 (d, 1H), 7.59 (m, 2H).

3-(3-Iodophenyl)-5-(2-pyridyl)-1,2,4-oxadiazole

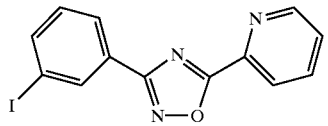

B184

A mixture of picolinic acid (300 mg, 2.4 mmol) in dichloromethane (2 mL) was treated with 2M oxalyl chloride (2 ml, 4 mmol, dichloromethane). The mixture was stirred 5 hours at room temperature. The solvent and excess reagent were removed in vacuo. The residue was treated with 3-iodophenyl-amidoxime (263 mg, 1 mmol) and triethylamine (303 mg, 3 mmol) in dichloromethane (2 mL). The mixture was then heated in dimethylformamide (2 mL) for 1 hours at 120~130° C. Standard work up, afforded 64.5 mg (18.5%) of 3-(3-iodophenyl)-5-(2-pyridyl)-1,2,4-oxadiazole. $^1$H-NMR (CDCl$_3$), δ (ppm): 8.88 (d, 1H), 8.61 (s, 1H), 8.31 (d, 1H), 8.20 (d, 1H), 7.96 (t, 1H), 7.87 (d, 1H), 7.56 (m, 1H), 7.25 (m, 1H).

3-(3-Cyanophenyl)-5-(2-pyridyl)-1,2,4-oxadiazole

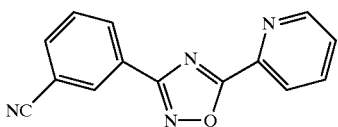

B186

A mixture of picolinic acid (300 mg, 2.4 mmol) in dichloromethane (2 mL) was treated with 2M oxalyl chloride (2 ml, 4 mmol, dichloromethane). The mixture was stirred 5 hours at room temperature. The solvent and excess reagent were removed in vacuo. The residue was treated with 3-iodophenyl-amidoxime (161 mg, 1 mmol) and triethylamine (303 mg, 3 mmol) in dichloromethane (2 mL). The mixture was then heated in dimethylformamide (2 mL) for 1 hours at 120~130° C. Standard work up, afforded 21.1 mg (8.5%) of 3-(3-cyanophenyl)-5-(2-pyridyl)-1,2,4-oxadiazole. $^1$H-NMR (CDCl$_3$), δ (ppm): 8.89 (d, 1H), 8.55 (s, 1H), 8.47 (d, 1H), 8.32 (d, 1H), 7.97 (t, 1H), 7.82 (d, 1H), 7.65 (t, 1H), 7.58 (m, 1H).

3-(3-Cyano-5-dimethylamino-phenyl)-5-(2-pyridyl)-1,2,4-oxadiazole

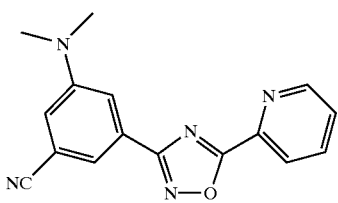

B187

A mixture of picolinic acid (300 mg, 2.4 mmol) in dichloromethane (2 mL) was treated with 2M oxalyl chloride (2 ml, 4 mmol, dichloromethane). The mixture was stirred 5 hours at room temperature. The solvent and excess reagent were removed in vacuo. The residue was treated with 3-cyano-5-dimethylaminophenyl-amidoxime (100 mg, 0.5 mmol) and triethylamine (303 mg, 3 mmol) in dichloromethane (2 mL). The mixture was then heated in dimethylformamide (2 mL) for 1 hours at 120~130° C. Standard work up, afforded 11.8 mg (8.1%) of 3-(3-cyano-5-dimethylamino-phenyl)-5-(2-pyridyl)-1,2,4-oxadiazole. $^1$H-NMR (CDCl$_3$), δ (ppm): 8.88 (d, 1H), 8.32 (d, 1H), 7.97 (t, 1H), 7.81 (s, 1H), 7.69 (s, 1H), 7.57 (m, 1H), 7.01 (s, 1H), 3.08 (s, 6H).

3-(3-Cyano-5-methylphenyl)-5-(5-fluoro-pyrid-2-yl)-1,2,4-oxadiazole

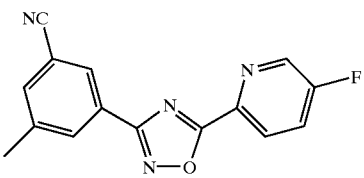

B188

A mixture of 5-fluoro-picolinic acid hydrochloride (177 mg, 1 mmol) in dichloromethane (2 mL) was treated with 2M oxalyl chloride (2 ml, 4 mmol, dichloromethane). The mixture was stirred 2 hours at room temperature. The solvent and excess reagent were removed in vacuo. The residue was treated with 3-cyano-5-methylphenyl-amidoxime (90 mg, 0.5 mmol) and triethylamine (303 mg, 3 mmol) in dichloromethane (2 mL). The mixture was then heated in dimethylformamide (2 mL) for 1 hours at 120° C. Standard work up, afforded 37.4 mg (26.7%) of 3-(3-cyano-5-methylphenyl)-5-(5-fluoro-pyrid-2-yl)-1,2,4-oxadiazole. $^1$H-NMR (CDCl$_3$), δ (ppm): 8.73 (d, 1H), 8.36 (m, 1H), 8.32 (s, 1H), 8.27 (s, 1H), 7.69 (m, 1H), 7.62 (s, 1H), 2.50 (s, 3H).

3-(3-Cyano-5-fluorophenyl)-5-(5-fluoro-pyrid-2-yl)-1,2,4-oxadiazole

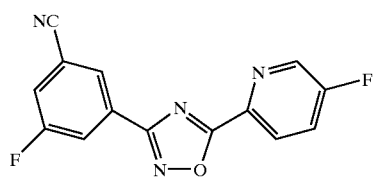

B189

A mixture of 5-fluoro-picolinic acid hydrochloride (177 mg, 1 mmol) in dichloromethane (2 mL) was treated with 2M oxalyl chloride (2 ml, 4 mmol, dichloromethane). The mixture was stirred 2 hours at room temperature. The solvent and excess reagent were removed in vacuo. The residue was treated with 3-cyano-5-fluorophenyl-amidoxime (120 mg, 0.67 mmol) and triethylamine (303 mg, 3 mmol) in dichloromethane (2 mL). The mixture was then heated in dimethylformamide (2 mL) for 1 hours at 120° C. Standard work up, afforded 33 mg (17.3%) of 3-(3-cyano-5-fluorophenyl)-5-(5-fluoro-pyrid-2-yl)-1,2,4-oxadiazole. $^1$H-NMR (CDCl$_3$), δ (ppm): 8.73 (d, 1H), 8.36 (m, 2H), 8.18 (dd, 1H), 7.69 (dt, 1H), 7.53 (d, 1H).

5-(4-Cyanophenyl)-3-(6-cyano-pyrid-2-yl)-1,2,4-oxadiazole

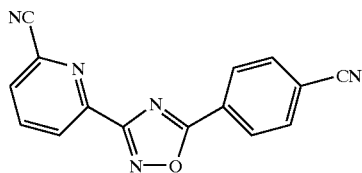

B190

To a dichloromethane solution (1 mL) of 6-cyanopyrid-2-ylamidoxime (81 mg, 0.5 mmol) and triethylamine (202 mg, 2 mmol), 4-cyanobenzoyl chloride (91 mg, 0.55 mmol) was added at room temperature. The mixture was then heated in dimethylformamide (1 mL) for 2 hours at 120~130° C. Standard work up, afforded 63.4 mg (46.4%) of 5-(4-cyanophenyl)-3-(6-cyano-pyrid-2-yl)-1,2,4-oxadiazole. $^1$H-NMR (CDCl$_3$), δ (ppm): 8.24 (m, 3H), 8.06 (t, 1H), 7.92 (d, 3H).

5-(3-Cyano-5-trifluoromethoxyphenyl)-3-(2-pyridyl)-1,2,4-oxadiazole

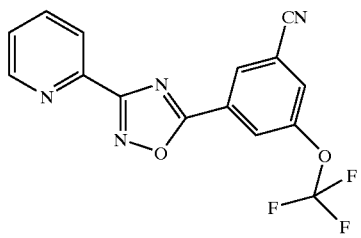

B191

A mixture of 3-cyano-5-trifluoromethoxybenzoic acid, which 3-[imino(methoxy)methyl]-5-trifluoromethoxybenzoic acid (3:1, 50 mg, 0.2165 mmoles) in dichloromethane (1 mL) was treated with 2M oxalyl chloride (0.433 ml, 0.866 mmol, dichloromethane). The mixture was stirred 3 hours at room temperature. The solvent and excess reagent were removed in vacuo. The residue was treated with 2-pyridyl-amidoxime (29.7 mg, 0.216 mmol) and triethylamine (87 mg, 0.866 mmol) in dichloromethane (1 mL). The mixture was then heated in dimethylformamide (0.5 mL) for 3 hours at 120° C. Standard work up, purified by prep HPLC (C18 column, $CH_3CN:H_2O=60:40$), afforded 3.2 mg (4.5%) of 5-(3-Cyano-5-trifluoromethoxyphenyl)-3-(2-pyridyl)-1,2,4-oxadiazole [$^1$H-NMR (CDCl$_3$), δ (ppm): 8.86 (w, 1H), 8.56 (s, 1H), 8.40 (s, 1H), 8.24 (d, 1H), 7.92 (t, 1H), 7.72 (s, 1H), 7.73 (m, 1H)]

5-(3-methoxycarbonyl-5-trifluoromethoxyphenyl)-3-(2-pyridyl)-1,2,4-oxadiazole

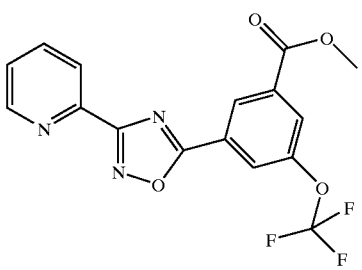

B192

A mixture of 3-cyano-5-trifluoromethoxybenzoic acid, which 3-[imino(methoxy)methyl]-5-trifluoromethoxybenzoic acid (3:1, 50 mg, 0.2165 mmoles) in dichloromethane (1 mL) was treated with 2M oxalyl chloride (0.433 ml, 0.866 mmol, dichloromethane). The mixture was stirred 3 hours at room temperature. The solvent and excess reagent were removed in vacuo. The residue was treated with 2-pyridyl-amidoxime (29.7 mg, 0.216 mmol) and triethylamine (87 mg, 0.866 mmol) in dichloromethane (1 mL). The mixture was then heated in dimethylformamide (0.5 mL) for 3 hours at 120° C. Standard work up, purified by prep HPLC (C18 column, $CH_3CN:H_2O=60:40$), afforded 1.2 mg (1.5%) of 5-(3-methoxycarbonyl-5-trifluoromethoxyphenyl)-3-(2-pyridyl)-1,2,4-oxadiazole [$^1$H-NMR (CDCl$_3$), δ (ppm): 8.86 (d, w, 2H), 8.36 (s, 1H), 8.25 (d, 1H), 8.15 (s, 1H), 7.90 (t, 1H), 7.51 (m, 1H), 4.01 (s, 3H)].

5-(3-Cyano-5-trifluoromethoxyphenyl)-3-(5-fluoro-pyrid-2-yl)-1,2,4-oxadiazole

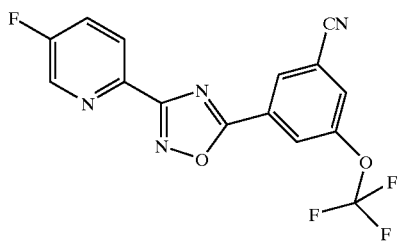

B193

A mixture of 3-cyano-5-trifluoromethoxybenzoic acid, which contained 3-[imino(methoxy)methyl]-5-trifluoromethoxybenzoic acid (3:1, 50 mg, 0.2165 mmoles) in dichloromethane (1 mL) was treated with 2M oxalyl chloride (0.433 ml, 0.866 mmol, dichloromethane). The mixture was stirred 3 hours at room temperature. The solvent and excess reagent were removed in vacuo. The residue was treated with 5-fluoropyrid-2-ylamidoxime (33.6 mg, 0.216 mmol) and triethylamine (87 mg, 0.866 mmol) in dichloromethane (1 mL). The mixture was then heated in dimethylformamide (0.5 mL) for 3 hours at 120° C. Standard work up, purified by prep HPLC (C18 column, $CH_3CN:H2O=60:40$), afforded 14.9 mg (19.6%) of 5-(3-cyano-5-trifluoromethoxyphenyl)-3-(5-fluoropyrid-2-yl)-1,2,4-oxadiazole. $^1$H-NMR (CDCl$_3$), δ (ppm): 8.72 (s, 1H), 8.56 (s, 1H), 8.39 (s, 1H), 8.25 (m, 1H), 7.78 (s, 1H), 7.61 (m, 1H).

3-(5-Cyano-pyrid-2-yl)-5-(3-cyano-5-trifluoromethoxyphenyl)-1,2,4-oxadiazole

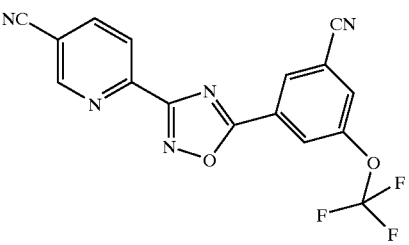

B194

A mixture of 3-cyano-5-trifluoromethoxybenzoic acid, which 3-[imino(methoxy)methyl]-5-trifluoromethoxybenzoic acid (3:1, 50 mg, 0.2165 mmoles) in dichloromethane (1 mL) was treated with 2M oxalyl chloride (0.433 ml, 0.866 mmol, dichloromethane). The mixture was stirred 3 hours at room temperature. The solvent and excess reagent were removed in vacuo. The residue was treated with 5-cyanopyrid-2-ylamidoxime (33.6 mg, 0.216 mmol) and triethylamine (87 mg, 0.866 mmol) in dichloromethane (1 mL). The mixture was then heated in dimethylformamide (0.5 mL) for 3 hours at 120° C. Standard work up, purified by prep HPLC (C18 column, $CH_3CN:H2O=60:40$), afforded 18 mg (22.2%) of 5-(3-cyano-5-trifluoromethoxyphenyl)-3-(5-fluoropyrid-2-yl)-1,2,4-oxadiazole. $^1$H-NMR (CDCl$_3$), δ (ppm): 9.12 (d, 1H), 8.50 (s, 1H), 8.38 (s, d, 2H), 8.20 (d, 1H), 7.79 (s, 1H).

3-(3-Cyano-5-dimethylaminophenyl)-5-(5-fluoro-pyrid-2-yl)-1,2,4-oxadiazole

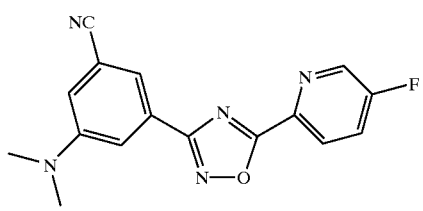

B195

A mixture of 5-fluoro-picolinic acid acid (177.5 mg, 1 mmol) in dichloromethane (2 mL) was treated with 2M oxalyl chloride (2 ml, 4 mmol, dichloromethane). The mixture was stirred 2 hours at room temperature. The solvent and excess reagent were removed in vacuo. The residue was treated with 3-cyano-5-dimethylaminophenyl-amidoxime (102 mg, 0.5 mmol) and triethylamine (404 mg, 4 mmol) in dichloromethane (2 mL). The mixture was then heated in dimethylformamide (1 mL) for 1 hours at 130° C. Standard work up, afforded 24 mg (15.5%) of 3-(3-cyano-5-dimethyaminophenyl)-5-(5-fluoro-pyrid-2-yl)-1,2,4-oxadiazole. $^1$H-NMR (CDCl$_3$), δ (ppm): 8.72 (d, 1H), 8.37 (dd, 1H), 7.81 (s, 1H), 7.68 (dt, 2H), 7.02 (d, 1H), 3.10 (s, 6H).

5-(5-Chloro-pyrid-2-yl)-3-(3-cyano-5-dimethylaminophenyl)-1,2,4-oxadiazole

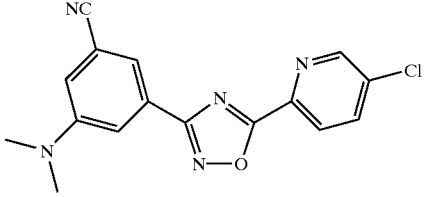

B196

A mixture of 5-chloro-picolinic acid hydrochloride (72 mg, 0.4 mmol) in dichloromethane (2 mL) was treated with 2M oxalyl chloride (0.8 ml, 1.6 mmol, dichloromethane). The mixture was stirred at room temperature overnight. The solvent and excess reagent were removed in vacuo. The residue was treated with 3-cyano-5-dimethylaminophenyl-amidoxime (40.8 mg, 0.2 mmol) and triethylamine (162 mg, 1.6 mmol) in dichloromethane (2 mL). The mixture was then heated in dimethylformamide (1 mL) for 4 hours at 130° C. Standard work up, afforded 3.8 mg (5.8%) of 5-(5-chloro-pyrid-2-yl)-3-(3-cyano-5-dimethyaminophenyl)-1,2,4-oxadiazole. $^1$H-NMR (CDCl$_3$), δ (ppm): 8.82 (d, 1H), 8.27 (d, 1H), 7.95 (dd, 1H), 7.78 (s, 1H), 7.66 (d, 1H), 7.01 (d, 1H), 3.06 (s, 6H).

5-(5-Chloro-pyrid-2-yl)-3-(3-cyano-5-methoxyphenyl)-1,2,4-oxadiazole

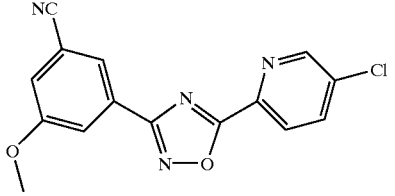

B197

A mixture of 5-chloropicolinic acid hydrochloride (72 mg, 0.4 mmol) in dichloromethane (2 mL) was treated with 2M oxalyl chloride (0.8 ml, 1.6 mmol, dichloromethane). The mixture was stirred at room temperature overnight. The solvent and excess reagent were removed in vacuo. The residue was treated with 3-cyano-5-methoxyphenyl-amidoxime (76 mg, 0.4 mmol) and triethylamine (162 mg, 1.6 mmol) in dichloromethane (2 mL). The mixture was then heated in dimethylformamide (1 mL) for 4 hours at 130° C. Standard work up, afforded 45.8 mg (36.6%) of 5-(5-chloro-pyrid-2-yl)-3-(3-cyano-5-methoxyphenyl)-1,2,4-oxadiazole. $^1$H-NMR (CDCl$_3$), δ (ppm): 8.85 (d, 1H), 8.27 (d, 1H), 8.10 (s, 1H), 7.95 (m, 2H), 7.12 (d, 1H), 3.92 (s, 3H).

5-(5-Chloro-pyrid-2-yl)-3-(6-cyano-4-methoxy-pyrid-2-yl)-1,2,4-oxadiazole

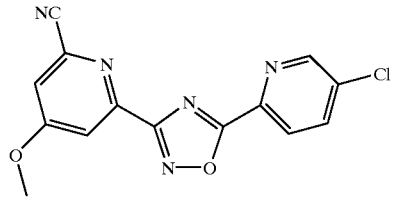

B198

A mixture of 5-chloropicolinic acid hydrochloride (72 mg, 0.4 mmol) in dichloromethane (2 mL) was treated with 2M oxalyl chloride (0.8 ml, 1.6 mmol, dichloromethane). The mixture was stirred at room temperature overnight. The solvent and excess reagent were removed in vacuo. The residue was treated with 6-cyano-4-methoxypyrid-2-yl-amidoxine (38.4 mg, 0.2 mmol) and triethylamine (162 mg, 1.6 mmol) in dichloromethane (2 mL). The mixture was then heated in dimethylformamide (1 mL) for 4 hours at 130° C. Standard work up, afforded 1.9 mg (3%) of 5-(5-chloro-pyrid-2-yl)-3-(6-cyano-4-methoxypyrid-2-yl)-1,2,4-oxadiazole. [$^1$H-NMR (CDCl$_3$), δ (ppm): 8.85 (d, 1H), 8.36 (d, 1H), 7.97 (m, 2H), 7.38 (d, $_1$ H), 4.03 (s, 3H)].

5-(5-chloro-pyrid-2-yl)-3-(6-cyano-4-hydroxy-pyrid-2-yl)-1,2,4-oxadiazole

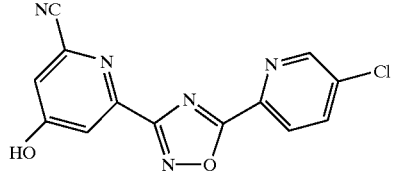

B199

A mixture of 5-chloropicolinic acid hydrochloride (72 mg, 0.4 mmol) in dichloromethane (2 mL) was treated with 2M oxalyl chloride (0.8 ml, 1.6 mmol, dichloromethane). The mixture was stirred at room temperature overnight. The solvent and excess reagent were removed in vacuo. The residue was treated with 6-cyano-4-methoxypyrid-2-yl-amidoxime (38.4 mg, 0.2 mmol) and triethylamine (162 mg, 1.6 mmol) in dichloromethane (2 mL). The mixture was then heated in dimethylformamide (1 mL) for 4 hours at 130° C. Standard work up, afforded 2.2 mg (3.67%) of 5-(5-chloro-pyrid-2-yl)-3-(6-cyano-4-hydroxypyrid-2-yl)-1,2,4-oxadiazole [$^1$H-NMR (CDCl$_3$), δ (ppm): 8.87 (d, 1H), 8.43 (d, 1H), 8.23 (dd, 1H), 7.91 (d, 1H), 7.57 (d, 1H).].

5-(5-Chloro-pyrid-2-yl)-3-(3-cyano-5-trifluoromethoxyphenyl)-1,2,4-oxadiazole

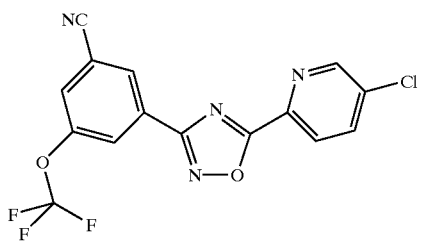

B200

A mixture of 5-chloropicolinic acid hydrochloride (72 mg, 0.4 mmol) in dichloromethane (2 mL) was treated with 2M oxalyl chloride (0.8 ml, 1.6 mmol, dichloromethane). The mixture was stirred at room temperature overnight. The solvent and excess reagent were removed in vacuo. The residue was treated with 3-cyano-5-trifluoromethoxyphenyl-amidoxime (68.6 mg, 0.28 mmol) and triethylamine (162 mg, 1.6 mmol) in dichloromethane (2 mL). The mixture was then heated in dimethylformamide (1 mL) for 4 hours at 130° C. Standard work up, afforded 17.4 mg (16.9%) of 5-(5-chloro-pyrid-2-yl)-3-(3-cyano-5-trifluoromethoxyphenyl)-1,2,4-oxadiazole. $^1$H-NMR (CDCl$_3$), δ (ppm): 8.84 (d, 1H), 8.46 (s, 1H), 8.30 (m, 2H), 7.96 (dd, $_1$ H), 7.68 (d, 1H).

5-(5-Chloro-pyrid-2-yl)-3-(3-cyanophenyl)-1,2,4-oxadiazole

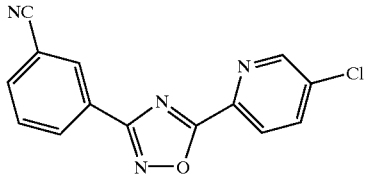

B201

A mixture of 5-chloropicolinic acid hydrochloride (72 mg, 0.4 mmol) in dichloromethane (2 mL) was treated with 2M oxalyl chloride (0.8 ml, 1.6 mmol, dichloromethane). The mixture was stirred at room temperature overnight. The solvent and excess reagent were removed in vacuo. The residue was treated with 3-cyanophenyl-amidoxime (64.4 mg, 0.4 mmol) and triethylamine (162 mg, 1.6 mmol) in dichloromethane (2 mL). The mixture was then heated in dimethylformamide (1 mL) for 4 hours at 130° C. Standard work up, afforded 24.5 mg (21.7%) of 5-(5-chloro-pyrid-2-yl)-3-(3-cyanophenyl)-1,2,4-oxadiazole. $^1$H-NMR (CDCl$_3$), δ (ppm): 8.84 (d, 1H), 8.53 (s, 1H), 8.45 (dd, 1H), 8.26 (d, 1H), 7.95 (dd, 1H), 7.83 (d, 1H), 7.66 (t, 1H).

5-(5-Chloro-pyrid-2-yl)-3-(3-cyano-5-methylphenyl)-1,2,4-oxadiazole

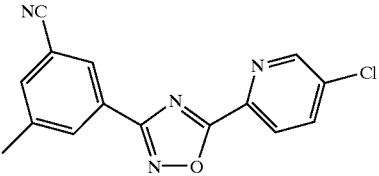

B202

A mixture of 5-chloropicolinic acid hydrochloride (72 mg, 0.4 mmol) in dichloromethane (2 mL) was treated with 2M oxalyl chloride (0.8 ml, 1.6 mmol, dichloromethane). The mixture was stirred at room temperature overnight. The solvent and excess reagent were removed in vacuo. The residue was treated with 3-cyano-5-methylphenyl-amidoxime (24 mg, 0.137 mmol) and triethylamine (162 mg, 1.6 mmol) in dichloromethane (2 mL). The mixture was then heated in dimethylformamide (1 mL) for 4 hours at 130° C. Standard work up, afforded 21.2 mg (52%) of 5-(5-chloro-pyrid-2-yl)-3-(3-cyano-5-methylphenyl)-1,2,4-oxadiazole. $^1$H-NMR (CDCl$_3$), δ (ppm): 8.84 (d, 1H), 8.28 (m, 3H), 7.9d (dd, 1H), 7.62 (s, 1H), 2.48 (s, 3H).

5-(5-Chloro-pyrid-2-yl)-3-(3-cyano-5-fluorophenyl)-1,2,4-oxadiazole

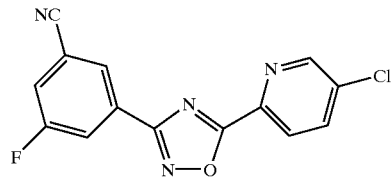

B203

A mixture of 5-chloropicolinic acid hydrochloride (72 mg, 0.4 mmol) in dichloromethane (2 mL) was treated with 2M oxalyl chloride (0.8 ml, 1.6 mmol, dichloromethane). The mixture was stirred at room temperature overnight. The solvent and excess reagent were removed in vacuo. The residue was treated with 3-cyano-5-fluorophenyl-amidoxime (71.6 mg, 0.4 mmol) and triethylamine (162 mg, 1.6 mmol) in dichloromethane (2 mL). The mixture was then heated in dimethylformamide (1 mL) for 4 hours at 130° C. Standard work up, afforded 70.4 mg (58.5%) of 5-(5-chloro-pyrid-2-yl)-3-(3-cyano-5-fluorophenyl)-1,2,4-oxadiazole. $^1$H-NMR (CDCl$_3$), δ (ppm): 8.82 (d, 1H), 8.34 (d, 1H), 8.27 (d, 1H), 8.16 (dd, 1H), 7.97 (dd, 1H), 7.52 (dd, 1H).

3-(3-Cyano-5-trifluoromethoxyphenyl)-5-(2-pyridyl)-1,2,4-oxadiazole

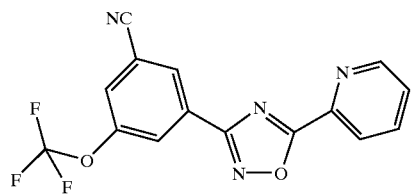

B204

A mixture of picolinic acid (123 mg, 1 mmol) and triethylamine (404 mg, 4 mmol) in tetrahydrofuran (2 mL) was treated with isobutylchloroformate (0.118 ml, 1.1 mmol) at room temperature. The mixture was stirred for 1.5 hours and treated with 3-cyano-5-trifluoromethoxyphenyl-amidoxime (50 mg, 0.204 mmol). The mixture was then heated in dimethylformamide (1 mL) for 4 hours at 130° C. Standard work up, afforded 7.1 mg (10.5%) 3-(3-cyano-5-trifluoromethoxyphenyl)-5-(2-pyridyl)-1,2,4-oxadiazole. $^1$H-NMR (CDCl$_3$), δ (ppm): 8.90 (d, 1H), 8.50 (s, 1H), 8.34 (m, 2H), 8.00 (dt, 1H), 7.66 (s, 1H), 7.60 (dd, 1H).

3-(3-Fluoro-5-methoxyphenyl)-5-(2-pyridyl)-1,2,4-oxadiazole

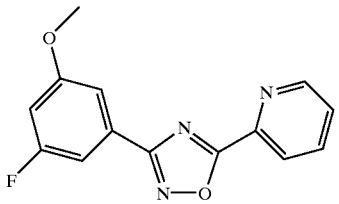
B205

A mixture of picolinic acid (123 mg, 1 mmol) and triethylamine (404 mg, 4 mmol) in tetrahydrofuran (2 mL) was treated with isobutylchloroformate (0.118 ml, 1.1 mmol) at room temperature. The mixture was stirred for 1.5 hours and treated with 3-fluoro-5-methoxyphenyl-amidoxime (73.8 mg, 0.4 mmol). The mixture was then heated in dimethylformamide (1 mL) for 4 hours at 130° C. Standard work up, afforded 40.1 mg (37%) 3-(3-fluoro-5-methoxyphenyl)-5-(2-pyridyl)-1,2,4-oxadiazole. $^1$H-NMR (CDCl$_3$), δ (ppm): 8.90 (d, 1H), 8.30 (d, 1H), 7.95 (dt, 1H), 7.56 (m, 3H), 6.80 (dd, 1H), 3.73 (s, 3H).

3-(3-Cyanophenyl)-5-(5-fluoro-pyrid-2-yl)-1,2,4-oxadiazole

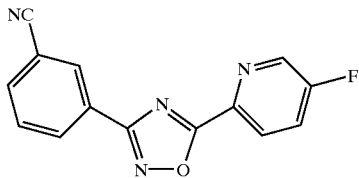
B206

A mixture of 5-fluoropicolinic acid hydrochloride (45.8 mg, 0.3 mmol) in dichloromethane (1 mL) was treated with 2M oxalyl chloride (0.6 ml, 1.2 mmol, dichloromethane). The mixture was stirred at room temperature for 3 hours. The solvent and excess reagent were removed in vacuo. The residue was treated with 3-cyanophenyl-amidoxime (24.2 mg, 0.15 mmol) and triethylamine (121 mg, 1.2 mmol) in dichloromethane (1 mL). The mixture was then heated in dimethylformamide (1 mL) for 6 hours at 130° C. Standard work up, afforded 10.6 mg (26.5%) of 3-(3-cyanophenyl)-5-(5-fluoro-pyrid-2-yl)-1,2,4-oxadiazole. $^1$H-NMR (CDCl$_3$), δ (ppm): 8.72 (d, 1H), 8.53 (s, 1H), 8.45 (dd, 1H), 8.37 (dd, 1H), 7.83 (d, 1H), 7.68 (m, 2H).

3-(3-Cyano-5-trifluoromethoxyphenyl)-5-(5-fluoro-pyrid-2-yl)-1,2,4-oxadiazole

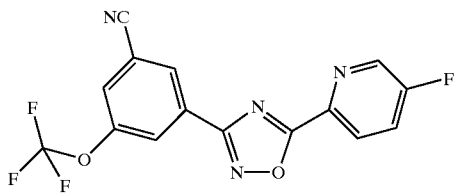
B207

A mixture of 5-fluoropicolinic acid hydrochloride (45.8 mg, 0.3 mmol) in dichloromethane (1 mL) was treated with 2M oxalyl chloride (0.6 ml, 1.2 mmol, dichloromethane). The mixture was stirred at room temperature for 3 hours. The solvent and excess reagent were removed in vacuo. The residue was treated with 3-cyano-5-trifluoromethoxyphenyl-amidoxime (36.5 mg, 0.15 mmol) and triethylamine (121mg, 1.2 mmol) in dichloromethane (1 mL). The mixture was then heated in dimethylformamide (1 mL) for 6 hours at 130° C. Standard work up, afforded 7.2 mg (14.4%) of 3-(3-cyano-5-trifluoromethoxyphenyl)-5-(5-fluoro-pyrid-2-yl)-1,2,4-oxadiazole. $^1$H-NMR (CDCl$_3$), δ (ppm): 8.74 (d, 1H), 8.49 (s, 1H), 8.38 (dd, 1H), 8.30 (s, 1H), 7.70 (m, 2H).

3-(3-Fluoro-5-methoxyphenyl)-5-(5-fluoropyrid-2-yl)-1,2,4-oxadiazole

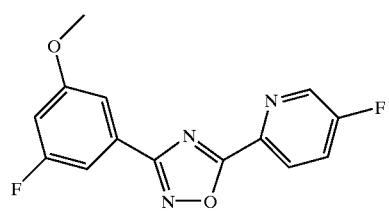
B208

A mixture of 5-fluoropicolinic acid hydrochloride (45.8 mg, 0.3 mmol) in dichloromethane (1 mL) was treated with 2M oxalyl chloride (0.6 ml, 1.2 mmol, dichloromethane). The mixture was stirred at room temperature for 3 hours. The solvent and excess reagent were removed in vacuo. The residue was treated with 3-fluoro-5-methoxyphenyl-amidoxime (27.7 mg, 0.15 mmol) and triethylamine (121 mg, 1.2 mmol) in dichloromethane (1 mL). The mixture was then heated in dimethylformamide (1 mL) for 6 hours at 130° C. Standard work up, afforded 9.0 mg (20%) of 3-(3-fluoro-5-methoxyphenyl)-5-(5-fluoropyrid-2-yl)-1,2,4-oxadiazole. $^1$H-NMR (CDCl$_3$), δ (ppm): 8.73 (d, 1H), 8.35 (dd, 1H), 7.65 (m, 1H), 7.55 (m, 2H), 6.80 (dd, 1H), 3.92 (s, 3H).

3-(3,5-Dimethoxyphenyl)-5-(5-fluoropyrid-2-yl)-1,2,4-oxadiazole

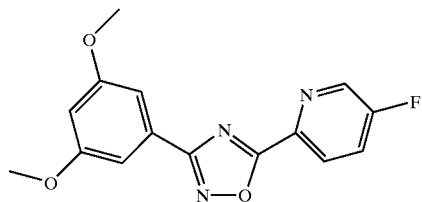
B209

A mixture of 5-fluoropicolinic acid hydrochloride (45.8 mg, 0.3 mmol) in dichloromethane (1 mL) was treated with 2M oxalyl chloride (0.6 ml, 1.2 mmol, dichloromethane). The mixture was stirred at room temperature for 3 hours. The solvent and excess reagent were removed in vacuo. The residue was treated with 3,5-dimethoxyphenyl-amidoxime (29.4 mg, 0.15 mmol) and triethylamine (121mg, 1.2 mmol) in dichloromethane (1 mL). The mixture was then heated in dimethylformamide (1 mL) for 6 hours at 130° C. Standard work up, afforded 12 mg (26.6%) of 3-(3,5-dimethoxyphenyl)-5-(5-fluoropyrid-2-yl)-1,2,4-oxadiazole. $^1$H-NMR (CDCl$_3$), δ (ppm): 8.71 (d, 1H), 8.37 (dd, 1H), 7.64 (dt, 1H), 7.37 (s, 2H), 6.61 (s, 1H), 3.87 (s, 6H).

3-[3-Fluoro-5-(1H-imidazol-1-yl)]phenyl]-5-(2-pyridyl)-1,2,4-oxadiazole

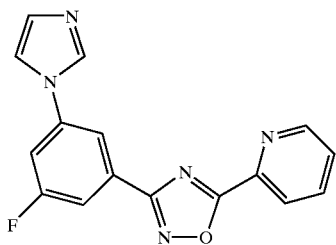

B210

A mixture of picolinic acid (62 mg, 0.5 mmol) and triethylamine (202 mg, 2 mmol) in tetrahydrofuran (1 mL) was treated with isobutylchloroformate (0.059 ml, 0.55 mmol) at room temperature. The mixture was stirred for 2 hours and treated with 3-fluoro-5-(1H-imidazol-1-yl)]phenyl-amidoxime (100 mg, 0.45 mmol). The mixture was then heated in dimethylformamide (1 mL) at 130° C. overnight. Standard work up, afforded 24.4 mg (17.6%) 3-[3-fluoro-5-(1H-imidazol-1-yl)]phenyl]-5-(2-pyridyl)-1,2,4-oxadiazole. $^1$H-NMR (CDCl$_3$), δ (ppm): 8.90 (d, 1H), 8.32 (d, 1H), 8.10 (s, 1H), 7.7.98 (m, 3H), 7.58 (dd, 1H), 7.39 (s, 1H), 7.29 (m, 2H).

3-(5-Fluoro-2-pyridyl)-5-(3-fluoro-5-(3-pyridyl)phenyl)-1,2,4-oxadiazole

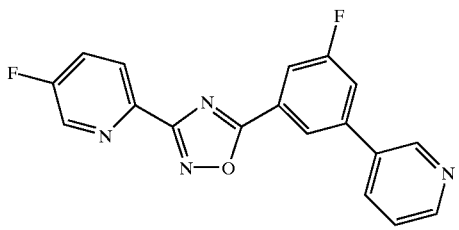

B211

A mixture of the hydrochloride salt of 3-Fluoro-5-(3-pyridyl)benzoic acid (1.00 g, 3.93 mmol) in dichloromethane (10 ml) was treated with oxalyl chloride (5.9 ml, 11.8 mmol, 2M dichloromethane) and 3 drops of N,N-dimethylformamide. The mixture was stirred 4 hours at room temperature. The solvent and excess reagent were removed in-vacuo. The residue was treated with 5-Fluoro-2-pyridylamidoxime (0.61 g, 3.93 mmol) and triethylamine (1.64 ml, 11.8 mmol) in dichloromethane (10 mL). The mixture was then heated in dimethylformamide (10 mL) at 120° C., overnight. Standard work up followed by trituration with diethyl ether afforded 3-(5-Fluoro-2-pyridyl)-5-(3-fluoro-5-(3-pyridyl)phenyl)-1,2,4-oxadiazole (452 mg) as a light yellow solid.

3-(5-Fluoro-2-pyridyl)-5-(3-bromo-5-(3-pyridyl)phenyl)-1,2,4-oxadiazole

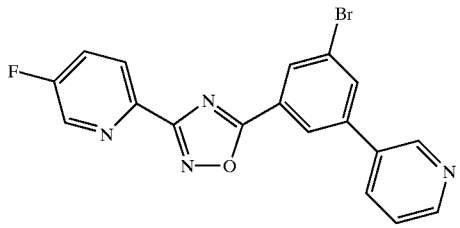

B212

A mixture of the hydrochloride salt of 3-Bromo-5-(3-pyridyl)benzoic acid (1.50 g, 4.78 mmol) in dichloromethane (10 ml) was treated with oxalyl chloride (7.2 ml, 14.3 mmol, 2M dichloromethane) and 3 drops of N,N-dimethylformamide. The mixture was stirred 4 hours at room temperature. The solvent and excess reagent were removed in-vacuo. The residue was treated with 5-Fluoro-2-pyridylamidoxime (0.74 g, 4.78 mmol) and triethylamine (2.0 ml, 14.3 mmol) in dichloromethane (10 mL). The mixture was then heated in dimethylformamide (10 mL) at 120° C., overnight. Standard work up followed by trituration with diethyl ether afforded 3-(5-Fluoro-2-pyridyl)-5-(3-bromo-5-(3-pyridyl)phenyl)-1,2,4-oxadiazole (457 mg) as an off white solid. $^1$H-NMR (CDCl$_3$), δ (ppm): 8.91 (s, 1H), 8.70 (s, 2H), 8.42 (d, 2H), 8.27 (dd, 1H), 7.94 (m, 2H), 7.61 (dt, 1H), 7.44 (dd, 1H).

3-(5-Fluoro-2-pyridyl)-5-(3-fluoro-5-methoxyphenyl)-1,2,4-oxadiazole

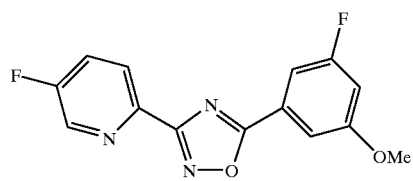

B213

A mixture of 3-Fluoro-5-methoxybenzoic acid (0.20 g, 1.18 mmol) in dichloromethane (2.5 mL) was treated with oxalyl chloride (1.76 ml, 3.53 mmol, 2M dichloromethane) and 3 drops of N,N-dimethylformamide. The mixture was stirred 4 hours at room temperature. The solvent and excess reagent were removed in-vacuo. The residue was treated with 5-Fluoro-2-pyridylamidoxime (182 mg, 1.18 mmol) and triethylamine (0.49 ml, 3.53 mmol) in dichloromethane (2.5 mL). The mixture was then heated in dimethylformamide (2.5 mL) at 120° C., overnight. Standard work up followed by purification on silica gel using 20% ethyl acetate in hexanes afforded the title compound (43.1 mg, 13%) as a light yellow solid. $^1$H-NMR (CDCl$_3$), δ (ppm): 8.69 (d, 1H), 8.26 (dd, 2H), 7.60 (m, 3H), 6.87 (m, 1H).

3-(Pyrid-2-yl)-5-(3-cyano-5-thiomethylphenyl)-1,2,4-oxadiazole

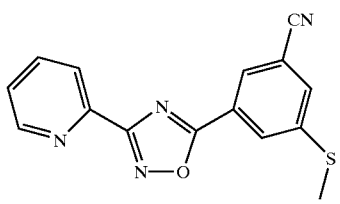

B214

Using the general procedure for the preparation of acid chlorides, 3-cyano-5-thiomethylbenzoyl chloride was prepared from 3-cyano-5-thiomethylbenzoic acid (330 mg, 1.71 mmol). A suspension of pyrid-2-ylamidoxime (123 mg, 0.9 mmol) in dichloromethane (4 mL) was treated with 3-cyano-5-thiomethylbenzoyl chloride (190 mg, 0.9 mmol) and the mixture stirred 30 minutes. The solvent was removed in vacuo and the intermediate dissolved in N,N-dimethylformamide (8 mL). The reaction was heated, under an argon atmosphere, for 20 hours at 120° C. The reaction mixture was cooled and the solvent removed in vacuo. Silica gel chromatography using a gradient of 0% to 10% ethyl acetate in dichloromethane afforded 159 mg (60%) of 3-(pyrid-2-yl)-5-(3-cyano-5-thiomethylphenyl)-1,2,4-oxadiazole as a white solid: $^1$H-NMR (CDCl$_3$), δ (ppm): 8.82 (t, 1H), 8.31 (d, 2H), 8.24 (d, 1H), 7.91 (t, 1H), 7.66 (s, 1H), 7.49 (t, 1H), 2.61 (s, 3H).

3-(5-Fluoro-pyrid-2-yl)-5-(3-cyano-5-thiomethylphenyl)-1,2,4-oxadiazole

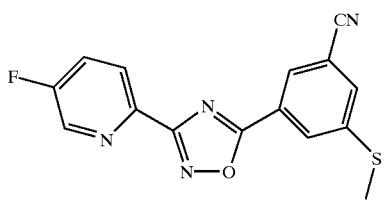

B215

Using the general procedure for the preparation of acid chlorides, 3-cyano-5-thiomethylbenzoyl chloride was prepared from 3-cyano-5-thiomethylbenzoic acid (330 mg, 1.71 mmol). A suspension of 5-fluoro-pyrid-2-ylamidoxime (161 mg, 1.04 mmol) in dichloromethane (4 mL) was treated with 3-cyano-5-thiomethylbenzoyl chloride (220 mg, 1.04 mmol) and the mixture stirred 30 minutes. The solvent was removed in vacuo and the intermediate dissolved in N,N-dimethylformamide (8 mL). The reaction was heated, under an argon atmosphere, for 20 hours at 120° C. After this time, the reaction mixture was cooled and the solvent removed in vacuo. Silica gel chromatography using a gradient of 5% to 50% ethyl acetate in hexanes afforded product that was not yet pure. The product was recrystallized from hexanes and methanol to yield 78 mg (24%) of 3-(5-fluoro-pyrid-2-yl)-5-(3-cyano-5-thiomethylphenyl)-1,2,4-oxadiazole as white solid: $^1$H-NMR (CDCl$_3$), δ (ppm): 8.70 (s, 1H), 8.27 (t, 3H), 7.62 (m, 2H), 2.61 (s, 3H).

3-(Pyrid-2-yl)-5-(3-fluoro-5-thiomethylphenyl)-1,2,4-oxadiazole

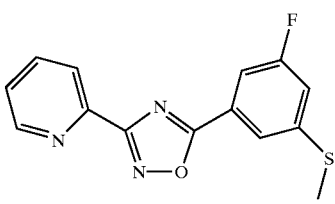

B216

Using the general procedure for the preparation of acid chlorides, 5-fluoro-3-thiomethylbenzoyl chloride was prepared from 5-fluoro-3-thiomethylbenzoic acid (470 mg, 2.52 mmol). A suspension of pyrid-2-ylamidoxime (346 mg, 2.52 mmol) in dichloromethane (3 mL) was treated with 5-fluoro-3-thiomethylbenzoyl chloride and the mixture was stirred 3 hours. The solvent was removed in vacuo and the intermediate dissolved in N,N-dimethylformamide (10 mL). The reaction was heated, under an argon atmosphere, for 4 hours at 120° C. After this time, the reaction mixture was cooled and the solvent removed in vacuo. Silica gel chromatography using a gradient of 0% to 4% ethyl acetate in dichloromethane afforded 567 mg (78%) of 3-(pyrid-2-yl)-5-(5-fluoro-3-thiomethylphenyl)-1,2,4-oxadiazole as a white solid: $^1$H-NMR (CDCl$_3$), δ (ppm): 8.85 (t, 1H), 8.21 (d, 1H), 7.89 (m, 2H), 7.72 (m, 1H), 7.47 (m, 1H), 7.15 (m, 1H), 2.57 (s, 3H).

3-(Pyrid-2-yl)-5-(3-fluoro-5-thiomethylsulphoxidephenyl)-1,2,4-oxadiazole

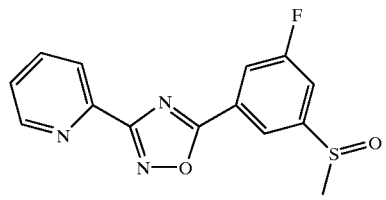

B217

3-(Pyrid-2-yl)-5-(3-fluoro-5-thiomethylphenyl)-1,2,4-oxadiazole (50 mg, 0.17 mmol) was dissolved in dichloromethane in an argon atmosphere at −78° C. and a solution of m-chloroperoxybenzoic acid (30 mg, 0.17 mmol) in dichloromethane was added. After 10 minutes, the reaction was allowed to warm to 0° C. and quenched with aqueous sodium bicarbonate. The reaction extracted with dichloromethane, washed with water and dried over anhydrous sodium sulphate. Column chromatography using 5% methanol in dichloromethane yielded 31 mg (59%) of 3-(Pyrid-2-yl)-5-(3-fluoro-5-thiomethylsulphoxidephenyl)-1,2,4-oxadiazole as an off-white solid. $^1$H-NMR (CDCl$_3$), δ (ppm): 8.83 (d, 1H), 8.20 (t, 2H), 8.06 (m, 1H), 7.89 (m, 1H), 7.73 (m, 1H), 7.47 (m, 1H), 2.82 (s, 3H).

3-(Pyrid-2-yl)-5-(3-fluoro-5-thioethylphenyl)-1,2,4-oxadiazole

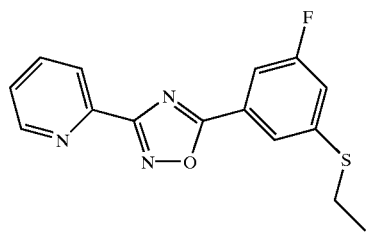

B218

Using the general procedure for the preparation of acid chlorides, 5-fluoro-3-thioethylbenzoyl chloride was prepared from 5-fluoro-3-thioethylbenzoic acid (274 mg, 1.37 mmol). A suspension of pyrid-2-ylamidoxime (188 mg, 1.37 mmol) in dichloromethane (3 mL) was treated with 5-fluoro-3-thioethylbenzoyl chloride and the mixture was stirred 3 hours. The solvent was removed in vacuo and the intermediate dissolved in N,N-dimethylformamide (5 mL). The reaction was heated, under an argon atmosphere, for 12 hours at 120° C. After this time, the reaction mixture was cooled and the solvent removed in vacuo. Silica gel chromatography using a gradient of 0% to 4% ethyl acetate in dichloromethane afforded 245 mg (59%) of 3-(pyrid-2-yl)-5-(5-fluoro-3-thioethylphenyl)-1,2,4-oxadiazole as a white solid: $^1$H-NMR (CDCl$_3$), δ (ppm): 8.76 (t, 1H), 8.12 (d, 1H), 7.83 (t, 1H), 7.77 (m, 1H), 7.65 (m, 1H), 7.39 (m, 1H), 7.12 (m, 1H), 2.96 (q, 2H), 1.28 (t, 3H).

3-(Pyrid-2-yl)-5-(3-fluoro-5-thioethylphenyl)-1,2,4-oxadiazole

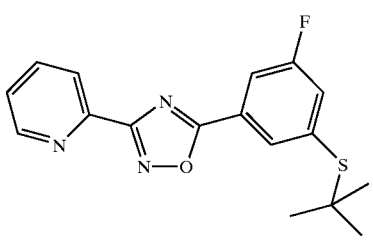

B219

Using the general procedure for the preparation of acid chlorides, 5-fluoro-3-thioethylbenzoyl chloride was prepared from 5-fluoro-3-thioethylbenzoic acid (274 mg, 1.20 mmol). A suspension of pyrid-2-ylamidoxime (165 mg, 1.20 mmol) in dichloromethane (3 mL) was treated with 5-fluoro-3-thiotertbutylbenzoyl chloride and the mixture was stirred 3 hours. The solvent was removed in vacuo and the intermediate dissolved in N,N-dimethylformamide (6 mL). The reaction was heated, under an argon atmosphere, for 12 hours at 120° C. After this time, the reaction mixture was cooled and the solvent removed in vacuo. Silica gel chromatography using dichloromethane afforded 31 mg (8%) of 3-(pyrid-2-yl)-5-(5-fluoro-3-thiotertbutylphenyl)-1,2,4-oxadiazole as a white solid: $^1$H-NMR (CDCl$_3$), δ (ppm): 8.85 (t, 1H), 8.24 (d, 1H), 7.97 (m, 1H), 7.89 (m, 1H), 7.48 (m, 1H), 1.34 (t, 9H).

(a) 3-(5-Fluoropyrid-2-yl)-5-(3-cyano-5-methylphenyl)-1,2,4-oxadiazole

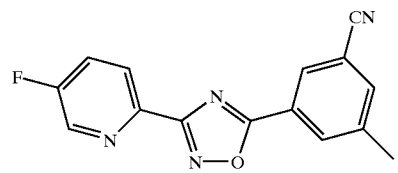

B220

To a mixture of 3-cyano-5-methylbenzoic acid (80 mg, 0.5 mmol), oxalyl chloride (1 mls, 2M solution in CH$_2$Cl$_2$, 2 mmol) in CH$_2$Cl$_2$ (5 ml) was added a few drops of DMF (one pipette drops) and the mixture was stirred at room temperature for 3 h. The solvent was then removed in vacuo. The residue was then dissolved in CH$_2$Cl$_2$ (5 ml) followed by the addition of 5-Fluoro-2-pyridyl amidoxime (78 mg, 0.5 mmol) and Et3N (0.2 ml) and stirring was continued for a further 1 h. Removal of the solvent in vacuo gave the crude residue which was dissolved in DMF (5 ml). The resulting solution was heated to 120° C. overnight after which the solvent was removed in vacuo and the residue was triturated with 20% ethylacetate/hexane giving the product as a white solid (21 mg, 15% yield). 1HNMR(CDCl$_3$) []: 8.70 (d, 1H), 8.37 (s, 1H), 8.34 (s, 1H), 8.28 (dd, 1H), 7.70 (s, 1H), 7.60 (dt, 1H), 2.50 (s, 3H).

(b) 3-(5-cyanopyrid-2-yl)-5-(3-cyano-5-methylphenyl)-1,2,4-oxadiazole

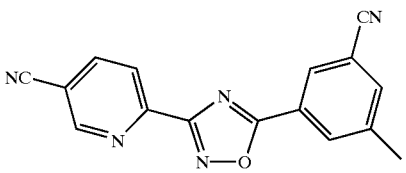

B221

To a mixture of 3-cyano-5-methylbenzoic acid (81 mg, 0.5 mmol), oxalyl chloride (1 mls, 2M solution in CH$_2$Cl$_2$, 2 mmol) in CH$_2$Cl$_2$ (5 ml) was added a few drops of DMF (one pipette drops) and the mixture was stirred at room temperature for 3 h. The solvent was then removed in vacuo. The residue was then dissolved in CH$_2$Cl$_2$ (5 ml) followed by the addition of 5-cyano-2-pyridyl amidoxime (78 mg, 0.5 mmol) and Et3N (0.2 ml) and stirring was continued for a further 1 h. Removal of the solvent in vacuo gave the crude residue which was dissolved in DMF (5 ml). The resulting solution was heated to 120° C. overnight after which the solvent was removed in vacuo and the residue was triturated with 20% ethylacetate/hexane giving the product as an off-white solid (10 mg, 7% yield). 1HNMR(CDCl3)[]: 9.10 (d, 1H), 8.39 (d,1H), 8.37 (s,1H), 8.34 (s, 1H), 8.20 (dd, 1H), 7.75 (s, 1H), 2.60 (s, 3H).

(c) 3-(5-Fluoropyrid-2-yl)-5-(4-cyano-2-thienyl)-1,2,4-oxadiazole

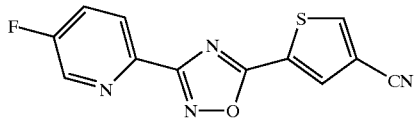

B222

To a mixture of 4-cyano-2-thiophenecarboxylic acid (70 mg, 0.46 mmol), oxalyl chloride (1 mls, 2M solution in CH$_2$Cl$_2$, 2 mmol) in CH$_2$Cl$_2$ (5 ml) was added a few drops of DMF (one pipette drops) and the mixture was stirred at room temperature for 3 h. The solvent was then removed in vacuo. The residue was then dissolved in CH$_2$Cl$_2$ (5 ml) followed by the addition of 5-cyano-2-pyridyl amidoxime (71 mg, 0.46 mmol) and Et3N (0.2 ml) and stirring was continued for a further 1 h. Removal of the solvent in vacuo gave the crude residue which was dissolved in DMF (2 ml). The resulting solution was heated to 120° C. overnight after which the solvent was removed in vacuo and the residue was triturated with 20% ethylacetate/hexane giving the product as an off-white solid (20 mg, 16% yield). 1HNMR(CDCl3): 8.68 (d, 1H), 8.25 (d,1H), 8.22 (s,1H), 8.17 (s, 1H), 7.61 (s, 1H).

Example 6

3-(2-Pyridyl)-5-(5-cyano-2-methoxyphenyl)-1,2,4-oxadiazole

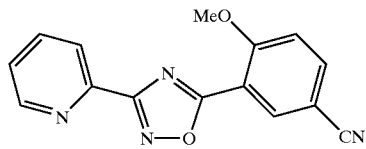

B97

A mixture of 3-(2-pyridyl)-5-(5-bromo-2-methoxyphenyl)-1,2,4-oxadiazole (66.4 mg, 0.2 mmol), zinc cyanide (35.1 mg, 0.3 mmol), and tetrakis(triphenylphosphine)palladium (Pd(PPh$_3$)$_4$, 23.1 mg, 0.02 mmol) in N,N-dimethylformamide (2 mL) was heated under an argon atmosphere at 80° C. for 16 hours. After cooling, the reaction mixture was poured into water and the crude product extracted with dichloromethane. Silica gel chromatography using 30% ethyl acetate in hexane afforded 6.9 mg (12%) of 3-(2-pyridyl)-5-(5-cyano-2-methoxyphenyl)-1,2,4-oxadiazole.

3-(2-pyridyl)-5-(2-cyano-5-methoxyphenyl)-1,2,4-oxadiazole

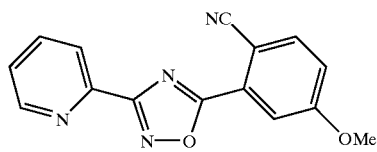

B98

In a similar fashion, a mixture of 3-(2-pyridyl)-5-(2-bromo-5-methoxyphenyl)-1,2,4-oxadiazole (33.2 mg, 0.1 mmol), zinc cyanide (17.6 mg, 0.15 mmol) and Pd(PPh$_3$)$_4$ (11.5 mg, 0.01 mmol) in N,N-dimethylformamide (1 mL) was heated under an argon atmosphere at 80° C. for 16 hours. After cooling, the reaction mixture was poured into water and the crude product extracted with dichloromethane. Silica gel chromatography using 50% ethyl acetate in hexane afforded 1.1 mg (4%) of 3-(2-pyridyl)-5-(2-cyano-5-methoxyphenyl)-1,2,4-oxadiazole.

3-(2-Pyridyl)-5-(5-cyano-pyrid-3-yl)-1,2,4-oxadiazole

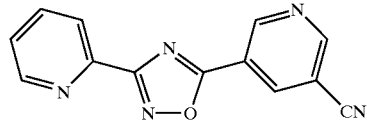

B99

In a similar fashion, mixture of 3-(2-pyridyl)-5-[3-(5-bromo-pyridyl)]-1,2,4-oxadiazole (90.9 mg, 0.3 mmol), zinc cyanide (24.6 mg, 0.21 mmol) and Pd(PPh$_3$)$_4$ (34.7 mg, 0.03 mmol) in N,N-dimethylformamide (1 mL) was stirred under an argon atmosphere at 80° C. for 16 hours. After cooling, the reaction mixture was poured into water and the crude product extracted with dichloromethane. Silica gel chromatography afforded 16 mg (21%) of 3-(2-pyridyl)-5-(5-cyano-pyrid-3-yl)-1,2,4-oxadiazole.

3-(2-Pyridyl)-5-(3-cyano-5-(methoxycarbonyl)phenyl)-1,2,4-oxadiazole

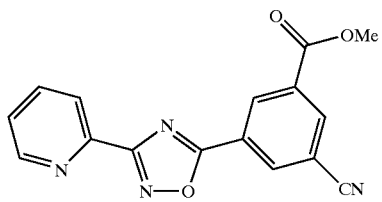

B100

In a similar fashion, a solution of 3-(2-pyridyl)-5-(3-iodo-5-(methoxycarbonyl)phenyl)-1,2,4-oxadiazole (50 mg, 0.122 mmol) in N,N-dimethylformamide (2 mL) was treated with zinc cyanide (22.5 mg, 0.191 mmol), and Pd(PPh$_3$)$_4$ (14 mg, 0.012 mmol). The reaction mixture was heated at 80° C. under an argon atmosphere for 2 hours. The mixture was then diluted with ethyl acetate (25 mL) and washed with water (3×5 mL) and brine (3×5 mL). The organic solution was then dried over anhydrous MgSO$_4$, filtered and concentrated in vacuo. Silica gel chromatography using 30% ethyl acetate in hexane afforded 29.2 mg (78%) of 3-(2-pyridyl)-5-(3-cyano-5-(methoxycarbonyl)phenyl)-1,2,4-oxadiazole: $^1$H-NMR (CDCl$_3$), δ (ppm): 9.19 (s, 1H), 8.89 (d, 1H), 8.80 (s, 1H), 8.59 (s, 1H), 8.25 (d, 1H), 7.95 (t, 1H), 7.50 (m, 1H), 4.09 (s, 3H).

3-(2-Pyridyl)-5-(3-cyano-5-trifluoromethylphenyl)-1,2,4-oxadiazole

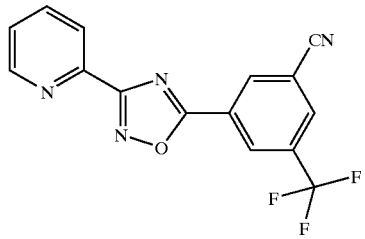

B223

Using the general procedure for the preparation of acid chlorides, 3-iodo-5-trifluoromethylbenzoyl chloride was prepared from 3-iodo-5-trifluoromethylbenzoic acid (711 mg, 4.46 mmol). To a solution of the acid chloride in dichloromethane (10 mL), pyridylamidoxime (217.7 mg, 1.588 mmol) was added. The solution was stirred at room temperature for 10 minutes and then concentrated in vacuo. DMF (8 mL) was added to the residue and the resulting solution was stirred at 120° C. for 16 h under argon. After the reaction mixture was cooled to room temperature, the solvent was removed in vacuo. Flash chromatography on silica gel (10%–20% ethyl acetate in hexane) yielded 439 mg (66%) of 3-(2-pyridyl)-5-(3-iodo-5-trifluoromethylphenyl)-1,2,4-oxadiazole. This intermediate (100.8 mg, 241.6 mmol), zinc cyanide (34.7 mg, 296 mmol) and tetrakistriphenyphosphine palladium(0) (Pd(PPh$_3$)$_4$, 30.5mg, 0.026 mmol) were mixed and flushed with argon. DMF (1 mL) was added and the resulting solution was stirred for 2 h at 80° C. After cooling to room temperature the reaction mixture was filtered through celite and washed with ethyl acetate (50 mL). The crude mixture was extracted into ethyl acetate (100 mL), washed sequentially with water (3×50 mL) and brine (50 mL), and dried over sodium sulfate. Flash chromatography on silica gel (50% ethyl acetate in hexane) yielded 53 mg (69%, GC/MS purity 97%) of 3-(2-pyridyl)-5-(3-cyano-5-trifluoromethylphenyl)-1,2,4-oxadiazole. $^1$H-NMR (CDCl$_3$), δ (ppm): 8.87 (d, 1H), 8.80 (s, 1H), 8.78 (s, 1H), 8.24 (d, 1H), 8.15 (s, 1H), 7.92 (m, 1H), 7.51 (m, 1H).

3-(5-Fluoro-2-pyridyl)-5-(3-cyano-5-trifluoromethylphenyl)-1,2,4-oxadiazole

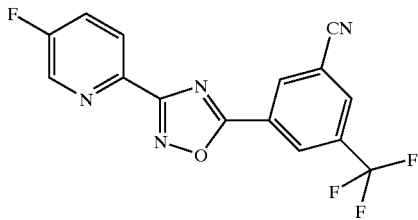

B224

In a similar fashion, 3-iodo-5-trifluoromethylbenzoyl chloride was prepared from 3-iodo 5-trifluoromethylbenzoic acid (118.2 mg, 0.374 mmol). To a solution of the acid chloride in dichloromethane (2 mL), 5-fluoropyridylamidoxime (124.4 mg, 0.3861 mmol) was added. The solution was stirred at room temperature for 10 minutes and then concentrated in vacuo. DMF (8 mL) was added to the residue and the resulting solution was stirred at 120° C. for 16 h under argon. After the reaction mixture was cooled to room temperature, the solvent was removed in vacuo. Flash chromatography on silica gel (10%–20% ethyl acetate in hexane) yielded 38.6 mg (24.4%) of 3-(5-fluoro-2-pyridyl)-5-(3-iodo-5-trifluoromethylphenyl)-1,2,4-oxadiazole. This intermediate (38.6 mg, 0.089 mmol), zinc cyanide (16.8 mg, 0.143 mmol) and Pd(PPh$_3$)$_4$ (11.8mg, 0.01 mmol) were mixed and flushed with argon. DMF (2 mL) was added and the resulting solution was stirred for 1 h at 80° C. After cooling to room temperature the reaction mixture was filtered through celite and washed with ethyl acetate (50 mL). The crude mixture was extracted into ethyl acetate (300 mL), washed sequentially with water (6×50 mL) and brine (50 mL), and dried over sodium sulfate. Trituration of the solid with ether yielded 7.5 mg (26%) of 3-(5-fluoro-2-pyridyl)-5-(3-cyano-5-trifluoromethylphenyl)-1,2,4-oxadiazole. $^1$H-NMR (CDCl$_3$), δ (ppm): 8.78 (s, 1H), 8.75 (s, 1H), 8.72 (s, 1H), 8.27 (m, 1H), 8.16 (s, 1H), 7.63 (m, 1H).

EXAMPLE 7

3-(2-Pyridyl)-5-(3-cyano-5-(4-pyridyl)phenyl)-1,2,4-oxadiazole

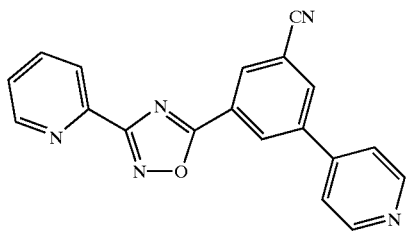

B101

A mixture of 3-(2-pyridyl)-5-(3-bromo-5-cyanophenyl)-1,2,4-oxadiazole (70 mg, 0.21 mmol), 4-pyridylboronic acid (53 mg, 0.43 mmol), and tetrakis(triphenylphosphine) palladium(0) (Pd(PPh$_3$)$_4$, 25 mg, 0.021 mmol) in a solution of ethylene glycol dimethyl ether (3 mL) and 2M sodium carbonate (3 mL) was headed in a sealed vial at 100° C. for 1 hour with vigorous stirring. The reaction was cooled and diluted with chloroform. The organic solution was washed with water and saturated brine, filtered, and concentrated. Silica gel chromatography of the residue using a gradient of 50% ethyl acetate in hexane to 100% ethyl acetate followed by trituration with 5% ethyl acetate in diethyl ether afforded 6 mg (9%) of 3-(2-pyridyl)-5-(3-cyano-5-(4-pyridyl)phenyl)-1,2,4-oxadiazole: $^1$H NMR (CDCl$_3$): δ-8.88 (d, 1H), 8.78 (m, 3H), 8.64 (s, 1H), 8.26 (d, 1H), 8.15 (s, 1H), 7.93 (t, 1H), 7.61 (m, 2H), 7.52 (m, 1H).

3-(2-Pyridyl)-5-[2-methoxy-5-(4-pyridyl)phenyl]-1,2,4-oxadiazole

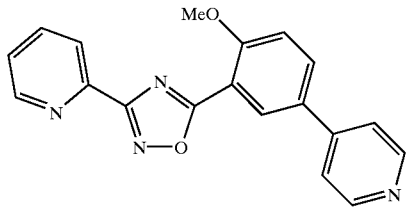

B102

In a similar fashion, 3-(2-pyridyl)-5-(5-bromo-2-methoxyphenyl)-1,2,4-oxadiazole (66.4 mg, 0.2 mmol), 4-pyridylboronic acid (48.8 mg, 0.4 mmol), and Pd(PPh$_3$)$_4$ (23 mg, 0.02 mmol) in a solution of 2M sodium carbonate (2 mL) and ethylene glycol dimethyl ether (2 mL) was heated overnight at 105° C. Standard work up, afforded 6.6 mg (10%) of 3-(2-pyridyl)-5-[2-methoxy-5-(4-pyridyl) phenyl]-1,2,4-oxadiazole.

3-(2-Pyridyl)-5-[2-fluoro-5-(4-pyridyl)phenyl]-1,2,4-oxadiazole

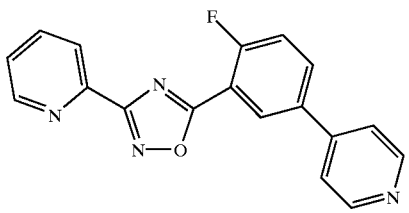

B103

In a similar fashion, 3-(2-pyridyl)-5-(5-bromo-2-fluorophenyl)-1,2,4-oxadiazole (100 mg, 0.312 mmole), 4-pyridylboronic acid (76.7 mg, 0.6265 mmol) and Pd(PPh$_3$)$_4$ (36.1 mg, 0.03123 mmol) in a solution of 2M sodium carbonate (4 mL) and ethylene glycol dimethyl ether (4 mL) was heated overnight at 105° C. Standard work up, afforded 4.1 mg (4%) of 3-(2-pyridyl)-5-[2-fluoro-5-(4-pyridyl)phenyl]-1,2,4-oxadiazole.

3-(2-Pyridyl)-5-(3-fluoro-5-(4-pyridyl)phenyl)-1,2,4-oxadiazole

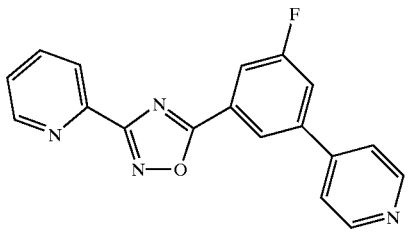

B104

In a similar fashion, 3-(2-pyridyl)-5-(3-bromo-5-fluorophenyl)-1,2,4-oxadiazole (30 mg, 0.093 mmol), pyridine-4-boronic acid (17.1 mg, 0.093 mmol), and Pd(PPh$_3$)$_4$ (10.4 mg, 0.0093 mmol) in a solution of and ethylene glycol dimethyl ether (1 mL) and 2M sodium carbonate (1 mL) was heated in a sealed vial at 100° C. for 1 hour. Standard work up and silica gel chromatography using a gradient of 50% ethyl acetate in hexane to 100% ethyl acetate afforded 2 mg (7%) of 3-(2-pyridyl)-5-(3-fluoro-5-(4-pyridyl)phenyl)-1,2,4-oxadiazole: $^1$H-NMR (CDCl$_3$), δ (ppm): 8.88 (d, 1H), 8.79 (d, 2H), 8.40 (s, 1H), 8.25 (d, 1H), 8.06 (md, 1H), 7.90 (td, 1H), 7.60 (m, 3H), 7.50 (ddd, 1H).

3-(2-Pyridyl)-5-(3-fluoro-5-(3-pyridyl)phenyl)-1,2,4-oxadiazole

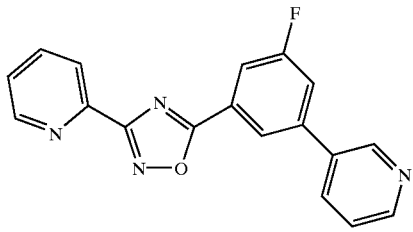

B105

A mixture of 3-(2-pyridyl)-5-(3-bromo-5-fluorophenyl)-1,2,4-oxadiazole (100 mg, 0.312 mmol), pyridine-3-boronic acid 1,3-propanediol cyclic ester (102 mg, 0.624 mmol), and tetrakis(triphenylphosphine)palladium(0) (Pd(PPh$_3$)$_4$, 35.8 mg, 0.031 mmol), in a solution of ethylene glycol dimethyl ether (3 mL) and 2M sodium carbonate (3 mL) was heated in a sealed vial at 100° C. for 1 hour. The reaction was cooled, diluted with chloroform, washed with water and saturated brine, filtered, and concentrated. Silica gel chromatography using a gradient of 50% ethyl acetate in hexane to 100% ethyl acetate afforded 19 mg (19%) 3-(2-pyridyl)-5-(3-fluoro-5-(3-pyridyl)phenyl)-1,2,4-oxadiazole: $^1$H-NMR (CDCl$_3$), δ (ppm): 8.92 (s, 1H), 8.84 (d, 1H), 8.70 (d, 1H), 8.39 (s, 1H), 8.25 (d, 1H), 8.00 (m, 2H), 7.90 (td, 1H), 7.65 (m, 1H), 7.55 (m, 2H).

3-(2-Pyridyl)-5-[2-fluoro-5-(3-pyridyl)phenyl]-1,2,4-oxadiazole

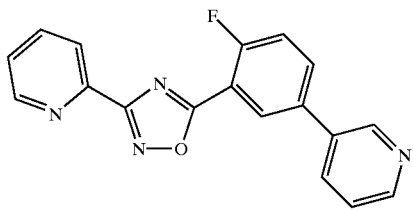

B106

In a similar fashion, 3-(2-pyridyl)-5-(5-bromo-2-fluorophenyl)-1,2,4-oxadiazole (100 mg, 0.312 mmol), pyridine-3-boronic acid 1,3-propanediol cyclic ester (101.8 mg, 0.625 mmol) and Pd(PPh$_3$)$_4$ (36.1 mg, 0.0312 mmole) in a solution of 2M sodium carbonate (4 mL) and ethylene glycol dimethyl ether (4 mL) was heated overnight at 105° C. Standard work up afforded 8.7 mg (9%) 3-(2-pyridyl)-5-[2-fluoro-5-(3-pyridyl)phenyl]-1,2,4-oxadiazole.

3-(2-Pyridyl)-5-[2-methoxy-5-(3-pyridyl)phenyl]-1,2,4-oxadiazole

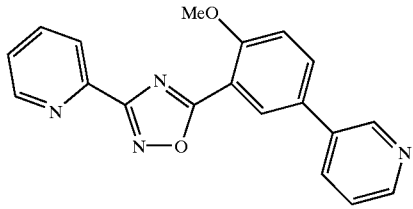

B107

In a similar fashion, 3-(2-pyridyl)-5-(5-bromo-2-methoxyphenyl)-1,2,4-oxadiazole (66.4 mg, 0.2 mmol), pyridine-3-boronic acid 1,3-propanediol cyclic ester (65 mg, 0.4 mmol), and Pd(PPh₃)₄ (23 mg, 0.02 mmol) in a solution of 2M sodium carbonate (2 mL) and ethylene glycol dimethyl ether (2 mL) was heated overnight at 105° C. Standard work up afforded 21 mg (32%) 3-(2-pyridyl)-5-[2-methoxy-5-(3-pyridyl)phenyl]-1,2,4-oxadiazole.

3-(2-Pyridyl)-5-(3-cyano-5-(3-pyridyl)phenyl)-1,2,4-oxadiazole

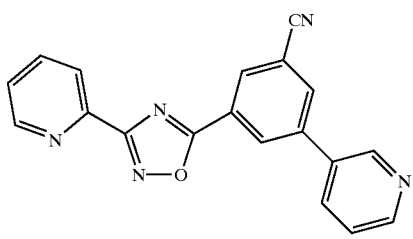

B108

In a similar fashion, 3-(2-pyridyl)-5-(3-bromo-5-cyanophenyl)-1,2,4-oxadiazole (71 mg, 0.22 mmol), pyridine-3-boronic acid 1,3-propanediol cyclic ester (70 mg, 0.43 mmol), and Pd(PPh₃)₄ (25 mg, 0.022 mmol) in a solution of ethylene glycol dimethyl ether (3 mL) and 2M sodium carbonate (3 mL) was heated in a sealed vial at 100° C. for 1 hour. Standard work up and silica gel chromatography using a gradient of 50% ethyl acetate in hexane to 100% ethyl acetate followed by trituration with 5% ethyl acetate in diethyl ether afforded 16 mg (22%) of 3-(2-pyridyl)-5-(3-cyano-5-(3-pyridyl)phenyl)-1,2,4-oxadiazole: ¹H NMR (CDCl₃): δ-8.94 (d, 1H), 8.88 (d, 1H), 8.74 (m, 2H), 8.61 (s, 1H), 8.25 (d, 1H), 8.00 (s, 1H), 7.98 (m, 1H), 7.93 (m, 1H), 7.50 (m, 2H).

3-(5-Fluoro-2-pyridyl)-5-(3-fluoro-5-(3-pyridyl)phenyl)-1,2,4-oxadiazole

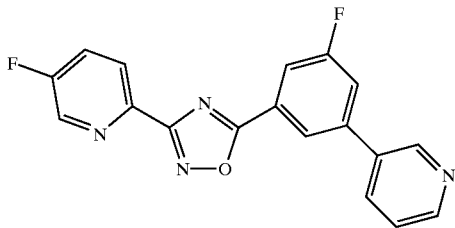

B109

In a similar fashion, 3-(5-fluoro-2-pyridyl)-5-(3-bromo-5-fluorophenyl)-1,2,4-oxadiazole (60 mg, 0.154 mmol), pyridine-3-boronic acid 1,3-propanediol cyclic ester (50.4 mg, 0.309 mmol), and Pd(PPh₃)₄ (17.8 mg, 0.015 mmol), in a solution of ethylene glycol dimethyl ether (2 mL) and 2M sodium carbonate (2 mL) was heated in a selaed vial at 100° C. for 1 hour. Standard work up and silica gel chromatography using a gradient of 50% to 70% ethyl acetate in hexane afforded 24.7 mg (48%) of 3-(5-fluoro-2-pyridyl)-5-(3-fluoro-5-(3-pyridyl)phenyl)-1,2,4-oxadiazole: ¹H-NMR (CDCl₃), δ (ppm): 8.92 (d, 1H), 8.71 (m, 2H), 8.31 (s, 1H), 8.30 (dd, 1H), 8.00 (m, 2H), 7.62 (td, 1H), 7.57 (td, 1H), 7.45 (dd, 1H).

3-(5-Fluoropyrid-2-yl)-5-[5-(3-pyridyl)-pyrid-3-yl)]-1,2,4-oxadiazole

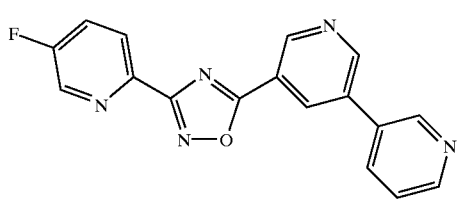

B110

In a similar fashion, 3-(5-fluoropyrid-2-yl)-5-(5-bromo-pyrid-3-yl)-1,2,4-oxadiazole (164 mg, 0.5 mmole), pyridine-3-boronic acid 1,3-propanediol cyclic ester (163.0 mg, 1 mmol) and Pd(PPh₃)₄ (57.8 mg, 0.05 mmol) in a solution of 2M sodium carbonate (2.5 mL) and ethylene glycol dimethyl ether (2.5 mL) was heated at 105° C. for 1 hour. Standard work up afforded 57 mg (18%) of 3-(5-fluoropyrid-2-yl)]-5-[5-(3-pyridyl)-pyrid-3-yl)]-1,2,4-oxadiazole.

3-(2-Pyridyl)-5-[5-(3-pyridyl)-pyrid-3-yl]-1,2,4-oxadiazole

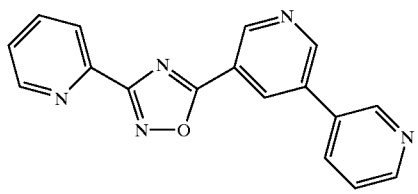

B111

In a similar fashion, 3-(2-pyridyl)-5-(5-bromo-pyrid-3-yl)-1,2,4-oxadiazole (60.6 mg, 0.2 mmole), pyridine-3-boronic acid 1,3-propanediol cyclic ester (48.9 mg, 0.3 mmol) and Pd(PPh₃)₄ (34.65 mg, 0.03 mmole) in a solution of 2M sodium carbonate (2 mL) and ethylene glycol dimethyl ether (2 mL) was heated overnight at 105° C. Standard work up afforded 21 mg (35%) 3-(2-pyridyl)-5-[5-(3-pyridyl)-pyrid-3-yl]-1,2,4-oxadiazole.

3-(5-Cyanopyrid-2-yl)-5-(3-(pyrid-3-yl) phenyl)-1,2,4-oxadiazole

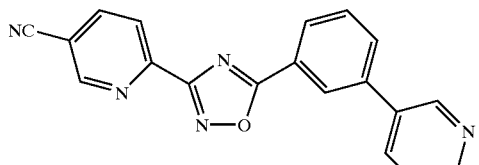

B112

In a similar fashion, 3-(5-cyanopyrid-2-yl)-5-(3-bromophenyl)-1,2,4-oxadiazole (50 mg, 0.15 mmol), pyridine-3-boronic acid 1,3-propanediol cyclic ester (50.5 mg, 0.31 mmol) and Pd(PPh₃)₄ (24 mg, 0.021 mmol) in a solution of ethylene glycol dimethyl ether (2 mL) and 2M sodium carbonate (2 mL) were heated in a sealed tube at 90° C. for 45 min. Standard work up, silica gel chromatography (gradient of 20% to 50% ethyl acetate in hexane) and trituration (diethyl ether) of the hydrochloride salt, afforded 11.7 mg (42%) of 3-(5-cyanopyrid-2-yl)-5-(3-(pyrid-3-yl)

phenyl)-1,2,4-oxadiazole dihydrochloride: $^1$H-NMR (CDCl$_3$),δ (ppm):☐9.15 (s, 1H), 9.00 (s, 1H), 8.80 (s, 1H), 8.66 (d, 1H), 8.52 (s, 1H), 8.34 (m, 2H), 8.17 (dd, 1H), 8.02 (m, 1H), 7.95 (d, 1H), 7.75 (t, 1H).

3-(5-Cyanopyrid-2-yl)-5-(3-fluoro-5-(pyrid-3-yl)phenyl)-1,2,4-oxadiazole

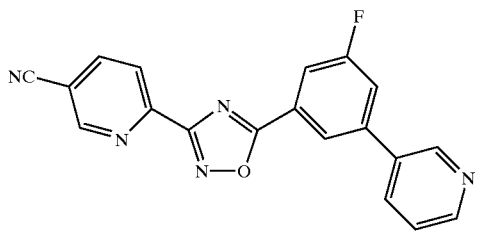

B113

In a similar fashion, 3-(5-cyanopyrid-2-yl)-5-(3-bromo-5-fluorophenyl)-1,2,4-oxadiazole (16.7 mg, 0.048 mmol), pyridine-3-boronic acid 1,3-propanediol cyclic ester (24 mg, 0.15 mmol) and Pd(PPh$_3$)$_4$ (12 mg, 0.01 mmol) in a solution of ethylene glycol dimethyl ether (1 mL) and 2M sodium carbonate (1 mL) were heated in a sealed tube at 90° C. for for 1 hour. Standard work up, silica gel chromatography (gradient of 20% to 50% ethyl acetate in hexane) and trituration (dichloromethane) of the hydrochloride salt, afforded 4.9 mg (24%) of 3-(5-cyanopyrid-2-yl)-5-(3-fluoro-5-(pyrid-3-yl)phenyl)-1,2,4-oxadiazole dihydrochloride (4.9 mg, 24%): $^1$H-NMR (CD$_3$OD/CDCl$_3$), δ (ppm): ☐☐9.36 (s, 1H), 9.10 (s, 1H), 9.06 (d, 1H), 8.95 (d, 1H), 8.55 (s, 1H), 8.45 (m, 2H), 8.27 (t, 1H), 8.20 (d, 1H), 8.01 (d, 1H).

3-(2-Pyridyl)-5-[(3-(3-fluorophenyl)-5-fluorophenyl)]-1,2,4-oxadiazole

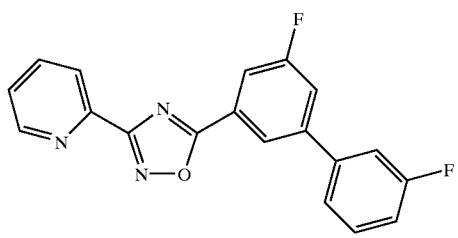

B114

A mixture of 3-(2-pyridyl)-5-[(3-bromo-5-fluorophenyl)]-1,2,4-oxadiazole (55.5mg, 0.173 mmol), 3-fluorophenyl boronic acid (48.4mg, 0.346 mmol), tetrakis(triphenylphosphine)palladium(0) (Pd(PPh$_3$)$_4$ (20mg, 0.017 mmol) in a solution of dimethoxy ethane (1.5 mL) and 2M sodium carbonate (1.5 mL) was heated in a sealed vial overnight at 100° C. After cooling, the reaction mixture was treated with water and the product extracted with dichloromethane (3×). Silica gel chromatography of the crude product using 30% ethyl acetate in hexane afforded 21.2mg (37%) of 3-(2-pyridyl)-5-[3-(3-fluorophenyl)-5-fluorophenyl)]-1,2,4-oxadiazole: m.p. 146–150° C.

3-(2-Pyridyl)-5-(3-cyano-5-(3-thiophene)phenyl)-1,2,4-oxadiazole

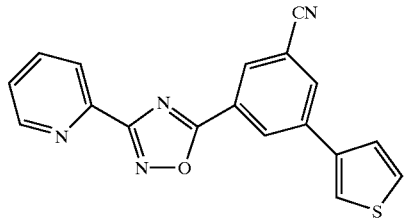

B115

In a similar fashion, 3-(2-pyridyl)-5-(3-bromo-5-cyanophenyl)-1,2,4-oxadiazole (70 mg, 0.21 mmol), 3-thiopheneboronic acid (55 mg, 0.43 mmol), Pd(PPh$_3$)$_4$ (25 mg, 0.021 mmol) in a solution of 2M sodium carbonate (3 mL) and ethylene glycol dimethyl ether (3 mL) was heated at 100° C. for 1 hour. Standard work up and silica gel chromatography using a gradient of 10% to 30% ethyl acetate in hexane afforded 22 mg (31%) of 3-(2-pyridyl)-5-(3-cyano-5-(3-thiophene)phenyl)-1,2,4-oxadiazole: $^1$H NMR (CDCl$_3$): δ-8.87 (d, 1H), 8.71 (s, 1H), 8.46 (s, 1H), 8.25 (d, 1H), 8.08 (s, 1H), 7.92 (t, 1H), 7.69 (s, 1H), 7.50 (m, 3H).

3-(2-Pyridyl)-5-[5-(3-thienyl)-pyrid-3-yl ]-1,2,4-oxadiazole

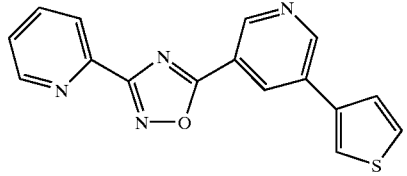

B116

In a similar fashion, 3-(2-pyridyl)-5-(5-bromo-pyrid-3-yl)-1,2,4-oxadiazole (42 mg, 0.1385 mmol), 3-thiopheneboronic acid (26.6 mg, 0.208 mmol), and Pd(PPh$_3$)$_4$ (24.0 mg, 0.021 mmole) in a solution of 2M sodium carbonate (1.5 mL) and ethylene glycol dimethyl ether (1.5 mL) was heated overnight at 105° C. Standard work up afforded 3.2 mg (8%) of 3-(2-pyridyl)-5-[5-(3-thienyl)-pyrid-3-yl ]-1,2,4-oxadiazole.

3-(2-Pyridyl)-5-[5-(3-furyl)-pyrid-3-yl ]-1,2,4-oxadiazole

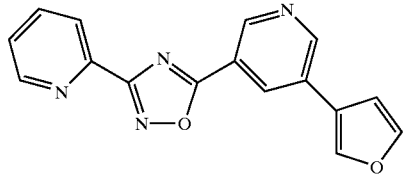

B117

In a similar fashion, 3-(2-pyridyl)-5-(5-bromo-pyrid-3-yl)-1,2,4-oxadiazole (152 mg, 0.5 mmol), 3-furylboronic acid (111.9 mg, 1.0 mmole) and Pd(PPh$_3$)$_4$ (57.8 mg, 0.05 mmole) in a solution of 2M sodium carbonate (3 mL) and ethylene glycol dimethyl ether (3 mL) was heated overnight at 105° C. Standard work up afforded 47 mg (32%) of 3-(2-pyridyl)-5-[5-(3-furyl)-pyrid-3-yl ]-1,2,4-oxadiazole.

3-(2-Pyridyl)-5-(5-phenyl-pyrid-3-yl)-1,2,4-oxadiazole

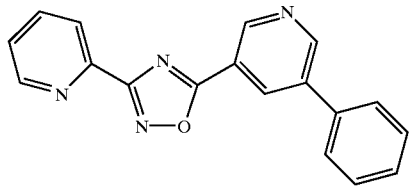

B118

In a similar fashion, 3-(2-pyridyl)-5-(5-bromo-pyrid-3-yl)-1,2,4-oxadiazole (152 mg, 0.5 mmol), phenylboronic acid (121.9 mg, 1.0 mmol) and Pd(PPh$_3$)$_4$ (57.8 mg, 0.05 mmol) in a solution of 2M sodium carbonate (3 mL) and ethylene glycol dimethyl ether (3 ml) was heated overnight at 105° C. Standard work up afforded 45 mg of 3-(2-pyridyl)-5-(5-phenyl-pyrid-3-yl)-1,2,4-oxadiazole.

3-(2-Pyridyl)-5-[5-(3-methoxyphenyl)-pyrid-3-yl]-1,2,4-oxadiazole

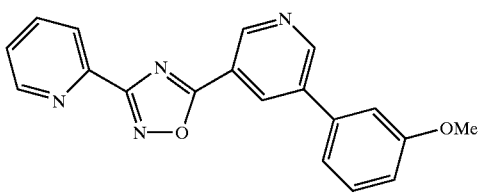

B119

In a similar fashion, 3-(2-pyridyl)-5-[3-(5-bromo-pyridyl)]-1,2,4-oxadiazole (45 mg, 0.148 mmol), 3-methoxyphenylboronic acid (45mg, 0.296 mmol), and Pd(PPh$_3$)$_4$ (25 mg, 0.022 mmol) in a solution of 2M sodium carbonate (1 mL) and ethylene glycol dimethoxy ether (1 mL) was heated at 105° C. for 2 hours. Standard work up afforded 14.8 mg of 3-(2-pyridyl)-5-[5-(3-methoxyphenyl)-pyrid-3-yl ]-1,2,4-oxadiazole.

3-(2-Pyridyl)-5-(3-cyano-5-(5-pyrimidyl)phenyl)-1,2,4-oxadiazole

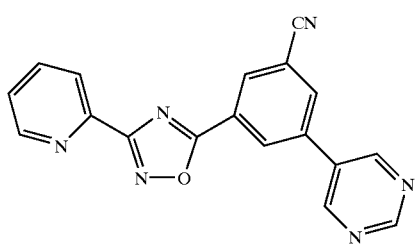

B120

In a similar fashion, 3-(2-pyridyl)-5-(3-bromo-5-cyanophenyl)-1,2,4-oxadiazole (71 mg, 0.22 mmol), pyrimidyl-5-boronic acid pinacolate (89 mg, 0.43 mmol), and Pd(PPh$_3$)$_4$ (25 mg, 0.022 mMol) in a solution of 2M sodium carbonate (3 mL) and ethylene glycol dimethyl ether (3 mL) was heated in a sealed vial at 100° C. for 1 hour. Standard work up and silica gel chromatography using a gradient of 30% ethyl acetate in hexane to 100% ethyl acetate, followed by trituration with ethyl acetate afforded 4 mg (6%) of 3-(2-pyridyl)-5-(3-cyano-5-(5-pyrimidyl)phenyl)-1,2,4-oxadiazole: $^1$H NMR (CDCl$_3$):δ-9.37 (s, 1H), 9.07 (s, 2H), 8.89 (d, 1H), 8.76 (s, 1H), 8.67 (s, 1H), 8.26 (d, 1H), 8.11 (s, 1H), 7.94 (t, 1H), 7.52 (m, 1H).

3-(2-Pyridyl)-5-(3-cyano-5-(3-aminophenyl)phenyl)-1,2,4-oxadiazole

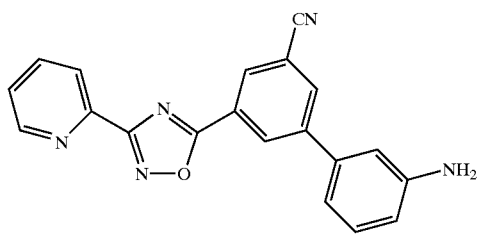

B121

In a similar fashion, 3-(2-pyridyl)-5-(3-bromo-5-cyanophenyl)-1,2,4-oxadiazole (70 mg, 0.21 mmol), 3-aminophenylboronic acid (66 mg, 0.43 mmol), and Pd(PPh$_3$)$_4$ (25 mg, 0.021 mmol), in a solution of ethylene glycol dimethyl ether (3 mL) and 2M sodium carbonate (3 mL) was heated in a sealed vial at 100° C. for 1 hour. Standard work up and silica gel chromatography using a gradient of 30% ethyl acetate in hexane to 100% ethyl acetate, followed by trituration with 50% ethyl acetate in hexane afforded 32mg (45%) of 3-(2-pyridyl)-5-(3-cyano-5-(3-aminophenyl)phenyl)-1,2,4-oxadiazole: $^1$H NMR (CDCl$_3$):δ-8.82 (d, 1H), 8.57 (s, 2H), 8.40 (s, 1H), 8.22 (d, 1H), 8.08 (t, 1H), 7.66 (m, 1H), 7.20 (t, 1H), 7.00 (m, 2H), 6.69 (d, 1H).

3-(2-Pyridyl)-5-(3-cyano-5-(3-fluorophenyl)phenyl)-1,2,4-oxadiazole

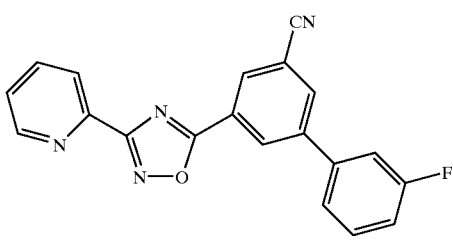

B122

In a similar fashion, 3-(2-pyridyl)-5-(3-bromo-5-cyanophenyl)-1,2,4-oxadiazole (70 mg, 0.21 mmol), 3-fluorophenylboronic acid (60 mg, 0.43 mmol), and Pd(PPh$_3$)$_4$ (25 mg, 0.022 mmol) in a solution of ethylene glycol dimethyl ether (3 mL) and 2M sodium carbonate (3 mL) was heated in a sealed vial at 100° C. for 1 hour. Standard work up and silica gel chromatography using a mixture of hexane:ethyl acetate:dichloromethane (3.5:0.5:4), followed by trituration with diethyl ether afforded 27 mg (36%) of 3-(2-pyridyl)-5-(3-cyano-5-(3-fluorophenyl)phenyl)-1,2,4-oxadiazole: $^1$H NMR (CDCl$_3$): δ-8.86 (d, 1H), 8.70 (s, 1H), 8.55 (s, 1H), 8.24 (d, 1H), 8.07 (s, 1H), 7.91 (t, 1H), 7.49 (m, 3H), 7.40 (m, 1H), 7.19 (m, 1H).

3-(2-pyridyl)-5-[5-(5-pyrimidyl)-pyrid-3-yl]-1,2,4-oxadiazole

B123

In a similar fashion, 3-(2-pyridyl)-5-(5-bromo-pyrid-3-yl)-1,2,4-oxadiazole (42 mg, 0.1385 mmole), 5-pyrimidylboronic acid (26.6 mg,0.208 mmole) and Pd(PPh₃)₄ (23.99 mg, 0.021 mmole) in a solution of 2M sodium carbonate (1.5 mL) and ethylene glycol dimethyl ether (1.5 mL) was heated overnight at 105° C. Standard workup afforded 3.2 mg (8%) of 3-(2-pyridyl)-5-[5-(5-pyrimidyl)-pyrid-3-yl ]-1,2,4-oxadiazole (3.2 mg, 7.6%).

3-(5-Fluoro-pyrid-2-yl)-5-[3-(3-pyridyl)phenyl]-1,2,4-oxadiazole

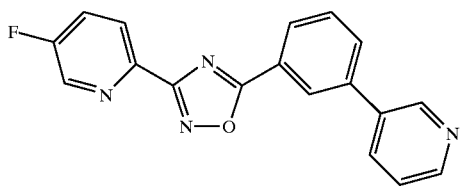

B225

A mixture of 3-(5-fluoro-pyrid-2-yl)-5-(3-bromophenyl)-1,2,4-oxadiazole (100 mg, 0.313 mmol), pyridine-3-boronic acid 1,3-propanediol cyclic ester (102 mg, 0.624 mmol), and tetrakis(triphenylphosphine)palladium(0) (Pd(PPh₃)₄, 50.8 mg, 0.044 mmol), in a solution of ethylene glycol dimethyl ether (2 mL) and 2M sodium carbonate (2 mL) was heated in a sealed vial at 110° C. for 1 hour. The reaction was cooled, diluted with dichloromethane, washed with water and saturated brine, filtered, and concentrated. Silica gel chromatography using a gradient of 50% ethyl acetate in hexane to 100% ethyl acetate afforded 50 mg (50.2%) 3-(5-fluoro-pyrid-2-yl)-5-[3-(3-pyridyl)phenyl]-1,2,4-oxadiazole. ¹H-NMR (CDCl₃), δ (ppm): 8.91 (d, 1H), 8.69 (d, 1H), 8.64 (d, 1H), 8.49 (s, 1H), 8.28 (m, 2H), 8.00 (m, 1H), 7.84 (dd, 1H), 7.69 (t, 1H), 7.60 (td, 1H), 7.44(dd, 1H).

5-[3-Methyl-5-(3-pyridyl)-pyrid-4-yl]-3-(2-pyridyl)-1,2,4-oxadiazole

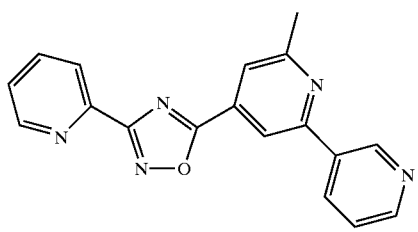

B226

A mixture of 5-(3-chloro-5-methyl-pyrid-4-yl)-3-(2-pyridyl)-1,2,4-oxadiazole (75 mg, 0.275 mmol), pyridine-3-boronic acid 1,3-propanediol cyclic ester (75 mg, 0.46 mmol), and tetrakis(triphenylphosphine)palladium(0) (Pd (PPh₃)₄, 30 mg, 0.026 mmol), in a solution of ethylene glycol dimethyl ether (1 mL) and 2M sodium carbonate (1 mL) was heated in a sealed vial at 100° C. for 1 hour. The reaction was cooled, diluted with dichloromethane, washed with water and saturated brine, filtered, and concentrated. Silica gel chromatography using a gradient of 40% ethyl acetate in hexane to 100% ethyl acetate afforded 5.4 mg (7.4%) of 5-[3-methyl-5-(3-pyridyl)-pyrid-4-yl]-3-(2-pyridyl)-1,2,4-oxadiazole. ¹H-NMR (CDCl₃), δ (ppm): 9.32 (s, 1H), 8.87 (d, 1H), 8.70 (d, 1H), 8.30 (m, 2H), 8.25 (s, 1H), 8.00 (s, 1H), 7.90 (d, 1H), 7.47 (m, 2H), 2.77 (s, 3H).

5-[3-Methoxy-5-(3-pyridyl)-pyrid-4-yl]-3-(2-pyridyl)-1,2,4-oxadiazole

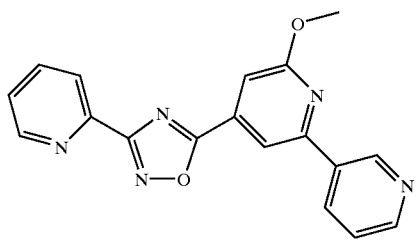

B227

A mixture of 3-(2-pyridyl)-5-(3-chloro-5-methoxy-pyrid-4-yl)-1,2,4-oxadiazole (75 mg, 0.260 mmol), pyridine-3-boronic acid 1,3-propanediol cyclic ester (75 mg, 0.46 mmol), and tetrakis(triphenylphosphine)palladium(0) (Pd (PPh₃)₄, 30 mg, 0.026 mmol), in a solution of ethylene glycol dimethyl ether (1 mL) and 2M sodium carbonate (1 mL) was heated in a sealed vial at 100° C. for 1 hour. The reaction was cooled, diluted with dichloromethane, washed with water and saturated brine, filtered, and concentrated. Silica gel chromatography using 40% ethyl acetate in hexane and 100% ethyl acetate afforded 3.5 mg (4.1%) 3-(2-pyridyl)-5-[3-methoxy-5-(3-pyridyl)-pyrid-4-yl]-1,2,4-oxadiazole. ¹H-NMR (CDCl₃), δ (ppm): 9.39 (s, 1H), 8.91 (d, 1H), 8.72 (d, 1H), 8.42 (d, 1H), 8.25 (d, 1H), 8.20 (s, 1H), 7.92 (dt, 1H), 7.63 (dd, 1H), 7.50 (m, 2H), 4.12 (s, 3H).

5-(2-pyridyl)-3-[5-(3-pyridyl)-pyrid-3-yl]-1,2,4-oxadiazole

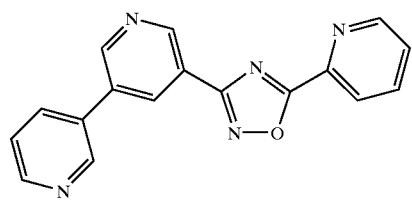

B228

A mixture of 3-(5-bromo-pyrid-3-yl)-5-(2-pyridyl)-1,2,4-oxadiazole 30.3 mg, 0.1 mmol), pyridine-3-boronic acid 1,3-propanediol cyclic ester (32.5 mg, 0.2 mmol), and tetrakis(triphenylphosphine)palladium(0) (Pd(PPh₃)₄, 15 mg, 0.013 mmol), in a solution of ethylene glycol dimethyl ether (1 mL) and 2M sodium carbonate (1 mL) was heated in a sealed vial at 100° C. for 1 hour. The reaction was cooled, diluted with dichloromethane, washed with water and saturated brine, filtered, and concentrated. Silica gel chromatography using 50% ethyl acetate in hexane and 100% ethyl acetate afforded 13 mg (43.2%) 5-(2-pyridyl)-3-[5-(3-pyridyl)-pyrid-3-yl]-1,2,4-oxadiazole. ¹H-NMR (CDCl₃), δ (ppm): 9.49 (d, 1H), 9.01 (d, 1H), 8.93 (dd, 2H), 8.72 (t, 2H), 8.35 (d, 2H), 8.00 (dt, 1H), 7.59 (m, 1H), 7.47 (dd, 1H).

5-(2-pyridyl)-3-[3-(3-pyridyl)-phenyl]-1,2,4-oxadiazole

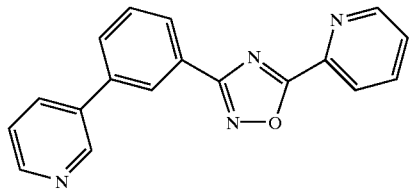

B229

A mixture of 3-(3-iodophenyl)-5-(2-pyridyl)-1,2,4-oxadiazole (55 mg, 0.158 mmol), pyridine-3-boronic acid 1,3-propanediol cyclic ester (51.4 mg, 0.3152 mmol), and tetrakis(triphenylphosphine)palladium(0) Pd(PPh₃)₄, 25 mg, 0.0216 mmol), in a solution of ethylene glycol dimethyl ether (1.5 mL) and 2M sodium carbonate (1.5 mL) was heated in a sealed vial at 100° C. for 1 hour. The reaction was cooled, diluted with dichloromethane, washed with water and saturated brine, filtered, and concentrated. Silica gel chromatography using 40% and 60% ethyl acetate in hexane and then the treatment of 1M HCl (0.2 mL) afforded 29.4 mg (55.45%) 5-(2-pyridyl)-3-[3-(3-pyridyl)-phenyl]-1,2,4-oxadiazole hydrochloride. ¹H-NMR (CDCl₃), δ (ppm): 9.34 (s, 1H), 8.88 (m, 3H), 8.54 (s, 1H), 8.40 (d, 1H), 8.28 (d, 1H), 8.16 (d, 1H), 8.00 (m, 3H), 7.82 (m, 2H).

5-(5-Fluoro-pyrid-2-yl)-3-[3-fluoro5-(3-pyridyl)-phenyl]-1,2,4-oxadiazole

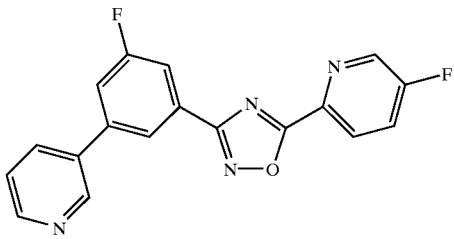

B230

A mixture of 5-fluoro-picolinic acid hydrochloride (177.5 mg, 1 mmol) in dichloromethane (2 mL) was treated with 2M oxalyl chloride (2 ml, 4 mmol, dichloromethane). The mixture was stirred 2 hours at room temperature. The solvent and excess reagent were removed in vacuo. The residue was treated with 3-bromo-5-fluorophenyl-amidoxime (102 mg, 0.5 mmol) and triethylamine (404 mg, 4 mmol) in dichloromethane (2 mL). The mixture was then heated in dimethylformamide (1 mL) for 1 hours at 130° C. Standard work up, afforded 80 mg (47%) of 3-(3-bromo-5fluorophenyl)-5-(5-fluoro-pyrid-2-yl)-1,2,4-oxadiazole.

A mixture of 3-(3-bromo-5-fluorophenyl)-5-(5-fluoro-pyrid-2-yl)-1,2,4-oxadiazole (80 mg, 0.236 mmol), pyridine-3-boronic acid 1,3-propanediol cyclic ester (80 mg, 0.49 mmol), and tetrakis(triphenylphosphine)palladium(0) (Pd(PPh₃)₄, 40 mg, 0.0346 mmol), in a solution of ethylene glycol dimethyl ether (1.5 mL) and 2M sodium carbonate (1.5 mL) was heated in a sealed vial at 100° C. for 1 hour. The reaction was cooled, diluted with dichloromethane, washed with water and saturated brine, filtered, and concentrated. Silica gel chromatography using a gradient of 50% ethyl acetate in hexane, afforded 14 mg (17.7%) 5-(5-fluoro-pyrid-2-yl)-3-[3-fluoro-5-(3-pyridyl)-phenyl]-1,2,4-oxadiazole. ¹H-NMR (CDCl₃), δ (ppm): 8.95 (s, 1H), 8.76 (d, 1H), 8.66 (d, 1H), 8.37 (dd, 2H), 8.25 (s, 1H), 7.95 (d, 2H), 7.43 (m, 2H).

3-(2-Pyridyl)-5-(3-cyano-5-(2-pyridyl)phenyl)-1,2,4-oxadiazole

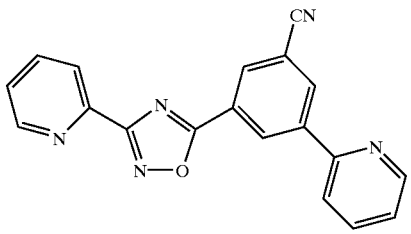

B124

A mixture of 3-(2-pyridyl)-5-(3-bromo-5-cyanophenyl)-1,2,4-oxadiazole (101 mg, 0.31 mmol), tetrakis (triphenylphosphine) palladium(0) (Pd(PPh₃)⁴, 25 mg, 0.021 mmol) and tri-n-butyl(2-pyridyl)tin in tetrahydrofuran (2 mL) was heated overnight at 100° C. The reaction mixture was cooled and transferred directly onto a flash silica column. Elution with a gradient of hexane:ethyl acetate:chloroform 3:1:4 to 2.5:1:4 followed by trituration with hexane in dichloromethane afforded 22 mg (22%) of 3-(2-pyridyl)-5-(3-cyano-5-(2-pyridyl)phenyl)-1,2,4-oxadiazole: ¹H NMR (CDCl₃): δ-9.12 (s, 1H), 8.88 (d, 1H), 8.78 (d, 1H), 8.64 (s, 1H), 8.61 (s, 1H), 8.26 (d, 1H), 7.89 (m, 3H), 7.51 (m, 1H), 7.40 (m, 1H).

3-(2-Pyridyl)-5-[2-methoxy-5-(2-pyridyl)phenyl]-1,2,4-oxadiazole

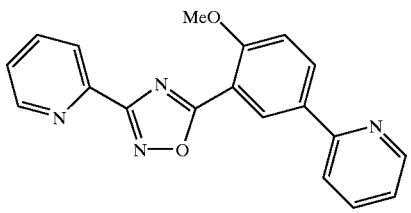

B125

In a similar fashion, a mixture of 3-(2-pyridyl)-5-(5-bromo-2-methoxyphenyl)-1,2,4-oxadiazole (110 mg, 0.331 mmol), pyridine-2-tributyltin (138.8 mg,0.663 mmole) and Pd(PPh₃)₄ (38.5 mg, 0.0333 mmole) in tetrahydrofuran (1 mL) was heated in a sealed vial overnight at 100° C. Standard work up afforded 13.9 mg (13%) 3-(2-pyridyl)-5-[2-methoxy-5-(2-pyridyl)phenyl]-1,2,4-oxadiazole.

3-(2-Pyridyl)-5-[2-fluoro-5-(2-pyridyl)phenyl]-1,2,4-oxadiazole

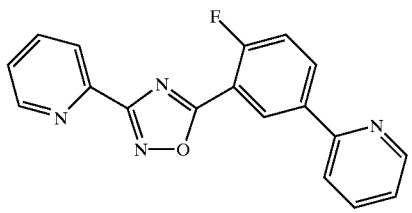

B126

In a similar fashion, 3-(2-pyridyl)-5-(5-bromo-2-fluorophenyl)-1,2,4-oxadiazole (100 mg, 0.312 mmol), pyridine-2-tributyltin (172 mg, 0.468 mmol) and Pd(PPh$_3$)$_4$ (36.1 mg, 0.0312 mmol) in tetrahydrofuran (1 mL) was heated in sealed vial overnight at 100° C. Standard work up afforded 11.3 mg (11%) of 3-(2-pyridyl)-5-[2-fluoro-5-(2-pyridyl)phenyl]-1,2,4-oxadiazole.

3-(2-Pyridyl)-5-(3-aminomethyl-5-cyanophenyl)-1,2,4-oxadiazole

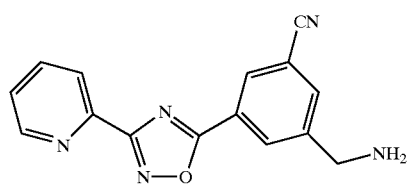

B127

A mixture of 3-(2-pyridyl)-5-(3-cyano-5-methylphenyl)-1,2,4-oxadiazole (0.5 g, 1.91 mmol), N-bromosuccinimide (0.339 g, 1.91 mmol), and benzoyl peroxide (0.0010 g, 0.04 mmol) in carbon tetrachloride (25 mL) was heated at 80° C. for 18 hours. After this time the reaction mixture was cooled and diluted with dichloromethane. The organic solution was washed with water and brine to afford 0.595 g (91%) of 3-(2-pyridyl)-5-(3-bromomethyl-5-cyanophenyl)-1,2,4-oxadiazole.

A solution of 3-(2-pyridyl)-5-(3-bromomethyl-5-cyanophenyl)-1,2,4-oxadiazole (0.5 g, 1.91 mmol) in dichloromethane (1.5 mL) was treated with a 0.5M ammonia (1.5 mL, 1.5 mmol, dioxane) and heated at 50° C. for 90 minutes. After this time the reaction mixture was cooled and diluted with dichloromethane. The organic solution was washed with water and brine. Silica gel chromatography of the crude product afforded 3.5 mg (5.5%) of 3-(2-pyridyl)-5-(3-aminomethyl-5-cyanophenyl)-1,2,4-oxadiazole.

3-(2-Pyridyl)-5-[5-(2-propenyl)-pyrid-3-yl]-1,2,4-oxadiazole

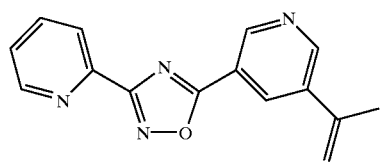

B128

Under an argon atmosphere, a solution of 5-bromonicotinic acid (1.01 g, 5 mmol) in tetrahydrofuran (10 mL) at −78° C. was treated dropwise with a 1.6M solution of n-butyllitium (6.99 ml, 11 mmol, hexane). After the reaction mixture was stirred for 15 minutes, acetone (1 mL) was added. The reaction mixture was then warmed to room temperature and quenched with 1N HCl. The solution was then concentrated in vacuo. The residue was treated with excess thionyl chloride (10 mL) and heated to 80° C. for 10 minutes. The excess thionyl chloride was then removed. The acid chloride in dichloromethane (10 mL) was treated with pyrid-2-ylamidoxime (0.685g, 5 mmol) and triethylamine (2.02 g, 20 mmoles) and stirred at room temperature for 15 minutes. N,N-Dimethylformamide (10 mL) was then added and the reaction mixture heated at 120° C. for 16 hours. The reaction was quenched by the addition of water and the precipitate collected and dried. Silica gel chromatograph of this material using 20% ethyl acetate in hexane afforded 153 mg (12%) of 3-(2-pyridyl)-5-[5-(2-propenyl)-pyrid-3-yl]-1,2,4-oxadiazole.

3-(2-Pyridyl)-5-(3-cyano-5-vinylphenyl)-1,2,4-oxadiazole

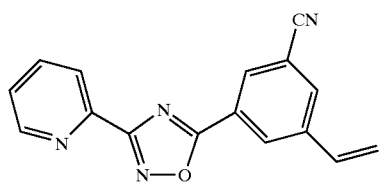

B129

A mixture of 3-(2-pyridyl)-5-(3-bromo-5-cyanophenyl)-1,2,4-oxadiazole (1.005 g, 3.21 mmol) and Pd(PPh$_3$)$_4$ (369 mg, 0.32 mmol) in tetrahydrofuran (10 mL) was treated with vinyl tributyl tin (0.985 mL, 3.36 mmol). The reaction mixture was heated in a sealed tube at 85° C. for 18 hours. After cooling, the mixture was diluted with dichloromethane and water. The organic layer was dried by filtration through an EX-TUBE. Silica gel chromatography afforded 691 mg (78%) of 3-(pyrid-2-yl)-5-(3-cyano-5-vinylphenyl)-1,2,4-oxadiazole: $^1$H-NMR (CDCl$_3$), δ (ppm):▯▯▯▯▯ (s, 1H), 8.52 (s, 1H), 8.43 (s, 1H), 8.23 (d, 1H), 7.90 (m, 2H), 7.48 (m, 1H), 6.78 (dd, 1H), 5.98 (d, 1H), 5.55 (d, 1H).

3-(2-Pyridyl)-5-(3-cyano-5-(2-hydroxyethyl)phenyl)-1,2,4-oxadiazole

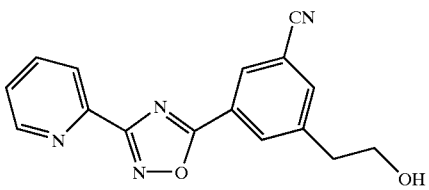

B130

A mixture of 3-(2-pyridyl)-5-(3-cyano-5-vinylphenyl)-1,2,4-oxadiazole (83 mg, 0.30 mmol) in dichloromethane (2 mL) was treated with 9-BBN dimer (40 mg, 0.16 mmol) and the reaction mixture stirred at room temperature for 4 hours. Sodium perborate tetrahydrate (157 mg, 1.02 mmol) and water (1 mL) were added and the resulting biphasic mixture was stirred vigorously for 18 hours. The mixture was diluted with dichloromethane and water and the organic layer dried by filtration through an EX-TUBE. Silica gel chromatography using a gradient of 20% to 75% ethyl acetate in hexane, followed by trituration in 10% ethyl acetate in hexane afforded 3.4 mg (3.7%) of 3-(2-pyridyl)-5-(3-cyano-5-(2-hydroxyethyl)phenyl)-1,2,4-oxadiazole: ¹H-NMR (CDCl₃), δ (ppm):⸮⸮08.85 (d, 1H), 8.43 (s, 2H), 8.22 (d, 1H), 7.90 (t, 1H), 7.80 (s, 1H), 7.48 (m, 1H), 3.99 (m, 2H), 3.02 (t, 2H).

3-(2-Pyridyl)-5-(3-cyano-5-(2,3-dichloropropoxy)phenyl)-1,2,4-oxadiazole

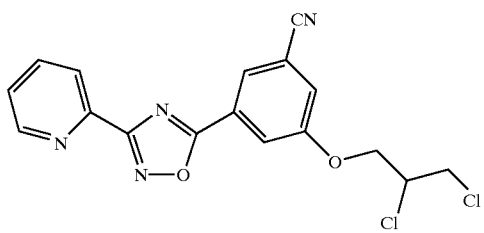

B131

A stirred suspension of 3-(2-pyridyl)-5-(3-alloxy-5-(methoxycarbonyl)phenyl)-1,2,4-oxadiazole (160 mg, 0.47 mmol) in methanol (5 mL) at ambient temperature was treated with 1M sodium hydroxide (0.8 mL, 0.80 mmol). The reaction was stirred 16 hours and solvent was removed in vacuo. The residue was dissolved in a small amount of water and then acidified with 1N hydrogen chloride. Extraction of the aqueous phase with dichloromethane followed by concentration in vacuo afforded 104.5mg of 3-(2-pyridyl)-5-(3-alloxy-5-(hydroxycarbonyl)phenyl)-1,2,4-oxadiazole.

The carboxylic acid (104.5 mg, 0.32 mMol) was treated with excess thionyl chloride (2.5 mL) and the resulting mixture heated at reflux for 2 hours. The thionyl chloride was then removed in vacuo the acid chloride dissolved in chloroform (2.5 mL). The solution was cooled to 0° C. and treated with 2 M ammonia in methanol. The reaction mixture was then stirred at ambient temperature for additional 2 hours. After this time the reaction was filtered and concentrated to afford 86 mg of crude 3-(2-pyridyl)-5-(3-alloxy-5-(carboxamide)phenyl)-1,2,4-oxadiazole.

The intermediate benzamide (86 mg) was treated with thionyl chloride (2 mL) and heated in a sealed vial for 16 hours. The thionyl chloride was then removed in vacuo. The residue was dissolved in water followed by addition of 10% sodium bicarbonate and the crude product extracted into ethyl acetate. Silica gel chromatography using a gradient of 30% ethyl acetate in hexanes to 40% ethyl acetate in hexanes afforded 15.4 mg (9%) of 3-(2-pyridyl)-5-(3-cyano-5-(2,3-dichloropropoxy)phenyl)-1,2,4-oxadiazole: ¹H NMR (CDCl₃): δ-8.87 (d, 1H), 8.30 (m, 2H), 8.10 (s, 1H), 7.89 (m, 1H), 7.50 (m, 2H), 4.50 (m, 3H), 3.91 (m, 2H).

3-(2-Pyridyl)-5-(3-carboxy-5-methoxyphenyl)-1,2,4-oxadiazole

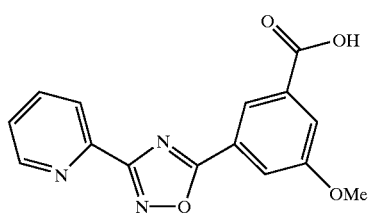

B132

A stirred suspension of 3-(2-pyridyl)-5-(3-methoxycarbonyl-5-methoxyphenyl)-1,2,4-oxadiazole (191.3 mg, 0.62 mmol) in methanol-tetrahydrofuran (1:1, 10 mL) was treated with 1M sodium hydroxide (1.5 mL, 1.5 mmol). The reaction was stirred at 50° C. for 5 hours and the solvent then removed in vacuo. The residue was dissolved in a small amount of water and then acidified (pH 4–5) by the addition of 2 N hydrogen chloride. The precipitate was collected and dried to afford 131.8 (72%) of 3-(2-pyridyl)-5-(3-carboxy-5-methoxyphenyl)-1,2,4-oxadiazole: ¹H NMR (DMSO): δ-8.81 (d, 1H), 8.28 (s, 1H), 8.21 (d, 1H), 8.06 (t, 1H), 7.88 (s, 1H), 7.74 (s, 1H), 7.65 (m, 1H), 3.95 (s, 3H).

3-(2-Pyridyl)-5-(3-(carboxamido)-5-methoxyphenyl)-1,2,4-oxadiazole

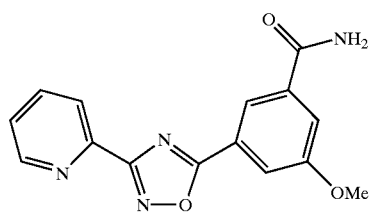

B133

A solution of 3-(2-pyridyl)-5-(3-carboxy-5-methoxyphenyl)-1,2,4-oxadiazole (131.8 mg, 0.44 mMol) in thionyl chloride (2 mL) and a catalytic amount of N,N-dimethylformamide was heated at reflux for 2 hours. The excess thionyl chloride was then removed in vacuo and the intermediate acid chloride dissolved in chloroform (2 mL). After cooling to 0° C. the solution was then treated with 2 M ammonia in methanol (2 mL). The reaction mixture was then stirred at ambient temperature for 30 minutes. The precipitate was collected, washed with water and dried in vacuo. Silica gel chromatography of this material using a gradient of 50% ethyl acetate in hexane to 100% ethyl acetate afforded 106.7 mg (81%) of 3-(2-pyridyl)-5-(3-(carboxamido)-5-methoxyphenyl)-1,2,4-oxadiazole: ¹H NMR (DMSO): δ-8.81 (d, 1H), 8.31 (s, 2H), 8.22 (d, 1H), 8.08 (t, 1H), 7.80 (d, 2H), 7.66 (t, 2H), 3.95 (s, 3H).

3-(2-Pyridyl)-5-(3-cyano-5-methoxyphenyl)-1,2,4-oxadiazole

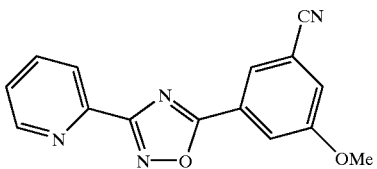

B134

A solution of 3-(2-pyridyl)-5-(3-(carboxamido)-5-methoxyphenyl)-1,2,4-oxadiazole (56.3 mg) in thionyl chloride (1.5 mL) was heated at reflux for 3 hours. The excess thionyl chloride was then removed in vacuo. Standard work up and silica gel chromatography using a mixture of hexanes, ethyl acetate, and dichloromethane (3.5:0.5:4) afforded 12.1 mg (23%) of 3-(2-pyridyl)-5-(3-cyano-5-methoxyphenyl)-1,2,4-oxadiazole: ¹H NMR (CDCl₃): δ-8.86 (d, 1H), 8.23 (d, 1H), 8.16 (s, 1H), 8.02 (s, 1H), 7.92 (t, 1H), 7.50 (t, 1H), 7.40 (s, 1H), 4.04 (s, 3H).

3-(2-Pyridyl)-5-(3-allyloxy-5-carboxyphenyl)-1,2,4-oxadiazole

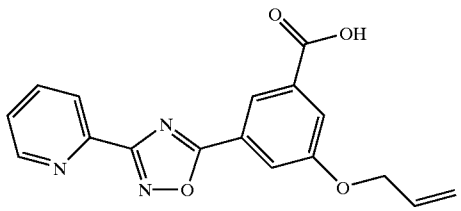
B135

A stirred suspension of 3-(2-Pyridyl)-5-(3-allyloxy-5-(methoxycarbonyl)phenyl)-1,2,4-oxadiazole (1.8 g, 5.28 mmol) in methanol (40 mL) was treated with 1M sodium hydroxide (7.9 mL, 7.9 mmol) and the reaction stirred at ambient temperature for 36 hours. The solvent was removed in vacuo, and the residue was dissolved in water (30 mL) and then acidified (pH 4–5) by the addition of 2N hydrogen chloride. The resulting precipitate was collected and dried to afford 1.6 (94%) of 3-(2-pyridyl)-5-(3-allyloxy-5-carboxyphenyl)-1,2,4-oxadiazole: $^1$H NMR (DMSO): δ-8.81 (d, 1H), 8.29 (s, 1H), 8.22 (d, 1H), 8.05 (m, 1H), 7.91 (s, 1H), 7.76 (s, 1H), 7.65 (m, 1H), 6.09 (m, 1H), 5.47 (dd, 1H), 5.33 (dd, 1H), 4.80 (d, 2H).

3-(2-Pyridyl)-5-(3-allyloxy-5-cyanophenyl)-1,2,4-oxadiazole

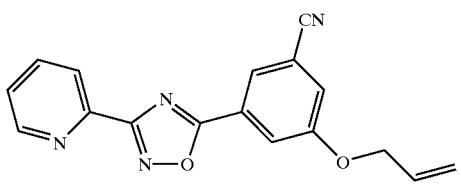
B136

A solution of 3-(2-pyridyl)-5-(3-allyloxy-5-(carboxy)phenyl)-1,2,4-oxadiazole (1.2 g, 3.7 mmol) in thionyl chloride (24 mL), and a catalytic amount of N,N-dimethylformamide was heated at reflux for 1.5 hours. The thionyl chloride was then removed in vacuo and the acid chloride was dissolved in chloroform (20 mL). The solution was cooled to 0° C. and treated with a solution of 0.5M ammonia in dioxane (22 mL). The reaction mixture was then stirred at ambient temperature for 30 minutes. The resulting precipitate was collected and dried to afford 1.1 g of 3-(2-pyridyl)-5-(3-allyloxy-5-(carboxamide)phenyl)-1,2,4-oxadiazole.

A suspension of 3-(2-pyridyl)-5-(3-allyloxy-5-(carboxamide)phenyl)-1,2,4-oxadiazole (1.1 g, 3.6 mmol) in a dichloromethane at 0° C. was treated with pyridine (0.6 mL, 7.6 mmol) and then trifluoroacetic anhydride (0.636 mL, 4.5 mmol). The reaction was stirred at 0° C. for 20 minutes and then stirred overnight at ambient temperature. The reaction mixture was then washed with water and saturated brine, dried over anhydrous sodium sulfate, filtered and concentrated. Silica gel chromatography using a mixture of hexanes, ethyl acetate, and dichloromethane (3.5:0.5:1) afforded 1.0 g (91%) of 3-(2-pyridyl)-5-(3-allyloxy-5-cyanophenyl)-1,2,4-oxadiazole: $^1$H NMR (CDCl$_3$): δ-8.87 (d, 1H), 8.23 (d, 1H), 8.16 (s, 1H), 8.03 (s, 1H), 7.91 (t, 1H), 7.50 (m, 1H), 7.41 (s, 1H), 6.06 (m, 1H), 5.48 (dd, 1H), 5.38 (dd, 1H), 4.68 (d, 2H).

3-(2-Pyridyl)-5-(3-cyano-5-hydroxyphenyl)-1,2,4-oxadiazole

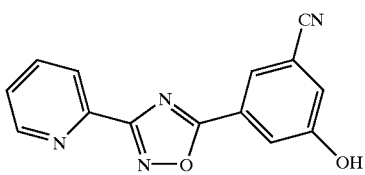
B137

A mixture of 3-(2-pyridyl)-5-(3-allyloxy-5-cyanophenyl)-1,2,4-oxadiazole (1.0 g, 3.4 mmol) and tetrabutylammonium iodide (1.4 g, 3.8 mmol) in dichloromethane (18 mL) at −78° C., under argon, was treated with a solution of 1M boron trichloride in dichloromethane (22 mL, 22 mmol). After 5 minutes at −78° C. the reaction mixture was stirred at ambient temperature for 1 hour. The reaction was then quenched with ice water and stirred for 30 minutes. The mixture was then washed with saturated sodium bicarbonate and extracted with dichloromethane. The combined organic layers were dried over anhydrous sodium sulfate, filtered and concentrated. Silica gel chromatography using a gradient of 10% ethyl acetate in hexanes to 80% ethyl acetate in hexanes afforded 460 mg (51%) of 3-(2-pyridyl)-5-(3-cyano-5-hydroxyphenyl)-1,2,4-oxadiazole: $^1$H NMR (CDCl$_3$/MeOD): δ-8.81 (d, 1H), 8.23 (d, 1H), 8.01 (s, 1H), 7.95 (m, 1H), 7.92 (m, 1H), 7.54 (m, 1H), 7.35 (m, 2H).

3-(2-Pyridyl)-5-(3-cyano-5-(2-N,N-dimethylaminoethoxy)phenyl)-1,2,4-oxadiazole

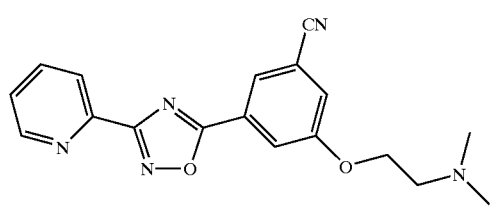
B138

A mixture of 3-(2-pyridyl)-5-(3-cyano-5-hydroxyphenyl)-1,2,4-oxadiazole (30 mg, 0.11 mmol), potassium carbonate (374mg, 2.7 mmol) and 2-dimethylaminoethyl chloride hydrochloride (46 mg, 0.32 mmol) in N,N-dimethylformamide (1 mL) were heated in a sealed vial at 150° C. for 5 minutes. The reaction was cooled, diluted with dichloromethane, washed with water (3×) and saturated brine, filtered and concentrated. Silica gel chromatography using a gradient of 1% methanol in dichloromethane to 5% methanol in dichloromethane afforded 24 mg (53%) of 3-(2-pyridyl)-5-(3-cyano-5-(2-dimethylaminoethoxy)phenyl)-1,2,4-oxadiazole: $^1$H NMR (CDCl$_3$): δ-8.86 (d, 1H), 8.23 (d, 1H), 8.15 (s, 1H), 8.04 (s, 1H), 7.91 (t, 1H), 7.49 (m, 1H), 7.43 (s, 1H), 4.20 (t, 2H), 2.80 (t, 2H), 2.37 (s, 6H).

3-(2-Pyridyl)-5-(3-cyano-5-(N,N-dimethylaminopropoxy)phenyl) -1,2,4-oxadiazole

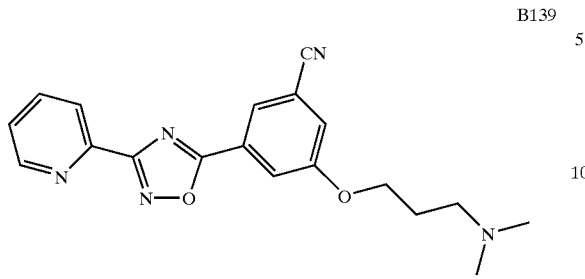

B139

In a similar fashion, 3-(2-pyridyl)-5-(3-cyano-5-hydroxyphenyl) -1,2,4-oxadiazole (31 mg, 0.12 mmol), potassium carbonate (381mg, 2.8 mmol) and 2-dimethylaminopropyl chloride hydrochloride (51 mg, 0.32 mmol) in N,N-dimethylformamide (1 mL) were heated in a sealed vial at 150° C. for 5 minutes. Standard work up and chromatography afforded 10 mg (24%) of 3-(2-pyridyl)-5-(3-cyano-5-(dimethylaminopropoxy)phenyl) -1,2,4-oxadiazole: $^1$H NMR (CDCl$_3$): δ-8.86 (d, 1H), 8.23 (d, 1H), 8.14 (s, 1H), 8.03 (s, 1H), 7.91 (t, 1H), 7.49 (m, 1H), 7.41 (s, 1H), 4.17 (t, 2H), 2.49 (t, 2H), 2.28 (s, 6H), 2.02 (q, 2H).

3-(2-Pyridyl)-5-(3-cyano-5-(2-aminoethoxy)phenyl)-1,2,4-oxadiazole

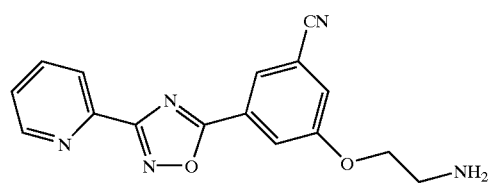

B140

In a similar fashion, 3-(2-pyridyl)-5-(3-cyano-5-hydroxyphenyl)-1,2,4-oxadiazole (63 mg, 0.24 mmol), triphenylphosphine (100 mg, 0.38 mmol), N-(tert-butoxycarbonyl)ethanolamine (60 mg, 0.37 mmol) in tetrahydrofuran (2 mL) was treated with diethyl azodicarboxylate (0.060 mL, 0.38 mmol) dropwise and the reaction mixture was stirred overnight. Standard work up and chromatography afforded the Boc-protected intermediate.

A solution of the Boc-protected intermdeiate in dichloromethane (2 mL) was treated with trifluoroacetic acid (1 mL) at 0° C. After stirring for 1.5 hours, saturated sodium bicarbonate was added to the reaction mixture and the crude product extracted with dichloromethane. Silica gel column chromatography using a gradient of 1% methanol in dichloromethane to 10% methanol in dichloromethane afforded 27 mg (37%) of 3-(2-pyridyl)-5-(3-cyano-5-(2-aminoethoxy)phenyl)-1,2,4-oxadiazole: $^1$H NMR (CDCl$_3$/MeOD): δ-8.85 (d, 1H), 8.23 (d, 1H), 8.17 (s, 1H), 8.04 (s, 1H), 7.93 (t, 1H), 7.49 (m, 1H), 7.44 (s, 1H), 4.17 (t, 2H), 3.17 (m, 2H).

3-(2-Pyridyl)-5-(3-cyano-5-propoxyphenyl)-1,2,4-oxadiazole

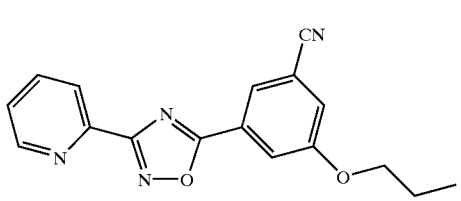

B141

A mixture of 3-(2-pyridyl)-5-(3-cyano-5-hydroxyphenyl)-1,2,4-oxadiazole (20 mg, 0.077 mmol), potassium carbonate (107 mg, 0.77 mmol) and propyl iodide (0.023 mL, 0.23 mmol) in N,N-dimethylformamide (1 mL) were heated in a sealed vial at 150° C. for 5 minutes. After cooling the reaction was diluted with dichloromethane, washed with water (3 times) and saturated brine, filtered and concentrated. Silica gel chromatography using a mixture of hexanes, ethyl acetate, and dichloromethane (3.5:0.5:4) followed by trituration with diethyl ether and hexanes afforded 9 mg (40%) of 3-(2-pyridyl)-5-(3-cyano-5-propoxyphenyl)-1,2,4-oxadiazole: $^1$H NMR (CDCl$_3$): δ-8.86 (d, 1H), 8.23 (d, 1H), 8.14 (s, 1H), 8.00 (s, 1H), 7.91 (t, 1H), 7.49 (m, 1H) 7.39 (s, 1H), 4.06 (t, 2H), 1.88 (m, 2H), 1.08 (t, 3H).

3-(2-Pyridyl)-5-(5-cyano-3-[3-hydroxypropyn-1-yl]phenyl)-1,2,4-oxadiazole

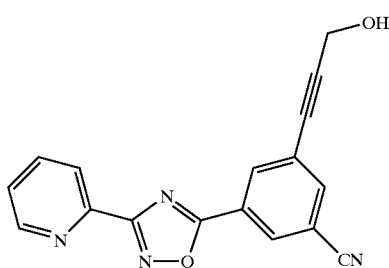

B142

A mixture of the 3-(2-pyridyl)-5-(5-cyano-3-iodophenyl)-1,2,4-oxadiazole (140 mg, 0.374 mmol), Pd(PPh$_3$)$_4$ (10 mg, 0.009), and CuI (30 mg, 0.158 mmol) in N,N-dimethylformamide (3 mL) was treated with triethylamine (1 mL, 726 mg, 7 mmol). The reaction mixture was cooled to 0° C. and treated with propargyl alcohol (56 mg, 1 mmol). The mixture was stirred at ambient temperature 5 hours and then filtered through a short plug of silica gel, washing with ethyl acetate. The organic solution was concentrated in vacuo. Silica gel chromatography afforded 20 mg (18%) of 3-(2-pyridyl)-5-(5-cyano-3-[3-hydroxypropyn-1-yl]phenyl)-1,2,4-oxadiazole: 1H-NMR (MeOH-d4), δ ppm: 8.80 (d, 1H), 8.60 (s, 1H), 8.58 (s, 1H), 8.30 (d, 1H), 8.10 (m, 2H), 7.60 (m, 1H), 4.5 (s, 2H).

3-(2-Pyridyl)-5-[5-(3-N-benzyl-1,2,5,6-tetrahydropyridine)-pyrid-3-yl]-1,2,4-oxadiazole

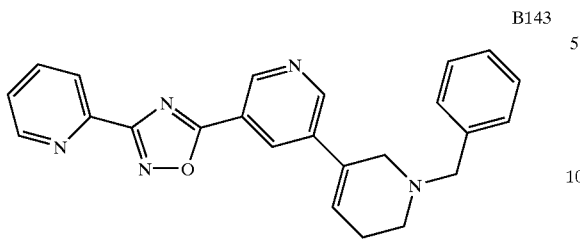

B143

A mixture of 5-bromonicotinic acid (1.01 g, 5 mmoles) in tetrahydrofuran (10 ml), under an argon atmophere, was cooled to −78° C. and treated dropwise with a solution of 1.6M n-butyllithium (6.99 mL, 11 mmole, hexane). The reaction mixture was stirred for 15 minutes at −78° C., and then treated with N-benzyl-3-piperidinone (1.89g, 10 mmoles). The reaction mixture was then allowed to warm to room temperature where it was quenched by the addition of 1N HCl. The reaction mixture was concentrated to dryness in vacuo. The residue was treated with thionyl chloride (10 mL) and the mixture heated for 10 minutes at 80° C. The excess thionyl chloride was removed in vacuo, and the residue treated with ethanol. Silica gel chromatograph using 1% methanol in dichloromethane afforded 120 mg (8%) of the nicotinic ethyl ester intermediate. Hydrolysis of the ester to the corresponding acid was accomplished using 1N sodium hydroxide (1 mL) and methanol (2 mL).

Activation of the intermediate acid using oxalyl chloride followed by treatment with pyrid-2-ylamidoxime (120 mg, 0.876 mmoles) and triethylamine (0.404 g, 4 mmol) in dichloromethane (10 mL) followed by heating at 120° C. in N,N-dimethylformamide (2 mL) for 4 hours, afforded, after standard work up 14.5 mg (10%) of 3-(2-pyridyl)-5-[5-(3-N-benzyl-1,2,3,6-tetrahydropyridine)-pyrid-3-yl]-1,2,4-oxadiazole.

3-(2-Pyridyl)-5-(2-N-methylaminophenyl)-1,2,4-oxadiazole

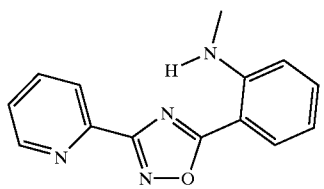

B144

A mixture of N-methyl-isatoic acid anhydride (177.2 mg, 1 mmol) and pyrid-2-ylamidoxime (137.14 mg, 1 mmol) in toluene (2 mL) was heated to 120° C. for 5 hours. After cooling, the solid was filtered, dissolved in ethylene glycol (1 mL) and heated at 125° C. for 6 hours. The solution was poured into water. Collection of the solid by filtration afforded 54 mg (21%) 3-(2-pyridyl)-5-(2-N-methylaminophenyl)-1,2,4-oxadiazole.

3-(2-Pyridyl)-5-(3-cyano-5-(2-hydroxyethoxy)phenyl)-1,2,4-oxadiazole

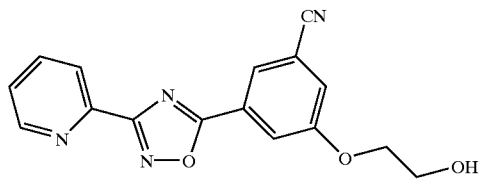

B231

A mixture of 3-(2-pyridyl)-5-(3-cyano-5-hydroxyphenyl)-1,2,4-oxadiazole (40 mg, 0.15 mmol), potassium carbonate (42 mg, 0.30 mmol) and bromoethane (30 mg, 0.23 mmol) in N,N-dimethylformamide (1 mL) was heated in a sealed vial at 100° C. for 2 hours. The reaction was cooled, diluted with dichloromethane, washed with water (3x) and saturated brine, filtered and concentrated. Silica gel chromatography using 2% methanol in dichloromethane afforded 18 mg (39%) of 3-(2-pyridyl)-5-(3-cyano-5-(2-hydroxyethoxy)phenyl)-1,2,4-oxadiazole: $^1$H NMR (CDCl$_3$/MeOD), δ (ppm): 8.80 (d, 1H), 8.27 (d, 1H), 8.17 (s, 1H), 8.07 (s, 1H), 8.00 (t, 1H), 7.58 (m, 1H), 7.53 (s, 1H), 4.24 (t, 2H), 3.99 (t, 2H).

3-(2-Pyridyl)-5-(3-cyano-5-isopropoxyphenyl)-1,2,4-oxadiazole

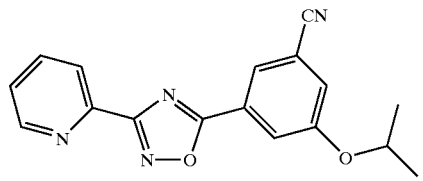

B232

A mixture of 3-(2-pyridyl)-5-(3-cyano-5-hydroxyphenyl)-1,2,4-oxadiazole (30 mg, 0.12 mmol), potassium carbonate (32 mg, 0.23 mmol) and 2-iodopropane (17 μL, 0.17 mmol) in N,N-dimethylformamide (1 mL) was heated in a sealed vial at 90° C. for 2 hours. The reaction was cooled, diluted with dichloromethane, washed with water (3x) and saturated brine, filtered and concentrated. Silica gel chromatography using a hexanes/ethyl acetate/dichloromethane (3.5:0.5:4) afforded 24 mg (68%) of 3-(2-pyridyl)-5-(3-cyano-5-isopropoxyphenyl)-1,2,4-oxadiazole: $^1$H NMR (CDCl$_3$), δ (ppm): 8.86 (d, 1H), 8.23 (d, 1H), 8.12 (s, 1H), 7.98 (s, 1H), 7.91 (m, 1H), 7.49 (m, 1H), 7.36 (s, 1H), 4.71 (m, 1H), 1.41 (m, 6H).

3-(2-Pyridyl)-5-(3-cyano-5-ethoxyhenyl)-1,2,4-oxadiazole

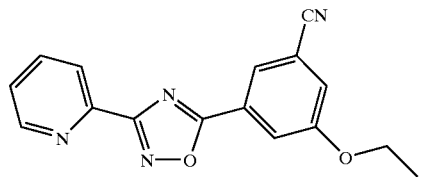

B233

A mixture of 3-(2-pyridyl)-5-(3-cyano-5-hydroxyphenyl)-1,2,4-oxadiazole (25 mg, 0.095 mmol), potassium carbonate (26 mg, 0.19 mmol) and iodoethane (11 μL, 0.14 mmol) in N,N-dimethylformamide (1 mL) was heated in a sealed vial at 70° C. for 1 hour. The reaction was cooled, diluted with dichloromethane, washed with water (3×) and saturated brine, filtered and concentrated. Silica gel chromatography of the residue using hexanes/ethyl acetate/dichlrormethane (3.5:0.5:4) followed by trituration with diethyl ether afforded 11 mg (39%) of 3-(2-pyridyl)-5-(3-cyano-5-ethoxyphenyl)-1,2,4-oxadiazole: $^1$H NMR (CDCl$_3$), δ (ppm): 8.86 (d, 1H), 8.23 (d, 1H), 8.14 (s, 1H), 7.99 (s, 1H), 7.91 (m, 1H), 7.49 (m, 1H), 7.38 (s, 1H), 4.17 (q, 2H), 1.49 (t, 3H).

3-(2-Pyridyl)-5-(3-cyano-5-(2,2,2-trifluoroethoxy)phenyl)-1,2,4-oxadiazole

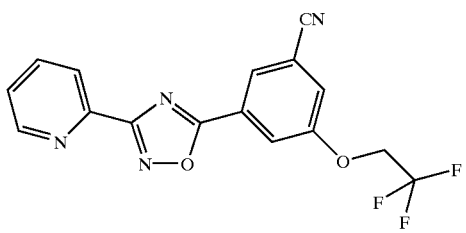

B234

A mixture of 3-(2-pyridyl)-5-(3-cyano-5-hydroxyphenyl)-1,2,4-oxadiazole (25 mg, 0.095 mmol), potassium carbonate (53 mg, 0.38 mmol) and 2-iodo-1,1,1-trifluoroethane (28 μL, 0.28 mmol) in N,N-dimethylformamide (1 mL) was heated in a sealed vial at 150° C. for 5 minutes hour. The reaction was cooled, diluted with dichloromethane, washed with water (3×) and saturated brine, filtered and concentrated. Silica gel chromatography of the residue using hexanes/ethyl acetate/dichlrormethane (3.5:0.5:4) afforded 9 mg (27%) of 3-(2-pyridyl)-5-(3-cyano-5-(2,2,2-trifluoroethoxy)phenyl)-1,2,4-oxadiazole: $^1$H NMR (CDCl$_3$), δ (ppm): 8.87 (d, 1H), 8.27 (s, 1H), 8.24 (d, 1H), 8.08 (s,1H), 7.92 (t, 1H), 7.50 (m, 2H), 4.53 (q, 2H).

3-(2-Pyridyl)-5-(3-cyano-5-cyclopropylmethoxyphenyl)-1,2,4-oxadiazole

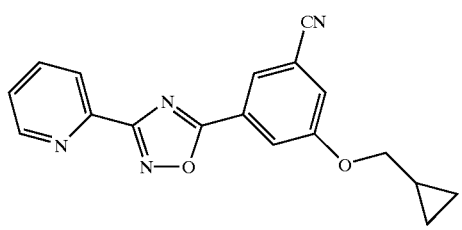

B235

A mixture of 3-(2-pyridyl)-5-(3-cyano-5-hydroxyphenyl)-1,2,4-oxadiazole (25 mg, 0.095 mmol), potassium carbonate (26 mg, 0.19 mmol) and (bromomethyl)cyclopropane (14 μL, 0.14 mmol) in N,N-dimethylformamide (1 mL) was heated in a sealed vial at 90° C. for 2 hours. The reaction was cooled, diluted with dichloromethane, washed with water (3×) and saturated brine, filtered and concentrated. Silica gel chromatography of the residue using hexanes/ethyl acetate/dichlrormethane (3.5:0.5:4) followed by trituration with diethyl ether afforded 12 mg (41%) of 3-(2-pyridyl)-5-(3-cyano-5-cylopropylmethoxyphenyl)-1,2,4-oxadiazole: $^1$H NMR (CDCl$_3$), δ (ppm): 8.86 (d, 1H), 8.23 (d, 1H), 8.14 (s, 1H), 7.99 (s, 1H), 7.91 (t, 1H), 7.50 (m, 1H), 7.40 (s, 1H), 3.95 (d, 2H), 1.21 (m, 1H), 0.72 (m, 2H), 0.41 (m, 2H).

3-(2-Pyridyl)-5-(3-amino-5-cyanophenyl)-1,2,4-oxadiazole

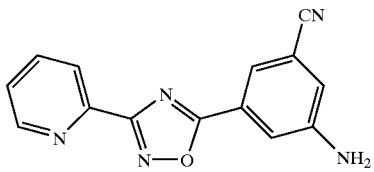

B236

3-(2-Pyridyl)-5-(3-cyano-5-nitrophenyl)-1,2,4-oxadiazole (30 mg, 0.10 mmol) and tin(II) chloride dihydrate (115 mg, 0.51 mmol) in ethanol (1 mL) were sealed in a glass vial and then heated at 78 oC for 2 hours. The reaction was cooled and dichloromethane was added to the reaction mixture. The organic layer was washed with water and saturated brine, dried over anhydrous sodium sulfate, filtered, and concentrated. Silica gel chromatography of the residue using hexanes:ethyl acetate:dichloromethane 1:3:4 followed by recrystallization using methanol afforded 2.8 mg (10%) of 3-(2-Pyridyl)-5-(3-amino-5-cyanophenyl)-1,2,4-oxadiazole: 1H NMR (CDCl$_3$), δ (ppm): 8.85 (d, 1H), 8.22 (d, 1H), 7.91 (m, 2H), 7.78 (s, 1H), 7.48 (m, 1H), 7.11 (s, 1H), 4.17 (bs, 2H).

3-(5-fluoropyrid-2-yl)-5-(3-amino-5-cyanophenyl)-1,2,4-oxadiazole

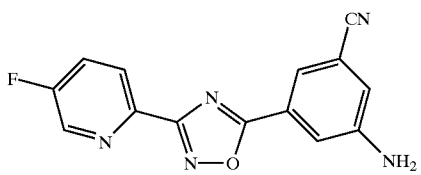

B237

3-(5-fluoropyrid-2-yl)-5-(3-cyano-5-nitrophenyl)-1,2,4-oxadiazole (30 mg, 0.096 mmol) and tin(II) chloride dihydrate (109 mg, 0.48 mmol) in ethanol (1 mL) were sealed in a glass vial and then heated at 78 oC for 2 hours. The reaction was cooled and dichloromethane was added to the reaction mixture. The organic layer was washed with water and saturated brine, dried over anhydrous sodium sulfate, filtered, and concentrated. Silica gel chromatography of the residue using hexanes:ethyl acetate:dichloromethane 1:3:4 followed by recrystallization using methanol afforded 6.3 mg (23%) of 3-(5-fluoropyrid-2-yl)-5-(3-amino-5-cyanophenyl)-1,2,4-oxadiazole: 1H NMR (CDCl$_3$), δ (ppm): 8.69 (d, 1H), 8.25 (m, 1H), 7.89 (s, 1H), 7.76 (s, 1H), 7.61 (m, 1H), 7.11 (s, 1H), 4.17 (bs, 2H).

201

3-(2-Pyridyl)-5-(3-cyano-5-(trifluoromethylsulfonyloxy)phenyl)-1,2,4-oxadiazole

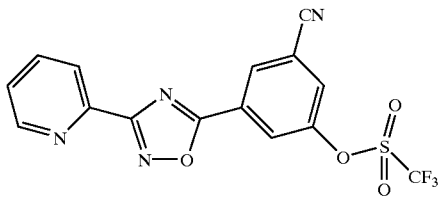

B238

Trifluoromethanesulfonic anhydride (22.9 µL, 0.14 mmol) and triethylamine (23.7 µL, 0.17) were added under argon to a vial containing 3-(2-pyridyl)-5-(3-cyano-5-hydroxyphenyl)-1,2,4-oxadiazole (30 mg, 0.11 mmol) in dichloromethane (1 mL). The vial was then sealed and the reaction was left stirring overnight at ambient temperature. The reaction mixture was placed directly onto a flash column and purified by eluting with hexanes:ethyl acetate:dichloromethane 3.5:0.5:4 to afford 11 mg (25%) of 3-(2-pyridyl)-5-(3-cyano-5-(trifluoromethylsulfonyloxy)phenyl)-1,2,4-oxadiazole: $^1$H NMR (CDCl$_3$), δ (ppm): 8.88 (d, 1H), 8.63 (s, 1H), 8.44 (s, 1H), 8.24 (d, 1H), 7.93 (t, 1H), 7.83 (s, 1H), 7.52 (m, 1H).

3-(2-Pyridyl)-5-(3-cyano-5-(2-methoxy-2-oxoethoxy)phenyl)-1,2,4-oxadiazole

B239

A mixture of 3-(2-pyridyl)-5-(3-cyano-5-hydroxyphenyl)-1,2,4-oxadiazole (30 mg, 0.11 mmol), potassium carbonate (31 mg, 0.23 mmol) and methyl bromoacetate (16 µL, 0.17 mmol) in N,N-dimethylformamide (1 mL) was heated in a sealed vial at 100° C. for 2 hours. The reaction was cooled, diluted with dichloromethane, washed with water (3×) and saturated brine, filtered and concentrated. Silica gel chromatography using hexanes:ethyl acetate:dichloromethane 3.5:0.5:4 followed by trituration with diethyl ether afforded 10 mg (26%) of 3-(2-pyridyl)-5-(3-cyano-5-(2-methoxy-2-oxoethoxy) phenyl)-1,2,4-oxadiazole: $^1$H NMR (CDCl$_3$), δ (ppm): 8.87 (d, 1H), 8.23 (d, 1H), 8.22 (s, 1H), 8.01 (s, 1H), 7.92 (t, 1H), 7.50 (t, 1H), 7.42 (s, 1H), 4.81 (s, 2H), 3.86 (s, 3H).

202

3-(2-Pyridyl)-5-(3-cyano-5-(2-tert-butoxy-2-oxoethoxy)phenyl)-1,2,4-oxadiazole

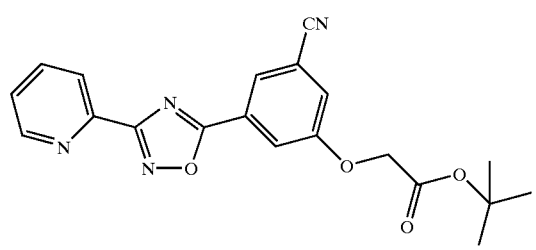

B240

A mixture of 3-(2-pyridyl)-5-(3-cyano-5-hydroxyphenyl)-1,2,4-oxadiazole (80 mg, 0.30 mmol), potassium carbonate (84 mg, 0.61 mmol) and tert-butylbromoacetate (67 µL, 0.46 mmol) in N,N-dimethylformamide (1 mL) was heated in a sealed vial at 90° C. for 1 hour. The reaction was cooled, diluted with dichloromethane, washed with water (3×) and saturated brine, filtered and concentrated. Silica gel chromatography using hexanes:ethyl acetate:dichloromethane 3.5:0.5:4 afforded 62 mg (62%) 3-(2-pyridyl)-5-(3-cyano-5-(2-tert-butoxy-2-oxoethoxy)phenyl)-1,2,4-oxadiazole: $^1$H NMR (CDCl$_3$), δ (ppm): 8.86 (d, 1H), 8.23 (d, 1H), 8.21 (s, 1H), 7.98 (s, 1H), 7.91 (t, 1H), 7.50 (t, 1H), 7.28 (s, 1H), 5.30 (s, 2H), 1.52 (s, 9H).

3-(2-Pyridyl)-5-(3-cyano-5-(methoxymethoxy) phenyl)-1,2,4-oxadiazole

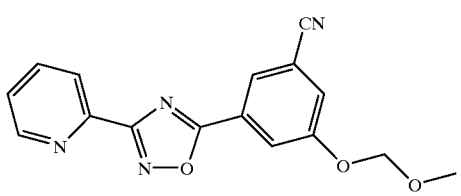

B241

A mixture of 3-(2-pyridyl)-5-(3-cyano-5-hydroxyphenyl)-1,2,4-oxadiazole (30 mg, 0.11 mmol), potassium carbonate (31 mg, 0.23 mmol) and chloromethyl methyl ether (26 µL, 0.34 mmol) in N,N-dimethylformamide (1 mL) was heated in a sealed vial at 70° C. for 2 hour. The reaction was cooled, diluted with dichloromethane, washed with water (3×) and saturated brine, filtered and concentrated. Silica gel chromatography using 20–30% hexanes/ethyl acetate afforded 19 mg (54%) of 3-(2-Pyridyl)-5-(3-cyano-5-(methoxymethoxy)phenyl)-1,2,4-oxadiazole: $^1$H NMR (CDCl$_3$), δ (ppm): 8.86 (d, 1H), 8.24 (d, 1H), 8.22 (s, 1H), 8.15 (s, 1H), 7.91 (t, 1H), 7.56 (s, 1H), 7.49 (m, 1H), 5.31 (s, 2H), 3.52 (s, 3H).

203

3-(2-Pyridyl)-5-(3-cyano-5-(2-methoxyethoxy)phenyl)-1,2,4-oxadiazole

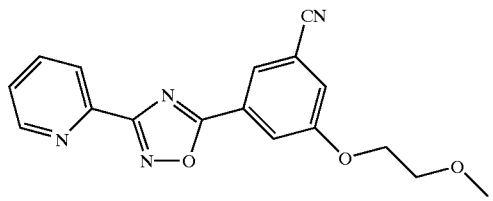

B242

A mixture of 3-(2-pyridyl)-5-(3-cyano-5-hydroxyphenyl)-1,2,4-oxadiazole (40 mg, 0.15 mmol), potassium carbonate (42 mg, 0.30 mmol) and 2-chloroethyl methyl ether (83 µL, 0.91 mmol) in N,N-dimethylformamide (1 mL) was heated in a sealed vial at 150° C. for 5 minutes. The reaction was cooled, diluted with dichloromethane, washed with water (3×) and saturated brine, filtered and concentrated. Silica gel chromatography using hexanes:ethyl acetate:dichloromethane 1:1:2 followed by trituration with diethyl ether afforded 24 mg (50%) of 3-(2-pyridyl)-5-(3-cyano-5-(2-methoxyethoxy)phenyl)-1,2,4-oxadiazole: $^1$H NMR (CDCl$_3$), δ (ppm): 8.87 (d, 1H), 8.23 (d, 1H), 8.17 (s, 1H), 8.04 (s, 1H), 7.91 (t, 1H), 7.49 (m, 1H), 7.45 (s, 1H), 4.27 (t, 2H), 3.81 (t, 2H), 3.48 (s, 3H).

204

3-(2-Pyridyl)-5-(3-cyano-5-hexyloxyphenyl)-1,2,4-oxadiazole

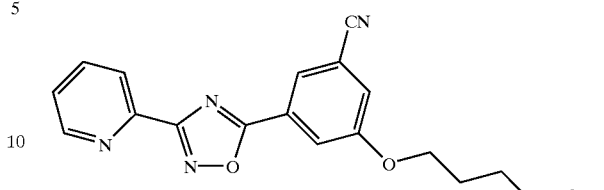

B244

A mixture of 3-(2-pyridyl)-5-(3-cyano-5-hydroxyphenyl)-1,2,4-oxadiazole (31 mg, 0.12 mmol), potassium carbonate (32 mg, 0.24 mmol) and hexyl bromide (25 µL, 0.18 mmol) in N,N-dimethylformamide (1 mL) was heated in a sealed vial at 90° C. for 35 minutes. The reaction was cooled, diluted with dichloromethane, washed with water (3×) and saturated brine, filtered and concentrated. Silica gel chromatography using 2% methanol in dichloromethane afforded 18 mg (39%) of 3-(2-pyridyl) -5-(3-cyano-5-(2-hydroxyethoxy)phenyl)-1,2,4-oxadiazole: $^1$H NMR (CDCl$_3$), δ (ppm): 8.86 (d, 1H), 8.23 (d, 1H), 8.13 (s, 1H), 8.00 (s, 1H), 7.91 (dd, 1H), 7.49 (dd, 1H), 7.38 (s, 1H), 4.09 (t, 2H), 1.84 (m, 2H), 1.49 (m, 2H), 1.37 (m, 4H), 0.93 (t, 3H).

3-(5-fluoropyrid-2-yl)-5-(3-cyano-5-cyclopentylaminophenyl) -1,2,4-oxadiazole

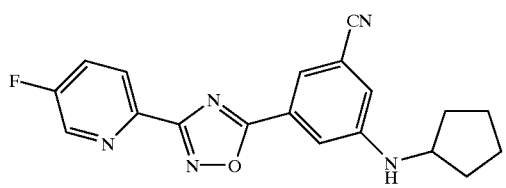

B243

A mixture of 3-(5-fluoropyrid-2-yl)-5-(3-amino-5-cyanophenyl) -1,2,4-oxadiazole (30 mg, 0.11 mmol), cyclopentanone (24 µL, 0.26 mmol), sodium cyanoborohydride, 1.0 M solution in tetrahydrofuran, (128 AL, 0.12 mmol) in acetic acid (4 mL) was heated at 60° C. for 1 hour. After cooling, the reaction mixture was diluted with ethyl acetate and then washed with water (2X) and saturated brine, dried over anhydrous sodium sulfate, filtered, and concentrated. Silica gel chromatography using 20% ethyl acetate/hexanes afforded 15 mg (39%) of 3-(5-fluoropyrid-2-yl)-5-(3-cyano-5-cyclopentylaminophenyl)-1,2,4-oxadiazole: $^1$H NMR (CDCl$_3$), δ (ppm): 8.69 (d, 1H), 8.25 (m, 1H), 7.79 (s, 1H), 7.61 (m, 2H), 6.99 (s, 1H), 4.17 (d, 1H), 3.88 (m, 1H), 2.10 (m, 1H), 1.74 (s, 2H), 1.50 (m, 1H), 1.27 (m, 2H), 0.87 (m, 2H).

3-(2-Pyridyl)-5-(3-cyano-5-(dimethylamino)carbonylphenyl)-1,2,4-oxadiazole

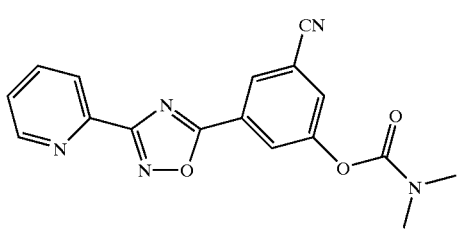

B245

A mixture of 3-(2-pyridyl)-5-(3-cyano-5-hydroxyphenyl)-1,2,4-oxadiazole (39 mg, 0.15 mmol), potassium carbonate (32 mg, 0.30 mmol) and dimethylcarbamyl chloride (27 µL, 0.30 mmol) in N,N-dimethylformamide (1 mL) was heated in a sealed vial at 140° C. for 2 hours. The reaction was cooled, diluted with dichloromethane, washed with water (3×) and saturated brine, filtered and concentrated. Silica gel chromatography using hexanes:ethyl acetate:dichloromethane 3.5:0.5:4 afforded 3 mg (29%) of 3-(2-pyridyl)-5-(3-cyano-5-(dimethylamino)carbonylphenyl)-1,2,4-oxadiazole: $^1$H NMR (CDCl$_3$), δ (ppm): 8.85 (d, 1H), 8.40 (s, 1H), 8.29 (s, 1H), 8.22 (d, 1H), 7.89 (m, 1H), 7.73 (s, 1H), 7.48 (dd, 1H), 3.14 (s, 3H), 3.06 (s, 3H).

3-(5-Fluoropyrid-2-yl)-5-(3-cyano-5-ethylaminophenyl)-1,2,4-oxadiazole

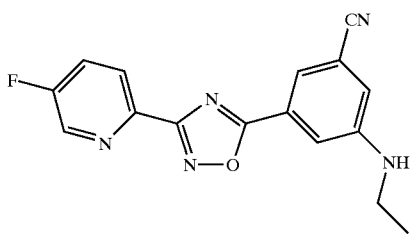

B246

A mixture of 3-(5-fluoropyrid-2-yl)-5-(3-cyano-5-nitrophenyl)-1,2,4-oxadiazole (30 mg, 0.11 mmol), potassium carbonate (29 mg, 0.21 mmol) and ethyl iodide (98 μL, 1.2 mmol) in N,N-dimethylformamide (1 mL) was heated in a sealed vial at 140° C. for 2 hours. The reaction was cooled, diluted with ethyl acetate, washed with water (3x) and saturated brine, filtered and concentrated. Silica gel chromatography using hexanes:ethyl acetate:dichloromethane 3:1:4 afforded 6 mg (38%) of 3-(5-fluoropyrid-2-yl)-5-(3-cyano-5-ethylaminophenyl)-1,2,4-oxadiazole: $^1$H NMR (CDCl$_3$), δ (ppm): 8.69 (d, 1H), 8.26 (dd, 1H), 7.80 (s, 1H), 7.61 (m, 2H), 6.99 (s, 1H), 4.12 (br, s, 1H), 3.26 (q, 2H), 1.32 (t, 3H).

3-(5-Fluoropyrid-2-yl)-5-(3-cyano-5-diethylaminophenyl)-1,2,4-oxadiazole

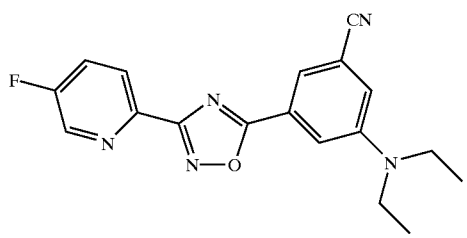

B247

A mixture of 3-(5-fluoropyrid-2-yl)-5-(3-cyano-5-nitrophenyl)-1,2,4-oxadiazole (30 mg, 0.11 mmol), potassium carbonate (29 mg, 0.21 mmol) and ethyl iodide (98 μL, 1.2 mmol) in N,N-dimethylformamide (1 mL) was heated in a sealed vial at 140° C. for 2 hours. The reaction was cooled, diluted with ethyl acetate, washed with water (3x) and saturated brine, filtered and concentrated. Silica gel chromatography using hexanes:ethyl acetate:dichloromethane 3:1:4 afforded 3 mg (20%) of 3-(5-fluoropyrid-2-yl)-5-(3-cyano-5-diethylaminophenyl)-1,2,4-oxadiazole: $^1$H NMR (CDCl$_3$), δ (ppm): 8.69 (d, 1H), 8.27 (dd, 1H), 7.78 (s, 1H), 7.60 (m, 2H), 7.04 (s, 1H), 3.45 (q, 4H), 1.23 (t, 6H).

3-(5-Fluoro-pyrid-2-yl)-5-[3-fluoro-5-(1H-tetraazol-5-yl)-phenyl]-1,2,4-oxadiazole

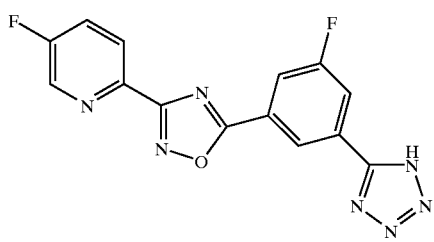

B248

To a mixture of 2 M trimethylaluminum (0.45 mL, 0.9 mmole, toluene) with toluene (1 mL) at 10° C., trimethylsilyl azide (0.119 mL, 0.9 mmole) was added, followed by the addition of 5-(3-cyano-5-fluorophenyl)-3-(5-fluoro-pyrid-2-yl)-1,2,4-oxadiazole. The reaction was heated at 80° C. for 2 hours and then quenched with 6 N hydrochloride (2 mL) and solid was collected by filtration. The product was recrystallized with dimethylformamide to give 59 mg (36%) of 3-(5-fluoro-pyrid-2-yl)-5-[3-fluoro-5-(1H-tetraazol-5-yl)-phenyl]-1,2,4-oxadiazole. $^1$H-NMR (DMSO-d 6), δ (ppm): 8.83 (d, 1H), 8.70 (s, 1H), 8.31 (m, 1H), 8.10 (m, 2H), 8.04 (dt, 1H).

5-[3-Fluoro-5-(1-methyl-1H-tetraazol-5-yl)-phenyl]-3-(5-fluoro-pyrid-2-yl)-1,2,4-oxadiazole

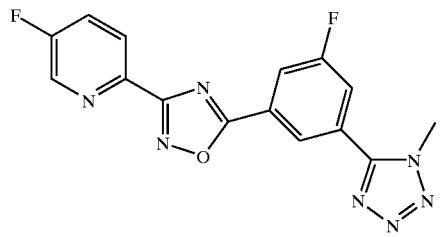

B249

To a solution of 3-(5-fluoro-pyrid-2-yl)-5-[3-fluoro-5-(1H-tetraazol-5-yl)-phenyl]-1,2,4-oxadiazole (30 mg, 0.092 mmol) in tetrahydrofuran (1 mL), 0.5 M diazomethane (1 mL, 0.5 mmol, ether) was added. The reaction was quenched with water and extracted with dichloromethane. The product was purified by column chromatography with 20% ethyl acetate in hexanes to give 6.7 mg (21.4%) of 5-[3-fluoro-5-(1-methyl-1H-tetraazol-5-yl)-phenyl]-3-(5-fluoro-pyrid-2-yl)-1,2,4-oxadiazole. $^1$H-NMR (CDCl$_3$), δ (ppm): 8.87 (s, 1H), 8.70 (d, 1H), 8.29 (dd, 1H), 8.10 (m, 2H), 7.62 (dt, 1H), 4.46 (s, 3H).

3-(5-Fluoro-2-pyridyl)-5-(3-(1-benzyl-1,2,5,6-tetrahydropyridin-3-yl)-5-fluorophenyl)-1,2,4-oxadiazole

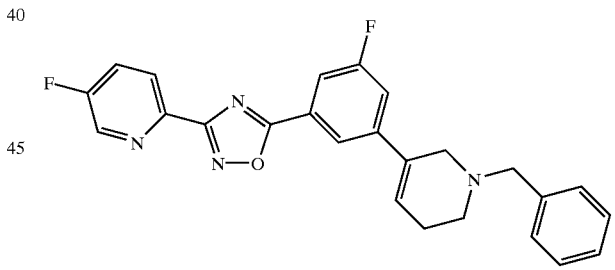

B250

In a screw cap vial equipped with stir bar added 3-(5-Fluoro-2-pyridyl)-5-(3-fluoro-5-(3-pyridyl)phenyl)-1,2,4-oxadiazole (100 mg, 0.30 mmol), acetonitrile (2 ml) and benzyl bromide (0.05 ml, 0.39 mmol). Stirred the resulting mixture at 90° C. for 4h. Cooled the mixture to room temperature, concentrated in-vacuo and triturated the residue with 30% ethyl acetate in hexanes to isolate the quarternary salt. The isolated solid was dissolved in methanol (2 ml) and treated with sodium borohydride (22.6 mg, 0.60 mmol) at 0° C. The bright yellow reaction mixture was stirred at room temperature for 2 h. The reaction mixture was concentrated in-vacuo and the residue was dissolved in dichloromethane (20 ml). The organic phase was sequentially washed with water (20 ml) and brine (20 ml), dried (sodium sulfate), filtered and concentrated in-vacuo. The crude residue was purified on silica gel using 30% ethyl acetate in hexanes to isolate the title compound (10.1 mg, 8%) as yellow oil. $^1$H-NMR (CDCl$_3$), δ (ppm): 8.69 (d, 1H), 8.26 (dd, 1H), 8.02 (s, 1H), 7.80 (dd, 1H), 7.60 (dt, 1H), 7.32 (m, 6H), 6.34 (m, 1H), 3.73 (s, 2H), 3.40 (bs, 2H), 2.63 (t, 2H), 2.39 (m, 2H).

3-(5-Fluoro-2-pyridyl)-5-(3-fluoro-5-(1H-imidazol-4-yl)phenyl) -1,2,4-oxadiazole

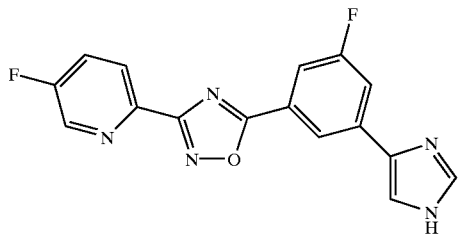

B251

A mixture of 3-Bromo-5-fluorobenzoic acid (0.41 g, 1.87 mmol) in dichloromethane (5 mL) was treated with oxalyl chloride (2.8 ml, 5.60 mmol, 2M dichloromethane) and 3 drops of N,N-dimethylformamide. The mixture was stirred 4 hours at room temperature. The solvent and excess reagent were removed in-vacuo. The residue was treated with 5-Fluoro-2-pyridylamidoxime (0.29 g, 1.87 mmol) and triethylamine (0.78 ml, 5.60 mmol) in dichloromethane (5 mL). The mixture was then heated in dimethylformamide (5 mL) at 120° C., overnight. Standard work up followed by purification on silica gel using 20% ethyl acetate in hexanes afforded 3-(5-Fluoro-2-pyridyl)-5-(3-bromo-5-fluorophenyl)-1,2,4-oxadiazole (150 mg).

To the solution of 4-Tributylstannyl-1-trityl-1H-imidazole (106 mg, 0.18 mmol) in tetrahydrofuran (5 ml) added 3-(5-Fluoro-2-pyridyl)-5-(3-bromo-5-fluorophenyl)-1,2,4-oxadiazole (50.0 mg, 0.15 mmol) and tetrakis (triphenylphoshine)palladium (0) (17.1 mg, 0.01 mmol), sequentially. The resulting brownish yellow reaction mixture was heated at 100° C. under argon overnight. The reaction mixture was cooled to room temperature and concentrated in-vacuo. The residue was purified on silica gel using 30% ethyl acetate in hexanes to isolate 3-(5-Fluoro-2-pyridyl)-5-(3-fluoro-5-(1-trityl-1H-imidazol-4-yl) phenyl)-1,2,4-oxadiazole (20.0 mg).

To a solution of 3-(5-Fluoro-2-pyridyl)-5-(3-fluoro-5-(1-trityl-1H-imidazol-4-yl)phenyl)-1,2,4-oxadiazole (20.0 mg, 0.04 mmol) in tetrahydrofuran (0.5 ml) added hydrochloric acid (0.14 ml, 2N aqueous). The resulting reaction mixture was heated at reflux for 45 min. The reaction mixture was cooled to room temperature, diluted with ethyl acetate (30 ml), washed successively with sodium hydroxide (30 ml, 1N aqueous), water (30 ml) and brine (30 ml), dried (sodium sulfate), filtered and concentrated in-vacuo. The isolated residue was purified on silica gel using 5% methanol in dichloromethane to yield the title compound (1.7 mg) as a beige solid. $^1$H-NMR (CDCl$_3$), δ (ppm): 9.64 (bs, 1H), 8.69 (d, 1H), 8.44 (s, 1H), 8.29 (dd, 1H), 7.81 (m, 3H), 7.61 (dt, 1H), 7.54 (s, 1H).

1-(3-Cyanophenyl)-4-(5-fluoro-2-pyridyl)-1 H-imidazole

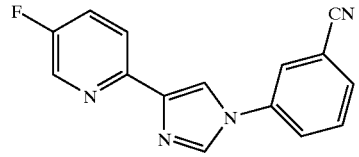

B252

To a solution of 4-Iodo-1-trityl-1H-imidazole (5.0 g, 11.6 mmol) in dichloromethane (100 ml) added Ethylmagnesium bromide (3M in diethyl ether) (4.6 ml, 13.9 mmol). Stirred the reaction under argon atmosphere at room temperature for 1 h. At this point added tributyltin chloride (4.1 ml, 13.9 mmol) to the reaction mixture and left the resulting mixture stirring at room temperature overnight. The reaction mixture was diluted with dichloromethane (100 ml), successively washed with saturated ammonium chloride (100 ml), water (100 ml) and brine (100 ml). The organic phase was dried (sodium sulfate), filtered and concentrated in-vacuo to yield 4-Tributylstannyl-1-trityl-1H-imidazole (2.35 g) as a white waxy solid.

To the solution of 4-Tributylstannyl-1-trityl-1H-imidazole (1.00 g, 1.67 mmol) in toluene (10 ml) added 2-Chloro-5-fluoropyridine (0.31 g, 2.38 mmol) and tetrakis (triphenylphoshine)palladium (0) (0.19 g, 0.17 mmol), sequentially. The resulting brownish yellow reaction mixture was heated at reflux under argon overnight. The reaction mixture was cooled to room temperature and concentrated in-vacuo. The residue was purified on silica gel using 30% diethyl ether in hexanes to isolate 4-(5-Fluoro-2-pyridyl)-1-trityl-1H-imidazole (0.23 g) as a clear oil.

To a solution of 4-(5-Fluoro-2-pyridyl)-1-trityl-1H-imidazole (0.23 g, 0.56 mmol) in tetrahydrofuran (4 ml) added hydrochloric acid (2.4 ml, 2N aqueous). The resulting reaction mixture was heated at reflux for 45 min. The reaction mixture was cooled to room temperature and concentrated in-vacuo. The isolated residue was triturated with diethyl ether to yield 4-(5-Fluoro-2-pyridyl)imidazole (0.06 g) as the hydrochloride salt.

In a screw-cap vial, added 4-(5-Fluoro-2-pyridyl) imidazole (0.06 g, 0.30 mmol), 3-Fluorobenzonitrile (0.04 ml, 0.36 mmol), potassium carbonate (0.21 g, 1.5 mmol) and dimethylformamide (1 ml). Stirred the resulting reaction mixture at 110° C. overnight. Cooled the reaction mixture to room temperature, diluted with chloroform (50 ml), sequentially washed with water (50 ml) and brine (50 ml). The organic phase was dried (sodium sulfate), filtered and concentrated in-vacuo. The crude residue was triturated with 10% diethyl ether in hexanes to yield the title compound (45 mg) as a dirty yellow colored solid. $^1$H-NMR (CDCl$_3$), δ (ppm): 8.43 (d, 1H), 8.04 (dd, 1H), 7.93 (dd, 2H), 7.70 (m,4H), 7.48 (dt, 1H).

3-(2-Pyridyl)-5-(3-(1H-imidazol-1-yl)-5-thiomethoxyphenyl)-1,2,4-oxadiazole

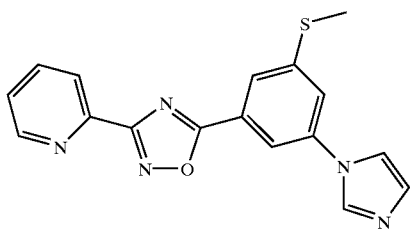

B253

In a screw cap vial equipped with stir bar added 3-(2-Pyridyl)-5-(3-fluoro-5-thiomethoxyphenyl)-1,2,4-oxadiazole (20 mg, 0.07 mmol), potassium carbonate (17.5 mg, 0.13 mmol), imidazole (4.3 mg, 0.06 mmol) and dimethylformamide (1 ml). Stirred the resulting mixture at 150° C. for 4 days. The reaction mixture was diluted with chloroform (30 ml) and washed with water (30 ml). The aqueous phase was re-extracted with chloroform (30 ml) and the combined organic phase was dried (sodium sulfate), filtered and concentrated in-vacuo. The crude residue was purified on silica gel using 2% methanol in dichloromethane to isolate the free base of the desired compound. The free base was converted to it's hydrochloride salt (4.5 mg), yellow solid. $^1$H-NMR (DMSO), δ (ppm): 9.64 (bs, 1H), 8.83 (d, 1H), 8.43 (s, 1H), 8.35 (s, 1H), 8.13 (m, 4H), 7.86 (bs, 1H), 7.70 (dt, 1H).

3-(3-Cyano-5-(1H-imidazol-1-yl)phenyl)-5-(2-pyridyl)-1,2,4-oxadiazole

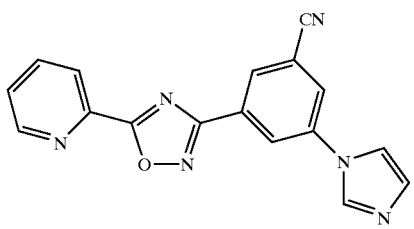

B254

In a screw cap vial equipped with stir bar added 3-(3-Cyano-5-fluorophenyl)-5-(2-Pyridyl)-1,2,4-oxadiazole (20 mg, 0.08 mmol), potassium carbonate (20.8 mg, 0.15 mmol), imidazole (7.7 mg, 0.11 mmol) and dimethylformamide (1 ml). Stirred the resulting mixture at 120° C. for 2 h. The reaction mixture was diluted with chloroform (30 ml) and washed with water (30 ml). The aqueous phase was re-extracted with chloroform (30 ml) and the combined organic phase was dried (sodium sulfate), filtered and concentrated in-vacuo. The crude residue was purified on silica gel using 1% methanol in dichloromethane to isolate the free base of the desired compound as a white solid. The free base was converted to it's hydrochloride salt (11.7 mg), white solid. $^1$H-NMR (DMSO), δ (ppm): 9.81 (s, 1H), 8.83 (m, 4H), 8.42 (m, 2H), 8.19 (dt, 1H), 7.92 (s, 1H), 7.80 (dd, 1H).

3-(2-Pyridyl)-5-(3-cyano-5-(1H-imidazol-1-yl)phenyl)-1,2,4-oxadiazole

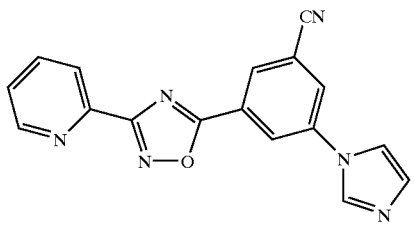

B255

In a screw cap vial equipped with stir bar added 3-(2-Pyridyl)-5-(3-cyano-5-fluorophenyl)-1,2,4-oxadiazole (20 mg, 0.08 mmol), potassium carbonate (20.8 mg, 0.15 mmol), imidazole (7.7 mg, 0.11 mmol) and dimethylformamide (1 ml). Stirred the resulting mixture at 120° C. for 2 h. The reaction mixture was diluted with chloroform (30 ml) and washed with water (30 ml). The aqueous phase was re-extracted with chloroform (30 ml) and the combined organic phase was dried (sodium sulfate), filtered and concentrated in-vacuo. The crude residue was purified on silica gel using 2% methanol in dichloromethane to isolate the free base of the desired compound as a white solid. The free base was converted to it's hydrochloride salt (10.0 mg), white solid. $^1$H-NMR (DMSO), δ (ppm): 9.85 (s, 1H), 8.86 (m, 4H), 8.49 (s, 1H), 8.23 (d, 1H), 8.13 (t, 1H), 7.95 (s, 1H), 7.73 (dd, 1H).

Example 8

2-(3-Iodophenyl)-4-(pyridin-2-yl)-1,3-thiazole

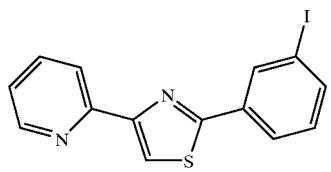

B145

A suspension of 3-iodobenzoic acid (4.04 g, 16.2 mmol) in dichloromethane (30 mL) was treated with 2M oxalyl chloride (16 mL, 32 mmol, hexane) followed by two drops of N,N-dimethylformamide and stirred at ambient temperature for 2 hours. After this time the solvent was removed in vacuo and the residue dissolved in tetrahydrofuran (30 ml). The solution was cooled to 0° C. and treated with 2M ammonia (20 mL, 40 mmol, methanol) and the mixture stirred for 30 minutes. The mixture was then filtered and the solvent removed in vacuo. Recrystallization of the residue from methanol afforded 3.5 g (87%) of 3-iodobenzamide, as a white solid.

A mixture of 3-iodobenzamide (500 mg, 2.0 mmol) in toluene (5 mL) was treated with Lawesson's reagent (404 mg, 1 mmol) and the mixture heated at reflux for 16 hours. After cooling, silica gel chromatography afforded 260 mg (99% yield) of 3-iodothiobenzamide, as a yellow solid.

A solution of 2-bromoacetylpyridine (400 mg, 2.0 mmol) in ethanol (5 mL) was treated with 3-iodothiobenzamide (1.2g, 6 mmol) and the mixture heated at reflux for 16 hours. After cooling the mixture was concentrated in vacuo. Silica gel chromatography of the residue using a gradient of hexane to ethyl acetate afforded 302 mg (55%) of 2-(3-iodophenyl)-4-(pyridin-2-yl)-1,3-thiazole, as a white solid.

2-(3-Cyanophenyl)-4-(pyridin-2-yl)-1,3-thiazole

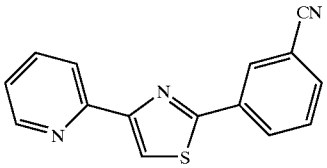

B146

A mixture of 2-(3-iodophenyl)-4-(pyridin-2-yl)-1,3-thiazole (130 mg, 0.36 mmol), zinc cyanide (117 mg, 1.0 mmol) and Pd(PPh$_3$)$_4$ (10 mg, 0.009 mmol) in N,N-dimethylformamide (2 mL) was heated overnight at 80° C. The mixture was cooled and diluted with toluene (5 mL). The organic solution was washed with 2N NH4OH (2×10 mL). The mixture was then extracted with ethyl acetate and the organic extract was washed with brine. The organic solution was dried over anhydrous sodium sulfate, filtered and concentrated in vacuo. Silica gel chromatography afforded 28 mg (30%) of 2-(3-cyanophenyl)-4-(pyridin-2-yl)-1,3-thiazole: 1H-NMR (CDCl$_3$), δ ppm: 8.65 (d, 1H), 8.38 (s, 1H), 8.25 (m, 2H), 8.15 (s, 1H), 7.85 (m, 1H), 7.72 (m, 1H), 7.6 (t, 1H), 7.28 (m, 1H). GC/EI-MS gave m/z 263 (M$^+$)

2-(3-Bromo-5-iodophenyl)-4-(pyridin-2-yl)-1,3-oxazole

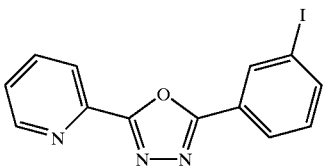

B147

A solution of 2-bromoacetylpyridine (1.0 g, 5 mmol) in toluene (5 mL) was treated with 3-bromo-5-iodobenzamide (2.0 g, 6 mmol) and the mixture heated at reflux for 60 hours. The mixture was then cooled and the solvent was removed in vacuo. Silica gel chromatography using a gradient of hexane to ethyl acetate afforded 10 mg (1%) of 2-(3-bromo-5-iodophenyl)-4-(pyridin-2-yl)-1,3-oxazole: 1H-NMR (CDCl$_3$), δ ppm: 8.62 (d, 1H), 8.42 (m, 1H), 8.38 (s, 1H), 8.24 (m, 1H), 8.00 (t, 1H), 7.95 (d, 1H), 7.8 (m, 1H), 7.27 (m, 1H).

2-(2-Pyridyl)-5-(3-iodophenyl)-1,3,4-oxadiazole

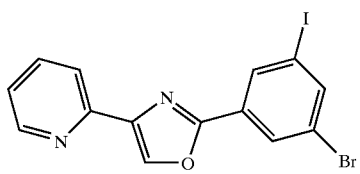

B148

A mixture of picolinic acid (0.47g, 3.82 mmol), 3-iodobenzhydrazide (1.00 g, 3.82 mmol), 1-(3-dimethylaminopropyl)-3-ethylcarbodiimide hydrochloride (0.80 g, 4.20 mmol), and 4-dimethylaminopyridine (0.05 g, 0.38 mmol) in dichloromethane (10 mL) was stirred overnight at ambient temperature. After this time, the reaction mixture was diluted with dichloromethane (200 mL). The organic solution was washed sequentially with water (100 mL), saturated sodium bicarbonate (150 mL), water (100 mL) and brine (100 mL). The organic phase was dried over anhydrous sodium sulfate, filtered and concentrated in vacuo to afford 0.33 g of the intermediate diacyl hydrazide.

The intermediate diacyl hydrazide.(0.15g, 0.41 mmol) was then treated with phosphorus oxychloride (2 mL) and heated at 110° C. for 40 minutes. After cooling the reaction was diluted with dichloromethane (10 ml). The organic solution was washed sequentially with 1N sodium hydroxide (10 mL), water (100 mL) and brine (100 mL). The organic phase was dried over anhydrous sodium sulfate, filtered and concentrated in vacuo. Silica gel chromatography using 30% ethyl acetate in hexanes afforded 0.03 g (22%) of 2-(2-pyridyl)-5-(3-iodophenyl)-1,3,4-oxadiazole.

2-(2-Pyridyl)-5-(3-cyanophenyl)-1,3,4-oxadiazole

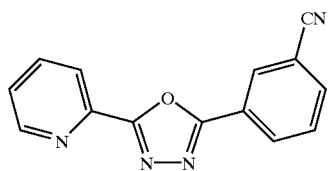

B149

Under an argon atmosphere, a mixture of 2-(2-pyridyl)-5-(3-iodophenyl)-1,3,4-oxadiazole (0.03 g, 0.08 mmol), zinc cyanide (0.01 g, 0.12 mmol), and Pd(PPh$_3$)$_4$ (9.1 mg, 0.01 mmol) in N,N-dimethylformamide (2ml) was heated at 80° C. for 2.5 hours. After cooling the reaction mixture was diluted with ethyl acetate and sequentially washed with water (3×50 mL) and brine (50 mL). The organic phase was dried over anhydrous sodium sulfate, filtered, and concentrated in vacuo. Recrystallization of the crude product from 5% ethyl acetate in hexanes, afforded 5.8 mg (30%) of 2-(2-pyridyl)-5-(3-cyanophenyl)-1,3,4-oxadiazole.

2-(2-Pyridyl)-5-(3-cyanophenyl)-1,3,4-triazole

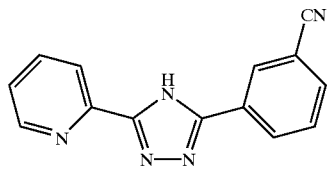

B150

A solution of 3-cyanobenzoic acid (1.0 g, 6.80 mmol) in tetrahydrofuran (10 mL) at 0° C. was treated with triethylamine (2.84 mL, 20.4 mmol) and ethyl chloroformate (0.78 mL, 8.16 mmol) and stirred at 0° C. for 1 h. The resulting white precipitate was removed by filtration and the filtrate cooled back to 0° C. Hydrazine monohydrate (1.00 mL, 20.4 mmol) was added and the mixture stirred at ambient temperature for 3.5 hours. The reaction mixture was then concentrated to dryness in vacuo and the residue was dissolved in dichloromethane (150 mL). The organic phase was sequentially washed with water (100 mL), 1N sodium hydroxide (100 mL), water (100 mL) and brine (100 mL). The organic phase was dried over anhydrous sodium sulfate, filtered and concentrated in vacuo. Silica gel chromatography using 3% methanol in dichloromethane afforded 0.32 g (30%) of 3-cyanobenzhydrazide.

A solution of 2-cyanopyridine (0.18 mL, 1.86 mmol) in methanol (5 mL) was treated with sodium metal (12.8 mg, 0.56 mmol) a stirred at ambient temperature for 1 hour. The reaction mixture was then treated with a solution of 3-cyanobenzhyrazide (0.30 g, 1.86 mmol) in methanol (5 mL) and heated at reflux for 3 hours. The reaction mixture was then concentrated in vacuo. The resulting yellow solid was dissolved in toluene (2 mL) and heated overnight at 175° C. The reaction mixture was concentrated in vacuo. Silica gel chromatography using 2% methanol in dichloromethane afforded 0.12 g (26%) of 2-(2-pyridyl)-5-(3-cyanophenyl)-1,3,4-triazole.

4-(3-Cyanophenyl)-1-(2-pyridyl)-1H-imidazole

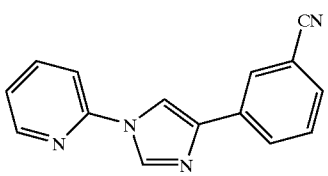

B151

A mixture of 4-bromo-1-trityl-1H-imidazole (0.2g, 0.51 mmol), 3-cyanophenylboronic acid (0.11 g, 0.77 mmol), and Pd(PPh$_3$)$_4$ (0.06g, 0.05 mmol) in a solution of ethylene glycol dimethyl ether (2 mL) and 2M sodium carbonate (2 mL) was heated in a sealed vial overnight at 120° C. After cooling, the reaction mixture was diluted with dichloromethane (30 mL) and washed with water (50 mL) and brine (30 mL). The organic phase was dried over anhydrous sodium sulfate, filtered and concentrated in vacuo. Silica gel chromatography of the crude residue using 2% ethyl acetate in hexanes afforded 0.07 g (34%) 4-(3-cyanophenyl)-1-trityl-1H-imidazole as white foam.

A solution of 4-(3-cyanophenyl)-1-trityl-1H-imidazole (0.07 g, 0.17 mmol) in tetrahydrofuran (1.36 mL) was treated with 2N hydrochloric acid (0.68 mL) and the resulting mixture was heated at reflux for 45 minutes. After cooling the reaction mixture was concentrated in vacuo and the residue dissolved in dichloromethane (20 mL). The organic phase was successively washed with 1N sodium hydroxide (10 mL), water (20 mL) and brine (20 mL). The organic solution was dried over anhydrous sodium sulfate, filtered, and concentrated in vacuo. Silica gel chromatography of the residues using 3% methanol in dichloromethane afforded 0.02 g (72%) of 4-(3-cyanophenyl)imidazole as a white solid.

A solution of 4-(3-cyanophenyl)imidazole (0.02 g, 0.11 mmol) in N-methylpyrrolidinone (0.5 mL) was treated with 2-bromopyridine (1.05 mL, 11.1 mmol) and the reaction mixture heated overnight at 160° C. After cooling the reaction mixture was diluted with dichloromethane (40 mL) and the organic phase was successively washed with water (10×50 mL) and brine (50 mL). The organic phase was dried over anhydrous sodium sulfate, filtered and concentrated in vacuo. Silica gel chromatography using 30% ethyl acetate in hexanes afforded 2.5mg (9%) of 4-(3-cyanophenyl)-1-(2-pyridyl)-1H-imidazole, as an off-white solid.

4-(2-Pyridyl)-1-(3-cyanophenyl)-1H-imidazole

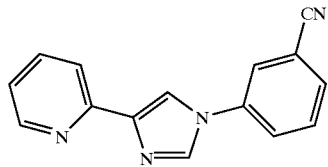

B152

Under an argon atmosphere, a solution of 4-iodo-1-trityl-1 H-imidazole (1.00 g, 2.29 mmol) in dichloromethane (10 mL) was treated with isopropylmagnesium bromide (2.75 mL of 1M, 2.75 mmol, in tetrahydrofuran) and stirred at ambient temperature for 1 hour. After this time, the reaction was treated with tributyltin chloride (0.81 mL, 2.98 mmol) and the resulting mixture stirred overnight at ambient temperature. The reaction mixture was then diluted with dichloromethane (50 mL) and successively washed with saturated ammonium chloride (50 mL), water (50 mL) and brine (50 mL). The organic phase was dried over anhydrous sodium sulfate, filtered and concentrated in vacuo to afford 1.37 g of crude 4-tributylstannyl-1-trityl-1H-imidazole.

The crude 4-tributylstannyl-1-trityl-1H-imidazole (1.37g) in toluene (10 mL) was treated sequentially with 2-bromopyridine (0.33 mL, 3.43 mmol) and Pd(PPh$_3$)$_4$ (0.26 g, 0.23 mmol). The reaction mixture was heated at reflux under an argon atmosphere for 4 hours. After cooling, the reaction mixture was concentrated in vacuo. The residue was dissolved in chloroform (50 mL) and sequentially washed with aqueous saturated potassium fluoride (75 mL), water (75 mL) and brine (100 mL). The organic phase was dried over anhydrous sodium sulfate, filtered and concentrated in-vacuo to afford 0.69 g of crude 4-(2-pyridyl)-1-trityl-1H-imidazole.

A solution of the crude 4-(2-pyridyl)-1-trityl-1H-imidazole (0.69g) in tetrahydrofuran (14 mL) was treated with 2 N hydrochloric acid (7.2 mL) and heated at reflux for 45 minutes. After cooling the reaction mixture was concentrated in vacuo and the residue was dissolved in dichloromethane (20 mL). The organic solution was successively washed with aqueous 1N sodium hydroxide (10 mL), water (20 mL) and brine (20 mL). The organic solution was then dried over anhydrous sodium sulfate, filtered, and concentrated in-vacuo to afford 0.12 g of crude 4-(2-pyridyl) imidazole, as a sticky white solid.

To a flame dried, argon purged screw-cap vial, containing copper (I) triflate.benzene complex (0.01 g, 0.03 mmol), 1,10-phenanthroline (0.10 g, 0.54 mmol), trans-dibenzylideneacetone (0.01 g, 0.03 mmol) and cesium carbonate (0.20g, 0.60 mmol) was added a solution of 4-(2-pyridyl)imidazole (0.08 g, 0.54 mmol) and 3-iodobenzonitrile (0.19 g, 0.82 mmol) in ortho-xylene (2 mL). The resulting brownish black reaction mixture was heated overnight at 120° C. After cooling, the reaction mixture was diluted with dichloromethane (20 mL) and washed sequentially with saturated ammonium chloride (20 mL) and brine (20 mL). The organic phase was then dried with sodium sulfate, filtered, and concentrated in vacuo. Silica gel chromatography of the crude residue using 1% methanol (2 M in ammonia) in dichloromethane afforded 11 mg of 4-(2-pyridyl)-1-(3-cyanophenyl)-1H-imidazole, as an off-white solid.

Example 9

3-(2-Pyridyl)-2-(3-cyanophenyl)-furan

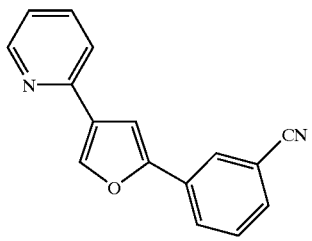

B256

A solution of n-butyllithium (6.8 mL, 1.6M in hexanes, 11.0 mmol) was added in a dropwise manner to a solution of tetrahydro-2-(2-propynyloxy)-2H-pyran (1.43 mL, 10.0 mmol) in THF (30 mL) at −78° C. and the reaction mixture was stirred at −50° C. for 30 min prior to the dropwise addition of 3-cyanobenzaldehyde (1.44 mL, 11.0 mmol) at −78° C. The resulting mixture was stirred for 30 min at −78° C. After the reaction mixture was warmed to room temperature, it was quenched by pouring over ice. The crude product was partitioned between ethyl acetate (450 mL) and sodium hydrogen sulfate (1M, aqueous). The organic layer was washed sequentially with water and brine, and dried over sodium sulfate. Removal of the solvent in vacuo yielded the crude product (2.87 g, 100%).

A solution of this crude product in dichloromethane (5 mL) was added to a mechanically stirred heterogenous mixture of manganese dioxide (9.660 g, 4.42 mol) in dichloromethane (25 mL) at 0° C. and stirred at this temperature for 1 hour. The reaction mixture was filtered through magnesium sulfate, and the solvent was removed in vacuo yielding the crude acetylenic ketone. Pyridinium-p-toluene sulfonate (220.0 mg) was added to a solution of the crude acetylenic ketone in ethanol (25 mL). The resulting mixture was stirred at 50° C. for 4 h. After allowing the mixture to cool to room temperature, it was diluted with ethyl acetate (80 mL), washed sequentially with water (3×50 mL) and brine (50 mL), and dried over sodium sulfate. After removal of the solvent in vacuo, flash chromatography on silica gel (10%–20% ethyl acetate in hexanes) yielded the crude deprotected alcohol (793.1 mg, 30% over 2 steps).

To a stirred solution of the deprotected alcohol (793.1 mg, 4.28 mmol) and dichloromethane (3 mL), HBr in acetic acid (30%, 1.69 mL) was added dropwise at 0° C. The reaction mixture was stirred for 1.5 h at 0° C. The reaction mixture was diluted with ethyl acetate (50 mL) and then quenched by pouring it over ice, ether and sodium bicarbonate. The crude product was then taken into ethyl acetate (300 mL), washed sequentially with water, sodium sulfite and brine, and dried over sodium sulfate. The solvent was removed in vacuo. Flash chromatography on silica gel (0–5% ethyl acetate in hexane) yielded 1.5098 g (100% yield) of 3-bromo-2-(3-cyanophenyl)-furan. The oil was taken on to the next step without further purification.

A solution of 3-bromo-2-(3-cyanophenyl)-furan (112 mg, 0.45 mmol), pyridyl 2-trimethyl stannane (240 mg, 0.996 mmol) and Pd(PPh$_3$)$_4$ (20 mg, 0.02 mmol) in anhydrous toluene (5 mL) was stirred at 110° C. for 3 days. After cooling to room temperature, the product was filtered through 1 g SPE tube and washed through with dichloromethane (50 mL), and the solvent was removed in vacuo. Flash chromatography on silica gel (15–50% ethyl acetate in hexanes) yielded 32.4 mg (42%, GC/MS RT 9.209 min, 100%pure) of 3-(2-pyridyl)-2-(3-cyanophenyl)-furan. $^1$H-NMR (CDCl$_3$), δ (ppm): 8.61 (d, 1H), 8.07 (s, 1H), 7.99 (s, 1H), 7.92 (m, 1H), 7.71 (m, 1H), 7.53 (m, 3H), 7.27 (s, 1H), 7.19 (m, 1H).

3-(5-fluoro-2-pyridyl)-2-(3-cyanophenyl)-furan

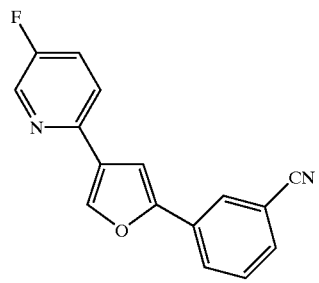

B257

In a similar fashion, a solution of 3-bromo-2-(3-cyanophenyl)-furan (110 mg, 0.44 mmol), 5-fluoro-pyridyl 2-trimethyl stannane (172 mg, 0.66 mmol) and Pd(PPh$_3$)$_4$ (20 mg, 0.02 mmol) in anhydrous toluene (5 mL) was stirred at 110° C. for 3 days. After cooling to room temperature, the product was filtered through 1 g SPE tube and washed through with dichloromethane (50 mL), and the solvent was removed in vacuo. Chromatography (5g silica SPE tube, 10% ethyl acetate in hexanes) yielded 29.3 mg (35%, GC/MS RT 9.029, 97%pure) of 3-(5-fluoro-2-pyridyl)-2-(3-cyanophenyl)-furan. $^1$H-NMR (CDCl$_3$), δ (ppm): 8.47 (d, 1H), 8.05 (s, 1H), 8.01 (s, 1H), 7.92 (dd, 1H), 7.40–7.57 (m, 5H), 7.21 (s, 1H).

3-(5-chloro-2-pyridyl)-2-(3-cyanophenyl)-furan

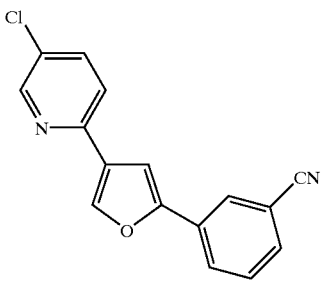

B258

In a similar fashion, a solution of 3-bromo-2-(3-cyanophenyl)-furan (98.04 mg, 0.395 mmol), 5-chloro-pyridyl 2-trimethyl stannane (170 mg, 0.35 mmol) and Pd(PPh$_3$)$_4$ (20 mg, 0.02 mmol) in anhydrous toluene (5 mL) was stirred at 110° C. for 3 days. After cooling to room temperature, the product was filtered through 1 g SPE tube and washed through with dichloromethane (50 mL), and the solvent was removed in vacuo. Chromatography (5g silica SPE tube, 10% ethyl acetate in hexanes) yielded 5.9 mg (7.3%, GC/MS RT 9.876 min., 100%pure) of 3-(5-chloro-2-pyridyl)-2-(3-cyanophenyl)-furan. $^1$H-NMR (CDCl$_3$), δ (ppm): 8.56 (d, 1H), 8.06 (s, 1H), 8.00 (s, 1H), 7.92 (d, 1H), 7.57 (dAB, 1H), 7.53 (dAB, 3H), 7.46 (d, 1H), 7.23 (s, 1H).

2-(2-Pyridyl)-5-(5-fluoro-3-(1-imidazolyl)phenyl)-furan

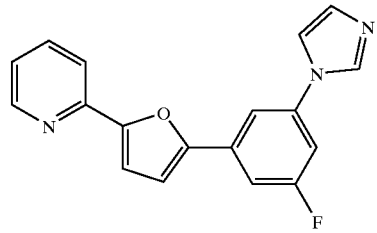

B259

Intermediates: 5-Bromo-2-(2-pyridyl)-furan

N-Bromosuccinimide (187 mg, 1.05 mmol) and p-toluensulfonic acid (11 mg) were added to a solution of 2-pyridyl-2-furan (150 mg, 1.03 mmol) in benzene (12.5 mL) under argon. The resulting solution was stirred at 80° C. for 2 h. After cooling to room temperature, the product was washed sequentially with aqueous sodium sulfite (3×5 mL), water (5 mL) and brine (5 mL), and dried by passing through an EX-TUBE (3 mL), using additional solvent (dichloromethane) to rinse. Chromatography (5g silica gel SPE tube, 70–100% dichloromethane in hexane) afforded 180 mg (69% based on 88% purity by GC/MS) of 5-bromo-2-(2-pyridyl)-furan as a light brown oil. 1-(3-bromo-5-fluoro-phenyl)-1H-imidazole: 1-Bromo-3,5-difluorobenzene (1.78 mL, 15.5 mmol) was added to a solution of imidazole (1.07 g, 15.7 mmol) and potassium carbonate (2.2 g, 15.9 mmol) in DMF (20 mL). The resulting mixture was stirred at 110° C. for 36 h. After cooling to room temperature, water (75 mL) was added and the product was extracted into ethyl acetate (3×150 mL). The organic layer was washed sequentially with water (3×100 mL) and brine (100 mL) and dried over sodium sulfate. The solvent was removed in vacuo to afford 2.35 g of the crude product, which was contaminated with 5-bromo-1,3-bis(1-imidazolyl)benzene. A 320 mg portion of the product was further purified by chromatography (5g silica gel SPE tube, 1–5% methanol in dichloromethane) afforded 193.6 mg (38%) of 1-(3-bromo-5-fluoro-phenyl)-1H-imidazole.

Title compound synthesis: Pd(PPh$_3$)$_4$ (10 mg, 0.009 mmol) was added to a solution of hexamethylditin (169 mg, 0.52 mmol) and 5-bromo-2-(2-pyridyl)-furan (90 mg, 88% purity, 0.36 mmol) in toulene (2 mL) under argon. The resulting solution was stirred at 80° C. for 19 h. After cooling to room temperature, a second portion of Pd(PPh$_3$)$_4$ (10 mg, 0.009 mmol) and 1-(3-bromo-5-fluoro-phenyl)-1H-imidazole (86 mg, 0.36 mmol) were added and the resulting solution was stirred at 110° C. for 36 h. After cooling to room temperature, the solvent was removed in vacuo. Chromatography (5g silica gel SPE tube, 0–3% methanol in 1:1 chloroform:ethyl acetate) afforded 72.3 mg (66%) of 2-(2-pyridyl)-5-(5-fluoro-3-(1-imidazolyl)phenyl)-furan. $^1$H-NMR (CDCl$_3$), δ (ppm): 8.63 (d, 1H), 7.93 (s, 1H), 7.78 (m, 2H), 7.57 (s, 1H), 7.45 (m, 1H), 7.35 (s, 1H), 7.23 (m, 3H), 7.03 (m, 1H), 6.91 (d, 1H).

3-(5-(2-pyridyl)-2-furyl)-benzonitrile

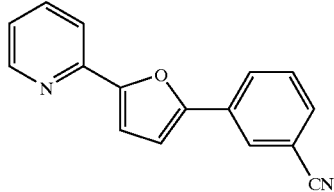

B260

Similarly, Pd(PPh$_3$)$_4$ (22 mg, 0.019 mmol) was added to a solution of 3-(5-bromofuran-2-yl)-benzonitrile (35 mg, 0.14 mmol) and 2-tributylstannylpyridine (71 mg, 0.19 mmol) in toluene (2 mL) under argon. In a similar manner, benzylbis(triphenylphosphine)palladium(II) chloride (10.5 mg, 0.014 mmol) was added to a solution of 3-(5-bromofuran-2-yl)-benzonitrile (35 mg, 0.14 mmol) and 2-tributylstannylpyridine (75 mg, 0.20 mmol) in toluene (2 mL) under argon. Both solutions were stirred at 110° C. for 18 h. After cooling to room temperature, the mixtures were combined since TLC of both reactions proved to be identical. The solvent was removed in vacuo from the combined product. Chromatography (5g silica gel SPE tube, dichloromethane) followed by triturating with 10% ethyl acetate in hexanes afforded 26.2 mg (38%) of 3-(5-(2-pyridyl)-2-furyl)-benzonitrile. $^1$H-NMR (CDCl$_3$), δ (ppm): 8.63 (d, 1H), 8.05 (s, 1H), 7.96 (d, 1H), 7.77 (m, 3H), 7.54 (m, 2H), 7.20 (m, 1H), 6.89 (d, 1H).

3-(5-(5-choro-2-pyridyl)-2-furyl)-benzonitrile

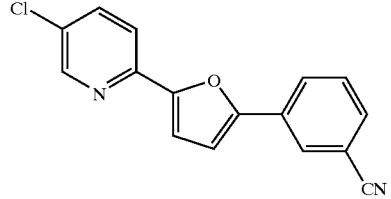

B261

Pd(PPh$_3$)$_4$ (5 mg, 0.004 mmol) was added to a solution of hexamethylditin (160 mg, 0.49 mmol) and 5-chloro-2-bromopyridine (76 mg, 0.395 mmol) in toulene (1 mL) under argon. The resulting solution was stirred at 80° C. for 16 h. After cooling to room temperature, a second portion of Pd(PPh$_3$)$_4$ (20 mg, 0.019 mmol) and 3-(5-bromofuran-2-yl)-benzonitrile (79 mg, 0.32 mmol) were added and the resulting solution was stirred at 110° C. for 14 h. After cooling to room temperature, the solvent was removed in vacuo. Chromatography (5g silica gel SPE tube, 25–50% chloroform in hexane to 2% ethyl acetate in 1:1 chloroform:hexane) followed by triturating with hexanes and purification by preparative TLC (90% dichloromethane in hexane) afforded 15.7 mg (17%) of 3-(5-(5-choro-2-pyridyl)-2-furyl)-benzonitrile (97.5% pure by GC/MS, contaminated with 2.5% dimer). $^1$H-NMR (CDCl$_3$), δ (ppm): 8.55 (d, 1H), 8.03 (s, 1H), 7.94 (dd, 1H), 7.73 (s, 2H), 7.54 (m, 12), 7.16 (d, 1H), 6.88 (d, 1H).

3-(5-(5-cyano-2-pyridyl)-2-furyl)-benzonitrile

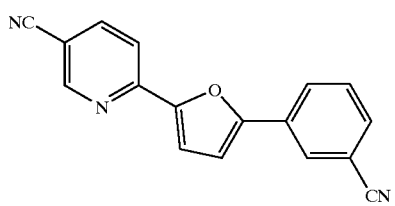

B262

In a similar fashion, Pd(PPh$_3$)$_4$ (10 Mg, 0.009 mmol) was added to a solution of 2-trimethylstannyl-5-cyano-pyridine (22.7 mg, 0.085 mmol) and 3-(5-bromofuran-2-yl)-benzonitrile (31 mg, 0.125 mmol) in toluene (1 mL) under argon. The resulting solution was stirred at 110° C. for 15 h. After cooling to room temperature, the solvent was removed in vacuo. Chromatography (5g silica gel SPE tube, 50% chloroform in hexane to 20% ethyl acetate in 1:1 chloroform:hexane) followed by triturating with 50% dichloromethane in hexane afforded 5.3 mg (23%) of 3-(5-(5-cyano-2-pyridyl)-2-furyl)-benzonitrile (91% pure by GC/MS, contaminated by 9% dimer). $^1$H-NMR (CDCl$_3$), δ (ppm): 8.85 (s, 1H), 7.87–8.05 (m, 5H), 7.52–7.63 (m, 3H), 7.36 (d, 1H), 6.95 (d, 1H), dimer impurity caused peak intensity to increase in region 8.00, 7.92, 7.49–7.57, plus 2 peaks additional peaks exactly overlapping with pure dimer @ δ (ppm): 6.87 (d) & 6.80 (d).

3-(5-(5-fluoro-2-pyridyl)-2-furyl)-benzonitrile

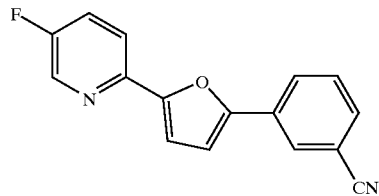

B263

In a similar fashion, Pd(PPh$_3$)$_4$ (25 mg, 0.022 mmol) was added to a solution of hexamethylditin (163 mg, 0.50 mmol) and 5-fluoro-2-bromopyridine (87 mg, 0.49 mmol) in toulene (4 mL) under argon. The resulting solution was stirred at 80° C. for 15 h. After cooling to room temperature, a second portion of Pd(PPh$_3$)$_4$ (25 mg, 0.022 mmol) and 3-(5-bromofuran-2-yl)-benzonitrile (105 mg, 0.42 mmol) were added and the resulting solution was stirred at 110° C. for 48 h. After cooling to room temperature, the mixture was diluted with dichloromethane and passed through a 1 g silica gel SPE tube using dichloromethane to elute the product. Flash chromatography (silica gel, 50–100% dichloromethane in hexane) afforded 48.4 mg (43%) of 3-(5-(5-fluoro-2-pyridyl)-2-furyl)-benzonitrile (pure by GC/MS). $^1$H-NMR (CDCl$_3$), δ (ppm): 8.48 (d, 1H), 8.03 (s, 1H), 7.95 (m, 1H), 7.81 (m, 1H), 7.51 (m, 3H), 7.11 (d, 1H), 6.87 (d, 1H).

3-Fluoro-5-(5-(2-pyridyl)-2-furyl)-benzonitrile

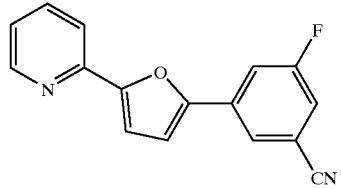

B264

3-(5-Bromofuran-2-yl)-5-fluoro-benzonitrile intermediate: In a similar fashion, 3-(5-Bromofuran-2-yl)-5-fluoro-benzonitrile was prepared from N-bromosuccinimide (123 mg, 0.69 mmol), p-toluensulfonic acid (8 mg) and 3-furan-2-yl-benzonitrile (128 mg, 0.68 mmol) in benzene (10 mL) at 80° C. for 2.5 h. Standard workup and chromatography (5g silica gel SPE tube, 2.5–5% ethyl acetate in hexane) afforded 181 mg (86% based on 86% purity by GC/MS) of 3-(5-bromofuran-2-yl)-5-fluoro-benzonitrile.

Pd(PPh$_3$)$_4$ (10 mg, 0.009 mmol) was added to a solution of 3-(5-bromofuran-2-yl)-5-fluoro-benzonitrile (180 mg, 86% purity, 0.59 mmol) and 2-trimethylstannylpyridine (193 mg, 0.80 mmol) in toluene (2.5 mL) under argon. The resulting solution was stirred at 110° C. for 48 h. After cooling to room temperature, the solvent was removed in vacuo. Flash chromatography (silica gel, 35–100% dichloromethane in hexane) afforded 67.7 mg (43%) of 3-fluoro-5-(5-(2-pyridyl)-2-furyl)-benzonitrile. $^1$H-NMR (CDCl$_3$), δ (ppm): 8.64 (d, 1H), 7.76–7.83 (m, 3H), 7.66 (m, 1H), 7.24 (m, 2H), 7.19 (d, 1H), 6.92 (d, 1H).

Example 10

Oxazoles via Oxazolone Intermediate

General Synthesis of 3-Cyano-5-Substituted Benzamides:

To a mixture of aqueous ammonium hydroxide and ethylacetate (ratio of 1:5) at 0° C. was added slowly the benzoyl chloride (also prepared from the acid and oxalyl chloride). The mixture was stirred at room temperature for 15 minutes after which the ethylacetate layer was seperated. The aqueous layer was extracted vigorously with ethylacetate, the combined organic layer was washed with brine, dried over anhydrous Na2SO$_4$ and concentrated in vacuo to give the product.

General Synthesis of the 2-Aryloxazolones:

To a solution of the benzamide in 1,2-dichloroethane was added oxalyl chloride (4–5 equivalents) and the mixture was heated to reflux for 18 h. The solvent was removed in vacuo and the crude acyl isocyanates dissolved in dry ether and diazomethane (prepared from N-methyl-N-nitrosourea and 50% aqueous KOH) in ether was added from a dropping funnel very slowly until the bubbling ceases. The mixture was then filtered to give the 2-aryloxazolone.

General Synthesis of the 2-Aryl-4-trifluoromethanesulphonyloxy-1,3-oxazole:

To a solution of the 2-Aryloxazolone and 2,6-lutidine (2 eqv.) in CH$_2$Cl$_2$ at 0° C. was added triflic anhydride (1.5 eqv.) dropwise over 15 minutes. The mixture was allowed to come to room temperature and stirred overnight. The solvent was removed in vacuo and then purified by flash column chromatography on silica gel with CH$_2$Cl$_2$ as eluant General Synthesis of 2-Aryl-4-pyrid-2-yl-1,3-oxazoles:

To a mixture of 2-Aryl-4-trifluoromethanesulphonyloxy-1,3-oxazole, LiCl, and 2-trimethylstannylpyridine in dioxane under argon was added Pd(PPh$_3$)$_4$ and the mixture was heated to 100° C. overnight. After cooling to room temperature, the solvent was removed in vacuo and the residue was purified by flash column chromatography on silica gel to afford the final product.

Thus, using the general method for synthesis of oxazoles via oxazolone intermediate the following compounds were obtained:

2-(3-cyanophenyl)-4-(5-Fluoropyrid-2-yl)-1,3-oxazole

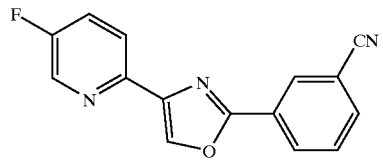

B265

2-(3-cyanophenyl)-4-(5-Fluoropyrid-2-yl)-1,3-oxazole (an off-white solid, 180 mg, 72% yield); 1HNMR(CDCl3) []: 8.48 (d, 1H), 8.41 (s,1H), 8.35 (m,1H), 8.30 (m, 1H), 8.00 (dd, 1H), 7.75 (m, 1H), 7.62 (t, 1H), 7.52 (dt, 1H).

2-(3-cyano-5-fluorophenyl)-4-(5-Fluoropyrid-2-yl)-1,3-oxazole

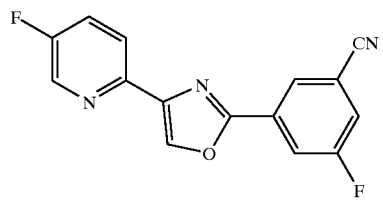

B266

2-(3-cyano-5-fluorophenyl)-4-(5-Fluoropyrid-2-yl)-1,3-oxazole (a white solid, 65 mg, 55% yield); 1HNMR(CDCl3) []: 8.48 (d, 1H), 8.31 (s,1H), 8.23 (d,1H), 8.07 (m, 1H), 8.00 (dd, 1H), 7.52 (m, 1H), 7.46 (m, 1H).

2-(3-cyano-5-fluorophenyl)-4-(2-pyridyl)-1,3-oxazole

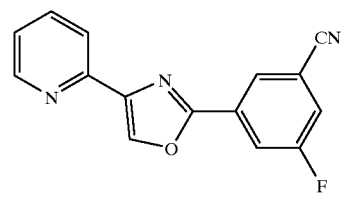

B267

2-(3-cyano-5-fluorophenyl)-4-(2-pyridyl)-1,3-oxazole (a white solid, 75 mg, 65% yield); 1HNMR(CDCl3) []: 8.62 (d, 1H), 8.38 (s,1H), 8.23 (s,1H), 8.07 (m, 1H), 8.00 (d, 1H), 7.80 (dt, 1H), 7.46 (m, 1H), 7.24 (m, 1H).

2-(5-allyloxy-3-cyanophenyl)-4-(5-Fluoropyrid-2-yl)-1,3-oxazole

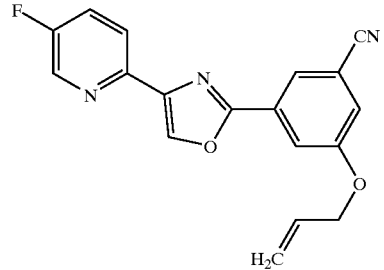

B268

2-(5-allyloxy-3-cyanophenyl)-4-(5-Fluoropyrid-2-yl)-1,3-oxazole (an off white solid, 11 mg, 15% yield); 1HNMR (CDCl3) []: 8.47 (d, 1H), 8.28 (s, 1H), 7.99 (m, 2H), 7.86 (s, 1H), 7.51 (m, 1H), 7.24 (s, 1H), 6.05 (m, 1H), 5.40 (m, 2H), 4.65 (d, 2H).

2-(3-cyano-5-methoxyphenyl)-4-(pyrid-2-yl)-1,3-oxazole

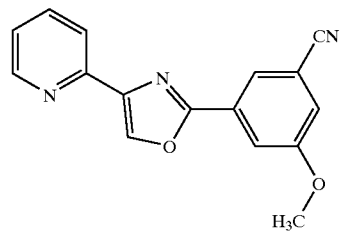

B269

2-(3-cyano-5-methoxyphenyl)-4-(pyrid-2-yl)-1,3-oxazole (a white solid, 600 mg, 65% yield); 1HNMR (CDCl3) []: 8.62 (d, 1H), 8.34 (s,1H), 7.92 (m, 2H), 7.84 (s, 1H), 7.78 (m, 1H), 7.78 (t, 1H), 7.25 (t, 1H), 3.94 (s, 3H).

2-(3-cyano-5-methoxyphenyl)-4-(5-Fluoropyrid-2-yl)-1,3-oxazole

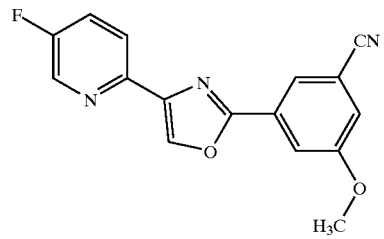

B270

2-(3-cyano-5-methoxyphenyl)-4-(5-Fluoropyrid-2-yl)-1,3-oxazole (a white solid, 35 mg, 35% yield); 1HNMR (CDCl3) []: 8.47 (d, 1H), 8.29 (s,1H), 8.02 (d,1H), 7.99 (s, 1H), 7.85 (s, 1H), 7.50 (m, 1H), 7.24 (s, 1H), 3.93 (s, 3H).

2-(3-cyano-5-n-propyloxyphenyl)-4-(5-Fluoropyrid-2-yl)-1,3-oxazole

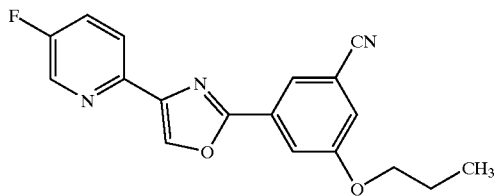

B271

2-(3-cyano-5-n-propyloxyphenyl)-4-(5-Fluoropyrid-2-yl)-1,3-oxazole (a white solid, 430 mg, 55% yield) 1HNMR (CDCl3) []: 8.46 (d, 1H), 8.27 (s,1H), 8.00 (m,1H), 7.95 (s, 1H), 7.83 (s, 1H), 7.50 (m, 1H), 7.23 (s, 1H), 4.02 (t, 3H), 1.85 (m, 1H), 1.07 (t, 3H).

2-(3-cya no-5-methoxyphenyl)-4-(pyrid-2-yl)-5-chloro-1,3-oxazole

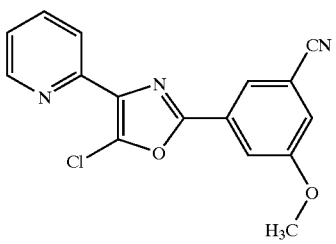

B272

N-chlorosuccinimide (32 mg, 0.24 mmol) and benzoyl peroxide (4.6 mg, 0.019 mmol) were added to a solution of 2-(3-cyano-5-methoxyphenyl)-4-(5-pyrid-2-yl)-1,3-oxazole (52 mg, 0.19 mmol) in carbon tetrachloride (2 mL). The reaction was heated at 80° C. for 4 hours. The solvent was removed in vacuo and the compound was purified by eluting through and 5 g SPE tube with a gradient of 5–10% ethyl acetate in hexanes. 2-(3-cyano-5-methoxyphenyl)-4-(pyrid-2-yl)-5-chloro-1,3-oxazole was afforded as a white solid (30 mg, 51% yield). 1HNMR(CDCl3): 8.75 (d, 1H), 8.03 (d,1H), 7.97 (s,1H), 7.82 (m, 2H), 7.29 (d, 2H), 3.93 (s, 3H).

Example 11

Assay of Group I Receptor Antagonist Activity

Primary astrocyte cultures were prepared from 3–5 day old Sprague-Dawley rat pups using a modification of Miller (Miller et al, *J. Neuroscience*, 15(9): 6103–6109, 1995). In brief, primary cultures were plated on poly-L lysine coated flasks in Dulbecco's modified Eagle's medium (DMEM) containing fetal calf serum (FCS). After 6 days, cell cultures were shaken over night at 280 rpm, then transferred to astrocyte-defined media (ADM) containing growth factors that up-regulate the expression of mGluR5 (Miller et al., 1995). For cuvette analysis, cultures were up-regulated with growth factors in flasks for 3–5 days, then harvested and prepared for measurement of $[Ca^{2+}]_i$ mobilization as previously described (Nemeth et al., 1998).

For FLIPR analysis, cells were seeded on poly-D lysine coated clear bottom 96-well plates with black sides and analysis of $[Ca^{2+}]_i$ mobilization was performed 3 days following the growth factor up-regulation. Cell cultures in the 96-well plates were loaded with a 4 μM solution of acetoxymethyl ester form of the fluorescent calcium indicator fluo-3 (Molecular Probes, Eugene, Oreg.) in 0.01% pluronic. All assays were performed in a buffer containing 127 mM NaCl, 5 mM KCl, 2 mM $MgCl_2$, 0.7 mM $NaH_2PO_4$, 2 mM $CaCl_2$, 0.422 mg/ml $NaHCO_3$, 2.4 mg/ml HEPES, 1.8 mg/ml glucose and 1 mg/ml BSA Fraction IV (pH 7.4).

FLIPR experiments were done using a laser setting of 0.800 W and a 0.4 second CCD camera shutter speed. Each FLIPR experiment was initiated with 180 μL of buffer present in each well of the cell plate. A 20 μL addition from the antagonist plate was followed by a 50 μL addition from the agonist plate. After each addition the fluorescence signal was sampled 50 times at 1 second intervals followed by 3 samples at 5 second intervals. Responses were measured as the peak height of the response within the sample period.

$EC_{50}/IC_{50}$ determinations were made from data obtained from 8 point concentration response curves (CRC) performed in duplicate. Agonist CRC were generated by scaling all responses to the maximal response observed for the plate. Antagonist block of the agonist challenge was normalized to the average response of the agonist challenge in 14 control wells on the same plate. Compounds of the present invention antagonized mGluR5 as determined by their $IC_{50}$ values which fell into the range of 11–9140 nM.

The invention thus has been disclosed broadly and illustrated in reference to representative embodiments described above. Those skilled in the art will recognize that various modifications can be made to the present invention without departing from the spirit and scope thereof.

What is claimed is:

1. A compound of formula I, or a pharmaceutically acceptable salt thereof:

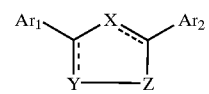

I wherein

---- represents a double or single bond;

X and Y are N;

Z is O;

$Ar_1$ and $Ar_2$ are independently selected from the group consisting of: optionally substituted phenyl and optionally substituted 2-pyridyl wherein at least one of $Ar_1$ and $Ar_2$ is phenyl and at least one of $Ar_1$ and $Ar_2$ is 2-pyridyl and at least one of $Ar_1$ and $Ar_2$ is substituted with at least one substituent G;

wherein

G is selected from the group consisting of: haloalkyl; pyridyl; thiophene; pyrimidine; furan; cycloalkene; alkenyl; alkynyl; A-alkenyl; A-alkynyl; A-alkyloxy; $-R_2OR_3$; $-R_2OC(O)R_3$; $(CH_2)_m-NR_2R_3$; $-OCH_2CH(Cl)CH_2Cl$; and substituted aryl wherein the aryl substituent is $R_4$, and wherein A is a linker selected from the group consisting of: $CH_2$; O; NH; S; SO; $SO_2$; $NSO_2$; $-OSO_2$; and $-C(NR_2)NR_3$;

m is selected from 0 and 1;

$R_2$ and $R_3$ may be independently selected from the group consisting of: H; alkyl; haloalkyl; alkyloxy; alkylamine; cycloalkyl; heterocycloalkyl; aryl; heteroaryl; alkylaryl; alkylheteroaryl; haloaryl; alkyloxyaryl; alkenylaryl; alkenyloxyaryl; and haloheteroaryl; and R$_4$ is selected from the group consisting of: halo; —OR$_2$; —SR$_2$; —SOR$_2$; —SO$_2$R$_2$; —SO$_2$NR$_2$R$_3$; —R$_2$OR$_3$; —R$_2$SR$_3$; —OCOR$_2$; —OCONR$_2$R$_3$; —NR$_2$COR$_3$; —NR$_2$CO$_2$R$_3$; —CN; —NO$_2$; —C(NR$_2$)NR$_3$; —CO$_2$R$_2$R$_3$; —CONR$_2$R$_3$; —C(O)R$_2$; —CH(OR$_2$)R$_3$; —CH$_2$(OR$_2$); —A—(CH$_2$)$_m$—NR$_2$R$_3$; NR$_2$R$_3$; aryl; aralkyl; heteroaryl; and heteroaralkyl; and Ar$_1$, Ar$_2$, and the substituent G are optionally further substituted with one or more substituents selected independently from the group consisting of R$_2$ and R$_4$, with the proviso that when ---- represents a double bond, then either of Ar$_1$ or Ar$_2$ is pyridyl and the compound is not:

3-(2-pyridyl)-5-(4-aminophenyl)-1,2,4-oxadiazole,
3-(2-pyridyl)-5-{2-[2-(N,N,dimethylamino)-ethyl]oxyphenyl}-1,2,4-oxadiazole,
3-(2-Pyridyl)-5-(2-chlorophenyl)-1,2,4-oxadiazole, or
3-(2-pyridyl)-5-phenyl-1,2,4-oxadiazole.

2. A compound of claim 1 wherein ---- a represents double bond.

3. A compound of claim 1 wherein Ar$_1$ is optionally substituted 2-pyridyl.

4. A compound as defined in claim 2 wherein the substituent G is bonded to Ar$_2$ and not Ar$_1$.

5. A compound of claim 4 wherein Ar$_2$ is further substituted with one or more substituents selected from the group consisting of R$_2$ and R$_4$.

6. A compound of claim 5 wherein Ar$_2$ is phenyl.

7. A compound of claim 5 wherein Ar$_2$ is 2-pyridyl.

8. A compound as defined in claim 5 wherein G is selected from the group consisting of: pyridyl; thiophene; pyrimidine; and furan, and wherein G is further substituted with one or more substituents selected from the group consisting of R$_2$, R$_3$, and R$_4$.

9. A compound as defined in claim 8 wherein G is selected from the group consisting of 2-pyridine, 3-pyridine and 4-pyridine.

10. A compound as defined in claim 9 wherein G is 3-pyridine.

11. A compound as defined in claim 8 wherein G is 3-thiophene.

12. A compound as defined in claim 8 wherein G is pyrimidine.

13. A compound as defined in claim 8 wherein G is furan.

14. A compound as defined in claim 8 wherein G is substituted aryl, wherein the substituent is R$_4$.

15. A compound as defined in claim 14 wherein G is substituted phenyl.

16. A compound as defined in claim 15 wherein G is substituted phenyl and R$_4$ is selected from the group consisting of halo, NR$_2$R$_3$, and CN.

17. A compound of claim 5 wherein G is (CH$_2$)$_m$-NR$_2$R$_3$ and m is selected from 0 and 1 and R$_2$ and R$_3$ may be independently selected from the group consisting of: H; alkyl; haloalkyl; alkyloxy; alkylamine; cycloalkyl; heterocycloalkyl; aryl; heteroaryl; alkylaryl; alkylheteroaryl; haloaryl; alkyloxyaryl; alkenylaryl; alkenyloxyaryl; and haloheteroaryl.

18. A compound as defined in claim 17 wherein R$_2$ and R$_3$ are independently selected from H and C$_{1-3}$ alkyl.

19. A compound of claim 5 wherein G is alkenyl.

20. A compound as defined in claim 19 wherein G is selected from the group consisting of: —CH$_2$=CH$_2$ and —CH(CH$_3$)=CH$_2$.

21. A compound as defined in claim 5 wherein G is alkynyl.

22. A compound of claim 5 wherein G is selected from the group consisting of A-alkenyl and A-alkynyl.

23. A compound as defined in claim 22 wherein A is O.

24. A compound as defined in claim 23 wherein G is —O—CH$_2$CH=CH$_2$.

25. A compound as defined in claim 5 wherein G is —OCH$_2$CH(Cl)CH$_2$Cl.

26. A compound as defined in claim 5 wherein G is selected from the group consisting of alkyloxy and A-alkyloxy.

27. A compound as defined in claim 5 wherein G is —CH$_2$CH$_2$OH.

28. A compound as defined in claim 5 wherein G is —CH$_2$OC(O)H.

29. A compound as defined in claim 5 wherein G is haloalkyl.

30. A compound as defined in claim 5 wherein G is cycloalkenyl.

31. A compound selected from the group consisting of:

3-(5-Methyl-pyrid-2-yl)-5-(3-cyanophenyl)-1,2,4-oxadiazole (B57), 3-(5-Cyano-pyrid-2-yl)-5-(3-cyanophenyl)-1,2,4-oxadiazole (B58), 3-(2-Pyridyl)-5-(5-bromo-2-methoxyphenyl)-1,2,4-oxadiazole (B62), 3-(2-Pyridyl)-5-(5-bromo-2-fluorophenyl)-1,2,4-oxadiazole (B63), 3-(2-Pyridyl)-5-(5-cyano-2-fluorophenyl)-1,2,4-oxadiazole (B64), 3-(2-Pyridyl)-5-(3-cyano-5-methylphenyl)-1,2,4-oxadiazole (B73), 3-(2-Pyridyl)-5-(3-fluoro-5-bromophenyl)-1,2,4-oxadiazole (B74), 3-(2-Pyridyl)-5-(3-iodo-5-bromophenyl)-1,2,4-oxadiazole (B75), 3-(5-Fluoro-2-pyridyl)-5-(3-fluoro-5-bromophenyl)-1,2,4-oxadiazole (B76), 3-(2-Pyridyl)-5-(3-iodo-5-(methylphenylester)-1,2,4-oxadiazole (B78), 3-(2-Pyridyl)-5-(3-methoxy-5-(methoxycarbonyl)phenyl)-1,2,4-oxadiazole (B79)

3-(2-Pyridyl)-5-(3-bromo-5-cyanophenyl)-1,2,4-oxadiazole (B80), 3-(2-Pyridyl)-5-(5-cyano-3-iodophenyl)-1,2,4-oxadiazole (B81), 3-(5-Cyano-2-pyridyl)-5-(3-bromophenyl)-1,2,4-oxadiazole (B59), 3-(5-Cyano-2-pyridyl)-5-(3-cyano-5-fluorophenyl)-1,2,4-oxadiazole (B60), 3-(5-Cyano-2-pyridyl)-5-(3-bromo-5-fluorophenyl)-1,2,4-oxadiazole (B61), 3-(2-Pyridyl)-5-(5-cyano-2-methoxyphenyl)-1,2,4-oxadiazole (B97), 3-(2-Pyridyl)-5-(2-cyano-5-methoxyphenyl)-1,2,4-oxadiazole (B98), 3-(2-Pyridyl)-5-(3-cyano-5-(methoxycarbonyl)phenyl)-1,2,4-oxadiazole (B100), 3-(2-Pyridyl)-5-(3-cyano-5-methoxyphenyl)-1,2,4-oxadiazole (B134), 3-(2-Pyridyl)-5-(3-cyano-5-hydroxyphenyl)-1,2,4-oxadiazole (B137), 3-(2-Pyridyl)-5-(3-cyano-5-propoxyphenyl)-1,2,4-oxadiazole (B141), 2-(2-Pyridyl)-5-(3-iodophenyl)-1,3,4-oxadiazole (B148),
2-(2-Pyridyl)-5-(3-cyanophenyl)-1,3,4-oxadiazole (B149),
3-(5-Chloropyrid-2-yl)-5-(3-cyano-5-fluorophenyl)-1,2,4-oxadiazole (B83),
3-(5-Chloropyrid-2-yl)-5-(3-cyano-5-chlorophenyl)-1,2,4-oxadiazole (B84),
3-(5-Chloropyrid-2-yl)-5-(3-chloro-5-fluorophenyl)-1,2,4-oxadiazole (B85),
3-(5-Chloropyrid-2-yl)-5-(3-cyano-5-methoxyphenyl)-1,2,4-oxadiazole (B86),
3-(5-Fluoropyrid-2-yl)-5-(3-cyano-5-chlorophenyl)-1,2,4-oxadiazole (B87),
3-(5-Fluoropyrid-2-yl)-5-(3-fluoro-5-chlorophenyl)-1,2,4-oxadiazole (B88),
3-(5-Fluoropyrid-2-yl)-5-(3-cyano-5-methoxyphenyl)-1,2,4-oxadiazole (B89),
3-(5-Cyanopyrid-2-yl)-5-(3-cyano-5-chlorophenyl)-1,2,4-oxadiazole (B90),
3-(5-Cyanopyrid-2-yl)-5-(3-fluoro-5-chlorophenyl)-1,2,4-oxadiazole (B91)
3-(5-Cyanopyrid-2-yl)-5-(3-cyano-5-methoxyphenyl)-1,2,4-oxadiazole (B92),
3-(5-Fluoropyrid-2-yl)-5-(3,5-di-cyanophenyl)-1,2,4-oxadiazole (B93),
3-(3-(4-Dimethylaminobutoxy)-pyrid-2-yl)-5-(3-cyano-5-fluorophenyl)-1,2,4-oxadiazole (B94)
3-(3-(5-Dimethylaminopentyloxy)-pyrid-2-yl)-5-(3-Cyano-5-fluorophenyl)-1,2,4-oxadiazole (B95), and
[3-(3-(6-Dimethylaminohexyloxy)-pyrid-2-yl)-5-(3-cyano-5-fluorophenyl)-1,2,4-oxadiazole](B96).

32. A compound selected from the group consisting of:
3-(2-Pyridyl)-5-(methoxycarbonyl)phenyl)-1,2,4-oxadiazole (B77),
3-(2-Pyridyl)-5-(3-N,N-dimethylaminophenyl)-1,2,4-oxadiazole (B82),
3-(2-Pyridyl)-5-(3-cyano-5-(4-pyridyl)phenyl)-1,2,4-oxadiazole (B101),
3-(2-Pyridyl)-5-[2-methoxy-5-(4-pyridyl)phenyl]-1,2,4-oxadiazole (B102),
3-(2-pyridyl)-5-[2-fluoro-5-(4-pyridyl)phenyl]-1,2,4-oxadiazole (B103),
3-(2-Pyridyl)-5-(3-fluoro-5-(4-pyridyl)phenyl)-1,2,4-oxadiazole (B104),
3-(2-Pyridyl)-5-(3-fluoro-5-(3-pyridyl)phenyl)-1,2,4-oxadiazole (B105),
3-(2-Pyridyl)-5-[2-fluoro-5-(3pyridyl)phenyl]-1,2,4-oxadiazole (B106),
3-(2-Pyridyl)-5-[2-methoxy-5(3pyridyl)phenyl]-1,2,4-oxadiazole (B107),
3-(2-Pyridyl)-5-(3-cyano-5-(3-pyridyl)phenyl)-1,2,4-oxadiazole (B108),
3-(5-Fluoro-2pyridyl)-5(3-pyridyl)phenyl)-1,2,4-oxadiazole (B109),
3-(5-Cyanopyrid-2-yl-5-(3-(pyrid-3-yl)phenyl)-1,2,4-oxadiazole (B112),
3-(5-Cyanopyrid-2-yl)-5-(3-fluoro-5-(pyrid-3-yl)phenyl)-1,2,4-oxadiazole (B113),
3-(2-Pyridyl)-5-(3-cyano-5-(2-pyridyl)phenyl)-1,2,4-oxadiazole (B124),
3-(2Pyridyl)5-[2-methoxy-5-(2-pyridyl)phenyl]-1,2,4-oxadiazole (B125),
3-(2-Pyridyl)-5-[2-fluoro-5-(2-pyridyl)phenyl]-1,2,4-oxadiazole (B126),
3-(2-Pyridyl)-5-[(3-(3-fluorophenyl)-5-fluorophenyl)]-1,2,4-oxadiazole (B114),
3-(2-Pyridyl)-5-(3-cyano-5-(3-thiophene)phenyl)-1,2,4-oxadiazole (B115),
3-(2-Pyridyl)-5-(3-cyano-5-(5-pyrimidyl)phenyl)-1,2,4-oxadiazole (B120),
3-(2-Pyridyl)-5-(3-cyano-5-(3-aminophenyl)phenyl)-1,2,4-oxadiazole (B121),
3-(2-Pyridyl)-5-(3-fluorophenyl)phenyl)-1,2,4-oxadiazole (B122),
3-(2-Pyridyl)-5(3-aminomethyl-5-cyanophenyl)-1,2,4-oxadiazole (B127),
3-(2-Pyridyl)-5-(3-cyano-5-vinylphenyl)-1,2,4-oxadiazole (B129),
3-(2-Pyridyl)-5-(3-cyano-5-(2-hydroxyethyl)phenyl)-1,2,4-oxadiazole (B130),
3-(2-Pyridyl)-5-(3-cyano-5-(2,3-dichloropropoxy)phenyl)-1,2,4-oxadiazole (B131),
3-(2-Pyridyl)-5-(3-allyloxy-5-carboxyphenyl)-1,2,4-oxadiazole (B135),
3-(2-Pyridyl)-5-(3-allyloxy-5-cyanophenyl)-1,2,4-oxadiazole (B136),
3-(2-Pyridyl)-5-(5-cyano-3-[3-hydroxypropyn-1-yl]phenyl)-1,2,4-oxadiazole (B142), and
3-(2-Pyridyl)-5-(2-N-methylaminophenyl)-1,2,4-oxadiazole (B 144).

33. A compound of Formula I, or a pharmaceutically acceptable salt thereof:

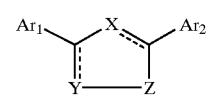

wherein
X and Y are N;
Z is O;
$Ar^1$ and $Ar^2$ are independently selected from the group consisting of optionally substituted phenyl and optionally substituted 2-pyridyl wherein at least one of $Ar_1$ and $Ar_2$ is phenyl and at least one of $Ar_1$ and $Ar_2$ is 2-pyridyl,
wherein
at least one of $Ar^1$ and $Ar^2$ is substituted with at least one substituents G,
wherein
G is selected from the group consisting of —F, —Cl, —Br, —I, —SR$_1$, —SOR, —SO$_2$R$_1$, —SO$_2$NR$_1$R$_2$, —OCOR$_1$, —OCONR$_1$R$_2$, —NR$_1$COR$_2$, —NR$_1$CO$_2$R$_2$, —CN, —NO$_2$, —CO$_2$R$_1$, —CONR$_1$R$_2$, —C(O)R$_1$, —CH(OR$_1$)R$_2$, —CH$_2$(OR$_1$), —R$_1$, and —A—(CH$_2$)$_n$—NR$_1$R$_2$,
wherein
R$_1$ and R$_2$ are independently selected from the group consisting of —H, —CF$_3$, —C$_1$-C$_{10}$ alkyl, -cycloalkyl, -alkyl-aryl, -alkyl-heteroaryl, -heterocycloalkyl, -aryl and where R$_1$ and R$_2$ may combine to form a ring, and A is defined as CH$_2$, O, NH, S, SO, or SO$_2$ and n is 1,2,3, or 4,
with the proviso that when ---- represents a double bond, then either of Ar$_1$ or Ar$_2$ is pyridyl and the compound is not:

3-(2-Pyridyl)-5-(2-nitrophenyl)-1,2,4-oxadiazole,
3-(2-Pyridyl)-5-(2-chlorophenyl)-1,2,4-oxadiazole,
3-(2-pyridyl)-5-(4-nitrophenyl)-1,2,4-oxadiazole,
3-(2-pyridyl)-5-(4-aminophenyl)-1,2,4-oxadiazole,
3-(2-pyridyl)-5-{2-[2-(N,N,dimethylamino)-ethyl] oxyphenyl}-1,2,4-oxadiazole, or
3-(2-pyridyl)-5-phenyl-1,2,4-oxadiazole.

34. A compound as defined in claim 33 wherein ---- represents a double bond.

35. The compound of claim 33 wherein Ar$^1$ is 2-pyridyl and Ar$^2$ is phenyl.

36. The compound of claim 35, wherein G is selected from the group consisting of —CF$_3$, —Cl, —F, —Br, —CH$_3$, —NO$_2$, —OCF$_3$, —SCH$_3$, and —CN.

37. The compound of claim 35, wherein Ar$_1$ is 2-pyridyl and substituted with one or more G, wherein G is selected from the group consisting of —CF$_3$, —F, and —Cl.

38. A compound selected from the group consisting of:
3-(2-pyridyl)-5-(3-methoxyphenyl)-1,2,4-oxadiazole (B1),
3-(2-pyridyl)-5-(3,5-dichlorophenyl)-1,2,4-oxadiazole (B2),
3-(2-pyridyl)-5-(3-chlorophenyl)-1,2,4-oxadiazole (B3),
3-(2-pyridyl)-5-(3-methylphenyl)-1,2,4-oxadiazole (B9),
3-(2-pyridyl)-5-[3-(trifluoromethoxy)phenyl]-1,2,4-oxadiazole (B11),
3-(2-pyridyl)-5-(2,3-difluorophenyl)-1,2,4-oxadiazole (B16),
3-(2-pyridyl)-5-(2,5-difluorophenyl)-1,2,4-oxadiazole (B17),
3-(2-pyridyl)-5-(3,5-difluorophenyl)-1,2,4-oxadiazole (B18),
3-(2-pyridyl)-5-(3-nitrophenyl)-1,2,4-oxadiazole (B19),
3-(2-pyridyl)-5-(3-cyanophenyl)-1,2,4-oxadiazole (B21),
3-(2-pyridyl)-5-(3-bromophenyl)-1,2,4-oxadiazole (B22),
3-(2-pyridyl)-5-(3,5-dimethoxyphenyl)-1,2,4-oxadiazol (B23),
3-(2-pyridyl)-5-(2,3-dichlorophenyl)-1,2,4-oxadiazole (B25),
3-(2-pyridyl)-5-(3-chloro-5-cyanophenyl)-1,2,4-oxadiazole (B26),
3-(2-pyridyl)-5-(3-fluoro-5-cyanophenyl)-1,2,4-oxadiazole (B27),
3-(2-pyridyl)-5-(3-chloro-5-fluorophenyl)-1,2,4-oxadiazole (B28),
3-(5-chloropyrid-2-yl)-5-(3-cyanophenyl)-1,2,4-oxadiazole (B29)
3-(5-fluoropyrid-2-yl)-5-(3-cyanophenyl)-1,2,4-oxadiazole (B30),
3-(5-fluoropyrid-2-yl)-5-(3-cyano-5-fluorophenyl)-1,2,4-oxadiazole (B31),
3-(3-fluoropyrid-2-yl)-5-(3-cyanophenyl)-1,2,4-oxadiazole (B32),
3-(5-fluoropyrid-2-yl)-5-(3,5-dimethoxyphenyl)-1,2,4-oxadiazole (B33),
3-(5-methoxypyrid-2-yl)-5-(3-cyanophenyl)-1,2,4-oxadiazole (B34),
3-(2-quinolinyl)-5-(3-cyanophenyl)-1,2,4-oxadiazole (B35),
3-(3-chloro-5-trifluoromethylpyrid-2-yl)-5-(3-cyanophenyl)-1,2,4-oxadiazole (B36),
3-(2pyridyl)-5-(5-chloro-2-methoxyphenyl)-1,2,4-oxadiazole (B37),
3-(2-pyridyl)-5-(2-chloro-5-methylthiophenyl)-1,2,4-oxadiazole (B39),
3-(2-pyridyl)-5-(2-bromo-5-methoxyphenyl)-1,2,4-oxadiazole (B42), and
3-(2-pyridyl)-5-(2,5,6-trifluorophenyl)-1,2,4-oxadiazole (B45).

39. A pharmaceutical composition comprising a pharmaceutically acceptable carrier and a therapeutically effective, non-toxic, amount of a compound of Formula I:

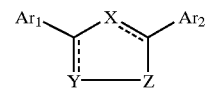

wherein
---- represents a double or single bond;
X and Y are N;
Z is O;
Ar$_1$ and Ar$_2$ are independently selected from the group consisting of: optionally substituted phenyl and optionally substituted 2-pyridyl wherein at least one of Ar$_1$ and Ar$_2$ is phenyl and at least one of Ar$_1$ and Ar$_2$ is 2-pyridyl and at least one of Ar$_1$ and Ar$_2$ is substituted with at least one substituent G;
wherein
  G is selected from the group consisting of: haloalkyl; pyridyl; thiophene; pyrimidine; furan; cycloalkene; alkenyl; alkynyl; A-alkenyl; A-alkynyl; A-alkyloxy; -R$_2$OR$_3$; —R$_2$OC(O)R$_3$; (CH$_2$)$_m$-NR$_2$R$_3$; —OCH$_2$CH(Cl)CH$_2$Cl; and substituted aryl wherein the aryl substituent is R$_4$, and
  wherein
    A is a linker selected from the group consisting of: CH$_2$; O; NH; S; SO; SO$_2$; NSO$_2$; —OSO$_2$; and —C(NR$_2$)NR$_3$;
    m is selected from 0 and 1;
    R$_2$ and R$_3$ may be independently selected from the group consisting of: H; alkyl; haloalkyl; alkyloxy; alkylamine; cycloalkyl; heterocycloalkyl; aryl; heteroaryl; alkylaryl; alkylheteroaryl; haloaryl; alkyloxyaryl; alkenylaryl; alkenyloxyaryl; and haloheteroaryl; and
    R$_4$ is selected from the group consisting of: halo; —OR$_2$; —SR$_2$; —SOR$_2$; —SO$_2$R$_2$; —SO$_2$NR$_2$R$_3$; —R$_2$OR$_3$; —R$_2$SR$_3$; —OCOR$_2$; —OCONR$_2$R$_3$; —NR$_2$COR$_3$; —NR$_2$CO$_2$R$_3$; —CN; —NO$_2$; —C(NR$_2$)NR$_3$; —CO$_2$R$_2$R$_3$; —CONR$_2$R$_3$; —C(O)R$_2$; —CH(OR$_2$)R$_3$; —CH$_2$(OR$_2$); —A—(CH$_2$)$_m$-NR$_2$R$_3$; NR$_2$R$_3$; aryl; aralkyl; heteroaryl; and heteroaralkyl; and
Ar$_1$, Ar$_2$, and the substituent G are optionally further substituted with one or more substituents selected independently from the group consisting of R$_2$ and R$_4$,
with the proviso that when ---- represents a double bond, then either of Ar$_1$ or Ar$_2$ is pyridyl and the compound is not:
3-(2-pyridyl)-5-(4-aminophenyl)-1,2,4-oxadiazole,
3-(2-Pyridyl)-5-(2-chlorophenyl)-1,2,4-oxadiazole,
3-(2-pyridyl)-5-(4-nitrophenyl)-1,2,4-oxadiazole,
3-(2-pyridyl)-5-phenyl-1,2,4-oxadiazole, and
3-(2-pyridyl)-5-{2-[2-(N,N,dimethylamino)-ehtyl] oxyphenyl}-1,2,4-oxadiazole.

40. A method for treating a disease associated with Group I mGluR activation comprising the step of administering to a patient in need of such treatment a pharmaceutical composition as defined in claim 39.

41. A method according to claim 40 wherein the disease is a disease associated with mGluR activation.

42. A method according to claim 41 wherein the disease is a neurological disease.

43. A method according to claim 41 wherein the disease is a psychiatric disease.

44. A method according to claim 41 wherein the disease is selected from the group consisting of stroke, head trauma, anoxic injury, ischemic injury, hypoglycemia, epilepsy, pain, migraine headaches, Parkinson's disease, senile dementia, Huntington's Chorea, anxiety, and Alzheimer's disease.

45. A pharmaceutical composition comprising a therapeutically effective, non-toxic, amount of a compound of claim 33 and a pharmaceutically acceptable carrier.

46. A method for treating a disease associated with Group I mGluR activation comprising the step of administering to a patient in need of such treatment a pharmaceutical composition as defined in claim 45.

47. A method according to claim 46 wherein the disease is a disease associated with mGluR activation.

48. A method according to claim 47 wherein the disease is a neurological disease.

49. A method according to claim 47 wherein the disease is a psychiatric disease.

50. A method according to claim 47 wherein the disease is selected from the group consisting of stroke, head trauma, anoxic injury, ischemic injury, hypoglycemia, epilepsy, pain, migraine headaches, Parkinson's disease, senile dementia, Huntington's Chorea, anxiety, and Alzheimer's disease.

51. A method according to claim 47 wherein the disease is selected from the group consisting of schizophrenia and depression.

52. A compound, or a pharmaceutically acceptable salt thereof, selected from the group consisting of compounds as set forth in the following table:

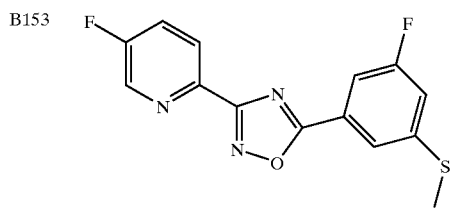

B153

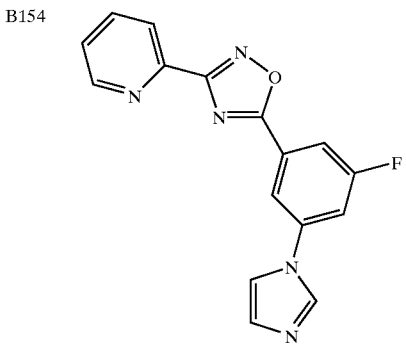

B154

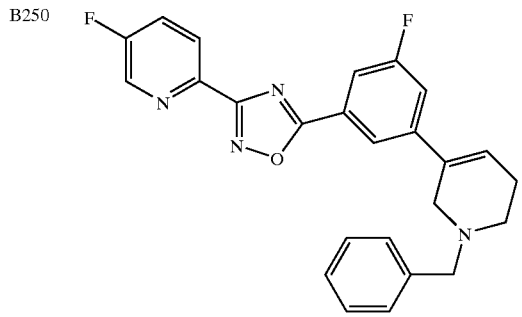

B250

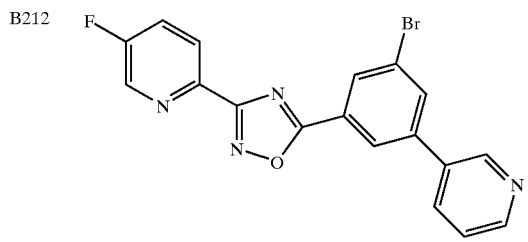

B212

-continued
B251
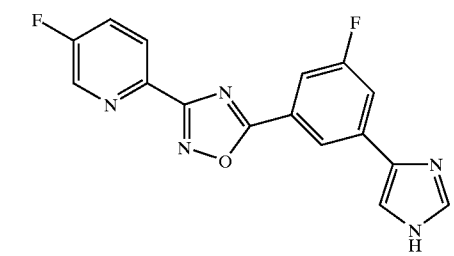
B213
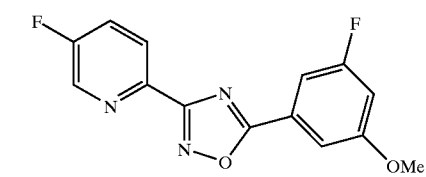
B253
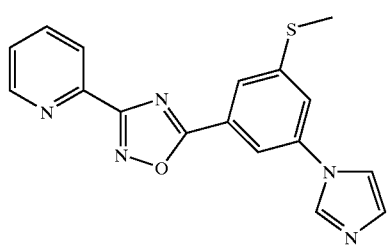
B254
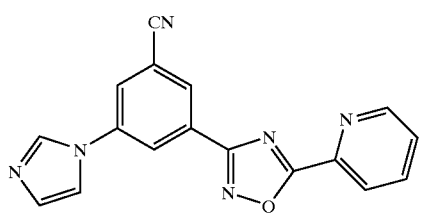
B255
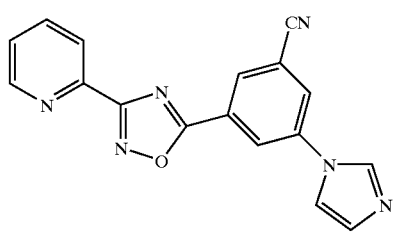
B216
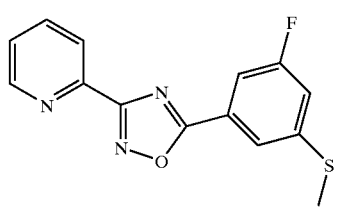
B217
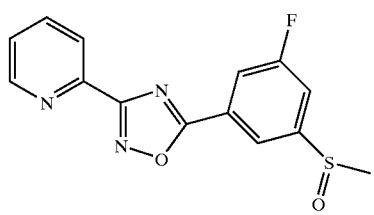

-continued
B214 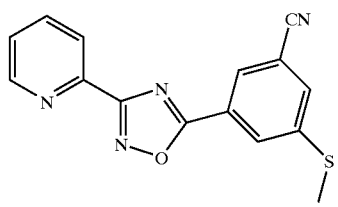
B215 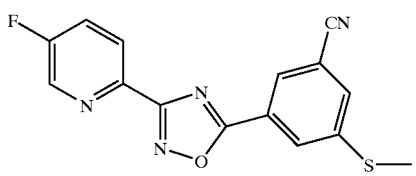
B218 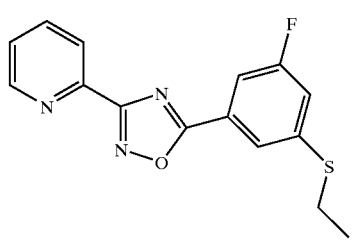
B219 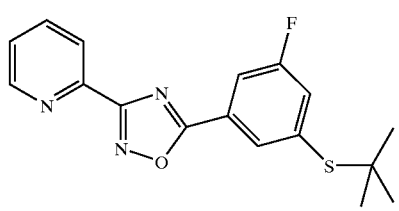
B155 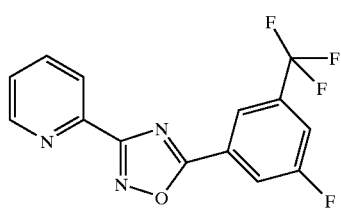
B156 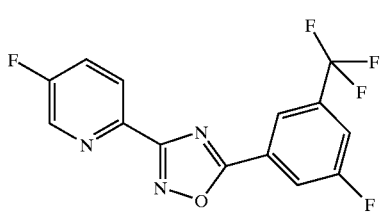
B223 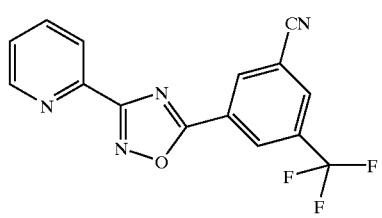

-continued
B224 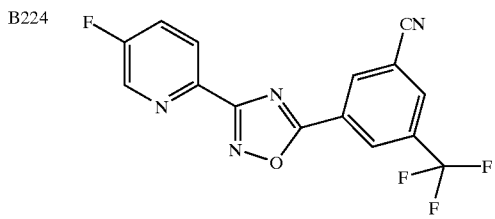
B244 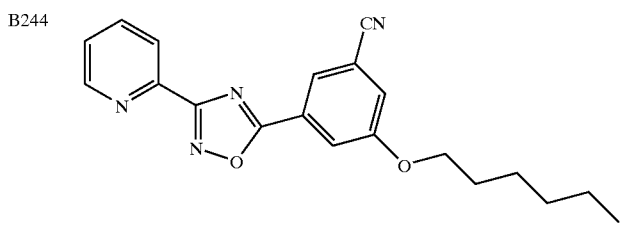
B167 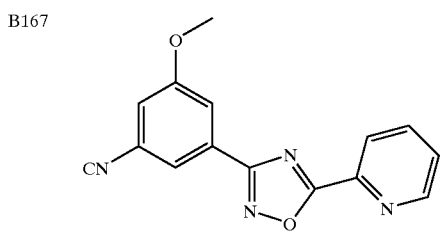
B168 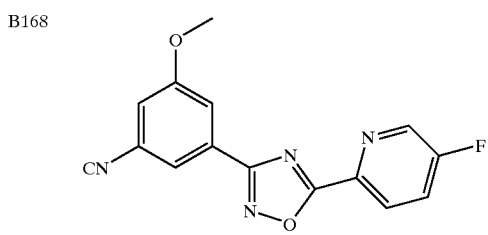
B169 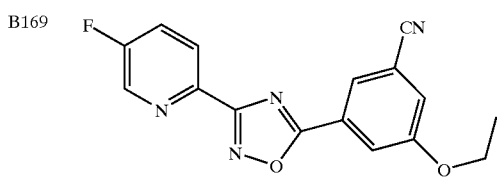
B170 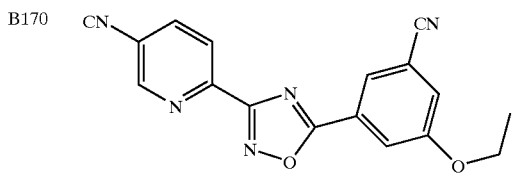
B171 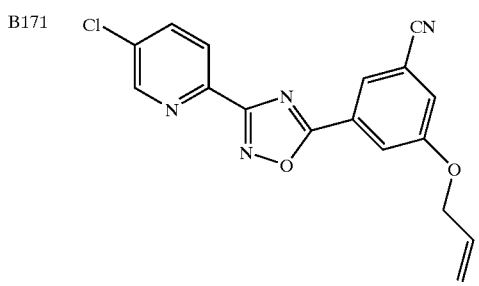

-continued
B172 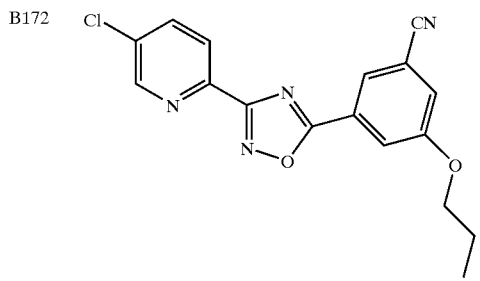
B173 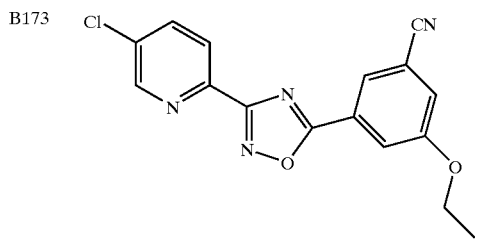
B174 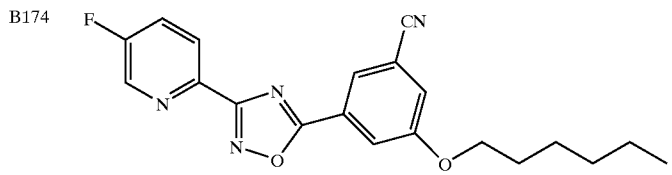
B175 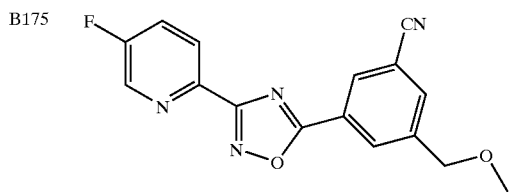
B245 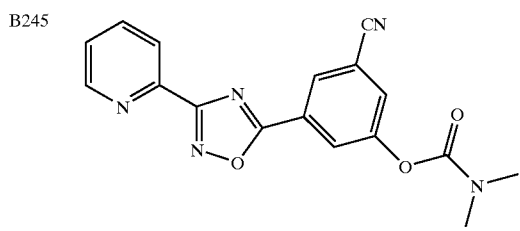
B246 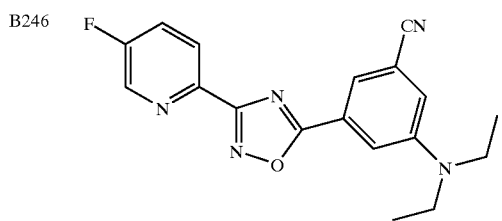
B247 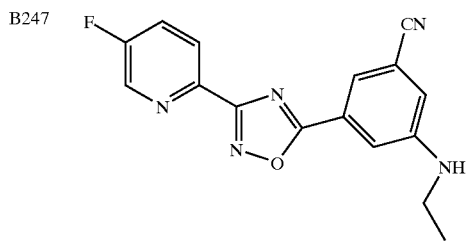

-continued
B274 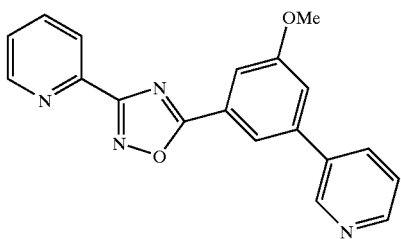
B275 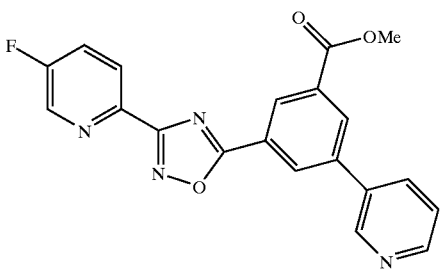
B276 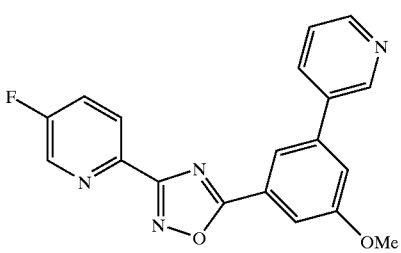
B277 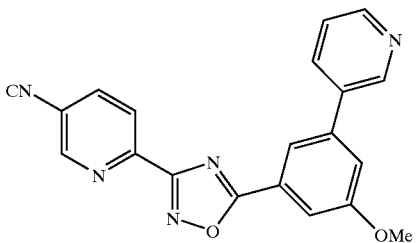
B220 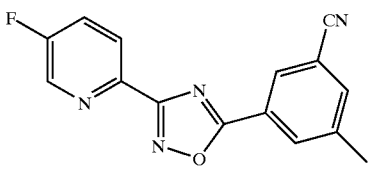
B221 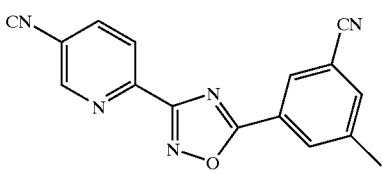
B176 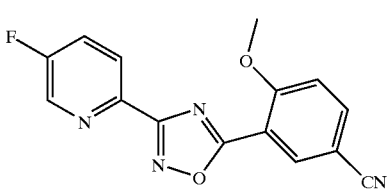

-continued
B177 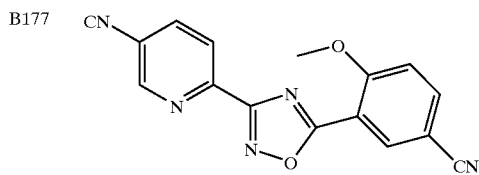
B225 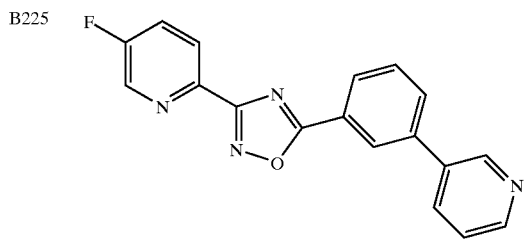
B226 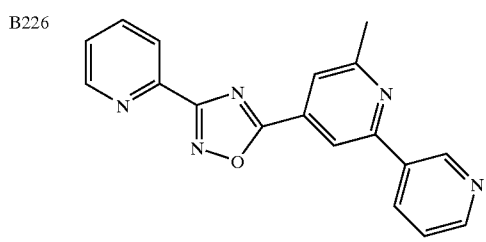
B181 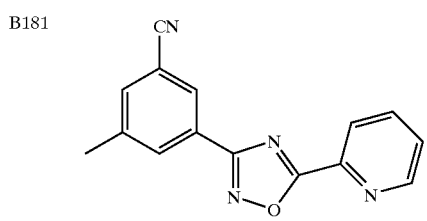
B183 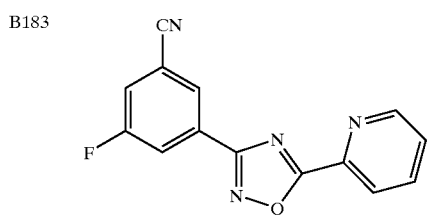
B184 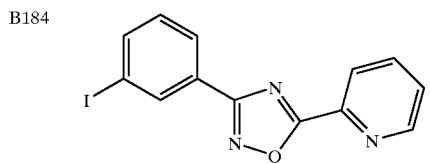
B186 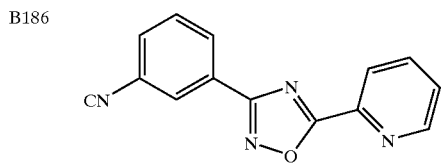

-continued
B187 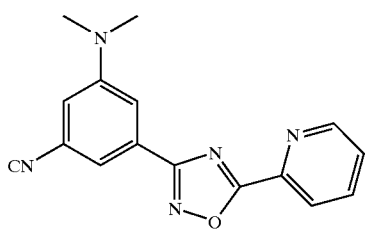
B188 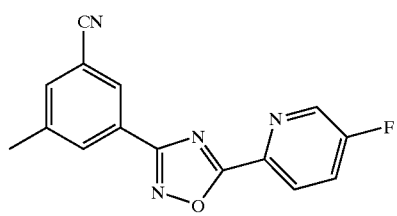
B189 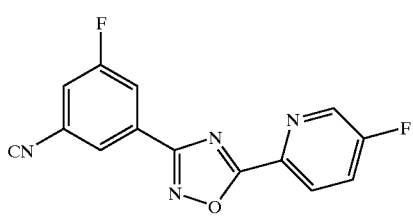
B229 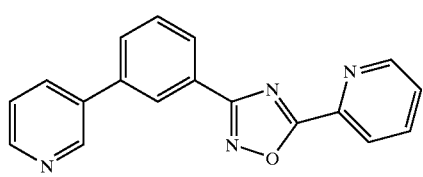
B190 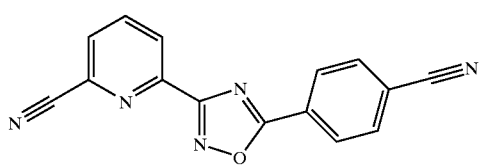
B191 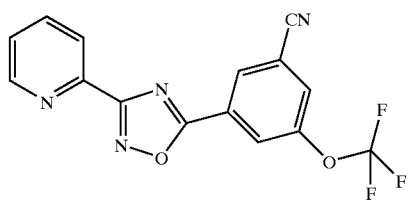
B192 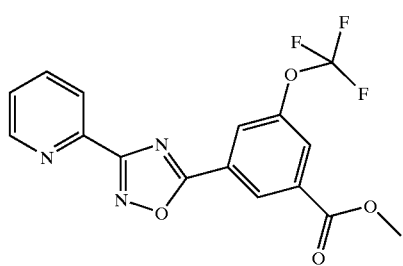

-continued
B193 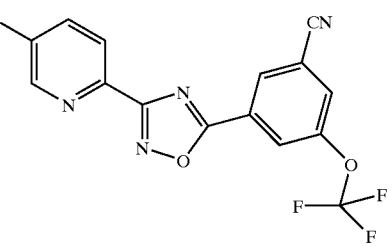
B194 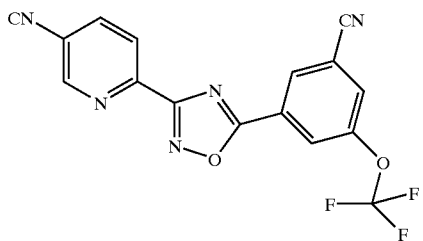
B195 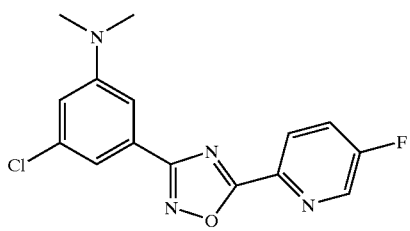
B230 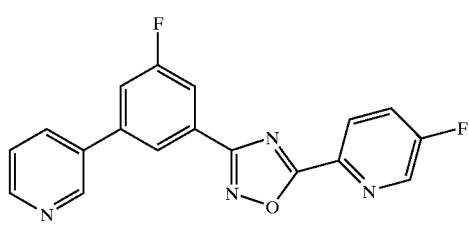
B197 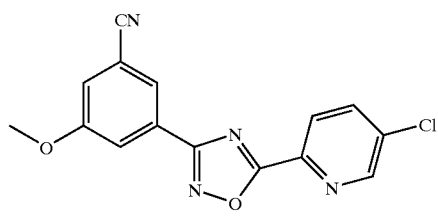
B196 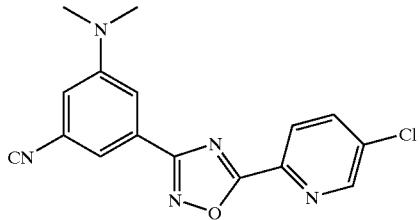

-continued
B200
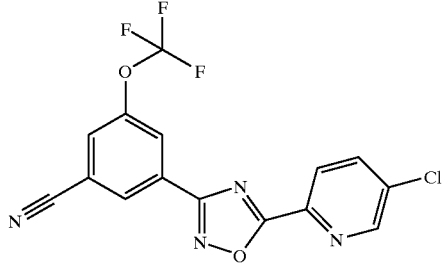
B201
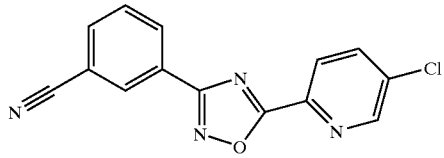
B202
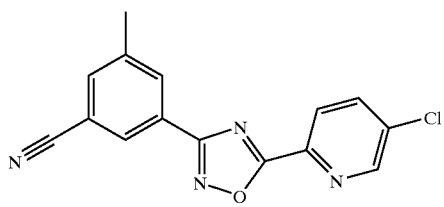
B203
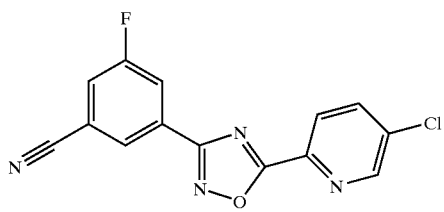
B204
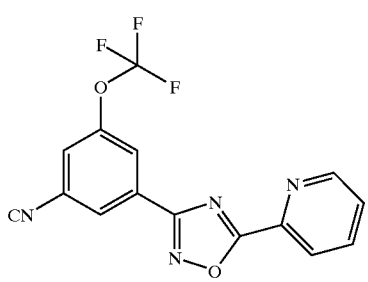
B205
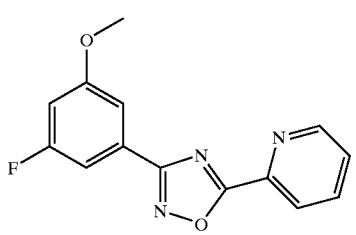
B206
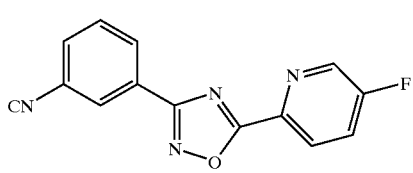

-continued
B208 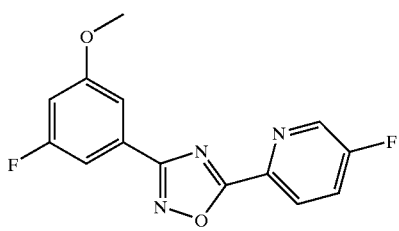
B207 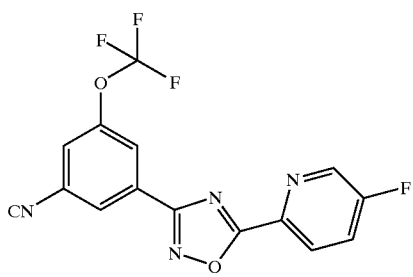
B209 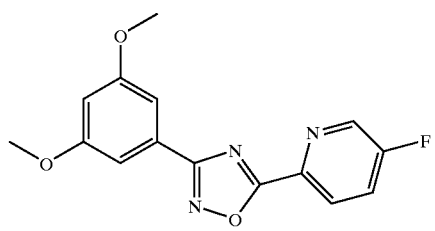
B248 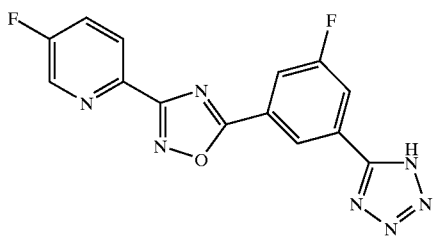
B249 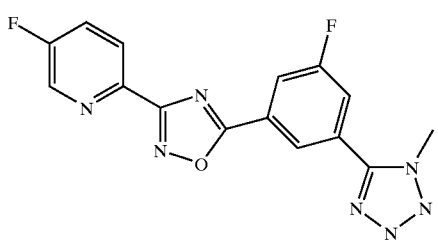
B231 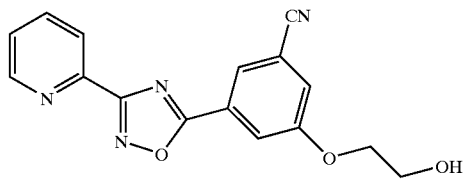
B157 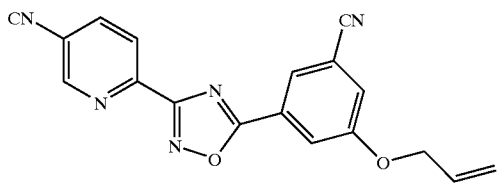

-continued
B158 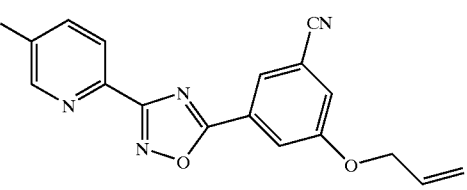
B159 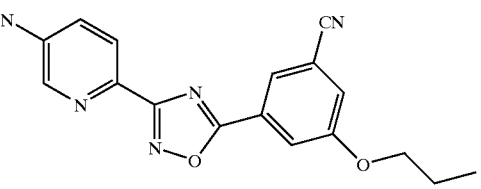
B160 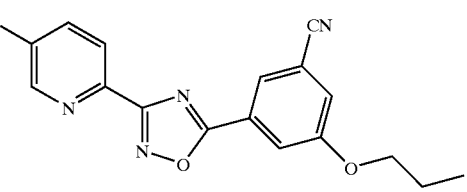
B232 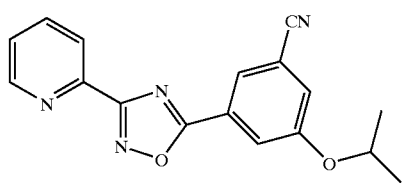
B233 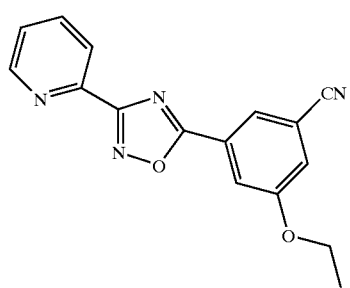
B234 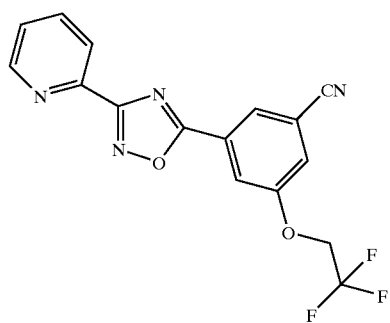
B161 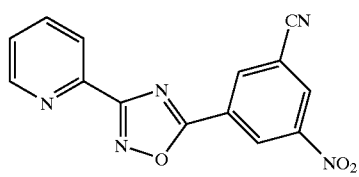

-continued
B162 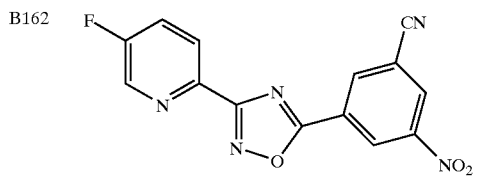
B235 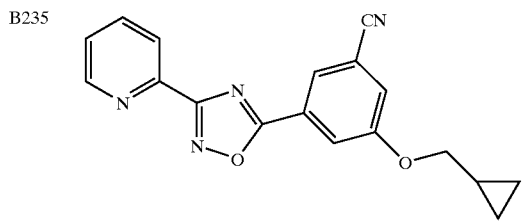
B236 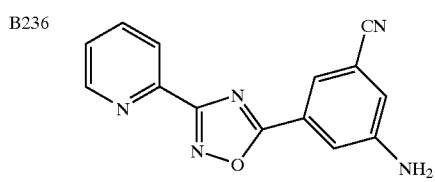
B237 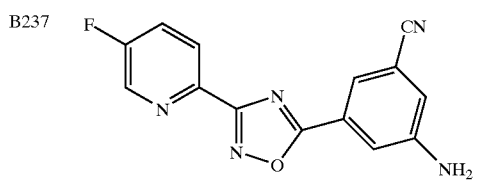
B238 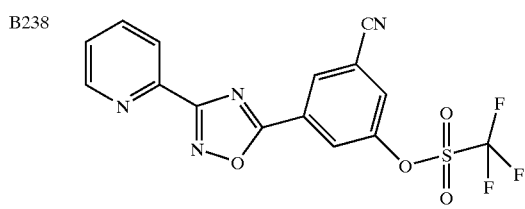
B239 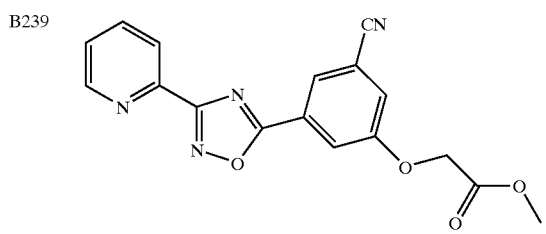
B240 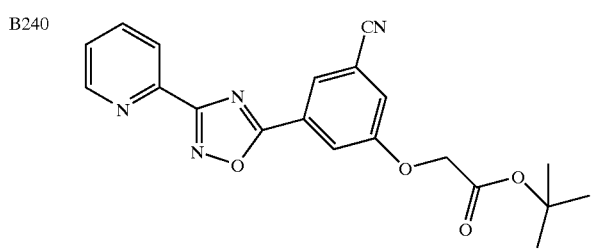

-continued
B241 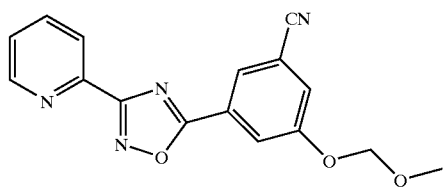
B163 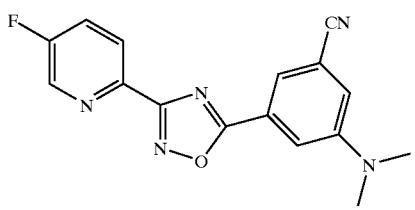
B242 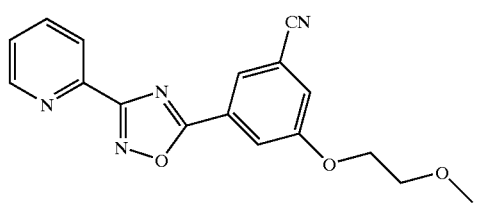
B164 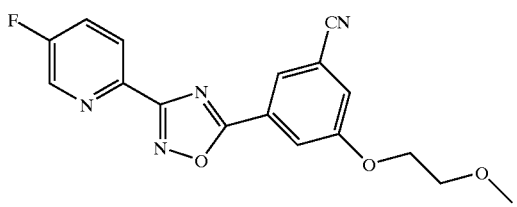
B165 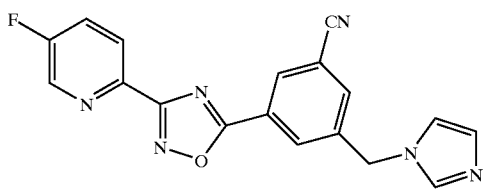
B243 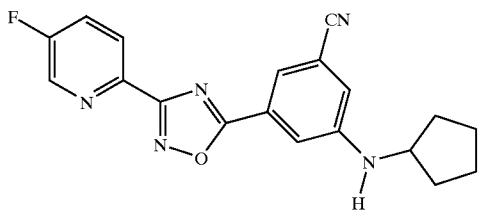
B166 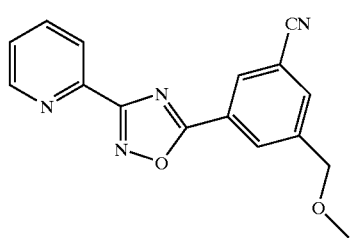

53. A pharmaceutical composition comprising a pharmaceutically acceptable carrier and a therapeutically effective, non-toxic, amount of a compound of Formula I:

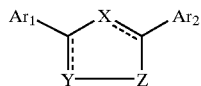

wherein
X and Y are N;
Z is O;
$Ar^1$ and $Ar^2$ are independently selected from the group consisting of optionally substituted phenyl and optionally substituted 2-pyridyl wherein at least one of $Ar_1$ and $Ar_2$ is phenyl and at least one of $Ar_1$ and $Ar2$ is 2-pyridyl, wherein
    $Ar^1$ and $Ar^2$ are optionally substituted with one or more substituents G,
    wherein
        G is selected from the group consisting of —F, —Cl, —Br, —I, —$SR_1$, —SOR, —$SO_2R_1$, —$SO_2NR_1R_2$, —$OCOR_1$, —$OCONR_1R_2$, —$NR_1CO_2R_2$, —$NR_1CO_2R_2$, —CN, —$NO_2$, —$CO_2R_1$, —$CONR_1R_2$, —C(O)$R_1$, —CH(O$R_1$)$R_2$, —$CH_2$(O$R_1$), —$R_1$, and —A—(C$H_2$)$_n$—N$R_1R_2$,
        wherein
            $R_1$ and $R_2$ are independently selected from the group consisting of —H, —$CF_3$, —$C_{1-C10}$ alkyl, -cycloalkyl, -alkyl-aryl, -alkyl-heteroaryl, -heterocycloalkyl, -aryl and where $R_1$ and $R_2$ may combine to form a ring, and A is defined as $CH_2$, O, NH, S, SO, or $SO_2$ and n is 1, 2, 3, or 4, with the proviso that when ---- represents a double bond, then either of $Ar_1$ or $Ar_2$ is pyridyl and the compound is not:

3-(2-Pyridyl)-5-(2-chlorophenyl)-1,2,4-oxadiazole, 3-(2-pyridyl)-5-(4-nitrophenyl)-1,2,4oxadiazole, 3-(2pyridyl)5-(4-aminophenyl)-1,2,4-oxadiazole, 3-(2-pyridyl)-5-{2[2-(N,N,dimethylamino)-ethyl]oxyphenyl}-1,2,4-oxadiazole, or 3-(2-pyridyl)-5-phenyl-1,2,4-oxadiazole.

54. A method for treating a disease associated with Group I mGluR activation comprising the step of administering to a patient in need of such treatment a pharmaceutical composition as defined in claim 53.

55. A method according to claim 54 wherein the disease is a disease associated with mGluR activation.

56. A method according to claim 55 wherein the disease is a neurological disease.

57. A method according to claim 55 wherein the disease is a psychiatric disease.

58. A method according to claim 55 wherein the disease is selected from the group consisting of stroke, head trauma, anoxic injury, ischemic injury, hypoglycemia, epilepsy, pain, migraine headaches, Parkinson's disease, senile dementia, Huntington's Chorea, anxiety, and Alzheimer's disease.

* * * * *